(12) United States Patent
Klein et al.

(10) Patent No.: US 11,789,019 B2
(45) Date of Patent: *Oct. 17, 2023

(54) PEPTIDE MHCII TETRAMERS TO DETECT ENDOGENOUS CALNEXIN SPECIFIC CD4 T CELLS

(71) Applicant: Wisconsin Alumni Research Foundation, Madison, WI (US)

(72) Inventors: Bruce Steven Klein, Madison, WI (US); Marcel Wuethrich, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 1041 days.

This patent is subject to a terminal disclaimer.

(21) Appl. No.: 16/529,151

(22) Filed: Aug. 1, 2019

(65) Prior Publication Data

US 2019/0361022 A1    Nov. 28, 2019

Related U.S. Application Data

(62) Division of application No. 14/643,693, filed on Mar. 10, 2015, now Pat. No. 10,416,158.

(60) Provisional application No. 61/951,099, filed on Mar. 11, 2014.

(51) Int. Cl.
*G01N 33/569* (2006.01)
*A61K 39/002* (2006.01)

(52) U.S. Cl.
CPC .  *G01N 33/56972* (2013.01); *G01N 33/56961* (2013.01); *G01N 2333/70539* (2013.01)

(58) Field of Classification Search
None
See application file for complete search history.

(56) References Cited

U.S. PATENT DOCUMENTS

| | | | |
|---|---|---|---|
| 4,016,043 | A | 4/1977 | Schuurs |
| 4,590,159 | A | 5/1986 | Markovitz |
| 4,962,023 | A | 10/1990 | Todd |
| 5,266,497 | A | 11/1993 | Imai |
| 5,714,389 | A | 2/1998 | Charlton |
| 5,877,028 | A | 3/1999 | Chandler |
| 5,922,537 | A | 7/1999 | Ewart |
| 6,168,956 | B1 | 1/2001 | Chandler |
| 6,180,417 | B1 | 1/2001 | Hajizadeh |
| 6,548,309 | B1 | 4/2003 | Moore |
| 9,993,534 | B2 * | 6/2018 | Klein ............... C07K 14/37 |
| 10,806,776 | B2 * | 10/2020 | Klein ............... C07K 16/14 |
| 2001/0006821 | A1 | 7/2001 | Ching |
| 2003/0165970 | A1 | 9/2003 | Hu |
| 2004/0087036 | A1 | 5/2004 | Chung |
| 2004/0214347 | A1 | 10/2004 | LaBorde |
| 2014/0271720 | A1 | 9/2014 | Klein et al. |

OTHER PUBLICATIONS

Ali-Khan et al (Current Protocols in Protein Sci., 2002, John Wiley & Sons, Inc., Suppl. 30, 22.1.1-22.2.19) (Year: 2002).*
Nepom, G.T. (J. Immunol., 2012, 188: 2477-2482) (Year: 2012).*
Hurtgen et al (Infect. Immunity, 2012 80(11): 3960-3974) (Year: 2012).*
Tanaka et al (Gene, 1997, 204 (1-2): 159-163) (Year: 1997).*
Chen and Kolls (Ann. Rev. Immunol. 2013, 31: 605-633) (Year: 2013).*
Vollers and Stern (Immunol. 2008, 123: 305-313) (Year: 2008).*
Kozono et al (Nature 1994, 369: 151-154) (Year: 1994).*
Brandhorst, et al., Targeted Gene Disruption Reveals an Adhesin Indispensable for Pathogenicity of Blastomyces Dermatitidis, J. Exp. Med., 1999, 189(8):1207-1216.
Dos Santos Feitosa, et al., Cloning, Characterization and Expression of a Calnexin Homologue from the Pathogenic Fungus Paracoccidioides Brasiliensis, Yeast, 2007, 24:79-87.
Ellgaard, et al., Quality Control in the Endoplasmic Reticulum, Nature Reviews Molecular Cell Biology, 2003, 4:181-191.
Fisher, et al., Biostatistics, A Methodology for Health Sciences, A Wiley-Interscience Publication, Copyright 1993 by John Wiley & Sons, Inc., pp. 611-613.
Harvey, et al., Mouse Model of Pulmonary Blastomycosis: Utility, Simplicity, and Quantitative Parameters, The American Review of Respiratory Disease, 1978, 117(4):695-703.
Leibundgut-Landmann, et al., Syk- and CARD9-dependent Coupling of Innate Immunity to the Induction of T Helper Cells that Produce Interleukin 17, Nature Immunology, 2007, 8:630-638.
Levine, et al., Division of Microbiology: Immunity to Coccidioidomycosis Induced in Mice by Purified Spherule, Arthrospore, and Mycelial Vaccines, Transactions of the New York Academy of Sciences, 1960, 22(6):436-449.
Levine, et al., Immunization of Mice to Coccidioides Immitis: Dose, Regimen and Spherulation Stage of Killed Spherule Vaccines, Journal of Immunology, 1965, 94(1):132-142.
Myhill, et al., The Subcellular Distribution of Calnexin is Mediated by PACS-2, Molecular Biology of the Cell, 2008, 19:2777-2788.
Nemecek, et al., Global Control of Dimorphism and Virulence in Fungi, Science, 2006, 312:583-588.
Wuthrich, et al., Calnexin Induces Expansion of Antigen-Specific CD4+ T Cells that Confer Immunity to Fungal Ascomycetes via Conserved Epitopes, Cell Host Microbe, 2015, 17:452-465.
Scott, et al., Role of Chain Pairing for the Production of Functional Soluble IA Major Histocompatibility Complex Class II Molecules, The Journal of Experimental Medicine, 1996, 183:2087-2095.

(Continued)

*Primary Examiner* — Michael Szperka
*Assistant Examiner* — Marianne DiBrino
(74) *Attorney, Agent, or Firm* — Quarles & Brady LLP

(57) ABSTRACT

The present application discloses proteins or peptides and methods of using such proteins or peptides to evaluate the immune status of a patient. In one embodiment, proteins or peptides may be used to detect endogenous calnexin specific CD4 T cells. In one preferred embodiment, the proteins or peptides may comprise peptide-MHCII tetramers (pMHC tetramers).

15 Claims, 52 Drawing Sheets
(11 of 52 Drawing Sheet(s) Filed in Color)
Specification includes a Sequence Listing.

(56) References Cited

OTHER PUBLICATIONS

Wang, et al., Lentiviral Calnexin-Modified Dendritic Cells Promote Expansion of High-Avidity Effector T Cells with Central Memory Phenotype, Immunology, 2009, 128:43-57.
Williams, Beyond Lectins: The Calnexin/Calreticulin Chaperone System of the Endoplasmic Reticulum, Journal of Cell Science, 2006, 119:615-623.
Cassone, et al. Recent Progress in Vaccines Against Fungal Diseases, Current Opinion in Microbiology, 2012, 15:427-433.
Wuthrich, et al., Mutation of the WI-1 Gene Yields an Attenuated Blastomyces Dermatitidis Strain That Induces Host Resistance, Journal of Clinical Investigation, 2000, 106(11):1381-1389.
Wuthrich, et al., VB1+ JB1.1+ /Va2+ Ja49+ CD4+ T Cells Mediate Resistance Against Infection with Blastomyces Dermatitidis, Infection and Immunity, 2007, 75(1):193-200.
Wuthrich, et al., Vaccine-Induced Protection Against 3 Systemic Mycoses Endemic to North America Requires Th17 Cells in Mice, Journal of Clinical Investigation, 2011, 121(2):554-568.
Wuthrich, et al., A TCR Transgenic Mouse Reactive with Multiple Systemic Dimorphic Fungi, Journal of Immunology, 2011, 187:1421-1431.
Wuthrich, et al., Fungi Subvert Vaccine T Cell Priming at the Respiratory Mucosa by Preventing Chemokine-Induced Influx of Inflammatory Monocytes, Immunity, 2012, 36:680-692.
Beckett, et al., A Minimal Peptide Substrate in Biotin Holoenzyme Synthetase-Catalyzed Biotinylation, Protein Science, 1999, 8:921-929.
Hirota, et al., Fate Mapping of IL-17-Producing T Cells in Inflammatory Responses, Nature Immunology, 2011, 12:255-263.
Huang, et al., Robust Stimulation of Humoral and Cellular Immune Responses Following Vaccination with Antigen-Loaded Beta-Glucan Particles, mBio, 2010, 1(3):e00164-10, pp. 1-7.
Moon, et al., Tracking Epitope—Specific T Cells, Nature Protocols, 2009, 4:565-581.
Moon, et al., Naive CD4(+) T Cell Frequency Varies for Different Epitopes and Predicts Repertoire Diversity and Response Magnitude, Immunity, 2007, 27:203-213.
Rappleye, et al., Fungal Stealth Technology, Trends in Immunology, 2008, 29:8-24.
Soto, et al, Characterization of Multilayered Nanoparticles Encapsulated in Yeast Cell Wall Particles for DNA delivery, Bioconjugate Chemistry, 2008, 19:840-848.
Acosta-Rodriguez, E.V., et al. (2007). Surface phenotype and antigenic specificity of human interleukin 17-producing T helper memory cells. Nature immunology 8, 639-646.
Beck, O., et al. (2006). Generation of highly purified and functionally active human TH1 cells against Aspergillus fumigatus. Blood 107, 2562-2569.
Berge, S. M. et al. "Pharmaceutical salts." Journal of pharmaceutical sciences 66.1 (1977): 1-19.
Blyth, E., et al. (2013). Donor-derived CMV-specific T cells reduce the requirement for CMV-directed pharmacotherapy after allogeneic stem cell transplantation. Blood 121, 3745-3758.
Casadevall, A., et al. (2009). Vesicular transport across the fungal cell wall. Trends in microbiology 17, 158-162.
Da Gloria Sousa, M., et al. (2011). Restoration of pattern recognition receptor costimulation to treat chromoblastomycosis, a chronic fungal infection of the skin. Cell Host Microbe 9, 436-443.
Deepe, G.S., Jr., et al. (1995). Immunobiological activity of recombinant H antigen from Histoplasma capsulatum. Infection and immunity 63, 3151-3157.
Edwards, J.E., Jr. (2012). Fungal cell wall vaccines: an update. Journal of medical microbiology 61, 895-903.
Gomez, F.J., et al. (1991). Protective efficacy of a 62-kilodalton antigen, HIS-62, from the cell wall and cell membrane of Histoplasma capsulatum yeast cells. Infection and immunity 59, 4459-4464.
Harndahl, M., et al. "Peptide binding to HLA class I molecules: homogenous, high-throughput screening, and affinity assays." Journal of biomolecular screening 14.2 (2009): 173-180.
Hirota, K., et al. (2007). Preferential recruitment of CCR6-expressing Th17 cells to inflamed joints via CCL20 in rheumatoid arthritis and its animal model. The Journal of experimental medicine 204, 2803-2812.
Justesen, S., et al. "Functional recombinant MHC class II molecules and high-throughput peptide-binding assays." Immunome research 5.1 (2009): 2.
Kozono, H., et al. "Production of soluble MHC class II proteins with covalently bound single peptides." Nature 369.6476 (1994): 151.
Levitz, S.M., et al. (2006). The molecular basis for the immunogenicity of Cryptococcus neoformans mannoproteins. FEMS yeast research 6, 513-524.
Long, K.H., et al. (2003). Identification of heat shock protein 60 as the ligand on Histoplasma capsulatum that mediates binding to CD18 receptors on human macrophages. J Immunol 170, 487-494.
Lorch, J.M., et al. (2011). Experimental infection of bats with Geomyces destructans causes white-nose syndrome. Nature 480, 376-378.
Nanjappa, S.G., et al. (2012). Protective antifungal memory CD8(+) T cells are maintained in the absence of CD4(+) T cell help and cognate antigen in mice. J Clin Invest 122, 987-999.
Nanjappa, S.G., et al. (2012). Tc17 cells mediate vaccine immunity against lethal fungal pneumonia in immune deficient hosts lacking CD4+ T cells. PLoS pathogens 8, e1002771.
NCBI. "Calnexin" Gen Bank EGE86508.1. (2015) ncbi.nlm.nih.gov/protein/327357651; Protein database Accession No. EGE86508; Broad Institute predicted Gene name: BDDG_09453.
Nelson, R.W., et al. "T Cell Receptor Cross-Reactivity between Similar Foreign and Self Peptides Influences Naive Cell Population Size and Autoimmunity." Immunity 42 (2015): 95-107.
Nesvizhskii, A.I., et al. 2003. A statistical model for identifying proteins by tandem mass spectrometry. Anal Chem 75:4646-4658.
Nosanchuk, J.D., et al. (2003). Antibodies to a cell surface histone-like protein protect against Histoplasma capsulatum. J Clin Invest 112, 1164-1175.
O'Brien, C., et al. "Peptide length significantly influences in vitro affinity for MHC class II molecules." Immunome research 4.1 (2008): 6.
Park, B.J., et al. (2009). Estimation of the current global burden of cryptococcal meningitis among persons living with HIV/AIDS. AIDS 23, 525-530.
Peggs, K.S., et al. (2011). Directly selected cytomegalovirus-reactive donor T cells confer rapid and safe systemic reconstitution of virus-specific immunity following stem cell transplantation. Clin Infect Dis 52, 49-57.
Pepper, M., et al. (2010). Different routes of bacterial infection induce long-lived TH1 memory cells and short-lived TH17 cells. Nature immunology 11, 83-89.
Pfaller, M.A., et al. (2011). Candida Bloodstream Infections: Comparison of Species Distributions and Antifungal Resistance Patterns in Community-Onset and Nosocomial Isolates in the SENTRY Antimicrobial Surveillance Program, 2008-2009. Antimicrobial Agents and Chemotherapy 55, 561-566.
Singh, N., et al. (2005). Aspergillus infections in transplant recipients. Clinical microbiology reviews 18, 44-69.
Southwood, S., et al. "Several common HLA-DR types share largely overlapping peptide binding repertoires." The Journal of Immunology 160.7 (1998): 3363-3373.
Thompson, J.D., et al. 1994. Clustal W: improving the sensitivity of progressive multiple sequence alignment through sequence weighting, position-specific gap penalties and weight matrix choice. Nucleic Acids Res 22:4673-4680.
Torosantucci, A., et al. (2005). A novel glyco-conjugate vaccine against fungal pathogens. The Journal of experimental medicine 202, 597-606.
U.S. Pharmacopeia National Formulary, 1857-1859, (1990).
Walsh, T.J., et al. (2008). Treatment of aspergillosis: clinical practice guidelines of the Infectious Diseases Society of America. Clin Infect Dis 46, 327-360.
Wisniewski, J.R., et al. 2009. Universal sample preparation method for proteome analysis. Nat Methods 6:359-362.

(56) References Cited

OTHER PUBLICATIONS

Young, S.H., et al. (2007). A comparison of the pulmonary inflammatory potential of different components of yeast cell wall. J Toxicol Environ Health A 70, 1116-1124.

Zancope-Oliveira, R.M., et al. (1999). Molecular cloning, characterization, and expression of the M antigen of Histoplasma capsulatum. Infection and immunity 67, 1947-1953.
Jenkins Lab. MHC Class II Tetramer Production Protocol. Updated Jan. 27, 2016. Accessed online at jenkinslab.umn.edu/Jenkins_Lab_2/assets/pdf/New%20tetramer%20production%20010816-TD.pdf on Nov. 6, 2019.

* cited by examiner

Crude Ags

CW/M Eluate#1

Gel free fractions of Eluate#1

Gel free fraction number

CD4+ T cell responses

Figure 4B  Expression of Calnexin in *B. dermatitidis* vaccine yeast #55 non-immune serum anti-Calnexin serum

Figure 4C  Expression of Calnexin in *A. fumigatus* hyphae and spores

Calnexin Alignment

```
B.d. 26199  1   MRLNASLASLILSSIALIGNVHAEDEVKEDATSTSSVIEKPTFTPTTLKAPFLEQFTDGWETRWT  65
H.c. G217B  1   MRLNASLASLILSSVALIGNVRAEEEVKGDAPSRSSAIEKPTFTPTTLKAPFLEQFTDDWETRWT  65
C.p. C735   1   MRLNARIASLILSYIALLGGVHASEATKEEPIATSISRPTFTPTTLKAPFLEQFTDDWQTRWT   64
P.b. Pb01   1   MRLNASLASLIITSIALIGNVHAEDEVEGKPSSTSSVIEKPIFTPTTLKAPFLEQFTDDWETRWT  65

IEDB-B                              IEDB-D    Peptide 1
B.d. 26199  66  PSHAKKEDSKSEEDWAYVGTWAVEEPHVENGMVGDKGLVVKNAAAHHAISAKFPKKIDNKGKTLV  130
H.c. G217B  66  PSHAKKEDSSSDEDWAYIGTWAVEEPHVUNGMVGDKGLVVKNAAAHHAISAKFPKKIDNKGKTLV  130
C.p. C735   65  PSHAKKEDSKSEELWAYVGEWAVEEPTVFKGIGGDKGLVVKNAAAHHAISAKFPKKIDNKGKTLV  129
P.b. Pb01   66  PSHAKKQDSSSEEDWAYVGTWAVEEPHVENGMKGDKGLVIKNAAAHHAISAKFPKKIDNKGRTLV  130

B.d. 26199  131 VQYEVKLQNSLNCGGAYMKLLQDNKKLHAEEFSNTSPYVIMFGPDKCGVTNKVHFIRHKNPKTG  195
H.c. G217B  131 VQYEVKLQESLVCGGAYMKLLQDNKKLHAEEFSNASPYVIMFGPDKCGVTNKVHFIRHKNPKTG  195
C.p. C735   130 VQYEVKLQNSLNCGGAYMKLLQDNKKLHAEEFSNASPYVIMFGPDKCAVTNKVHFIRHKNPKTG  194
P.b. Pb01   131 VQYEVKLQNGLNCGGAYMKLLQDNKKLHAEEFSNASPYVIMFGPDKCGVTNKVHFIRHKNPKTG  195

IEDB-E    Peptide 3                                      Peptide 5
B.d. 26199  196 EYEEKHMKLPPAVRVSKLSTLYTLIVNPDQSFQIRIDGAAVKNGTLLEDFSPAVNPEKEIDDPED  260
H.c. G217B  196 EYEEKHLNNAAPAAKINKLSTLYTLIVKPDQSIFQIQINGEAVKNGTLLEDFQPEVNPPKEDDPED  260
C.p. C735   195 EYEEKHLNNAPTARVSKLSTLYTLIVKPDQTFQIQINGEAVKNGTLLEDFQPEVNPPKEIDDPND  259
P.b. Pb01   196 EYEEKHLKNPPAARVSKLSTLYTLIVKPDQSFQIIDGEAVKNGTLLEDFSPAVNPQKEIDDPED  260

Peptide 8   Peptide 6                                  Peptide 7
B.d. 26199  261 KKPEDWVDEAHIPDPEATKPEDWDEDAPYEIVDTDATQPEDWLVDERISIPDPEAQKPEDWDDEE  325
H.c. G217B  261 KKPEDWVDEARIADPDATKPEDWDEDAPYEIVDTDAVQPEDWLVDERISIPDPEAKPEDWDDEE  325
C.p. C735   260 KKPADWVDEKIPDPEAKKPEDWDEDAPREIVDTEAKKPDDWLQDEPSIPDPEAQKPEDWDDEE  324
P.b. Pb01   261 KKPKDWVDSFRIPDPTATKPDDWDEDAPYEITDTATKPDDWLDSEPISIPDPEAQKPEDWDDEE  325

Peptide 4                              IEDB-C    Peptide 9
B.d. 26199  326 DGDWRPTIPNPKCSEVSGCGMWEPMKKNPYKGKWTAPMIDNPAYKGPWAPRKIANPNYFEDK  390
H.c. G217B  326 DGDWRPTIPNPKCSEVSGCGKWQQPMKKNPDYKGKWVAPMIDNPAYKGPWAPRKIPNPDYFEDK  390
C.p. C735   325 DGDWFAPTVPNPKCEASGCGKWBPMKRNPDYKGKWTAPUIDNPAYKGPWSPRKIANRDHFEDK  389
P.b. Pb01   326 DGDWAAPTIPNPKCSEVSGCGKWEAPMKKNPDYKGKWTPPMIDNPAYKGPWTPRKIPNPNYFEDK  390

B.d. 26199  391 TRSNFEPMGAIGFEIWTMQNDILRDNIYIGHSVEDAKKLKAETWQLKHPVEVAEEEAAPKDEEK  455
H.c. G217B  391 TRSNFEPMGAIGFEIWTMQSDILRDNIYIGHSIEDAKKLKAETWDRKHPVEVAEEEASRPKDEEK  455
C.p. C735   390 KPANFEPMGAIGFEIWTMQNDILRDNIYIGHSIEDAKKLKAETRDIKQPIEVAEEEAAKPKDEPS  454
P.b. Pb01   391 TRANFEPMGAIGFEIWTMQNDILRDNIYIGHSIEDAQKLKSETWDLKHPIEVAEEEATRPKDDEK  455

B.d. 26199  456 KEGTSFKEAPVKYIRGKTELFISQALHNPVEAVKAVPEVAGGIDALVTLUVLIIVGAMGLGSPIS  520
H.c. G217B  456 EAGTSFKEDPVQYIRKKIQLFISIALHNPVEAVKAVPEVAGGIDALVTITULIIVSGLSUGSSS   519
C.p. C735   455 TDSGLNFKDDPVKYIRSKIVDQFILMAKDNPVEAVKTVPEVAGGIDAALITITULVVBGAIGLSSPA  519
P.b. Pb01   456 DSSFVSFKEAPVQFVREKINLFISTARKDPVQAAKSVPEVAGGIDALVITIALIIVGACIGSPA  520

Peptide 2 & 10
B.d. 26199  521 PAPAAKHQAEKGKEK------AEAVSTAADNVKQAKKRSQKAGE-   560
H.c. G217B  520 -GPAPKKQAEKGKEKEKAS---ASEAVSTGADNVKQQAKKRSTKTSE-  562
C.p. C735   520 PAPAKKDAGK-GKEKAKEK---AAEAVSTGAENIKAGATKRS-KSSE-  561
P.b. Pb01   521 PAPAVAKKVD-GKENDGASKEKAAEAVSTADNVKGAATRRSGKANNE  567
```

```
-----------180----------190-----------200----------210-----------220-----------230----------
NTSPYVIMFGPDKCGVTNKVHFIFKHKNPKTGEYEEKHMKLPPAVRVSKLSTLYTLIVN
SNTSPYVIMFGPDKCGVTNKVHFIFKHKNPKTGEYEEKHMKLPPAVRVSKLSTLYTL
EFSNTSPYVIMFGPDKCGVTNKVHFIFKHKNPKTGEYEEKHMKLPPAVRVSKLSTLYTL
EEFSNTSPYVIMFGPDKCGVTNKVHFIFKHKNPKTGEYEEKHMKLPPAVRVSKLSTLY
AEEFSNTSPYVIMFGPDKCGVTNKVHFIFKHKNPKTGEYEEKHMKLPPAVRVSKLSTLYT
HAEEFSNTSPYVIMFGPDKCGVTNKVHFIFKHKNPKTGEYEEKHMKLPPAVRVSKLSTL
HAEEFSNTSPYVIMFGPDKCGVTNKVHFIFKHKNPKTGEYEEKHMKLPPAVRVSKLSTL
EFSNTSPYVIMFGPDKCGVTNKVHFIFKHKNPKTGEYEEKHMKLPPAVRVSKLSTLYTI
IAEEFSNTSPYVIMFGPDKCGVTNKVHFIFKHKNPKTGEYEEKHMKLPPAVRVSKLSTLY
EEFSNTSPYVIMFGPDKCGVTNKVHFIFKHKNPKTGEYEEKHMKLPPAVRVSKLSTLY
FSNTSPYVIMFGPDKCGVTNKVHFIFKHKNPKTGEYEEKHMKLPPAVRVSKLSTLYTLIV
EFSNTSPYVIMFGPDKCGVTNKVHFIFKHKNPKTGEYEEKHMKLPPAVRVSKLSTLYTI
SNTSPYVIMFGPDKCGVTNKVHFIFKHKNPKTGEYEEKHMKLPPAVRVSKLSTLYTLIVN
EFSNTSPYVIMFGPDKCGVTNKVHFIFKHKNPKTGEYEEKHMKLPPAVRVSKLSTLYT
SNTSPYVIMFGPDKCGVTNKVHFIFKHKNPKTGEYEEKHMKLPPAVRVSKLSTLYTLIV
EFSNTSPYVIMFGPDKCGVTNKVHFIFKHKNPKTGEYEEKHMKLPPAVRVSKLSTLYTLI
EFSNTSPYVIMFGPDKCGVTNKVHFIFKHKNPKTGEYEEKHMKLPPAVRVSKLSTLY
EFSNTSPYVIMFGPDKCGVTNKVHFIFKHKNPKTGEYEEKHMKLPPAVRVSKLSTLYTL
SNTSPYVIMFGPDKCGVTNKVHFIFKHKNPKTGEYEEKHMKLPPAVRVSKLSTLYTL
SNTSPYVIMFGPDKCGVTNKVHFIFKHKNPKTGEYEEKHMKLPPAVRVSKLSTLYTI
EFSNTSPYVIMFGPDKCGVTNKVHFIFKHKNPKTGEYEEKHMKLPPAVRVSKLSTLYT
EFSNTSPYVIMFGPDKCGVTNKVHFIFKHKNPKTGEYEEKHMKLPPAVRVSKLSTLY
SNTSPYVIMFGPDKCGVTNKVHFIFKHKNPKTGEYEEKHMKLPPAVRVSKLSTLYTLI
SNTSPYVIMFGPDKCGVTNKVHFIFKHKNPKTGEYEEKHMKLPPAVRVSKLSTLYTLI
SNTSPYVIMFGPDKCGVTNKVHFIFKHKNPKTGEYEEKHMKLPPAVRVSKLSTLYTL
EFSNTSPYVIMFGPDKCGVTNKVHFIFKHKNPKTGEYEEKHMKLPPAVRVSKLSTLYT
EFSNTSPYVIMFGPDKCGVTNKVHFIFKHKNPKTGEYEEKHMKLPPAVRVSKLSTLYT
FSNTSPYVIMFGPDKCGVTNKVHFIFKHKNPKTGEYEEKHMKLPPAVRVSKLSTLYT
EFSNTSPYVIMFGPDKCGVTNKVHFIFKHKNPKTGEYEEKHMKLPPAVRVSKLSTLY
EFSNTSPYVIMFGPDKCGVTNKVHFIFKHKNPKTGEYEEKHMKLPPAVRVSKLSTLY
EEFSNTSPYVIMFGPDKCGVTNKVHFIFKHKNPKTGEYEEKHMKLPPAVRVSKLSTLY
SNTSPYVIMFGPDKCGVTNKVHFIFKHKNPKTGEYEEKHMKLPPAVRVSKLSTLYTI
NTSPYVIMFGPDKCGVTNKVHFIFKHKNPKTGEYEEKHMKLPPAVRVSKLSTLYTLI
SNTSPYVIMFGPDKCGVTNKVHFIFKHKNPKTGEYEEKHMKLPPAVRVSKLSTLYTI
TSPYVIMFGPDKCGVTNKVHFIFKHKNPKTGEYEEKHMKLPPAVRVSKLSTLYTLIVNP
SNTSPYVIMFGPDKCGVTNKVHFIFKHKNPKTGEYEEKHMKLPPAVRVSKLSTLYTLIVI
NTSPYVIMFGPDKCGVTNKVHFIFKHKNPKTGEYEEKHMKLPPAVRVSKLSTLYTLI
FSNTSPYVIMFGPDKCGVTNKVHFIFKHKNPKTGEYEEKHMKLPPAVRVSKLSTLYTL
TSPYVIMFGPDKCGVTNKVHFIFKHKNPKTGEYEEKHMKLPPAVRVSKLSTLYTLIVNP
FSNTSPYVIMFGPDKCGVTNKVHFIFKHKNPKTGEYEEKHMKLPPAVRVSKLSTLYT
EFSNTSPYVIMFGPDKCGVTNKVHFIFKHKNPKTGEYEEKHMKLPPAVRVSKLSTLYT
SNTSPYVIMFGPDKCGVTNKVHFIFKHKNPKTGEYEEKHMKLPPAVRVSKLSTLYTL
FSNTSPYVIMFGPDKCGVTNKVHFIFKHKNPKTGEYEEKHMKLPPAVRVSKLSTLYT
FSNTSPYVIMFGPDKCGVTNKVHFIFKHKNPKTGEYEEKHMKLPPAVRVSKLSTLYT
FSNTSPYVIMFGPDKCGVTNKVHFIFKHKNPKTGEYEEKHMKLPPAVRVSKLSTLYTLI
FSNTSPYVIMFGPDKCGVTNKVHFIFKHKNPKTGEYEEKHMKLPPAVRVSKLSTLYTLIV
SNTSPYVIMFGPDKCGVTNKVHFIFKHKNPKTGEYEEKHMKLPPAVRVSKLSTLYTLI
TSPYVIMFGPDKCGVTNKVHFIFKHKNPKTGEYEEKHMKLPPAVRVSKLSTLYTLIVNPD
SNTSPYVIMFGPDKCGVTNKVHFIFKHKNPKTGEYEEKHMKLPPAVRVSKLSTLYTLI
ITSPYVIMFGPDKCGVTNKVHFIFKHKNPKTGEYEEKHMKLPPAVRVSKLSTLYTLIVN
ITSPYVIMFGPDKCGVTNKVHFIFKHKNPKTGEYEEKHMKLPPAVRVSKLSTLYTLIVN
```

Figure 7C

```
----240-------------250-------------260-------------270-------------280-------------290----------300----------
IPDQSFQIRIDGAAVKNGTLLEDFSPAVNPEKEIDDPEDKKPEDWVDEAHIPDPEATKPEDWDEDAPYEI
IVNPDQSFQIRIDGAAVKNGTLLEDFSPAVNPEKEIDDPEDKKPEDWVDEAHIPDPEATKPEDWDEDAP
.IVNPDQSFQIRIDGAAVKNGTLLEDFSPAVNPEKEIDDPEDKKPEDWVDEAHIPDPEATKPEDWDED
'TLIVNPDQSFQIRIDGAAVKNGTLLEDFSPAVNPEKEIDDPEDKKPEDWVDEAHIPDPEATKPEDWD
TLIVNPDQSFQIRIDGAAVKNGTLLEDFSPAVNPEKEIDDPEDKKPEDWVDEAHIPDPEATKPEDWDED
YTLIVNPDQSFQIRIDGAAVKNGTLLEDFSPAVNPEKEIDDPEDKKPEDWVDEAHIPDPEATKPEDWDE
YTLIVNPDQSFQIRIDGAAVKNGTLLEDFSPAVNPEKEIDDPEDKKPEDWVDEAHIPDPEATKPEDWDE
LIVNPDQSFQIRIDGAAVKNGTLLEDFSPAVNPEKEIDDPEDKKPEDWVDEAHIPDPEATKPEDWDEI
'TLIVNPDQSFQIRIDGAAVKNGTLLEDFSPAVNPEKEIDDPEDKKPEDWVDEAHIPDPEATKPEDWDE
'TLIVNPDQSFQIRIDGAAVKNGTLLEDFSPAVNPEKEIDDPEDKKPEDWVDEAHIPDPEATKPEDWD
/NPDQSFQIRIDGAAVKNGTLLEDFSPAVNPEKEIDDPEDKKPEDWVDEAHIPDPEATKPEDWDEDAPYE
LIVNPDQSFQIRIDGAAVKNGTLLEDFSPAVNPEKEIDDPEDKKPEDWVDEAHIPDPEATKPEDWDED.
IPDQSFQIRIDGAAVKNGTLLEDFSPAVNPEKEIDDPEDKKPEDWVDEAHIPDPEATKPEDWDEDAPYE
LIVNPDQSFQIRIDGAAVKNGTLLEDFSPAVNPEKEIDDPEDKKPEDWVDEAHIPDPEATKPEDWDED.
(NPDQSFQIRIDGAAVKNGTLLEDFSPAVNPEKEIDDPEDKKPEDWVDEAHIPDPEATKPEDWDEDAPY
VNPDQSFQIRIDGAAVKNGTLLEDFSPAVNPEKEIDDPEDKKPEDWVDEAHIPDPEATKPEDWDEDAF
TLIVNPDQSFQIRIDGAAVKNGTLLEDFSPAVNPEKEIDDPEDKKPEDWVDEAHIPDPEATKPEDWDE
IVNPDQSFQIRIDGAAVKNGTLLEDFSPAVNPEKEIDDPEDKKPEDWVDEAHIPDPEATKPEDWDED.
.IVNPDQSFQIRIDGAAVKNGTLLEDFSPAVNPEKEIDDPEDKKPEDWVDEAHIPDPEATKPEDWDEDAF
LIVNPDQSFQIRIDGAAVKNGTLLEDFSPAVNPEKEIDDPEDKKPEDWVDEAHIPDPEATKPEDWDED,
LIVNPDQSFQIRIDGAAVKNGTLLEDFSPAVNPEKEIDDPEDKKPEDWVDEAHIPDPEATKPEDWDEDAI
'TLIVNPDQSFQIRIDGAAVKNGTLLEDFSPAVNPEKEIDDPEDKKPEDWVDEAHIPDPEATKPEDWDE
VNPDQSFQIRIDGAAVKNGTLLEDFSPAVNPEKEIDDPEDKKPEDWVDEAHIPDPEATKPEDWDEDAF
IVNPDQSFQIRIDGAAVKNGTLLEDFSPAVNPEKEIDDPEDKKPEDWVDEAHIPDPEATKPEDWDEDAPY
LIVNPDQSFQIRIDGAAVKNGTLLEDFSPAVNPEKEIDDPEDKKPEDWVDEAHIPDPEATKPEDWDEDAF
LIVNPDQSFQIRIDGAAVKNGTLLEDFSPAVNPEKEIDDPEDKKPEDWVDEAHIPDPEATKPEDWDEDAI
LIVNPDQSFQIRIDGAAVKNGTLLEDFSPAVNPEKEIDDPEDKKPEDWVDEAHIPDPEATKPEDWDED,
LIVNPDQSFQIRIDGAAVKNGTLLEDFSPAVNPEKEIDDPEDKKPEDWVDEAHIPDPEATKPEDWDEDAI
TLIVNPDQSFQIRIDGAAVKNGTLLEDFSPAVNPEKEIDDPEDKKPEDWVDEAHIPDPEATKPEDWDED
TLIVNPDQSFQIRIDGAAVKNGTLLEDFSPAVNPEKEIDDPEDKKPEDWVDEAHIPDPEATKPEDWDED
'TLIVNPDQSFQIRIDGAAVKNGTLLEDFSPAVNPEKEIDDPEDKKPEDWVDEAHIPDPEATKPEDWD
LIVNPDQSFQIRIDGAAVKNGTLLEDFSPAVNPEKEIDDPEDKKPEDWVDEAHIPDPEATKPEDWDEDAF
VNPDQSFQIRIDGAAVKNGTLLEDFSPAVNPEKEIDDPEDKKPEDWVDEAHIPDPEATKPEDWDEDAPY
LIVNPDQSFQIRIDGAAVKNGTLLEDFSPAVNPEKEIDDPEDKKPEDWVDEAHIPDPEATKPEDWDEDAF
'DQSFQIRIDGAAVKNGTLLEDFSPAVNPEKEIDDPEDKKPEDWVDEAHIPDPEATKPEDWDEDAPYEIV
NPDQSFQIRIDGAAVKNGTLLEDFSPAVNPEKEIDDPEDKKPEDWVDEAHIPDPEATKPEDWDEDAPYE
VNPDQSFQIRIDGAAVKNGTLLEDFSPAVNPEKEIDDPEDKKPEDWVDEAHIPDPEATKPEDWDEDAPY
.IVNPDQSFQIRIDGAAVKNGTLLEDFSPAVNPEKEIDDPEDKKPEDWVDEAHIPDPEATKPEDWDEDA
'DQSFQIRIDGAAVKNGTLLEDFSPAVNPEKEIDDPEDKKPEDWVDEAHIPDPEATKPEDWDEDAPYEIV
'LIVNPDQSFQIRIDGAAVKNGTLLEDFSPAVNPEKEIDDPEDKKPEDWVDEAHIPDPEATKPEDWDEDAI
TLIVNPDQSFQIRIDGAAVKNGTLLEDFSPAVNPEKEIDDPEDKKPEDWVDEAHIPDPEATKPEDWDED,
.IVNPDQSFQIRIDGAAVKNGTLLEDFSPAVNPEKEIDDPEDKKPEDWVDEAHIPDPEATKPEDWDEDAF
TLIVNPDQSFQIRIDGAAVKNGTLLEDFSPAVNPEKEIDDPEDKKPEDWVDEAHIPDPEATKPEDWDEDA
TLIVNPDQSFQIRIDGAAVKNGTLLEDFSPAVNPEKEIDDPEDKKPEDWVDEAHIPDPEATKPEDWDEDA
/NPDQSFQIRIDGAAVKNGTLLEDFSPAVNPEKEIDDPEDKKPEDWVDEAHIPDPEATKPEDWDEDAPY
'NPDQSFQIRIDGAAVKNGTLLEDFSPAVNPEKEIDDPEDKKPEDWVDEAHIPDPEATKPEDWDEDAPYE
/NPDQSFQIRIDGAAVKNGTLLEDFSPAVNPEKEIDDPEDKKPEDWVDEAHIPDPEATKPEDWDEDAPY
IQSFQIRIDGAAVKNGTLLEDFSPAVNPEKEIDDPEDKKPEDWVDEAHIPDPEATKPEDWDEDAPYEIVD'
VNPDQSFQIRIDGAAVKNGTLLEDFSPAVNPEKEIDDPEDKKPEDWVDEAHIPDPEATKPEDWDEDAPY
IPDQSFQIRIDGAAVKNGTLLEDFSPAVNPEKEIDDPEDKKPEDWVDEAHIPDPEATKPEDWDEDAPYE
IPDQSFQIRIDGAAVKNGTLLEDFSPAVNPEKEIDDPEDKKPEDWVDEAHIPDPEATKPEDWDEDAPYI
```

Figure 7D

```
----310------------320-------------330-------------340-------------350-------------360-------------370--------
VDTDATQPEDWLVDEPTSIPDPEAQKPEDWDDEEDGDWIPPTIPNPKCSEVSGCGMWEPPMKKNPEY
YEIVDTDATQPEDWLVDEPTSIPDPEAQKPEDWDDEEDGDWIPPTIPNPKCSEVSGCGMWEPPMKKNP
DAPYEIVDTDATQPEDWLVDEPTSIPDPEAQKPEDWDDEEDGDWIPPTIPNPKCSEVSGCGMWEPPM
DEDAPYEIVDTDATQPEDWLVDEPTSIPDPEAQKPEDWDDEEDGDWIPPTIPNPKCSEVSGCGMWEPP
DAPYEIVDTDATQPEDWLVDEPTSIPDPEAQKPEDWDDEEDGDWIPPTIPNPKCSEVSGCGMWEPPM
EDAPYEIVDTDATQPEDWLVDEPTSIPDPEAQKPEDWDDEEDGDWIPPTIPNPKCSEVSGCGMWEPP
EDAPYEIVDTDATQPEDWLVDEPTSIPDPEAQKPEDWDDEEDGDWIPPTIPNPKCSEVSGCGMWEPP
DAPYEIVDTDATQPEDWLVDEPTSIPDPEAQKPEDWDDEEDGDWIPPTIPNPKCSEVSGCGMWEPPM
DAPYEIVDTDATQPEDWLVDEPTSIPDPEAQKPEDWDDEEDGDWIPPTIPNPKCSEVSGCGMWEPPM
EDAPYEIVDTDATQPEDWLVDEPTSIPDPEAQKPEDWDDEEDGDWIPPTIPNPKCSEVSGCGMWEPP
EIVDTDATQPEDWLVDEPTSIPDPEAQKPEDWDDEEDGDWIPPTIPNPKCSEVSGCGMWEPPMKKNPE
APYEIVDTDATQPEDWLVDEPTSIPDPEAQKPEDWDDEEDGDWIPPTIPNPKCSEVSGCGMWEPPMKK
IVDTDATQPEDWLVDEPTSIPDPEAQKPEDWDDEEDGDWIPPTIPNPKCSEVSGCGMWEPPMKKNPE
APYEIVDTDATQPEDWLVDEPTSIPDPEAQKPEDWDDEEDGDWIPPTIPNPKCSEVSGCGMWEPPMKK
EIVDTDATQPEDWLVDEPTSIPDPEAQKPEDWDDEEDGDWIPPTIPNPKCSEVSGCGMWEPPMKKNPE
PYEIVDTDATQPEDWLVDEPTSIPDPEAQKPEDWDDEEDGDWIPPTIPNPKCSEVSGCGMWEPPMKK
DAPYEIVDTDATQPEDWLVDEPTSIPDPEAQKPEDWDDEEDGDWIPPTIPNPKCSEVSGCGMWEPPMK
APYEIVDTDATQPEDWLVDEPTSIPDPEAQKPEDWDDEEDGDWIPPTIPNPKCSEVSGCGMWEPPMK
YEIVDTDATQPEDWLVDEPTSIPDPEAQKPEDWDDEEDGDWIPPTIPNPKCSEVSGCGMWEPPMKKNP
APYEIVDTDATQPEDWLVDEPTSIPDPEAQKPEDWDDEEDGDWIPPTIPNPKCSEVSGCGMWEPPMKK
PYEIVDTDATQPEDWLVDEPTSIPDPEAQKPEDWDDEEDGDWIPPTIPNPKCSEVSGCGMWEPPMKKN
DAPYEIVDTDATQPEDWLVDEPTSIPDPEAQKPEDWDDEEDGDWIPPTIPNPKCSEVSGCGMWEPPM
PYEIVDTDATQPEDWLVDEPTSIPDPEAQKPEDWDDEEDGDWIPPTIPNPKCSEVSGCGMWEPPMKKN
EIVDTDATQPEDWLVDEPTSIPDPEAQKPEDWDDEEDGDWIPPTIPNPKCSEVSGCGMWEPPMKKNPE
PYEIVDTDATQPEDWLVDEPTSIPDPEAQKPEDWDDEEDGDWIPPTIPNPKCSEVSGCGMWEPPMKKN
PYEIVDTDATQPEDWLVDEPTSIPDPEAQKPEDWDDEEDGDWIPPTIPNPKCSEVSGCGMWEPPMKKN
APYEIVDTDATQPEDWLVDEPTSIPDPEAQKPEDWDDEEDGDWIPPTIPNPKCSEVSGCGMWEPPMKK
PYEIVDTDATQPEDWLVDEPTSIPDPEAQKPEDWDDEEDGDWIPPTIPNPKCSEVSGCGMWEPPMKKN
APYEIVDTDATQPEDWLVDEPTSIPDPEAQKPEDWDDEEDGDWIPPTIPNPKCSEVSGCGMWEPPMKK
APYEIVDTDATQPEDWLVDEPTSIPDPEAQKPEDWDDEEDGDWIPPTIPNPKCSEVSGCGMWEPPMKK
EDAPYEIVDTDATQPEDWLVDEPTSIPDPEAQKPEDWDDEEDGDWIPPTIPNPKCSEVSGCGMWEPP
PYEIVDTDATQPEDWLVDEPTSIPDPEAQKPEDWDDEEDGDWIPPTIPNPKCSEVSGCGMWEPPMKKN
EIVDTDATQPEDWLVDEPTSIPDPEAQKPEDWDDEEDGDWIPPTIPNPKCSEVSGCGMWEPPMKKNPE
PYEIVDTDATQPEDWLVDEPTSIPDPEAQKPEDWDDEEDGDWIPPTIPNPKCSEVSGCGMWEPPMKKN
DTDATQPEDWLVDEPTSIPDPEAQKPEDWDDEEDGDWIPPTIPNPKCSEVSGCGMWEPPMKKNPEYK
IVDTDATQPEDWLVDEPTSIPDPEAQKPEDWDDEEDGDWIPPTIPNPKCSEVSGCGMWEPPMKKNPE
EIVDTDATQPEDWLVDEPTSIPDPEAQKPEDWDDEEDGDWIPPTIPNPKCSEVSGCGMWEPPMKKNPE
PYEIVDTDATQPEDWLVDEPTSIPDPEAQKPEDWDDEEDGDWIPPTIPNPKCSEVSGCGMWEPPMKKN
DTDATQPEDWLVDEPTSIPDPEAQKPEDWDDEEDGDWIPPTIPNPKCSEVSGCGMWEPPMKKNPEYK
PYEIVDTDATQPEDWLVDEPTSIPDPEAQKPEDWDDEEDGDWIPPTIPNPKCSEVSGCGMWEPPMKKN
APYEIVDTDATQPEDWLVDEPTSIPDPEAQKPEDWDDEEDGDWIPPTIPNPKCSEVSGCGMWEPPMKK
YEIVDTDATQPEDWLVDEPTSIPDPEAQKPEDWDDEEDGDWIPPTIPNPKCSEVSGCGMWEPPMKKNP
PYEIVDTDATQPEDWLVDEPTSIPDPEAQKPEDWDDEEDGDWIPPTIPNPKCSEVSGCGMWEPPMKKN
PYEIVDTDATQPEDWLVDEPTSIPDPEAQKPEDWDDEEDGDWIPPTIPNPKCSEVSGCGMWEPPMKKN
EIVDTDATQPEDWLVDEPTSIPDPEAQKPEDWDDEEDGDWIPPTIPNPKCSEVSGCGMWEPPMKKNPE
EIVDTDATQPEDWLVDEPTSIPDPEAQKPEDWDDEEDGDWIPPTIPNPKCSEVSGCGMWEPPMKKNPE
EIVDTDATQPEDWLVDEPTSIPDPEAQKPEDWDDEEDGDWIPPTIPNPKCSEVSGCGMWEPPMKKNPE
TDATQPEDWLVDEPTSIPDPEAQKPEDWDDEEDGDWIPPTIPNPKCSEVSGCGMWEPPMKKNPEYKI
EIVDTDATQPEDWLVDEPTSIPDPEAQKPEDWDDEEDGDWIPPTIPNPKCSEVSGCGMWEPPMKKNPE
EIVDTDATQPEDWLVDEPTSIPDPEAQKPEDWDDEEDGDWIPPTIPNPKCSEVSGCGMWEPPMKKNPE
EIVDTDATQPEDWLVDEPTSIPDPEAQKPEDWDDEEDGDWIPPTIPNPKCSEVSGCGMWEPPMKKNPE
```

```
----------460---------------470-----------480---------------490---------------500--------
"WDLKHPVEVAEEEAARPKDEEKKEGTLSFKEAPVKYIRGKIELFISLA
AETWDLKHPVEVAEEEAARPKDEEKKEGTLSFKEAPVKYIRGKIELFI
EKLKAETWDLKHPVEVAEEEAARPKDEEKKEGTLSFKEAPVKYIRGI
:DAEKLKAETWDLKHPVEVAEEEAARPKDEEKKEGTLSFKEAPVKY
:KLKAETWDLKHPVEVAEEEAARPKDEEKKEGTLSFKEAPVKYIRGK
AEKLKAETWDLKHPVEVAEEEAARPKDEEKKEGTLSFKEAPVKYIRG
AEKLKAETWDLKHPVEVAEEEAARPKDEEKKEGTLSFKEAPVKYIRG
)AEKLKAETWDLKHPVEVAEEEAARPKDEEKKEGTLSFKEAPVKYIF
.EKLKAETWDLKHPVEVAEEEAARPKDEEKKEGTLSFKEAPVKYIRGI
AEKLKAETWDLKHPVEVAEEEAARPKDEEKKEGTLSFKEAPVKYIRC
"WDLKHPVEVAEEEAARPKDEEKKEGTLSFKEAPVKYIRGKIELFISL
:AETWDLKHPVEVAEEEAARPKDEEKKEGTLSFKEAPVKYIRGKIELI
TWDLKHPVEVAEEEAARPKDEEKKEGTLSFKEAPVKYIRGKIELFISL
:AETWDLKHPVEVAEEEAARPKDEEKKEGTLSFKEAPVKYIRGKIELF
TWDLKHPVEVAEEEAARPKDEEKKEGTLSFKEAPVKYIRGKIELFISL
_KAETWDLKHPVEVAEEEAARPKDEEKKEGTLSFKEAPVKYIRGKIEL
_KAETWDLKHPVEVAEEEAARPKDEEKKEGTLSFKEAPVKYIRGKIEI
KLKAETWDLKHPVEVAEEEAARPKDEEKKEGTLSFKEAPVKYIRGKII
:TWDLKHPVEVAEEEAARPKDEEKKEGTLSFKEAPVKYIRGKIELFIS
.AETWDLKHPVEVAEEEAARPKDEEKKEGTLSFKEAPVKYIRGKIELF
_KAETWDLKHPVEVAEEEAARPKDEEKKEGTLSFKEAPVKYIRGKIEI
AEKLKAETWDLKHPVEVAEEEAARPKDEEKKEGTLSFKEAPVKYIRG
:AETWDLKHPVEVAEEEAARPKDEEKKEGTLSFKEAPVKYIRGKIEL
.ETWDLKHPVEVAEEEAARPKDEEKKEGTLSFKEAPVKYIRGKIELF
AETWDLKHPVEVAEEEAARPKDEEKKEGTLSFKEAPVKYIRGKIELFI
:AETWDLKHPVEVAEEEAARPKDEEKKEGTLSFKEAPVKYIRGKIEL
.AETWDLKHPVEVAEEEAARPKDEEKKEGTLSFKEAPVKYIRGKIELF
(ETWDLKHPVEVAEEEAARPKDEEKKEGTLSFKEAPVKYIRGKIELFIS
:AETWDLKHPVEVAEEEAARPKDEEKKEGTLSFKEAPVKYIRGKIELF
:AETWDLKHPVEVAEEEAARPKDEEKKEGTLSFKEAPVKYIRGKIELF
)AEKLKAETWDLKHPVEVAEEEAARPKDEEKKEGTLSFKEAPVKYIR
_KAETWDLKHPVEVAEEEAARPKDEEKKEGTLSFKEAPVKYIRGKIEL
AETWDLKHPVEVAEEEAARPKDEEKKEGTLSFKEAPVKYIRGKIELFI
ETWDLKHPVEVAEEEAARPKDEEKKEGTLSFKEAPVKYIRGKIELFIS
"WDLKHPVEVAEEEAARPKDEEKKEGTLSFKEAPVKYIRGKIELFISLA
TWDLKHPVEVAEEEAARPKDEEKKEGTLSFKEAPVKYIRGKIELFISL
:AETWDLKHPVEVAEEEAARPKDEEKKEGTLSFKEAPVKYIRGKIELF
AETWDLKHPVEVAEEEAARPKDEEKKEGTLSFKEAPVKYIRGKIELFIS
TWDLKHPVEVAEEEAARPKDEEKKEGTLSFKEAPVKYIRGKIELFISLA
LKAETWDLKHPVEVAEEEAARPKDEEKKEGTLSFKEAPVKYIRGKIEI
.AETWDLKHPVEVAEEEAARPKDEEKKEGTLSFKEAPVKYIRGKIELF
:TWDLKHPVEVAEEEAARPKDEEKKEGTLSFKEAPVKYIRGKIELFIS
AETWDLKHPVEVAEEEAARPKDEEKKEGTLSFKEAPVKYIRGKIELFI
LKAETWDLKHPVEVAEEEAARPKDEEKKEGTLSFKEAPVKYIRGKIE
:TWDLKHPVEVAEEEAARPKDEEKKEGTLSFKEAPVKYIRGKIELFISI
TWDLKHPVEVAEEEAARPKDEEKKEGTLSFKEAPVKYIRGKIELFISL
"WDLKHPVEVAEEEAARPKDEEKKEGTLSFKEAPVKYIRGKIELFISL
.KHPVEVAEEEAARPKDEEKKEGTLSFKEAPVKYIRGKIELFISLALE
TWDLKHPVEVAEEEAARPKDEEKKEGTLSFKEAPVKYIRGKIELFISL
:TWDLKHPVEVAEEEAARPKDEEKKEGTLSFKEAPVKYIRGKIELFISL
:TWDLKHPVEVAEEEAARPKDEEKKEGTLSFKEAPVKYIRGKIELFISI
```

>Bd_26199 calnexin (deduced from genomic sequence)
MRLNASLASLILSSIALGNVHAEDEVKEDATSTSSVEKPTTTPTTLKAPPLEQFTDQWETRWTPSHAKEDKKSEEDWAYVGTWAVEE
PHVPNGMVQDKGLVVKNPAMHAISAKEPKKIDNKGKTLVVQYEVKLQNSLNCGGAYMKLLQDNKKLHAEFSWTSPYVMFQPDKC
GVTNRKVHFIFKHKNPKTGEYEEKHMRLPPAYRVSKLSTLYTLIVNPQKSFQIRIDOAAVKNGTLLEDFSPAVNPEKGIDPEDKKPEDWV
DEAHPDPEATKPEDWDEDAPYEIVDTDATQPEDWLVDEPTSIPPEAQKPEDWDDEEDGQWIPPTIPNPKCSEVSGCGMWEPMKKNP
BYKGKWTAPMIDNPAYKQPWAPRNIANPNYFEDKTPSNFPMQGAGFEIWTMQNDILPDNIYGHSVIEDAEKLKAETWDLKIPVEVAEE
EAARPKDEEKEGTLSFKEAPVKYIRGKIELFISLALENPVEAVKAVPEVAGGLGALLVTLLIVGAVGLGSPSPAPAAKKQAEKQKEKT
AEAVSTAADWVKGEAKKRSGKAGE Links to Calnexin Protein sequence in GenBank:

*Note that these links are for a the Calnexin sequence for the strain 10188, but the protein sequence is identical to than in strain 26199

Protein database Accession number: EGE86398
Broad Institute predicted Gene name: BDDG_08453

Figure 8

Simple calnexin pro Alignments
Fri, Jan 25, 2013 3:17 PM

ClustalW (v1.83) multiple sequence alignment

7 Sequences Aligned          Processing time: 0.7 seconds
Gaps Inserted = 95           Conserved Identities = 152
Score = 51436

Pairwise Alignment Mode: Fast
Pairwise Alignment Parameters:
  Ktup = 1    Gap Penalty = 3    Top Diagonals = 5    Window Size = 5
  Similarity Matrix: gonnet Multiple Alignment Parameters:
  Open Gap Penalty = 10.0    Extend Gap Penalty = 0.2
  Delay Divergent = 40%      Gap Distance = 8
  Similarity Matrix: gonnet Identity Scores (%)

|  | B.d. 26199 | P.b. Pb01 | C.i. RS | H.C. 86AR | H.C. G186ARs | A.flavu | C.a.5314 | C. neoform. |
|---|---|---|---|---|---|---|---|---|
| B.d. 26199 | 100.0 | 82.9 | 78.9 | 87.1 | 73.9 | 32.5 | 49.0 |
| P.b. Pb01 | 90.3 | 100.0 | 77.5 | 80.5 | 72.6 | 33.1 | 49.7 |
| C.i. RS | 87.6 | 85.9 | 100.0 | 77.5 | 72.3 | 33.8 | 50.0 |
| H.C. G186AR | 92.0 | 88.4 | 87.1 | 100.0 | 72.6 | 33.6 | 48.9 |
| A.flavus | 85.5 | 84.4 | 85.5 | 83.6 | 100.0 | 34.6 | 51.7 |
| C.a.5314 | 46.0 | 47.8 | 47.3 | 46.8 | 46.6 | 100.0 | 33.5 |
| C. neoform. | 63.1 | 63.6 | 64.0 | 62.8 | 64.4 | 46.4 | 100.0 |

Similarity Scores (%)

Figure 9 simple calnexin pro Alignments
Friday, January 25, 2013 2:25 PM

*Formatted Alignments*

```
B.d. 26199    1   MRLNASLASLILSSIALIGNVHAEDVKEDATSTSSVIEK   40
P.b. Pb01     1   MRLNASLASLIISIALIGNVHAEDVEGKPSSTSSVIEK   40
C.i. RS       1   MRLNARTASLILSYIALGQVHAESATKEEP-TATSISR   39
H.c. G186AR   1   MRLNASLASLILSSVALIGNVRAEEVKGDAPSPSGAIEK   40
A flavus      1   MRFNAVASALVSSATLMG--YAHAEEAEKNPDATSVVLEK  38
C.a.5314      1   ---------------MKYALVLLLSLVNALKYVPFDK   22
C. neoform.   1   MRP---------------QNVAGVAGTGALIMAAGALADR 25

B.d. 26199    41  PTFTPTTLKAPFLEQFTDGW-ETRWTPSHAKKEDSKSEED   79
P.b. Pb01     41  PLFTPTTLKAPFLEQFTDDW-ETRWTPSHAKKQDSSSEED   79
C.i. RS       40  PTFTPTTLKAPFLEQFTDDW-QTRWTPSHAKKEDSKSEHE   78
H.c. G186AR   41  PTFTPTTLKAPFLEQFTDDW-ETRWTPSHAKKEDSSQDED   79
A flavus      39  PTFTPTTLKAPFLEQFTDDW-ESRWTPSHAKKDDSQTEED  77
C.a.5314      23  TQLDPSSVFEQHDYPSLNSS---PWQVSTAKKPDEGRDEI  59
C. neoform.   26  AVHHPTSITAPHIEQRLESIPESRWTVSRATKQTPVGDEI  65

B.d. 26199    80  WAYVGTWAVEEPH-VRNGMVGDKGLVVKNPAAHHAISAKP  118
P.b. Pb01     80  WAYVGTWAVEEPH-VRNGMKGDKGLVIKNAAAHHAISAKP  118
C.i. RS       79  WAYVGEWAVEEPT-VHKGIDGDKGLVVKNAAAHHAISAKP  117
H.c. G186AR   80  WAYIGTWAVEEPH-VLNGMVGDKGLVVKNPAAHHAISAKP  118
A flavus      78  WAYVGEWSVEEPT-VHKGIDGDKGLVVKNPAAHHAISAKP  116
C.a.5314      60  VRYSGEWKIESSTSKYPGLEGLIGLVMKSRASHYAISYKL  99
C. neoform.   66  FSYVGQWEIEED-VYPGISGDKGLVLKTKAAHHAISTLP  104

B.d. 26199    119 PKKID-----NKGKTLVVQYEVKLQNSLNCGGAYMKLLQ  152
P.b. Pb01     119 PKKID-----NKGNTLVVQYEVKLQNGLNCGGAYMKLLQ  152
C.i. RS       118 PQKID-----NKGKTLVVQYEVKLQNSLVCGGAYMKLLQ  151
H.c. G186AR   119 PKKID-----NKGKTLVVQYEVKLQNSLVCGGAYMKLLQ  152
A flavus      117 PKKID-----NKGKTLVVQYEVKPQNSLVCGGAYLKLLQ  150
C.a.5314      100 PHEVTNTNPNNKTQDLVLQYEVKLQQGLTCGGAYIKLLD  139
C. neoform.   105 DEPID-----PKGKSLVVQYEVKLQKGLECGGAYIKLLT  138

B.d. 26199    153 DNKK--LHA-EEFSNTSPYVIMFGPDKCGVTNKVHFIKH  189
P.b. Pb01     153 DNKK--LHA-EEFSNASPYVIMFGPDKCGVTNKVHFIRH  189
C.i. RS       152 DNKK--LHA-EEFSNASPYVIMFGPDKCGATNKVHFIKH  188
H.c. G186AR   153 DNKK--LHA-EEFSNASPYVIMFGPDKCGVTNKVHFIRH  189
A flavus      151 ENKK--LHA-EEFSNAPYVIMFGPDKCGATNKVHFIFRH  187
C.a.5314      140 SSPS----GYKIHNSETPYQIMFGPDVCGSDNKIHFIIRK 175
C. neoform.   139 QQDEGIRAGDYTDKTPFTIMFGPDKCGSTNKVHFIRH   178
```

Figure 10

```
simple  calnexin  pro  Alignments
Friday, January 25, 2013  2:25 PM

B.d. 26199    190  KNPKTGEY EEKHMK LPPAVRV SKLST LYTLIVN - -PDQSF  227
P.b. Pb01     190  KNPKTGEY EEKHLKNPPAARV SKLST LYTLIVK - -PDQSF  227
C.i. RS       189  KNPKTGEY EEKHLNNAPTARI SKLST LYTLIVK - -PDQTF  226
H.c. G186AR   190  KNPKTGEY EEKHMNAAPAAKI NKLST LYTLIVK - -PDQSF  227
A flavus      186  KNPKTGEY EEKHLKAPPAART NKVTSLYTLIVR - -PDQSF  225
C.a.5314      176  KLP-NGAI EEKHLKHKPMART NEITNLYTLITK - -SNQDF  212
C. neoform.   179  KNPITGEWEEKHLKNPPAPKI TKTTALYTLITKT SPDQTF  218

B.d. 26199    228  QIRIDGAAVKNGTLLED - - RSPAVNPQKEIDDPEDKKPE  264
P.b. Pb01     228  QILIDGEAVKNGTLLED - - RSPAVNPQKEIDDPEDKKPK  264
C.i. RS       227  QIQINGEAVKNGTLLED - - RQPPVNPPKEIDDPNDKKPA  263
H.c. G186AR   228  QIRIDGKAVKNGTLLED - - RSPAVNPPKEIDDPEDKKPE  264
A flavus      226  QILIDGEAVKNGTLLED - - RNPPVNPEKEIDDPKDKKPD  262
C.a.5314      213  EIRVNGQVAKAGNLYKNQKLNPPFEPPKEIPDVDDKKPD  252
C. neoform.   219  EILINDESVRKGSLLED - - RQPPVNPPKEIDDPEDRKPE  255

B.d. 26199    265  DWVDEAHIPDPEATKPEDWDEDAPY-EIVDTDATQPEDWL  303
P.b. Pb01     265  DWVDETRIPDPTATKPDDWDEDAPY-EIIDTEATKPDDWL  303
C.i. RS       264  DWVDEAKIPDPEAKKPEDWDEDAPF-EIVDTEAKKPDDWL  302
H.c. G186AR   265  DWVDEARIADPDATKPEDWDEDAPY-EIVDADAVQPEDWL  303
A flavus      263  DWVDDVKIPDPEATKPEDWDEEAPY-EIVDEEATKPEDWL  301
C.a.5314      253  DWDDRAYIPDPNVKPEDYELKHEYPQIRDPNAVKPDEWD   292
C. neoform.   256  TWVDEAEIDDVTATKPDDWDEDAPI-MITDTSAVKPEDWL  294

B.d. 26199    304  VDEPTSIPDPEAQKPEDWDDEEDGDWIPPTIPNPKCEVS  343
P.b. Pb01     304  DSEPDSIPDPEAQKPEDWDDEEDGDWAAPTIPNPKCEVS  343
C.i. RS       303  DDEPSSIPDPEAQKPEDWDDEEDGDWVAPTVPNPKCEAS  342
H.c. G186AR   304  IDEPTSIPDPEAEKPEDWDDEEDGDWTPPTIPNPKCEVS  343
A flavus      302  EEEPTSIPDPEAEKPEDWDDEEDGDWIPPTVPNPKCNDVS 341
C.a.5314      293  ESAPRYIPDPDAVKPKDWNDAEK-QWFPPLIVNPKC--AT  329
C. neoform.   295  EEEPETIPDPEAEKPEEWDDEEDGDWIPPMVPNPKCEDVS 334

B.d. 26199    344  GCGMWEPPMKKNPEYKGKWTAPMIDNPAYKGPWAPRKIAN  383
P.b. Pb01     344  GCGKWEAPMKKNPDYKGKWTPPMIDNPAYKGPWTPRKIPN  383
C.i. RS       343  GCGKWEPPMKRNPDYKGKWTAPLIDNPAYKGPWSPRKIAN  382
H.c. G186AR   344  GCGKWQQPMKKNPDYKGKWVAPMIDNPAYKGPWAPRKIPN  383
A flavus      342  GCGPWSAPMKKNPAYKGKWTAPMIDNPAYKGPWSPRKIAN  381
C.a.5314      330  GCGPWEAPLIPNHDYIGPWFPPDIKNPNYNGIWTPRIPN   369
C. neoform.   335  GCGPWTAPKVRNPAYKGKWIPKIPNPDYKGPWAPRKIAN   374

B.d. 26199    384  PNYFEDKTPSNFEP-MGAIGFEIWTMQNDILFDNIYIGHS  422
P.b. Pb01     384  PNYFEDKTPANFEP-MGAIGFEIWTMQNDILFNNIYIGHS  422
C.i. RS       383  PDFFEDKKPANFEP-MGAIGFEIWTMQNDILFDNIYIGHS  421
H.c. G186AR   384  PDYFEDKTPANFEP-MGAIGFEIWTMQSDILHNNIYIGHS  422
A flavus      382  PAYFEDKTPSNFEP-MGAIGFEIWTMQNDILFDNIYIGHS  420
C.a.5314      370  PYYYQVKTPGKLDKPIQGIGFEIWSIESDILFDNIYLGNS 409
C. neoform.   375  PAHFEDLHPSDFTK-TGVGIEIWTMEDILFDNIYIGHD   413
```

Figure 10 - continued simple calnexin pro Alignments
Friday, January 25, 2013 2:25 PM

```
B.d. 26199    423  VEDAEKLKAETWDLKHPVEVAEEEAARPK-DEKKEGTLS  461
P.b. Pb01     423  IEDAQKLKSETWDIKHPIEVAEEEATRPK-DDEKDSSFVS  461
C.i. RS       422  IEDAKKLKAETHDIKHPIEVAEEEAAKPK-DEPSTDSGLN  460
H.c. G186AR   423  IEDAEKLKAETWDLKHPVEVAEEEASRPK-DEKEAGT-S   460
A flavus      421  HEDAEQLRKETHDVKHPVEVAEEEASKPKKELTAPATSVS  460
C.a.5314      410  DADAELIGNTIFKIKYELEADQRRENKPRVKNEPVAPPRN  449
C. neoform.   414  AAQAKKFAEEIYHVKPIEKEAEGSNEDE--------LE   444

B.d. 26199    462  FKEAPVKYIRGKIELFISLALEMPVEAVKAVP--------  493
P.b. Pb01     462  FKEAPVQFVRKINLFISIARKDPVQAAKSVP--------  493
C.i. RS       461  FKDDPVKYIRSKVDQFILMAKDNPVEAVKAVP--------  492
H.c. G186AR   461  FKEDPVQYIRKKIDLFISLALEMPVEAVKTVP--------  492
A flavus      461  HQEDPITFVRKVDHFVGLAKQDPVNAVKQAP--------  492
C.a.5314      450  HEDIIRDDSISTFQQHLIFIKLFWLKQYVQLKDFYFELTL  489
C. neoform.   445  EPSSLIDKVQLKVYEHLLATFDISQAVKQMP--------  476

B.d. 26199    494  ----EVAGGLGALLVTLLIIVGAVGLGSPSPAPAAKKQ  528
P.b. Pb01     494  ----EVAGGLGAIVITLALIIVGAIGLSSPAPAPAVAKK  528
C.i. RS       493  ----EVAGGAALLITLLVVHGAIGLSSPAPAPA-KKD   526
H.c. G186AR   493  ----EVAGGLGALLVTLLITIVSGISLGS-SSPAPKKQ  526
A flavus      493  ----EVAGTLGAIVLSMVLIIVGAIKASSPAPAPVKKGK 527
C.a.5314      490  DPIGLIMANPKTLLYAFLFLFSFTIFFGFASTIMFLLQG  529
C. neoform.   477  ----EVAAGLAAAVITILGMLLALRGFIGSAPTKVKQTS  511

B.d. 26199    529  AEKGKEK-------TAEAVSTAADNV-----KGEAKKRS  555
P.b. Pb01     529  VD-GKEKDGASKEKAAEAVSTIADNV-----KGAATRRS  561
C.i. RS       527  AGKGKEK---AKEKAAEAVSTGAENV-----KAGATKRS  557
H.c. G186AR   527  AEKGKEKE---KASAESAVSTGADNV-----KGGAKKRS  557
A flavus      528  EAAGAAK-----EKVSEAVSSSALTG-----KGGASKRT  556
C.a.5314      530  GEAFGSSSSITTTTTTDSNRKNVLTAEEIEMPSNHVQKIE 569
C. neoform.   512  VKTKSVAP---VAPAGEEEKKALQQAGVEVPAVEGSKKRV 548

B.d. 26199    556  GKAGE-------  560
P.b. Pb01     562  GKANNE------ 567
C.i. RS       558  -KSSE------- 561
H.c. G186AR   558  TKTSE------- 562
A flavus      557  TRSSAQ------ 562
C.a.5314      570  ILDEQIHVQRK  581
C. neoform.   549  TRSTKE------ 554
```

Figure 10 - continued

*H. capsulatum*

FIGURE 11 - continued

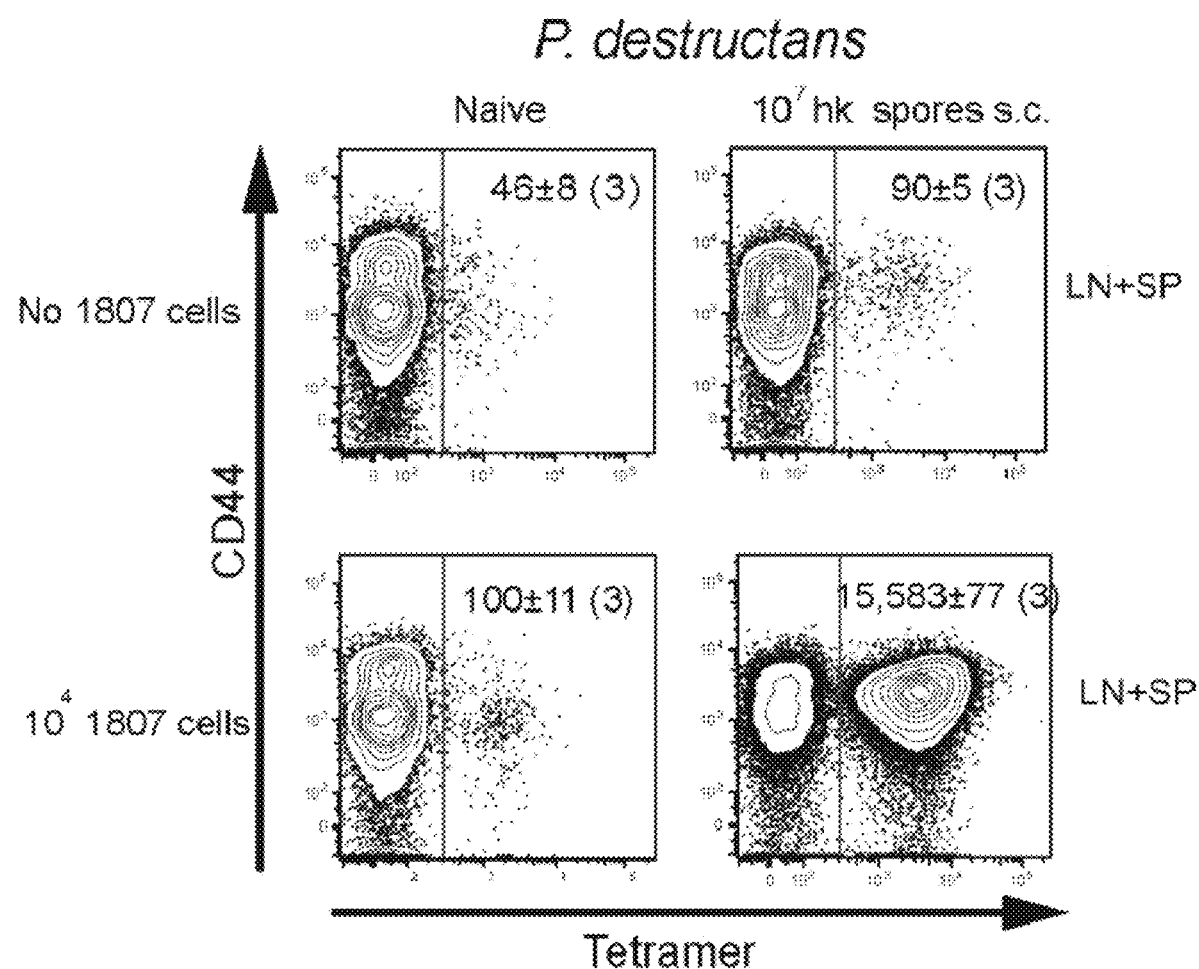
FIGURE 11 - continued

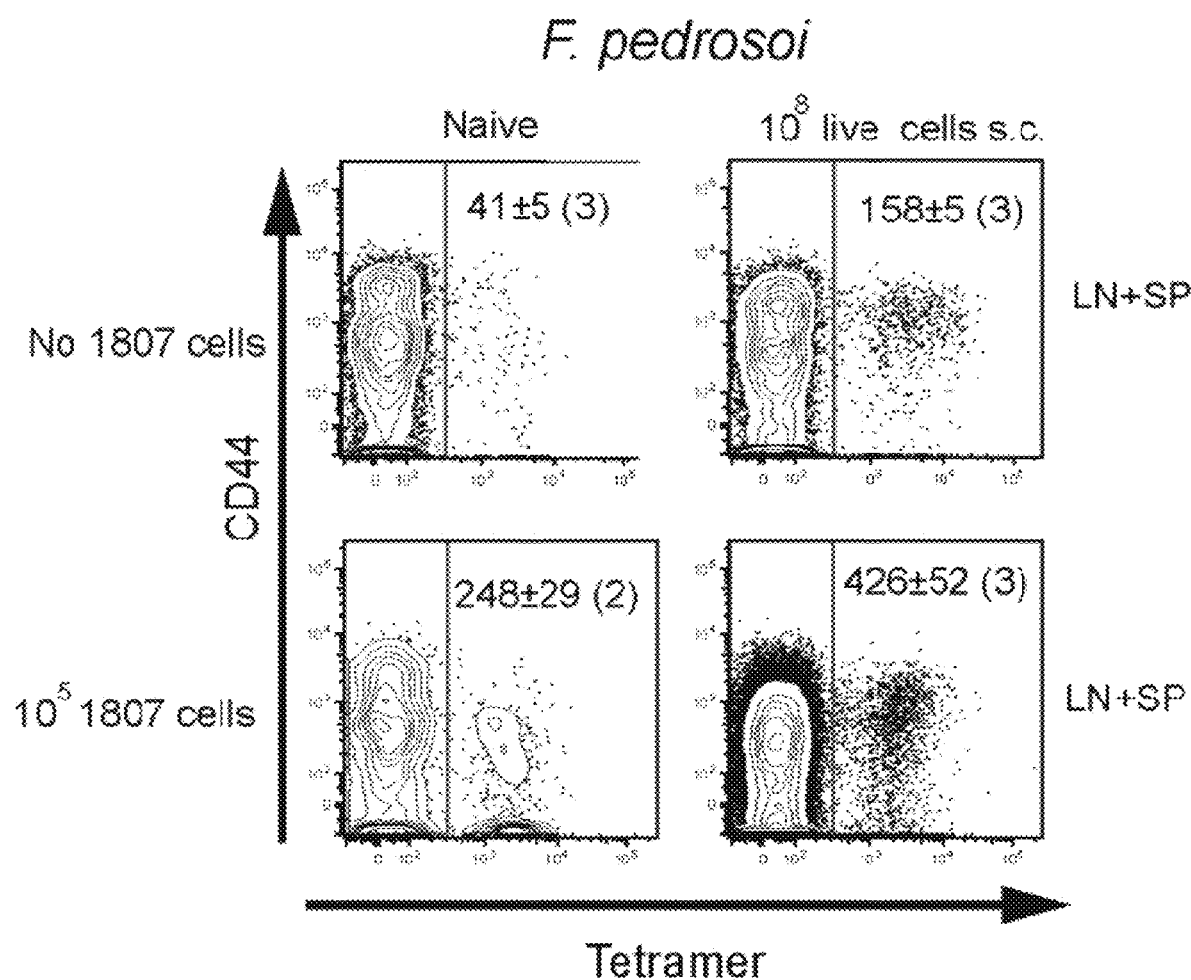
FIGURE 11 - continued

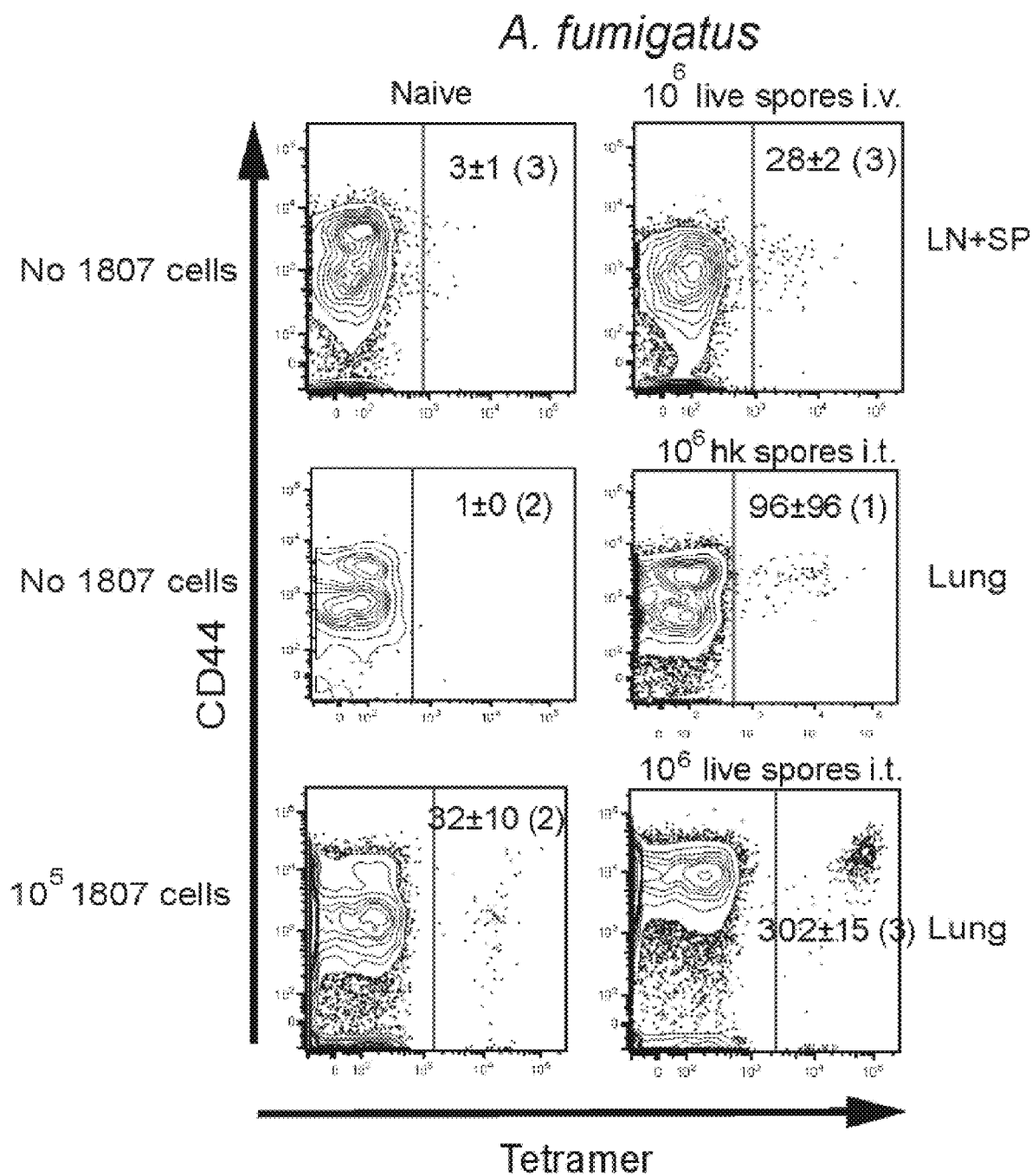
FIGURE 11 - continued

FIGURE 12A

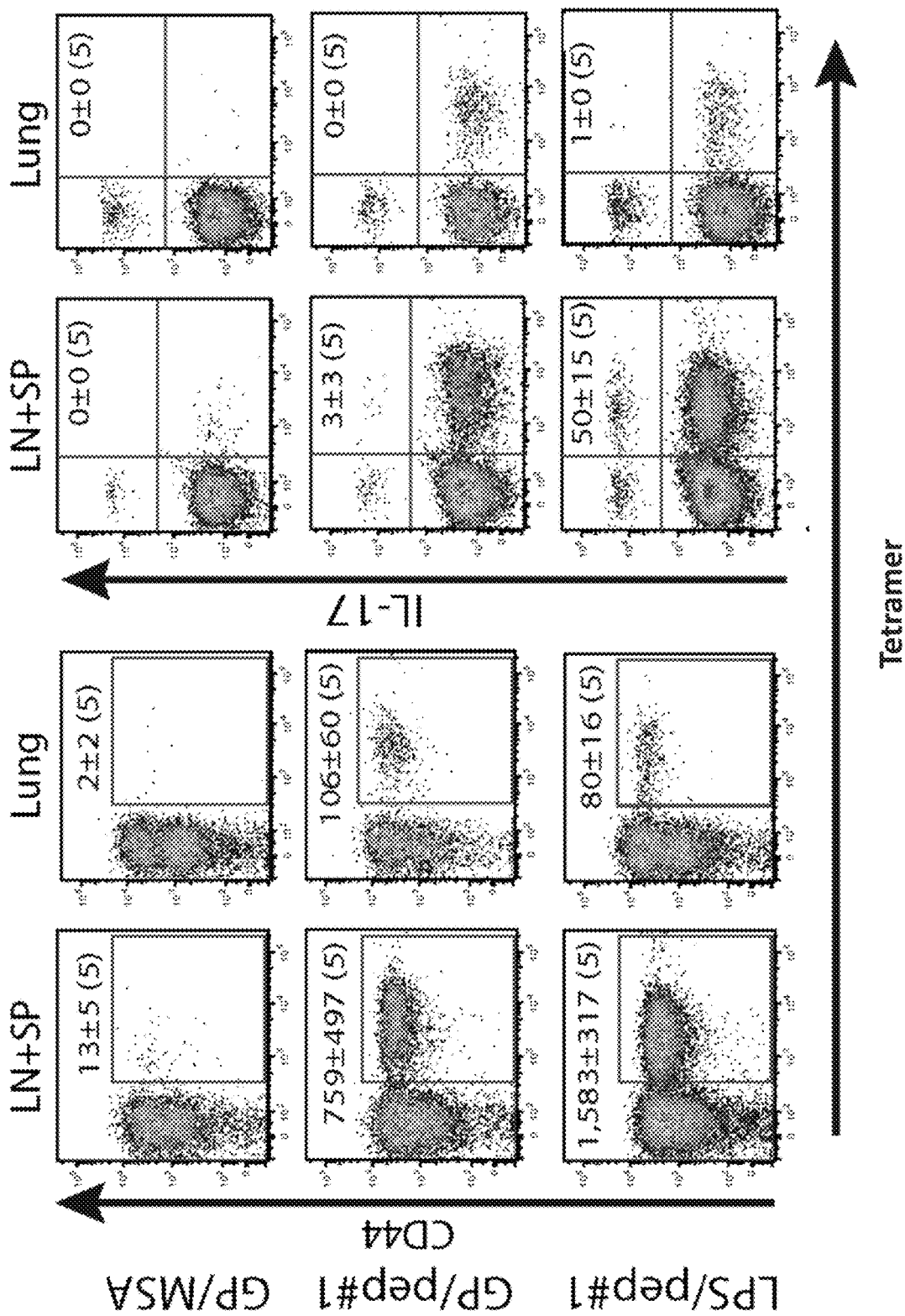
FIGURE 13C - continued

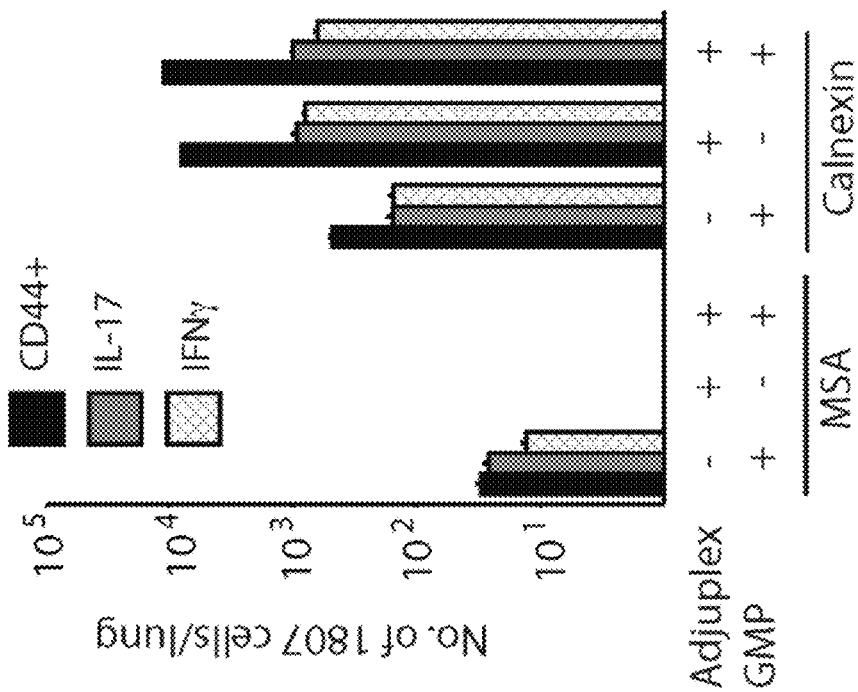
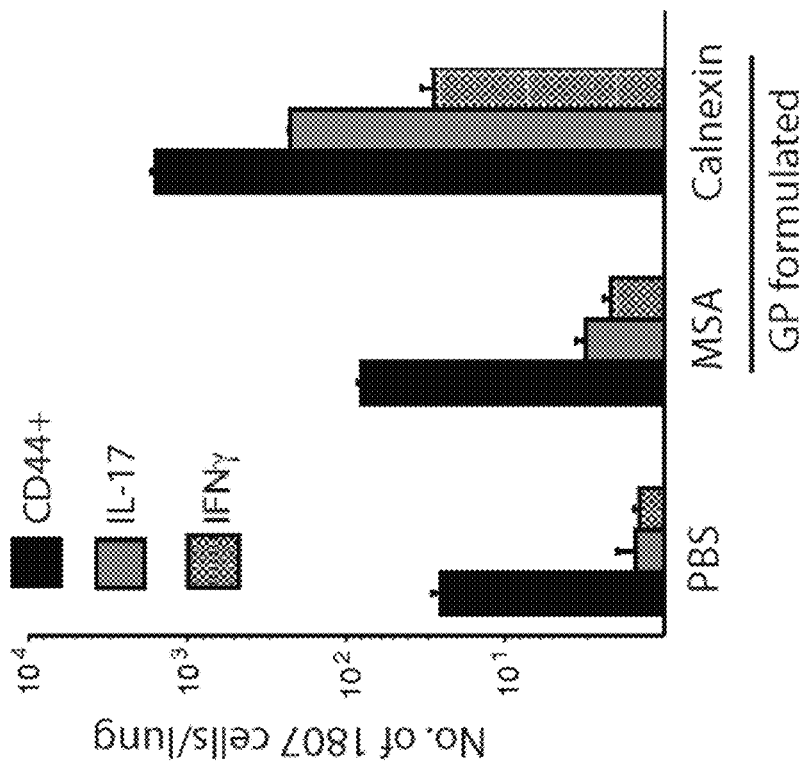
FIGURE 14A-B

FIGURE 15 - continued

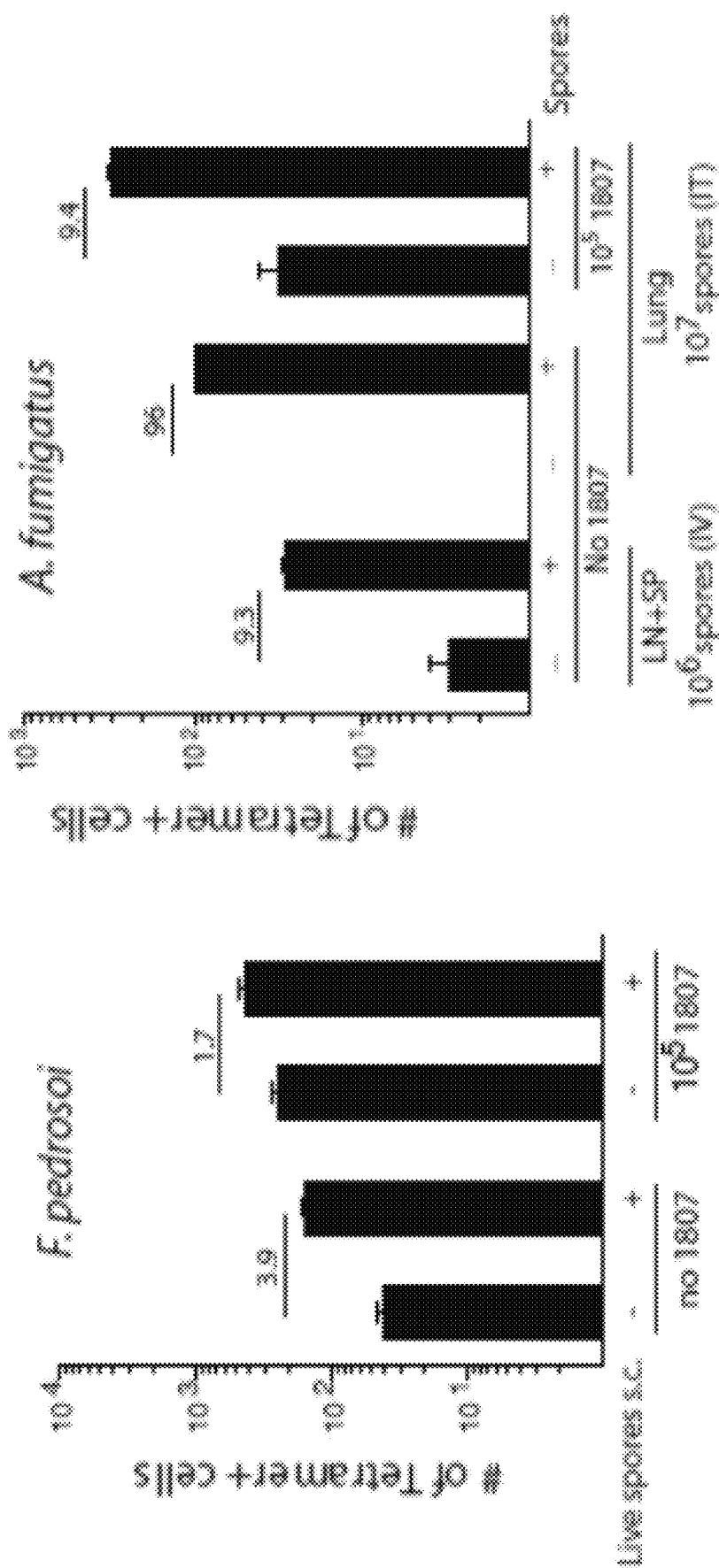
FIGURE 15 - continued

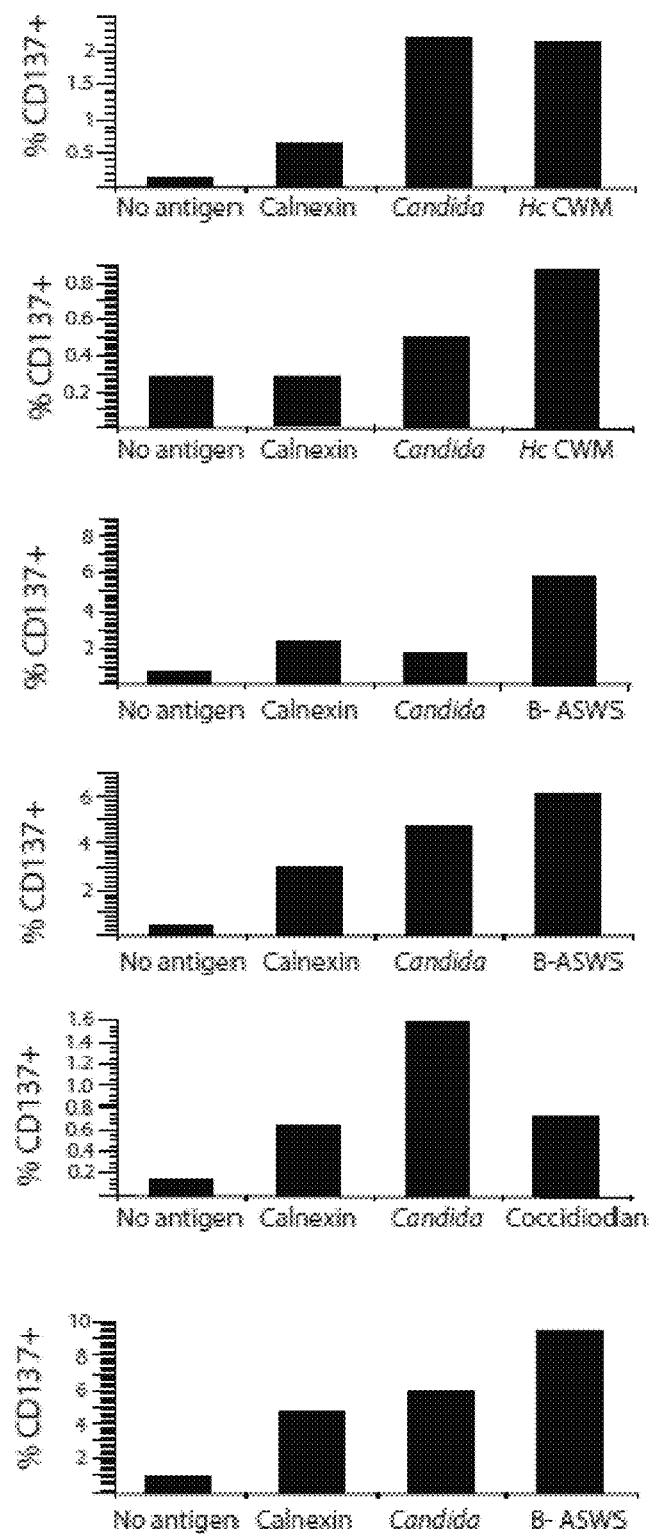
FIGURE 16B - continued

SEQUENCE LISTING

```
<160> NUMBER OF SEQ ID NOS: 59

<210> SEQ ID NO 1
<211> LENGTH: 13
<212> TYPE: PRT
<213> ORGANISM: Artificial Sequence
<220> FEATURE:
<223> OTHER INFORMATION: Blastomyces dermatitidis of strains 26199,
      18808, Er-3, 14081; Histoplasma capsulatum of strains G186AR,
      Nam1, H88, H143; Aspergillus sp.1 of strain group.1; Ajellomyces
      capsulatus; Ajellomyces dermatitidis; Arthroderma benhamiae;
      Arthroderma

<400> SEQUENCE: 1

Leu Val Val Lys Asn Pro Ala Ala His His Ala Ile Ser
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Trichoderma virens; Paracoccidioides lutzii;
      Paracocciodioides brasiliensis

<400> SEQUENCE: 2

Leu Val Ile Lys Asn Ala Ala Ala His His Ala Ile Ser
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Byssochlamys spectabilis; Cladophialophora
      carrionii; Coccidioides immittis; Coccidioides posadasii; Eutypa
``` lata; Exophiala dermatitidis; Marssonina brunnea; Myceliophthora
thermophile; Neurospora crassa; Neurospora tetrasperma;

<400> SEQUENCE: 3

Leu Val Val Lys Asn Ala Ala Ala His His Ala Ile Ser
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Talaromyces stipitatus; Talaromyces marneffei;
      Cyphellophora europaea; Gaeumannomyces graminis; Penicillium
      marneffei

<400> SEQUENCE: 4

Leu Val Leu Lys Asn Pro Ala Ala His His Ala Ile Ser
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Aspergillus nidulans; Aspergillus clavatus;
      Aspergillus fumigatus; Aspergillus kawachii; Aspergillus niger;
      Chaetomium thermophilum ; Neosartorya fischeri; Penicillium
      oxalicum; Tuber melanosporum; Aspergillus sp. 2

<400> SEQUENCE: 5

Leu Val Val Lys Asn Val Ala Ala His His Ala Ile Ser
1               5                   10

<210> SEQ ID NO 6
<211> LENGTH: 13
<212> TYPE: PRT
<213> ORGANISM: Pneumocystis carinii

<400> SEQUENCE: 6

Leu Val Leu Lys Asn Glu Ala Ala His His Ala Ile Ser
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Cryptococcus neoformans; Cryptococcus gattii;
      Pneumocystis murina; Rhodosporidium toruloides; Candida temuis

<400> SEQUENCE: 7

Leu Val Leu Lys Thr Lys Ala Ala His His Ala Ile Ser
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Coniophora puteana; Schizophyllum commeune;
      Dichomitus squalens; Trametes versicolor; Phanerochaete carnosa;
      Ceriporiopsis subvermispora; Fibroporia radiculosa; Serpula
      lacrymans; Gloeophyllum trabeum; Fomitopsis pinicola

<400> SEQUENCE: 8

Leu Val Ala Lys Thr Lys Ala Ala His His Ala Ile Ser
1               5                   10

<210> SEQ ID NO 9
<211> LENGTH: 13
<212> TYPE: PRT
<213> ORGANISM: Candida albicans

<400> SEQUENCE: 9

Leu Val Met Lys Ser Arg Ala Ser His Tyr Ala Ile Ser
1               5                   10

<210> SEQ ID NO 10
<211> LENGTH: 13
<212> TYPE: PRT
<213> ORGANISM: Homo sapiens

<400> SEQUENCE: 10

Leu Val Leu Lys Ser Arg Ala Lys His His Ala Ile Ser
1               5                   10

<210> SEQ ID NO 11
<211> LENGTH: 13
<212> TYPE: PRT
<213> ORGANISM: Homo sapiens

<400> SEQUENCE: 11

Leu Val Leu Met Ser Arg Ala Lys His His Ala Ile Ser
1               5                   10

<210> SEQ ID NO 12
<211> LENGTH: 560
<212> TYPE: PRT
<213> ORGANISM: Blastomyces dermatitidis

<400> SEQUENCE: 12

Met Arg Leu Asn Ala Ser Leu Ala Ser Leu Ile Leu Ser Ser Ile Ala
1               5                   10                  15

Leu Ile Gly Asn Val His Ala Glu Asp Glu Val Lys Glu Asp Ala Thr
            20                  25                  30

Ser Thr Ser Ser Val Ile Glu Lys Pro Thr Phe Thr Pro Thr Thr Leu
        35                  40                  45

Lys Ala Pro Phe Leu Glu Gln Phe Thr Asp Gly Trp Glu Thr Arg Trp
    50                  55                  60

Thr Pro Ser His Ala Lys Lys Glu Asp Ser Lys Ser Glu Glu Asp Trp
65                  70                  75                  80

Ala Tyr Val Gly Thr Trp Ala Val Glu Glu Pro His Val Phe Asn Gly
                85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
        115                 120                 125

Leu Val Val Gln Tyr Glu Val Lys Leu Gln Asn Ser Leu Asn Cys Gly
    130                 135                 140

Gly Ala Tyr Met Lys Leu Leu Gln Asp Asn Lys Lys Leu His Ala Glu
145                 150                 155                 160

Glu Phe Ser Asn Thr Ser Pro Tyr Val Ile Met Phe Gly Pro Asp Lys
                165                 170                 175

Cys Gly Val Thr Asn Lys Val His Phe Ile Phe Lys His Lys Asn Pro
            180                 185                 190

Lys Thr Gly Glu Tyr Glu Glu Lys His Met Lys Leu Pro Pro Ala Val

```
                195                 200                 205
Arg Val Ser Lys Leu Ser Thr Leu Tyr Thr Leu Ile Val Asn Pro Asp
210                 215                 220

Gln Ser Phe Gln Ile Arg Ile Asp Gly Ala Ala Val Lys Asn Gly Thr
225                 230                 235                 240

Leu Leu Glu Asp Phe Ser Pro Ala Val Asn Pro Glu Lys Glu Ile Asp
                245                 250                 255

Asp Pro Glu Asp Lys Pro Glu Asp Trp Val Asp Glu Ala His Ile
            260                 265                 270

Pro Asp Pro Glu Ala Thr Lys Pro Glu Asp Trp Asp Glu Asp Ala Pro
        275                 280                 285

Tyr Glu Ile Val Asp Thr Asp Ala Thr Gln Pro Glu Asp Trp Leu Val
290                 295                 300

Asp Glu Pro Thr Ser Ile Pro Asp Pro Glu Ala Gln Lys Pro Glu Asp
305                 310                 315                 320

Trp Asp Asp Glu Glu Asp Gly Asp Trp Ile Pro Pro Thr Ile Pro Asn
                325                 330                 335

Pro Lys Cys Ser Glu Val Ser Gly Cys Gly Met Trp Glu Pro Pro Met
            340                 345                 350

Lys Lys Asn Pro Glu Tyr Lys Gly Lys Trp Thr Ala Pro Met Ile Asp
        355                 360                 365

Asn Pro Ala Tyr Lys Gly Pro Trp Ala Pro Arg Lys Ile Ala Asn Pro
370                 375                 380

Asn Tyr Phe Glu Asp Lys Thr Pro Ser Asn Phe Glu Pro Met Gly Ala
385                 390                 395                 400

Ile Gly Phe Glu Ile Trp Thr Met Gln Asn Asp Ile Leu Phe Asp Asn
                405                 410                 415

Ile Tyr Ile Gly His Ser Val Glu Asp Ala Glu Lys Leu Lys Ala Glu
            420                 425                 430

Thr Trp Asp Leu Lys His Pro Val Glu Val Ala Glu Glu Ala Ala
        435                 440                 445

Arg Pro Lys Asp Glu Lys Lys Glu Gly Thr Leu Ser Phe Lys Glu
450                 455                 460

Ala Pro Val Lys Tyr Ile Arg Gly Lys Ile Glu Leu Phe Ile Ser Leu
465                 470                 475                 480

Ala Leu Glu Asn Pro Val Glu Ala Val Lys Ala Val Pro Glu Val Ala
                485                 490                 495

Gly Gly Leu Gly Ala Leu Leu Val Thr Leu Val Leu Ile Ile Val Gly
            500                 505                 510

Ala Val Gly Leu Gly Ser Pro Ser Pro Ala Pro Ala Ala Lys Lys Gln
        515                 520                 525

Ala Glu Lys Gly Lys Glu Lys Thr Ala Glu Ala Val Ser Thr Ala Ala
530                 535                 540

Asp Asn Val Lys Gly Glu Ala Lys Lys Arg Ser Gly Lys Ala Gly Glu
545                 550                 555                 560

<210> SEQ ID NO 13
<211> LENGTH: 13
<212> TYPE: PRT
<213> ORGANISM: Artificial Sequence
<220> FEATURE:
<223> OTHER INFORMATION: Blastomyces dermatitidis of strains 26199,
      18808, Er-3, 14081

<400> SEQUENCE: 13
```

Leu Gln Asn Ser Leu Asn Cys Gly Gly Ala Tyr Met Lys
1               5                   10

<210> SEQ ID NO 14
<211> LENGTH: 66
<212> TYPE: DNA
<213> ORGANISM: Artificial Sequence
<220> FEATURE:
<223> OTHER INFORMATION: synthetic

<400> SEQUENCE: 14
ccgggactga gggcctcgtg gtgaagaatc cgccgccca ccacgcgatt tccggctgtg    60
gaggta                                                              66

<210> SEQ ID NO 15
<211> LENGTH: 66
<212> TYPE: DNA
<213> ORGANISM: Artificial Sequence
<220> FEATURE:
<223> OTHER INFORMATION: synthetic

<400> SEQUENCE: 15
ctagtacctc cacagccgga aatcgcgtgg tgggcggcgg gattcttcac cacgaggccc    60
tcagtc                                                              66

<210> SEQ ID NO 16
<211> LENGTH: 9
<212> TYPE: PRT
<213> ORGANISM: Artificial Sequence
<220> FEATURE:
<223> OTHER INFORMATION: Blastomyces dermatitidis of strains 26199,
      18808, Er-3, 14081; Histoplasma capsulatum of strains G186AR,
      Nam1, H88, and H143, Aspergillus sp.1 of strains group.1, A. flavus, and group.1, A. oryzae, A. terreus, and Magnaporthe oryzae_70-15.

<400> SEQUENCE: 16

Val Lys Asn Pro Ala Ala His His Ala
1 5

<210> SEQ ID NO 17
<211> LENGTH: 13
<212> TYPE: PRT
<213> ORGANISM: Artificial Sequence
<220> FEATURE:
<223> OTHER INFORMATION: Colletotrichum graminicola; Chaetomium globosum

<400> SEQUENCE: 17

Leu Val Ile Lys Asn Pro Ala Ala His His Ala Ile Ser
1 5 10

<210> SEQ ID NO 18
<211> LENGTH: 13
<212> TYPE: PRT
<213> ORGANISM: Artificial Sequence
<220> FEATURE:
<223> OTHER INFORMATION: Puccinia graminis; Melampsora larici-populina; Yarrowia lipolytica

<400> SEQUENCE: 18

Leu Val Val Lys Ser Pro Ala Ala His His Ala Ile Ser
1 5 10

<210> SEQ ID NO 19
<211> LENGTH: 13
<212> TYPE: PRT

```
<213> ORGANISM: Artificial Sequence
<220> FEATURE:
<223> OTHER INFORMATION: Grosmannia clavigera; Sporothrix schenckii

<400> SEQUENCE: 19

Leu Val Val Lys Asn Lys Ala Ala His His Ala Ile Ser
1               5                   10

<210> SEQ ID NO 20
<211> LENGTH: 13
<212> TYPE: PRT
<213> ORGANISM: Meyerozyma guilliermondii

<400> SEQUENCE: 20

Leu Val Met Lys Thr Pro Ala Ala His His Ala Ile Ser
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Debarymomyces hansenii; Wickerhamomyces
      ciferrii

<400> SEQUENCE: 21

Leu Val Leu Lys Thr Pro Ala Ala His His Ala Ile Ser
1               5                   10

<210> SEQ ID NO 22
<211> LENGTH: 13
<212> TYPE: PRT
<213> ORGANISM: Arthrobotrys oligospor

<400> SEQUENCE: 22

Leu Val Val Lys Asp Lys Ala Ala His His Ala Ile Ser
1               5                   10

<210> SEQ ID NO 23
<211> LENGTH: 13
<212> TYPE: PRT
<213> ORGANISM: Pichia pastoris

<400> SEQUENCE: 23

Leu Val Val Lys Ser Glu Ala Ala His His Ala Ile Ser
1               5                   10

<210> SEQ ID NO 24
<211> LENGTH: 13
<212> TYPE: PRT
<213> ORGANISM: Batrachochytrium dendrobatidis

<400> SEQUENCE: 24

Leu Val Val Lys Thr Thr Ala Ala His His Ala Ile Ser
1               5                   10

<210> SEQ ID NO 25
<211> LENGTH: 13
<212> TYPE: PRT
<213> ORGANISM: Bipolaris maydis

<400> SEQUENCE: 25

Leu Val Ile Lys Asp Gln Ala Ala His His Ala Ile Ser
1               5                   10
```

```
<210> SEQ ID NO 26
<211> LENGTH: 13
<212> TYPE: PRT
<213> ORGANISM: Agaricus bisporus

<400> SEQUENCE: 26

Leu Val Ala Lys Ser Pro Ala Ser His His Ala Ile Ser
1               5                   10

<210> SEQ ID NO 27
<211> LENGTH: 13
<212> TYPE: PRT
<213> ORGANISM: Ophiostoma piceae

<400> SEQUENCE: 27

Leu Val Leu Lys Asn Lys Ala Ala His His Ala Ile Ser
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Schizosaccharomyces japonicas;
      Schizosaccharomyces octosporus

<400> SEQUENCE: 28

Leu Val Met Lys Asp Ala Ala His His Ala Ile Ser
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Phaeosphaeria nodorum ; Neofusicoccum parvum;
      Macrophomina phaseolina; Pyrenophora teres; Pyrenophora tritici-
      repentis; Coniosporium apollinis

<400> SEQUENCE: 29

Leu Val Ile Lys Asp Lys Ala Ala His His Ala Ile Ser
1               5                   10

<210> SEQ ID NO 30
<211> LENGTH: 13
<212> TYPE: PRT
<213> ORGANISM: Setosphaeria turcica

<400> SEQUENCE: 30

Leu Ile Val Lys Asp Lys Ala Ala His His Ala Ile Ser
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Schizosaccharomyces pombe; Schizosaccharomyces
      cryophilus

<400> SEQUENCE: 31

Leu Val Met Lys Asp Glu Ala Ala His His Ala Ile Ser
1               5                   10

<210> SEQ ID NO 32
<211> LENGTH: 13
<212> TYPE: PRT
```

<213> ORGANISM: Millerozyma farinose

<400> SEQUENCE: 32

Leu Val Met Lys Lys Ala Ala Ala His His Ala Ile Ser
1               5                   10

<210> SEQ ID NO 33
<211> LENGTH: 13
<212> TYPE: PRT
<213> ORGANISM: Glarea lozoyensis

<400> SEQUENCE: 33

Leu Val Met Lys Asp Val Ala Ala His His Ala Ile Ser
1               5                   10

<210> SEQ ID NO 34
<211> LENGTH: 13
<212> TYPE: PRT
<213> ORGANISM: Pneumocystis jirovecii

<400> SEQUENCE: 34

Leu Val Leu Lys Lys Gln Ala Ala His His Ala Ile Ser
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Stereum hirsutum; Pseudocercospora fijiensis

<400> SEQUENCE: 35

Leu Val Ala Lys Asp Lys Ala Ala His His Ala Ile Ser
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Sphaerulina musiva; Dothistroma septosporum;
      Zymoseptoria tritici; Leptosphaeria maculans; Baudoinia
      compniacensis

<400> SEQUENCE: 36

Leu Val Leu Lys Asp Lys Ala Ala His His Ala Ile Ser
1               5                   10

<210> SEQ ID NO 37
<211> LENGTH: 13
<212> TYPE: PRT
<213> ORGANISM: Blumeria graminis

<400> SEQUENCE: 37

Leu Val Met Lys Ser Lys Ala Ala His His Ala Ile Ser
1               5                   10

<210> SEQ ID NO 38
<211> LENGTH: 13
<212> TYPE: PRT
<213> ORGANISM: Tremella mesenterica

<400> SEQUENCE: 38

Leu Val Met Lys Ser Lys Ala Ala His His Ala Ile Ser
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Fomitiporia mediterranea; Punctularia
      strigosozonata; Laccaria bicolor; Coprinopsis cinerea;
      Moniliophthora roreri; Piriformospora indica; Heterobasidion
      irregulare

<400> SEQUENCE: 39

Leu Val Ala Lys Ser Lys Ala Ala His His Ala Ile Ser
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Trichosporon asahii; Scheffersomyces stipites

<400> SEQUENCE: 40

Leu Val Leu Lys Ser Lys Ala Ala His His Ala Ile Ser
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Ogataea parapolymorpha ; Ogataea angusta

<400> SEQUENCE: 41

Leu Val Ala Lys Thr Glu Ala Ala His His Ala Ile Ser
1               5                   10

<210> SEQ ID NO 42
<211> LENGTH: 13
<212> TYPE: PRT
<213> ORGANISM: Dactylellina haptotyla

<400> SEQUENCE: 42

Leu Val Val Lys Asp Lys Ala Arg His His Ala Ile Ser
1               5                   10

<210> SEQ ID NO 43
<211> LENGTH: 13
<212> TYPE: PRT
<213> ORGANISM: Dekkera bruxellensis

<400> SEQUENCE: 43

Leu Val Val Lys Ser Glu Ala Ala Leu His Ala Ile Ser
1               5                   10

<210> SEQ ID NO 44
<211> LENGTH: 13
<212> TYPE: PRT
<213> ORGANISM: Mixia osmundae

<400> SEQUENCE: 44

Leu Val Val Ala Ser Lys Ala Ala His His Ala Ile Ser
1               5                   10

<210> SEQ ID NO 45
<211> LENGTH: 13
<212> TYPE: PRT

<213> ORGANISM: Rhizoctonia solani

<400> SEQUENCE: 45

Leu Val Ala Lys Ser Lys Ala Ser His His Ala Ile Ser
1               5                   10

<210> SEQ ID NO 46
<211> LENGTH: 13
<212> TYPE: PRT
<213> ORGANISM: Spathaspora passalidarum

<400> SEQUENCE: 46

Leu Val Leu Lys Ser Lys Ala Ala His His Ala Ile Ala
1               5                   10

<210> SEQ ID NO 47
<211> LENGTH: 13
<212> TYPE: PRT
<213> ORGANISM: Auricularia delicate

<400> SEQUENCE: 47

Leu Val Ala Lys Ser Lys Ala Thr His His Ala Ile Ser
1               5                   10

<210> SEQ ID NO 48
<211> LENGTH: 13
<212> TYPE: PRT
<213> ORGANISM: Rhizophagus irregularis

<400> SEQUENCE: 48

Leu Ile Val Asp Ser Lys Ala Ala His His Ala Ile Ser
1               5                   10

<210> SEQ ID NO 49
<211> LENGTH: 13
<212> TYPE: PRT
<213> ORGANISM: Pyronema omphalodes

<400> SEQUENCE: 49

Leu Val Ala Lys Asn Val Ala Ala Phe His Ala Ile Ser
1               5                   10

<210> SEQ ID NO 50
<211> LENGTH: 13
<212> TYPE: PRT
<213> ORGANISM: Moniliophthora perniciosa

<400> SEQUENCE: 50

Leu Val Ala Lys Ser Lys Ala Ala His Gln Ala Ile Ser
1               5                   10

<210> SEQ ID NO 51
<211> LENGTH: 13
<212> TYPE: PRT
<213> ORGANISM: Dacryopinax sp.

<400> SEQUENCE: 51

Leu Val Ala Lys Thr Lys Ala Gly His His Ala Ile Ser
1               5                   10

<210> SEQ ID NO 52
<211> LENGTH: 562
<212> TYPE: PRT
<213> ORGANISM: Histoplasma capsulatum of strains G217B

<400> SEQUENCE: 52

```
Met Arg Leu Asn Ala Ser Leu Ala Ser Leu Ile Leu Ser Ser Val Ala
1               5                   10                  15

Leu Ile Gly Asn Val Arg Ala Glu Glu Val Lys Gly Asp Ala Pro
            20                  25                  30

Ser Pro Ser Ser Ala Ile Glu Lys Pro Thr Phe Thr Pro Thr Thr Leu
        35                  40                  45

Lys Ala Pro Phe Leu Glu Gln Phe Thr Asp Asp Trp Glu Thr Arg Trp
    50                  55                  60

Thr Pro Ser His Ala Lys Lys Glu Asp Ser Ser Asp Glu Asp Trp
65                  70                  75                  80

Ala Tyr Ile Gly Thr Trp Ala Val Glu Glu Pro His Val Leu Asn Gly
                    85                  90                  95

Met Val Gly Asp Lys Gly Leu Val Val Lys Asn Pro Ala Ala His His
            100                 105                 110

Ala Ile Ser Ala Lys Phe Pro Lys Lys Ile Asp Asn Lys Gly Lys Thr
            115                 120                 125

Leu Val Val Gln Tyr Glu Val Lys Leu Gln Asp Ser Leu Val Cys Gly
    130                 135                 140

Gly Ala Tyr Met Lys Leu Leu Gln Asp Asn Lys Lys Leu His Ala Glu
145                 150                 155                 160

Glu Phe Ser Asn Ala Ser Pro Tyr Val Ile Met Phe Gly Pro Asp Lys
                    165                 170                 175

Cys Gly Val Thr Asn Lys Val His Phe Ile Phe Arg His Lys Asn Pro
            180                 185                 190

Lys Thr Gly Glu Tyr Glu Glu Lys His Met Asn Ala Ala Pro Ala Ala
        195                 200                 205

Lys Ile Asn Lys Leu Ser Thr Leu Tyr Thr Leu Ile Val Lys Pro Asp
    210                 215                 220

Gln Ser Phe Gln Ile Arg Ile Asp Gly Lys Ala Val Lys Asn Gly Thr
225                 230                 235                 240

Leu Leu Glu Asp Phe Ser Pro Ala Val Asn Pro Pro Lys Glu Ile Asp
                245                 250                 255

Asp Pro Glu Asp Lys Lys Pro Glu Asp Trp Val Asp Glu Ala Arg Ile
            260                 265                 270

Ala Asp Pro Asp Ala Thr Lys Pro Glu Asp Trp Asp Glu Asp Ala Pro
        275                 280                 285

Tyr Glu Ile Val Asp Thr Asp Ala Val Gln Pro Glu Asp Trp Leu Val
    290                 295                 300

Asp Glu Pro Thr Ser Ile Pro Asp Pro Glu Ala Glu Lys Pro Glu Asp
305                 310                 315                 320

Trp Asp Asp Glu Glu Asp Gly Asp Trp Thr Pro Pro Thr Ile Pro Asn
                325                 330                 335

Pro Lys Cys Ser Glu Val Ser Gly Cys Gly Lys Trp Gln Gln Pro Met
            340                 345                 350

Lys Lys Asn Pro Asp Tyr Lys Gly Lys Trp Val Ala Pro Met Ile Asp
        355                 360                 365

Asn Pro Ala Tyr Lys Gly Pro Trp Ala Pro Arg Lys Ile Pro Asn Pro
    370                 375                 380

Asp Tyr Phe Glu Asp Lys Thr Pro Ser Asn Phe Glu Pro Met Gly Ala
385                 390                 395                 400

Ile Gly Phe Glu Ile Trp Thr Met Gln Ser Asp Ile Leu Phe Asn Asn
                405                 410                 415
```

```
Ile Tyr Ile Gly His Ser Ile Glu Asp Ala Glu Lys Leu Lys Ala Glu
            420                 425                 430

Thr Trp Asp Leu Lys His Pro Val Glu Val Ala Glu Glu Glu Ala Ser
        435                 440                 445

Arg Pro Lys Asp Glu Glu Lys Glu Ala Gly Thr Ser Phe Lys Glu Asp
    450                 455                 460

Pro Val Gln Tyr Ile Arg Lys Lys Ile Asp Leu Phe Ile Ser Leu Ala
465                 470                 475                 480

Leu Glu Asn Pro Val Glu Ala Val Lys Ala Val Pro Glu Val Ala Gly
                485                 490                 495

Gly Leu Cys Ala Leu Leu Val Thr Leu Ile Leu Ile Ile Val Ser Gly
            500                 505                 510

Leu Ser Leu Gly Ser Ser Ser Ser Pro Ala Pro Lys Lys Gln Ala Glu
        515                 520                 525

Lys Gly Lys Glu Lys Glu Lys Ala Ser Ala Ser Glu Ala Val Ser Thr
    530                 535                 540

Gly Ala Asp Asn Val Lys Gly Gly Ala Lys Lys Arg Ser Thr Lys Thr
545                 550                 555                 560

Ser Glu

<210> SEQ ID NO 53
<211> LENGTH: 561
<212> TYPE: PRT
<213> ORGANISM: Coccidioides posadasii

<400> SEQUENCE: 53

Met Arg Leu Asn Ala Arg Thr Ala Ser Leu Ile Leu Ser Tyr Ile Ala
1               5                   10                  15

Leu Leu Gly Gln Val His Ala Glu Ser Glu Ala Thr Lys Glu Glu Pro
            20                  25                  30

Thr Ala Thr Ser Ile Ser Arg Pro Thr Phe Thr Pro Thr Thr Leu Lys
        35                  40                  45

Ala Pro Phe Leu Glu Gln Phe Thr Asp Asp Trp Gln Thr Arg Trp Thr
    50                  55                  60

Pro Ser His Ala Lys Lys Glu Asp Ser Lys Ser Glu Glu Glu Trp Ala
65                  70                  75                  80

Tyr Val Gly Glu Trp Ala Val Glu Glu Pro Thr Val Phe Lys Gly Ile
                85                  90                  95

Asp Gly Asp Lys Gly Leu Val Val Lys Asn Ala Ala Ala His His Ala
            100                 105                 110

Ile Ser Ala Lys Phe Pro Lys Lys Ile Asp Asn Lys Gly Lys Thr Leu
        115                 120                 125

Val Val Gln Tyr Glu Val Lys Leu Gln Asn Ser Leu Val Cys Gly Gly
    130                 135                 140

Ala Tyr Met Lys Leu Leu Gln Asp Asn Lys Lys Leu His Ala Glu Glu
145                 150                 155                 160

Phe Ser Asn Ala Ser Pro Tyr Val Ile Met Phe Gly Pro Asp Lys Cys
                165                 170                 175

Gly Ala Thr Asn Lys Val His Phe Ile Phe Lys His Lys Asn Pro Lys
            180                 185                 190

Thr Gly Glu Tyr Glu Glu Lys His Leu Asn Asn Ala Pro Thr Ala Arg
        195                 200                 205

Val Ser Lys Leu Ser Thr Leu Tyr Thr Leu Ile Val Lys Pro Asp Gln
    210                 215                 220
```

Thr Phe Gln Ile Gln Ile Asn Gly Glu Ala Val Lys Asn Gly Thr Leu
225                 230                 235                 240

Leu Glu Asp Phe Gln Pro Val Asn Pro Lys Glu Ile Asp Asp
            245                 250                 255

Pro Asn Asp Lys Lys Pro Ala Asp Trp Val Asp Glu Ala Lys Ile Pro
            260                 265                 270

Asp Pro Glu Ala Lys Lys Pro Glu Asp Trp Asp Glu Asp Ala Pro Phe
            275                 280                 285

Glu Ile Val Asp Thr Glu Ala Lys Lys Pro Asp Asp Trp Leu Asp Asp
            290                 295                 300

Glu Pro Ser Ser Ile Pro Asp Pro Glu Ala Gln Lys Pro Glu Asp Trp
305                 310                 315                 320

Asp Asp Glu Glu Asp Gly Asp Trp Phe Ala Pro Thr Val Pro Asn Pro
                325                 330                 335

Lys Cys Glu Glu Ala Ser Gly Cys Gly Lys Trp Glu Pro Pro Met Lys
            340                 345                 350

Arg Asn Pro Asp Tyr Lys Gly Lys Trp Thr Ala Pro Leu Ile Asp Asn
            355                 360                 365

Pro Ala Tyr Lys Gly Pro Trp Ser Pro Arg Lys Ile Ala Asn Pro Asp
            370                 375                 380

Phe Phe Glu Asp Lys Lys Pro Ala Asn Phe Glu Pro Met Gly Ala Ile
385                 390                 395                 400

Gly Phe Glu Ile Trp Thr Met Gln Asn Asp Ile Leu Phe Asp Asn Ile
                405                 410                 415

Tyr Ile Gly His Ser Ile Glu Asp Lys Lys Leu Lys Ala Glu Thr
            420                 425                 430

Phe Asp Ile Lys Gln Pro Ile Glu Val Ala Glu Glu Ala Ala Lys
            435                 440                 445

Pro Lys Asp Glu Pro Ser Thr Asp Ser Gly Leu Asn Phe Lys Asp Asp
450                 455                 460

Pro Val Lys Tyr Ile Arg Ser Lys Val Asp Gln Phe Ile Leu Met Ala
465                 470                 475                 480

Lys Asp Asn Pro Val Glu Ala Val Lys Thr Val Pro Glu Val Ala Gly
                485                 490                 495

Gly Leu Ala Ala Leu Leu Ile Thr Leu Ile Leu Val Val Phe Gly Ala
            500                 505                 510

Ile Gly Leu Ser Ser Pro Ala Pro Ala Pro Ala Lys Lys Asp Ala Gly
            515                 520                 525

Lys Gly Lys Glu Lys Ala Lys Glu Lys Ala Ala Glu Ala Val Ser Thr
            530                 535                 540

Gly Ala Glu Asn Ile Lys Ala Gly Ala Thr Lys Arg Ser Lys Ser Ser
545                 550                 555                 560

Glu

<210> SEQ ID NO 54
<211> LENGTH: 567
<212> TYPE: PRT
<213> ORGANISM: Paracoccidioides brasiliensis

<400> SEQUENCE: 54

Met Arg Leu Asn Ala Ser Leu Ala Ser Leu Ile Leu Thr Ser Ile Ala
1               5                   10                  15

Leu Ile Gly Asn Val His Ala Glu Asp Glu Val Glu Gly Lys Pro Ser
                20                  25                  30

```
Ser Thr Ser Ser Val Ile Glu Lys Pro Leu Phe Thr Pro Thr Thr Leu
        35                  40                  45

Lys Ala Pro Phe Leu Glu Gln Phe Thr Asp Asp Trp Glu Thr Arg Trp
    50                  55                  60

Thr Pro Ser His Ala Lys Lys Gln Asp Ser Ser Glu Glu Asp Trp
65                  70                  75                  80

Ala Tyr Val Gly Thr Trp Ala Val Glu Glu Pro His Val Phe Asn Gly
                    85                  90                  95

Met Lys Gly Asp Lys Gly Leu Val Ile Lys Asn Ala Ala His His
                100                 105                 110

Ala Ile Ser Ala Lys Phe Pro Lys Lys Ile Asp Asn Lys Gly Asn Thr
            115                 120                 125

Leu Val Val Gln Tyr Glu Val Lys Leu Gln Asn Gly Leu Asn Cys Gly
        130                 135                 140

Gly Ala Tyr Met Lys Leu Leu Gln Asp Asn Lys Lys Leu His Ala Glu
145                 150                 155                 160

Glu Phe Ser Asn Ala Ser Pro Tyr Val Ile Met Phe Gly Pro Asp Lys
                165                 170                 175

Cys Gly Val Thr Asn Lys Val His Phe Ile Phe Arg His Lys Asn Pro
            180                 185                 190

Lys Thr Gly Glu Tyr Glu Glu Lys His Leu Lys Asn Pro Pro Ala Ala
        195                 200                 205

Arg Val Ser Lys Leu Ser Thr Leu Tyr Thr Leu Ile Val Lys Pro Asp
    210                 215                 220

Gln Ser Phe Gln Ile Leu Ile Asp Gly Glu Ala Val Lys Asn Gly Thr
225                 230                 235                 240

Leu Leu Glu Asp Phe Ser Pro Ala Val Asn Pro Gln Lys Glu Ile Asp
                245                 250                 255

Asp Pro Glu Asp Lys Lys Pro Lys Asp Trp Val Asp Glu Thr Arg Ile
            260                 265                 270

Pro Asp Pro Thr Ala Thr Lys Pro Asp Asp Trp Asp Glu Asp Ala Pro
        275                 280                 285

Tyr Glu Ile Ile Asp Thr Glu Ala Thr Lys Pro Asp Asp Trp Leu Asp
290                 295                 300

Ser Glu Pro Asp Ser Ile Pro Asp Pro Glu Ala Gln Lys Pro Glu Asp
305                 310                 315                 320

Trp Asp Asp Glu Glu Asp Gly Asp Trp Ala Ala Pro Thr Ile Pro Asn
                325                 330                 335

Pro Lys Cys Ser Glu Val Ser Gly Cys Gly Lys Trp Glu Ala Pro Met
            340                 345                 350

Lys Lys Asn Pro Asp Tyr Lys Gly Lys Trp Thr Pro Pro Met Ile Asp
        355                 360                 365

Asn Pro Ala Tyr Lys Gly Pro Trp Thr Pro Arg Lys Ile Pro Asn Pro
370                 375                 380

Asn Tyr Phe Glu Asp Lys Thr Pro Ala Asn Phe Glu Pro Met Gly Ala
385                 390                 395                 400

Ile Gly Phe Glu Ile Trp Thr Met Gln Asn Asp Ile Leu Phe Asn Asn
                405                 410                 415

Ile Tyr Ile Gly His Ser Ile Glu Asp Ala Gln Lys Leu Lys Ser Glu
            420                 425                 430

Thr Trp Asp Ile Lys His Pro Ile Glu Val Ala Glu Glu Glu Ala Thr
        435                 440                 445
```

Arg Pro Lys Asp Asp Glu Lys Asp Ser Ser Phe Val Ser Phe Lys Glu
450 455 460

Ala Pro Val Gln Phe Val Arg Glu Lys Ile Asn Leu Phe Ile Ser Ile
465 470 475 480

Ala Arg Lys Asp Pro Val Gln Ala Ala Lys Ser Val Pro Glu Val Ala
485 490 495

Gly Gly Leu Gly Ala Leu Val Ile Thr Leu Ala Leu Ile Ile Val Gly
500 505 510

Ala Ile Gly Leu Ser Ser Pro Ala Pro Ala Pro Ala Val Ala Lys Lys
515 520 525

Val Asp Gly Lys Glu Lys Asp Gly Ala Ser Lys Glu Lys Ala Ala Glu
530 535 540

Ala Val Ser Thr Thr Ala Asp Asn Val Lys Gly Ala Ala Thr Arg Arg
545 550 555 560

Ser Gly Lys Ala Asn Asn Glu
565

<210> SEQ ID NO 55
<211> LENGTH: 561
<212> TYPE: PRT
<213> ORGANISM: Coccidioides immitis

<400> SEQUENCE: 55

Met Arg Leu Asn Ala Arg Thr Ala Ser Leu Ile Leu Ser Tyr Ile Ala
1 5 10 15

Leu Leu Gly Gln Val His Ala Glu Ser Glu Ala Thr Lys Glu Glu Pro
20 25 30

Thr Ala Thr Ser Ile Ser Arg Pro Thr Phe Thr Pro Thr Thr Leu Lys
35 40 45

Ala Pro Phe Leu Glu Gln Phe Thr Asp Asp Trp Gln Thr Arg Trp Thr
50 55 60

Pro Ser His Ala Lys Lys Glu Asp Ser Lys Ser Glu Glu Glu Trp Ala
65 70 75 80

Tyr Val Gly Glu Trp Ala Val Glu Glu Pro Thr Val Phe Lys Gly Ile
85 90 95

Asp Gly Asp Lys Gly Leu Val Val Lys Asn Ala Ala Ala His His Ala
100 105 110

Ile Ser Ala Lys Phe Pro Gln Lys Ile Asp Asn Lys Gly Lys Thr Leu
115 120 125

Val Val Gln Tyr Glu Val Lys Leu Gln Asn Ser Leu Val Cys Gly Gly
130 135 140

Ala Tyr Met Lys Leu Leu Gln Asp Asn Lys Lys Leu His Ala Glu Glu
145 150 155 160

Phe Ser Asn Ala Ser Pro Tyr Val Ile Met Phe Gly Pro Asp Lys Cys
165 170 175

Gly Ala Thr Asn Lys Val His Phe Ile Phe Lys His Lys Asn Pro Lys
180 185 190

Thr Gly Glu Tyr Glu Glu Lys His Leu Asn Asn Ala Pro Thr Ala Arg
195 200 205

Ile Ser Lys Leu Ser Thr Leu Tyr Thr Leu Ile Val Lys Pro Asp Gln
210 215 220

Thr Phe Gln Ile Gln Ile Asn Gly Glu Ala Val Lys Asn Gly Thr Leu
225 230 235 240

Leu Glu Asp Phe Gln Pro Pro Val Asn Pro Pro Lys Glu Ile Asp Asp
245 250 255

Pro Asn Asp Lys Lys Pro Ala Asp Trp Val Asp Glu Ala Lys Ile Pro
           260                 265                 270

Asp Pro Glu Ala Lys Lys Pro Glu Asp Trp Asp Asp Ala Pro Phe
       275                 280                 285

Glu Ile Val Asp Thr Glu Ala Lys Lys Pro Asp Asp Trp Leu Asp Asp
290                 295                 300

Glu Pro Ser Ser Ile Pro Asp Pro Glu Ala Gln Lys Pro Glu Asp Trp
305                 310                 315                 320

Asp Asp Glu Glu Asp Gly Asp Trp Val Ala Pro Thr Val Pro Asn Pro
               325                 330                 335

Lys Cys Glu Glu Ala Ser Gly Cys Gly Lys Trp Glu Pro Pro Met Lys
               340                 345                 350

Arg Asn Pro Asp Tyr Lys Gly Lys Trp Thr Ala Pro Leu Ile Asp Asn
       355                 360                 365

Pro Ala Tyr Lys Gly Pro Trp Ser Pro Arg Lys Ile Ala Asn Pro Asp
   370                 375                 380

Phe Phe Glu Asp Lys Lys Pro Ala Asn Phe Glu Pro Met Gly Ala Ile
385                 390                 395                 400

Gly Phe Glu Ile Trp Thr Met Gln Asn Asp Ile Leu Phe Asp Asn Ile
               405                 410                 415

Tyr Ile Gly His Ser Ile Glu Asp Ala Lys Lys Leu Lys Ala Glu Thr
               420                 425                 430

Phe Asp Ile Lys His Pro Ile Glu Val Ala Glu Glu Ala Ala Lys
               435                 440                 445

Pro Lys Asp Glu Pro Ser Thr Asp Ser Gly Leu Asn Phe Lys Asp Asp
   450                 455                 460

Pro Val Lys Tyr Ile Arg Ser Lys Val Asp Gln Phe Ile Leu Met Ala
465                 470                 475                 480

Lys Asp Asn Pro Val Glu Ala Val Lys Ala Val Pro Glu Val Ala Gly
               485                 490                 495

Gly Leu Ala Ala Leu Leu Ile Thr Leu Ile Leu Val Val Phe Gly Ala
               500                 505                 510

Ile Gly Leu Ser Ser Pro Ala Pro Ala Pro Ala Lys Lys Asp Ala Gly
           515                 520                 525

Lys Gly Lys Glu Lys Ala Lys Glu Lys Ala Ala Glu Ala Val Ser Thr
           530                 535                 540

Gly Ala Glu Asn Val Lys Ala Gly Ala Thr Lys Arg Ser Lys Ser Ser
545                 550                 555                 560

Glu

<210> SEQ ID NO 56
<211> LENGTH: 598
<212> TYPE: PRT
<213> ORGANISM: Histoplasma capsulatum of strains G186AR

<400> SEQUENCE: 56

Met Ile Pro Ala Ser Asp Ile Ala Gln Arg Ile Glu Ile Trp Gln Ile
1               5                   10                  15

Asp Ser Gly Ser Lys Leu Gln Leu Ala Thr Thr Leu Ser Asn Trp Arg
           20                  25                  30

Pro Ser Val Thr Met Arg Leu Asn Ala Ser Leu Ala Ser Leu Ile Leu
       35                  40                  45

Ser Ser Val Ala Leu Ile Gly Asn Val Arg Ala Glu Glu Glu Val Lys
   50                  55                  60

```
Gly Asp Ala Pro Ser Pro Ser Ala Ile Glu Lys Pro Thr Phe Thr
 65                  70                  75                  80

Pro Thr Thr Leu Lys Ala Pro Phe Leu Glu Gln Phe Thr Asp Asp Trp
             85                  90                  95

Glu Thr Arg Trp Thr Pro Ser His Ala Lys Lys Glu Asp Ser Ser Ser
                100                 105                 110

Asp Glu Asp Trp Ala Tyr Ile Gly Thr Trp Ala Val Glu Glu Pro His
             115                 120                 125

Val Leu Asn Gly Met Val Gly Asp Lys Gly Leu Val Val Lys Asn Pro
    130                 135                 140

Ala Ala His His Ala Ile Ser Ala Lys Phe Pro Lys Lys Ile Asp Asn
145                 150                 155                 160

Lys Gly Lys Thr Leu Val Val Gln Tyr Glu Val Lys Leu Gln Asn Ser
                165                 170                 175

Leu Val Cys Gly Gly Ala Tyr Met Lys Leu Leu Gln Asp Asn Lys Lys
             180                 185                 190

Leu His Ala Glu Glu Phe Ser Asn Ala Ser Pro Tyr Val Ile Met Phe
    195                 200                 205

Gly Pro Asp Lys Cys Gly Val Thr Asn Lys Val His Phe Ile Phe Arg
210                 215                 220

His Lys Asn Pro Lys Thr Gly Glu Tyr Glu Glu Lys His Met Asn Ala
225                 230                 235                 240

Ala Pro Ala Ala Lys Ile Asn Lys Leu Ser Thr Leu Tyr Thr Leu Ile
                245                 250                 255

Val Lys Pro Asp Gln Ser Phe Gln Ile Arg Ile Asp Gly Lys Ala Val
             260                 265                 270

Lys Asn Gly Thr Leu Leu Glu Asp Phe Ser Pro Ala Val Asn Pro Pro
    275                 280                 285

Lys Glu Ile Asp Asp Pro Glu Asp Lys Lys Pro Glu Asp Trp Val Asp
290                 295                 300

Glu Ala Arg Ile Ala Asp Pro Asp Ala Thr Lys Pro Glu Asp Trp Asp
305                 310                 315                 320

Glu Asp Ala Pro Tyr Glu Ile Val Asp Ala Asp Ala Val Gln Pro Glu
                325                 330                 335

Asp Trp Leu Ile Asp Glu Pro Thr Ser Ile Pro Asp Pro Glu Ala Glu
             340                 345                 350

Lys Pro Glu Asp Trp Asp Asp Glu Glu Asp Gly Asp Trp Thr Pro Pro
    355                 360                 365

Thr Ile Pro Asn Pro Lys Cys Ser Glu Val Ser Gly Cys Gly Lys Trp
370                 375                 380

Gln Gln Pro Met Lys Lys Asn Pro Asp Tyr Lys Gly Lys Trp Val Ala
385                 390                 395                 400

Pro Met Ile Asp Asn Pro Ala Tyr Lys Gly Pro Trp Ala Pro Arg Lys
                405                 410                 415

Ile Pro Asn Pro Asp Tyr Phe Glu Asp Lys Thr Pro Ala Asn Phe Glu
             420                 425                 430

Pro Met Gly Ala Ile Gly Phe Glu Ile Trp Thr Met Gln Ser Asp Ile
    435                 440                 445

Leu Phe Asn Asn Ile Tyr Ile Gly His Ser Ile Glu Asp Ala Glu Lys
450                 455                 460

Leu Lys Ala Glu Thr Trp Asp Leu Lys His Pro Val Glu Val Ala Glu
465                 470                 475                 480
```

-continued

```
Glu Glu Ala Ser Arg Pro Lys Asp Glu Lys Glu Ala Gly Thr Ser
            485                 490                 495

Phe Lys Glu Asp Pro Val Gln Tyr Ile Arg Lys Ile Asp Leu Phe
            500                 505                 510

Ile Ser Leu Ala Leu Glu Asn Pro Val Glu Ala Val Lys Thr Val Pro
            515                 520                 525

Glu Val Ala Gly Gly Leu Gly Ala Leu Leu Val Thr Leu Ile Leu Ile
            530                 535                 540

Ile Val Ser Gly Ile Ser Leu Gly Ser Ser Ser Pro Ala Pro Lys
545                 550                 555                 560

Lys Gln Ala Glu Lys Gly Lys Glu Lys Glu Lys Ala Ser Ala Ser Glu
            565                 570                 575

Ala Val Ser Thr Gly Ala Asp Asn Val Lys Gly Gly Ala Lys Lys Arg
            580                 585                 590

Ser Thr Lys Thr Ser Glu
            595

<210> SEQ ID NO 57
<211> LENGTH: 562
<212> TYPE: PRT
<213> ORGANISM: Aspergillus flavus

<400> SEQUENCE: 57

Met Arg Phe Asn Ala Ala Val Ala Ser Ala Leu Val Ser Ala Thr
1               5                   10                  15

Leu Met Gly Tyr Ala His Ala Glu Glu Ala Lys Asn Pro Asp Ala
                20                  25                  30

Thr Ser Val Val Glu Lys Pro Thr Phe Thr Pro Thr Thr Leu Lys Ala
                35                  40                  45

Pro Phe Leu Glu Gln Phe Thr Asp Asp Trp Glu Ser Arg Trp Thr Pro
            50                  55                  60

Ser His Ala Lys Lys Asp Asp Ser Gln Thr Glu Glu Asp Trp Ala Tyr
65                  70                  75                  80

Val Gly Glu Trp Ser Val Glu Glu Pro Thr Val Phe Lys Gly Ile Asp
                85                  90                  95

Gly Asp Lys Gly Leu Val Val Lys Asn Pro Ala Ala His His Ala Ile
                100                 105                 110

Ser Ala Lys Phe Pro Lys Lys Ile Asp Asn Lys Gly Lys Thr Leu Val
                115                 120                 125

Val Gln Tyr Glu Val Lys Pro Gln Asn Ser Leu Val Cys Gly Gly Ala
            130                 135                 140

Tyr Leu Lys Leu Leu Gln Glu Asn Lys Lys Leu His Ala Glu Glu Phe
145                 150                 155                 160

Ser Asn Ala Thr Pro Tyr Val Ile Met Phe Gly Pro Asp Lys Cys Gly
                165                 170                 175

Ala Thr Asn Lys Val His Phe Ile Phe Arg His Lys Asn Pro Lys Thr
                180                 185                 190

Gly Glu Tyr Glu Glu Lys His Leu Lys Ala Pro Pro Ala Ala Arg Thr
            195                 200                 205

Asn Lys Val Thr Ser Leu Tyr Thr Leu Ile Val Arg Pro Asp Gln Ser
        210                 215                 220

Phe Gln Ile Leu Ile Asp Gly Glu Ala Val Lys Asn Gly Thr Leu Leu
225                 230                 235                 240

Glu Asp Phe Asn Pro Pro Val Asn Pro Glu Lys Glu Ile Asp Asp Pro
                245                 250                 255
```

```
Lys Asp Lys Lys Pro Asp Asp Trp Val Asp Val Lys Ile Pro Asp
                260                 265                 270

Pro Glu Ala Thr Lys Pro Glu Asp Trp Asp Glu Ala Pro Tyr Glu
            275                 280                 285

Ile Val Asp Glu Glu Ala Thr Lys Pro Glu Asp Trp Leu Glu Glu
        290                 295                 300

Pro Thr Ser Ile Pro Asp Pro Glu Ala Glu Lys Pro Glu Asp Trp Asp
305                 310                 315                 320

Asp Glu Glu Asp Gly Asp Trp Ile Pro Pro Thr Val Pro Asn Pro Lys
                325                 330                 335

Cys Asn Asp Val Ser Gly Cys Gly Pro Trp Ser Ala Pro Met Lys Lys
                340                 345                 350

Asn Pro Ala Tyr Lys Gly Lys Trp Thr Ala Pro Met Ile Asp Asn Pro
            355                 360                 365

Ala Tyr Lys Gly Pro Trp Ser Pro Arg Lys Ile Ala Asn Pro Ala Tyr
        370                 375                 380

Phe Glu Asp Lys Thr Pro Ser Asn Phe Glu Pro Met Gly Ala Ile Gly
385                 390                 395                 400

Phe Glu Ile Trp Thr Met Gln Asn Asp Ile Leu Phe Asp Asn Ile Tyr
                405                 410                 415

Ile Gly His Ser Pro Glu Asp Ala Glu Gln Leu Arg Lys Glu Thr Phe
            420                 425                 430

Asp Val Lys His Pro Val Glu Val Ala Glu Glu Ala Ser Lys Pro
                435                 440                 445

Lys Lys Glu Glu Thr Ala Pro Ala Thr Ser Val Ser Phe Gln Glu Asp
            450                 455                 460

Pro Ile Thr Phe Val Arg Glu Lys Val Asp His Phe Val Gly Leu Ala
465                 470                 475                 480

Lys Gln Asp Pro Val Asn Ala Val Lys Gln Ala Pro Glu Val Ala Gly
                485                 490                 495

Thr Leu Gly Ala Leu Val Leu Ser Met Val Leu Ile Ile Val Gly Ala
            500                 505                 510

Ile Lys Ala Ser Ser Pro Ala Pro Ala Pro Val Lys Lys Gly Lys Glu
        515                 520                 525

Ala Ala Gly Ala Ala Lys Glu Lys Val Ser Glu Ala Val Ser Ser Ser
        530                 535                 540

Ala Asp Thr Gly Lys Gly Gly Ala Ser Lys Arg Thr Thr Arg Ser Ser
545                 550                 555                 560

Ala Gln

<210> SEQ ID NO 58
<211> LENGTH: 581
<212> TYPE: PRT
<213> ORGANISM: Candida albicans

<400> SEQUENCE: 58

Met Lys Tyr Ala Leu Val Leu Leu Ser Leu Val Asn Ala Leu Lys
1               5                   10                  15

Tyr Val Pro Phe Asp Lys Thr Gln Leu Asp Pro Ser Ser Val Phe Glu
            20                  25                  30

Gln Phe Asp Tyr Pro Ser Leu Asn Ser Ser Pro Trp Gln Val Ser Thr
        35                  40                  45

Ala Lys Lys Phe Asp Glu Gly Arg Asp Glu Ile Val Arg Tyr Ser Gly
    50                  55                  60
```

```
Glu Trp Lys Ile Glu Ser Ser Thr Ser Lys Tyr Pro Gly Leu Glu Gly
65                  70                  75                  80

Asp Leu Gly Leu Val Met Lys Ser Arg Ala Ser His Tyr Ala Ile Ser
                85                  90                  95

Tyr Lys Leu Pro His Glu Val Thr Asn Thr Asn Pro Asn Asn Asn Lys
                100                 105                 110

Thr Gln Asp Leu Val Leu Gln Tyr Glu Val Lys Leu Gln Gln Gly Leu
            115                 120                 125

Thr Cys Gly Gly Ala Tyr Ile Lys Leu Leu Asp Ser Ser Pro Ser Gly
            130                 135                 140

Tyr Lys Phe Phe Asn Ser Glu Thr Pro Tyr Gln Ile Met Phe Gly Pro
145                 150                 155                 160

Asp Val Cys Gly Ser Glu Asn Lys Ile His Phe Ile Arg Lys Lys
                165                 170                 175

Leu Pro Asn Gly Ala Ile Glu Glu Lys His Leu Lys His Lys Pro Met
                180                 185                 190

Ala Arg Thr Asn Glu Leu Thr Asn Leu Tyr Thr Leu Ile Ile Lys Ser
            195                 200                 205

Asn Gln Asp Phe Glu Ile Arg Val Asn Gly Gln Val Ala Lys Ala Gly
    210                 215                 220

Asn Leu Tyr Lys Asn Gln Lys Leu Phe Asn Pro Pro Phe Glu Pro Pro
225                 230                 235                 240

Lys Glu Ile Pro Asp Val Asp Lys Lys Pro Asp Asp Trp Asp Asp
                245                 250                 255

Arg Ala Tyr Ile Pro Asp Pro Asn Val Glu Lys Pro Glu Asp Tyr Glu
                260                 265                 270

Leu Lys His Glu Tyr Pro Gln Ile Arg Asp Pro Asn Ala Val Lys Pro
            275                 280                 285

Asp Glu Trp Asp Glu Ser Ala Pro Arg Tyr Ile Pro Asp Pro Asp Ala
        290                 295                 300

Val Lys Pro Lys Asp Trp Asn Asp Ala Glu Lys Gln Trp Glu Pro Pro
305                 310                 315                 320

Leu Ile Val Asn Pro Lys Cys Ala Thr Gly Cys Gly Pro Trp Glu Ala
                325                 330                 335

Pro Leu Ile Pro Asn His Asp Tyr Ile Gly Pro Trp Phe Pro Pro Asp
        340                 345                 350

Ile Lys Asn Pro Asn Tyr Asn Gly Ile Trp Thr Pro Arg Leu Ile Pro
            355                 360                 365

Asn Pro Tyr Tyr Tyr Gln Val Lys Thr Pro Gly Lys Leu Asp Lys Pro
        370                 375                 380

Ile Gly Gly Ile Gly Phe Glu Leu Trp Ser Ile Glu Ser Asp Ile Leu
385                 390                 395                 400

Phe Asp Asn Ile Tyr Leu Gly Asn Ser Ile Ala Glu Ala Glu Leu Ile
                405                 410                 415

Gly Asn Thr Thr Phe Lys Ile Lys Tyr Glu Leu Glu Ala Asp Gln Arg
            420                 425                 430

Arg Glu Asn Lys Pro Arg Val Lys Asn Glu Pro Val Ala Pro Pro Arg
            435                 440                 445

Asn Phe Glu Asp Ile Ile Arg Asp Asp Ser Ile Ser Thr Phe Gln Gln
    450                 455                 460

Phe Leu Ile Phe Ile Lys Leu Phe Trp Leu Lys Gln Tyr Val Gln Leu
465                 470                 475                 480
```

```
Lys Asp Phe Tyr Phe Glu Leu Thr Leu Asp Pro Ile Gly Leu Ile Met
                485                 490                 495

Ala Asn Pro Leu Lys Thr Leu Leu Tyr Ala Phe Leu Phe Leu Phe Ser
            500                 505                 510

Phe Thr Ile Phe Gly Phe Ala Ser Thr Ile Met Phe Leu Leu Gln
        515                 520                 525

Gly Gly Glu Ala Phe Gly Ser Ser Ser Ile Thr Thr Thr Thr
        530                 535                 540

Thr Asp Ser Asn Arg Lys Asn Val Leu Thr Ala Glu Glu Ile Glu Met
545                 550                 555                 560

Pro Ser Asn His Val Gln Lys Ile Glu Ile Leu Asp Glu Gln Ile His
                565                 570                 575

Val Arg Gln Arg Lys
                580

<210> SEQ ID NO 59
<211> LENGTH: 554
<212> TYPE: PRT
<213> ORGANISM: Cryptococcus gattii

<400> SEQUENCE: 59

Met Arg Pro Gln Asn Val Ala Gly Val Ala Gly Thr Gly Ala Leu Ile
1               5                   10                  15

Met Ala Ala Gly Ala Leu Ala Asp Arg Ala Val Phe His Pro Thr Ser
            20                  25                  30

Leu Thr Ala Pro Phe Ile Glu Gln Phe Leu Glu Ser Ile Pro Glu Ser
        35                  40                  45

Arg Trp Thr Val Ser Arg Ala Thr Lys Gln Thr Pro Val Gly Asp Glu
    50                  55                  60

Ile Phe Ser Tyr Val Gly Gln Trp Glu Ile Glu Pro Asp Val Tyr
65                  70                  75                  80

Pro Gly Ile Ser Gly Asp Lys Gly Leu Val Leu Lys Thr Lys Ala Ala
                85                  90                  95

His His Ala Ile Ser Thr Leu Phe Asp Glu Pro Ile Asp Pro Lys Gly
            100                 105                 110

Lys Ser Leu Val Val Gln Tyr Glu Val Lys Leu Gln Lys Gly Leu Glu
        115                 120                 125

Cys Gly Gly Ala Tyr Ile Lys Leu Leu Thr Asp Gln Gln Asp Glu Gly
    130                 135                 140

Leu Arg Ala Gly Glu Asp Tyr Thr Asp Lys Thr Pro Phe Thr Ile Met
145                 150                 155                 160

Phe Gly Pro Asp Lys Cys Gly Ser Thr Asn Lys Val His Phe Ile Phe
                165                 170                 175

Arg His Lys Asn Pro Leu Thr Gly Glu Trp Glu Lys His Leu Lys
            180                 185                 190

Asn Pro Pro Ala Pro Lys Ile Thr Lys Thr Thr Ala Leu Tyr Thr Leu
        195                 200                 205

Ile Thr Lys Thr Ser Pro Asp Gln Thr Phe Glu Ile Leu Ile Asn Asp
    210                 215                 220

Glu Ser Val Arg Lys Gly Ser Leu Leu Glu Asp Phe Asp Pro Val
225                 230                 235                 240

Asn Pro Pro Lys Glu Ile Asp Asp Pro Glu Asp Phe Lys Pro Glu Thr
                245                 250                 255

Trp Val Asp Glu Ala Glu Ile Asp Asp Val Thr Ala Thr Lys Pro Asp
            260                 265                 270
```

```
Asp Trp Asp Glu Asp Ala Pro Ile Met Ile Thr Asp Thr Ser Ala Val
        275                 280                 285

Lys Pro Glu Asp Trp Leu Glu Glu Pro Glu Thr Ile Pro Asp Pro
    290                 295                 300

Glu Ala Glu Lys Pro Glu Glu Trp Asp Glu Glu Asp Gly Asp Trp
305                 310                 315                 320

Ile Pro Pro Met Val Pro Asn Pro Lys Cys Glu Asp Val Ser Gly Cys
                325                 330                 335

Gly Pro Trp Thr Ala Pro Lys Val Arg Asn Pro Ala Tyr Lys Gly Lys
                340                 345                 350

Trp Thr Ile Pro Lys Ile Pro Asn Pro Asp Tyr Lys Gly Pro Trp Ala
        355                 360                 365

Pro Arg Lys Ile Ala Asn Pro Ala Phe Phe Glu Asp Leu His Pro Ser
    370                 375                 380

Asp Phe Thr Lys Ile Gly Gly Val Gly Ile Glu Leu Trp Thr Met Thr
385                 390                 395                 400

Glu Asp Ile Leu Phe Asp Asn Leu Tyr Ile Gly His Asp Ala Ala Gln
                405                 410                 415

Ala Lys Lys Phe Ala Glu Glu Thr Tyr His Val Lys Lys Pro Ile Glu
                420                 425                 430

Lys Glu Ala Glu Gly Ser Asn Glu Asp Glu Leu Glu Glu Pro Ser Ser
            435                 440                 445

Leu Ile Asp Lys Val Gln Leu Lys Val Tyr Glu Phe Leu His Leu Ala
    450                 455                 460

Thr Phe Asp Ile Ser Gln Ala Val Lys Gln Met Pro Glu Val Ala Ala
465                 470                 475                 480

Gly Leu Ala Ala Ala Val Phe Thr Leu Leu Gly Met Leu Leu Ala Leu
                485                 490                 495

Phe Gly Phe Ile Gly Ser Ala Pro Thr Lys Val Lys Gln Thr Ser Val
                500                 505                 510

Lys Thr Lys Ser Val Ala Pro Val Ala Pro Ala Gly Glu Glu Glu Lys
        515                 520                 525

Lys Ala Leu Asp Gln Ala Gly Val Glu Val Pro Ala Val Glu Gly Ser
    530                 535                 540

Lys Lys Arg Val Thr Arg Ser Thr Lys Glu
545                 550
```

PEPTIDE MHCII TETRAMERS TO DETECT ENDOGENOUS CALNEXIN SPECIFIC CD4 T CELLS

CROSS-REFERENCE TO RELATED APPLICATIONS

This application is a divisional of U.S. patent application Ser. No. 14/643,693, filed Mar. 10, 2015, which claims the benefit of U.S. Provisional Patent Application Ser. No. 61/951,099 filed Mar. 11, 2014, each of which is incorporated herein by reference for all purposes.

STATEMENT REGARDING FEDERALLY SPONSORED RESEARCH/DEVELOPMENT

This invention was made with government support under AI105816 and AI093553 awarded by the National Institutes of Health. The government has certain rights in the invention.

BACKGROUND

Major killers such as poliomyelitis have been eradicated, but new pathogens are emerging. Fungi are one such group, which is linked partly to modern medical practices. Fungi, from yeasts colonizing the skin or mucosa, to molds from soil or water, are often harmless in the context of normal host responses. However, the success of cancer chemotherapy, as well as the AIDS pandemic, has led to immune deficiencies in a growing segment of the human population. Likewise, the routine use of intravenous catheters in hospitals provides a route of access for microbes that otherwise might not be able to infect human hosts. *Candida* is now among the leading agents of nosocomial blood stream infections (Pfaller et al., 2011). Infection with the mold *Aspergillus* is among the most feared complications in patients with hematological malignancies (Walsh et al., 2008). Over one million new cases per year of cryptococcosis are estimated worldwide in patients with AIDS, and over half those affected die of the infection (Park et al., 2009). Fungal infections have thus become an important cause of morbidity and mortality, and represent an increasing burden on the medical system. Effective ways to treat and prevent these infections are badly needed.

Vaccines have been hailed as one of the greatest achievements in public health during the past century. The global eradication of Smallpox virus in humans and Rinderpest virus in animals, and the near eradication or successful prevention of other viral or bacterial infections, for example meningitis in children due to Hemophilus influenze Type B, offer compelling examples. Yet, the development of safe and efficacious vaccines against fungi has been a major hurdle. This difficulty stems from the relative genetic complexity and intractability of fungi in the laboratory, limited knowledge of the mechanisms that underpin anti-fungal protective immunity, and a lack of defined antigen (Ag) candidates for vaccine protection against fungal pathogens. To date, only two vaccines against fungi have moved into clinical trials (Cassone and Casadevall, 2012). An investigational candidate vaccine containing rAls3p-N (NDV-3), directed against *Candida* (and also *S. aureus*), has been tested for safety and immunogenicity in volunteers in a Phase I trial. Another candidate vaccine containing rSap2p was found to be tolerated and effective in inducing specific antibodies and B cell memory in women with recurrent vulvovaginitis in a European clinical trial (Edwards, 2012). Highly conserved Ags that are shared across fungal pathogens in a family or taxon would be preferable, but the only such component that has shown promise is β-glucan. Cassone et. al. (Torosantucci et al., 2005) reported that this shared cell wall component served as the basis for a glyco-conjugate vaccine against *Candida* and *Aspergillus*. This preparation has not yet moved into clinical trials, but β-glucan particles (GPs) could serve as an experimental platform for the delivery of candidate vaccines against fungi.

The incidence of fungal infections and mycoses has increased significantly in the past two decades, mainly due to the growing number of individuals who have reduced immunological function (immuno-compromised patients), such as cancer patients, patients who have undergone organ transplantation, patients with AIDS, patients undergoing hemodialysis, critically ill patients, patients after major surgery, patients with catheters, patients suffering from severe trauma or burns, patients having debilitative metabolic illnesses such as diabetes mellitus, persons whose blood is exposed to environmental microbes such as individuals having indwelling intravenous tubes, and even in some elderly individuals. Fungal infections are often also attributed to the frequent use of cytotoxic and/or antibacterial drugs, which alter the normal bacterial flora. Fungi include moulds, yeasts and higher fungi. All fungi are eukaryotic and have sterols but not peptidoglycan in their cell membrane. They are chemoheterotrophs (requiring organic nutrition) and most are aerobic. Many fungi are also saprophytes (living off dead organic matter) in soil and water and acquire their food by absorption. Characteristically fungi also produce sexual and asexual spores. There are over 100,000 species recognized, with 100 infectious members for humans.

Human fungal infections are uncommon in generally healthy persons, being confined to conditions such as Candidiasis (thrush) and dermatophyte skin infections such as athlete's foot. Nevertheless, yeast and other fungi infections are one of the human ailments which still present a formidable challenge to modern medicine. In an immuno-compromised host, a variety of normally mild or nonpathogenic fungi can cause potentially fatal infections. Furthermore, the relative ease with which human can now travel around the world provides the means for unusual fungal infections to be imported from place to place. Therefore, wild and resistant strains of fungi are considered to be one of the most threatening and frequent cause of death mainly in hospitalized persons and immuno-compromised patients.

The identity of conserved antigens among pathogenic fungi is poorly understood. This is especially true for immunologically significant antigens that may serve as immunogens to vaccinate against infection. There are currently no commercial vaccines against fungi despite the growing problem of fungal infections. A vaccine against pathogenic fungi, especially one that protects against multiple fungal pathogens, would be of enormous clinical benefit, and of commercial interest.

An improved vaccine and a method of vaccination against fungi are needed in the art. Specifically, a vaccine antigenic to multiple fungi, e.g., multiple dimorphic fungi, and a method of using such vaccine are needed in the art.

There is currently no way to identify CD4 T cells in mammalian blood or tissue, and thus to determine an individuals profile of CD4 T cell based immune resistance or susceptibility. Therefore, needed in the art are compositions and methods for evaluating immune status of a patient by identifying and evaluating CD4 T cells in the patient.

SUMMARY OF THE INVENTION

In one aspect, the present invention discloses a method for evaluating the immune status of a patient against a fungus. The method comprises the steps of (a) obtaining peptide-MHCII tetramers; (b) exposing a patient's sample to a suitable amount of the pMHCII tetramers; (c) identifying helper T cells in the patient's sample; (d) quantifying the helper T cells in the patient's sample; and (e) monitoring the response, expansion and characteristics of the helper T cells the after infection and vaccination, wherein the immune status of a patient against the fungus is obtained by comparing the quantity, expansion and characteristics of the helper T cells before and after infection and vaccination.

In one embodiment, the sample is a fresh blood sample.

In one embodiment, the peptide-MHCII tetramers comprise a calnexin peptide.

In one embodiment, the calnexin peptide comprises or consists of a sequence selected from a group consisting of SEQ ID NOs:1-5, 7-8, and 12.

In one embodiment, the peptide-MHCII tetramers comprise at least one fluorescent label.

In one embodiment, the helper T cells are "endogenous" calnexin peptide #1 specific T cells.

In one embodiment, in the step (c) helper T cells are identified by using a spectroscopy technique. In one specific embodiment, the spectroscopy technique is fluorescence.

In one embodiment, the fungus is either a dimorphic fungus or non-dimorphic fungus.

In one specific embodiment, the dimorphic fungus is selected from a group consisting of *Histoplasma, Coccidioides, Paracoccidioides, Penicillium, Blastomyces*, and *Sporothrix*.

In one embodiment, the fungus is selected from a group consisting of *Blastomyces dermatitidis, Histoplasma capsulatum, Aspergillus fumigatus, Fonsecea pedrosoi*, and *Geomyces destructans*.

In one aspect, the present invention discloses a composition to evaluate the immune status of a patient against a fungus, wherein the composition comprises peptide-MHCII tetramers.

In one embodiment, the peptide-MHCII tetramers comprise a calnexin peptide.

In one embodiment, the calnexin peptide comprises or consists of a sequence selected from a group consisting of SEQ ID NOs:1-5, 7-8, and 12.

In one embodiment, the composition additionally comprises at least one of a stabilizer, a buffer, or an adjuvant.

In one embodiment, the peptide-MHCII tetramers comprise at least one fluorescent label.

In one aspect, the present invention discloses a kit for evaluating the immune status of a patient against a fungus. The kit comprises (1) a container or formulation wherein the container or formulation comprises peptide-MHCII tetramers, (2) means for exposing peptide-MHCII tetramers to a sample of a patient, and (3) means for detecting helper T cells in the patient's sample, wherein the peptide-MHCII tetramers are binding to the helper T cells.

In one embodiment, the peptide-MHCII tetramers comprise a calnexin peptide.

In one embodiment, the calnexin peptide comprises or consists of a sequence selected from a group consisting of SEQ ID NOs:1-5, 7-8, and 12.

In one embodiment, the sample is a fresh blood sample.

In one embodiment, the peptide-MHCII tetramers are in the form of a powder.

In one embodiment, the peptide-MHCII tetramers are in a solution.

In one embodiment, the peptide-MHCII tetramers comprise at least one fluorescent label.

In one embodiment, the means of detection is a fluorescence technique.

In one embodiment, the fungus is selected from a group consisting of *Blastomyces dermatitidis, Histoplasma capsulatum, Aspergillus fumigatus, Fonsecea pedrosoi*, and *Geomyces destructans*.

In one embodiment, the help T cells are "endogenous" calnexin peptide #1 specific T cells.

In one embodiment, the means for delivering peptide-MHCII tetramers is selected from a group consisting of subcutaneous administration, intramuscular administration, transcutaneous administration, intradermal administration, intraperitoneal administration, intraocular administration, intranasal administration and intravenous administration.

BRIEF DESCRIPTION OF THE DRAWINGS

The patent or application file contains at least one drawing in color. Copies of this patent or patent application publication with color drawings will be provided by the Office upon request and payment of the necessary fee.

FIGS. 4A, 4B, and 4C are a set of graphs of experimental observations showing that Calnexin is present on the yeast surface.

FIG. 4A shows the western-blot of the water-soluble extract, which is part of a set of graphs of experimental observations showing that Calnexin is present on the yeast surface.

FIG. 4B shows surface staining of vaccine and challenge yeast, which is part of a set of graphs of experimental observations showing that Calnexin is present on the yeast surface FIG. 4C shows surface staining of vaccine and challenge yeast, which is part of a set of graphs of experimental observations showing that Calnexin is present on the yeast surface.

FIG. 5A graphs experimental observations showing response to Calnexin, specifically, mice received adoptive transfer of $10^6$ 1807 T cells before vaccination, and were challenged with $2 \times 10^4$ B. dermatitidis yeast. 4 d after infection, lungs were collected and 1807 T cells analyzed for cytokine products by FACS.

FIG. 5B graphs experimental observations showing response to Calnexin, specifically, mice received adoptive transfer of $10^6$ 1807 T cells before vaccination, and were challenged with $2 \times 10^4$ B. dermatitidis yeast. 4 d after infection of the lungs.

FIG. 6 is a set of graphs of Calnexin's protein sequence alignment among different strains, showing that Calnexin is highly conserved in dimorphic fungi. The deduced Calnexin protein sequences of B. dermatitidis strain 26199 (B.d. 26199 SEQ ID NO:12), H. capsulatum strain G217B (H.c. G217B SEQ ID NO:52), C. posadasii strain C735 (C.p. C735 SEQ ID NO:53) and P. brasiliensis strain PB01 (P.b. Pb01 SEQ ID NO:54) were aligned using ClustalW software. Regions of identity (in at least three of the four species) are indicated in grey and boxed with a black border. Two different MHC class II peptide-binding prediction algorithms were use to analyze the Calnexin sequence of B. dermatitidis and the highest-ranking predictions are indicated on the sequence (Methods). The IEDB (red) boxes represent the regions where multiple overlapping peptides have been predicted. The six regions predicted to bind with an $IC_{50}$ value less that 500 nM are labeled -A through-E, based on lowest to highest value. The Marc Jenkins algorithm predicts nine amino-acid MHCII-binding peptides. Ten predicted binding nanomers are shown, with two amino acids added to each end. These 13-mers were synthesized to test epitope-specific 1807 T-cell activation (see the Example and FIGS. 3A, 3B, and 3C). The peptides are labeled 1 through 10, based on the highest-to-lowest strength of the predicted binding.

FIGS. 7A, 7B, 7C, 7D, 7E, 7F, 7G and 7H are diagrams showing an analysis of the predicted peptides that are suitable to work with the known epitope binding domain of several Human HLA DRB1 alleles. The diagram is produced by using the publicly available ProPred software (imtech.res.in/raghava/propred). In the output, the Blastomyces Calnexin sequence (SEQ ID NO:12) is shown on a separate line for each of 51 DRB1 alleles, and peptides that are predicted to fit in the MHCII groove of that allele are indicated in blue, with red used to indicate a so-called anchor amino acid that would be at position one of the 9 amino acid core sequence. A peptide of interest is "promiscuous" if it is predicted to interact with many different human MHCII molecules. Since the human HLA locus is so polymorphic, a good vaccine for human's will have to have epitopes that are promiscuous, and can work with many different HLA MHC molecules in order to stimulate an immune response. The webarchive shows that Blastomyces Calnexin does, indeed, have several peptide sequences (blue) that are predicted to fit into the MHC groove for presentation to T-Cells. Of particular interest is that there is a predicted epitope for the sequence of Peptide 1 (calnexin peptide #1; which was predicted for B6 mouse HLA interaction, and has been experimentally shown to do so with 1807 cells) at position 103 to 115. There are several other promiscuous epitopes throughout the Calnexin sequence as predicted by the ProPred software.

FIG. 8 is a list showing the protein sequences of Blastomyces Calnexin of strains ATCC 18188 and ATCC 26199 (SEQ ID NO:12). The sequences are deduced from genomic sequences. (ncbi.nlm.nih.gov/protein/327357651; Protein database Accession number: EGE86508; Broad Institute predicted Gene name: BDDG_09453).

FIG. 9 is a diagram showing the comparison analysis of Calnexin among dimorphic fungi, e.g., Blastomyces, Histoplasma, Coccidioides and Paracoccidioides and other, more distantly related fungi, e.g., Aspergillus, Candida and Cryptococcus.

FIG. 10 is a diagram showing the formatted alignment and the comparison analysis of Calnexin among dimorphic fungi, e.g., Blastomyces (B.d. 26199 SEQ ID NO:12), Histoplasma (H.c. G186AR SEQ ID NO:56), Coccidioides (C.i. RS SEQ ID NO:55) and Paracoccidioides (P.b. Pb01 SEQ ID NO:54) and other, more distantly related fungi, e.g., Aspergillus (A. flavus SEQ ID NO:57), Candida (C.a. 5314 SEQ ID NO:58) and Cryptococcus (C. neoform. SEQ ID NO:59).

FIGS. 12A, 12B and 12C are a set of graphs showing vaccine-induced resistance mediated by calnexin. FIG. 12A. Mice were vaccinated s.c. thrice, 2 wks apart with $10^8$ glucan particles (GP) loaded with 10 g r-calnexin (Cnx) or mouse serum albumin (MSA) as a control. 2 wk after the last boost, mice were challenged with $2 \times 10^3$ B. dermatitidis 26199 yeast or 86 spores of C. posadasii strain C735. Lung and spleen (latter for C. posadasii infection) CFU were assessed 2 wk post-infection. Numbers indicate the fold difference in lung CFUs vs. controls. FIG. 12B. Mice were vaccinated s.c. with 25 μg r-calnexin or MSA mixed with 5 or 20% ADJUPLEX adjuvant. 2 wk after the last boost, mice were challenged with 2×10³ *B. dermatitidis* and lung CFU measured as in FIG. 12A. Numbers are the fold difference in lung CFUs vs. controls. FIG. 12C. IL-17 reporter mice were vaccinated thrice with 25 g of calnexin encapsulated in GMP and mixed with 5% ADJUPLEX adjuvant. The histogram shows the mean number of tetramerpositive cells from the bound and unbound fractions combined. Dot plots show the mean±SEM number of tetramer-positive and percent of IL-17+(eYFP+) CD4+ T cells among tetramer-positive and –negative cells from the bound fraction, enumerated by FACS. Dot plots represent an overlay of 10 samples/group.

FIG. 13B. Mice were vaccinated i.v. with 10-250 μg soluble calnexin peptide #1 and 5 μg LPS. 7 d after vaccination in panels A and B, the skin draining lymph nodes and spleen were harvested and the number and activation (CD44) of tetramer-positive T cells assessed. The dot plots represent concatenated samples for 3-4 mice (noted in parenthesis) per group. The numbers of tetramer+ CD4+ T cells per concatenated sample is indicated inside the dot plots. The mean±SEM of tetramer+ CD4+ T cells per mouse is indicated in the histogram (right). The number over a bar denotes the fold change of tetramer+ T cells vs. indicated control mice. FIG. 13C. To assess resistance after i.v. delivery of calnexin peptide, mice were vaccinated thrice with 10 μg soluble peptide #1 plus 5 μg LPS or GP loaded with 10 or 50 μg peptide #1 or MSA as a control. 2 wk after the last boost, mice were challenged with 2×10³ *B. dermatitidis* 26199 yeast. Lung CFU was assayed 2 wk post-infection. * and **, denote fold change vs. the GMP/MSA or naïve control groups, respectively. Dot plots show the mean±SEM number of tetramer+, activated (CD44+) and IL-17 differentiated cells (as determined by eYFP fluorescence with IL-17A fate-reporter mice) in the draining lymph nodes and spleen at the time of challenge, and recalled to the lung 4d post-infection, concatenated for 5 mice/group.

FIGS. 14A, 14B and 14C are a set of graphs showing naïve T cell precursor frequency and adjuvant formulation impact the pool size of calnexin primed T cells and resistance to infection. FIG. 14A. Mice received 10⁶ naïve 1807 cells prior to vaccination s.c. with 10⁸ glucan particles (GP) loaded with 10 g r-calnexin or MSA as a negative control. 2 wk after the last boost, mice were challenged with 2×10³ *B. dermatitidis* 26199 yeast and the number of activated (CD44+) and cytokine-producing 1807 cells determined by FACS. FIG. 14B. Mice received 10⁶ naïve 1807 cells before vaccination s.c. with 50 μg calnexin or MSA formulated in GMP or ADJUPLEX adjuvant or in GMP and ADJUPLEX adjuvant together. At d4 post-challenge, the number of CD44+, IL-17 and IFN-γ producing 1807 cells were determined by FACS. FIG. 14C. Mice received 10⁶ naïve 1807 cells and were vaccinated as in B. 2 wk after the last boost, mice were challenged with *B. dermatitidis* and lung CFU assayed 2 wk post-infection when unvaccinated controls were moribund. Numbers in bold are the fold-change vs. MSA vaccinated controls.

FIG. 16C: The response to calnexin was assayed in the presence and absence of polymyxin B to chelate LPS. All calnexin responses in immune subjects were retained in the presence of polymyxin B. FIG. 16D: CD4+ T cells of immune subjects responded to calnexin in a concentration-dependent manner and the frequency of activated cells, measured by expression of CD154, was similar for calnexin and another immunodominant Ag Hsp60.

FIG. 17A: Mice were monitored for survival after they were vaccinated twice with 10 g calnexin peptide #1 formulated with GMP, GMP plus LPS, CFA or adjuvant control or not and challenged with 2×10³ 26199 yeast. * p<0.05 vs. control groups. FIG. 17B: In parallel, 2 wks post-infection, lung CFU was quantified. Numbers shown denote fold change in CFU vs. control. * p<0.05 vs. control groups.

FIG. 18A: Mice were vaccinated thrice with calnexin (25 g) encapsulated in GMP and mixed with 5% ADJUPLEX adjuvant or with live yeast. 4 days after challenge, the number of tetramer-positive and CD44+CD4+ T-cells that migrated to the lung were enumerated by FACS. The frequency of calnexin peptide-specific T-cells among CD44+CD4+ T-cells that migrated to the lung was calculated by dividing the average number of tetramer-positive cells by the average number of CD44+CD4+ T-cells (after subtracting the background from GMP-MSA vaccinated mice). Dot plots represent an overlay of 8 samples per group. FIG. 18B: C57BL6 mice were vaccinated s.c. with 10 μg calnexin peptide #1 emulsified in CFA, 50 μg calnexin protein emulsified in CFA, CFA alone or not. 7 d later, skin draining lymph nodes and spleen were harvested and CD4+ T cells were tetramer enriched and analyzed for tetramer and chemokine receptor (CCR6 and CXCR3) expression. The number and frequency of chemokine receptor-positive, tetramer-positive CD4+ T cells are shown.

DETAILED DESCRIPTION OF THE INVENTION

Figure 1A:
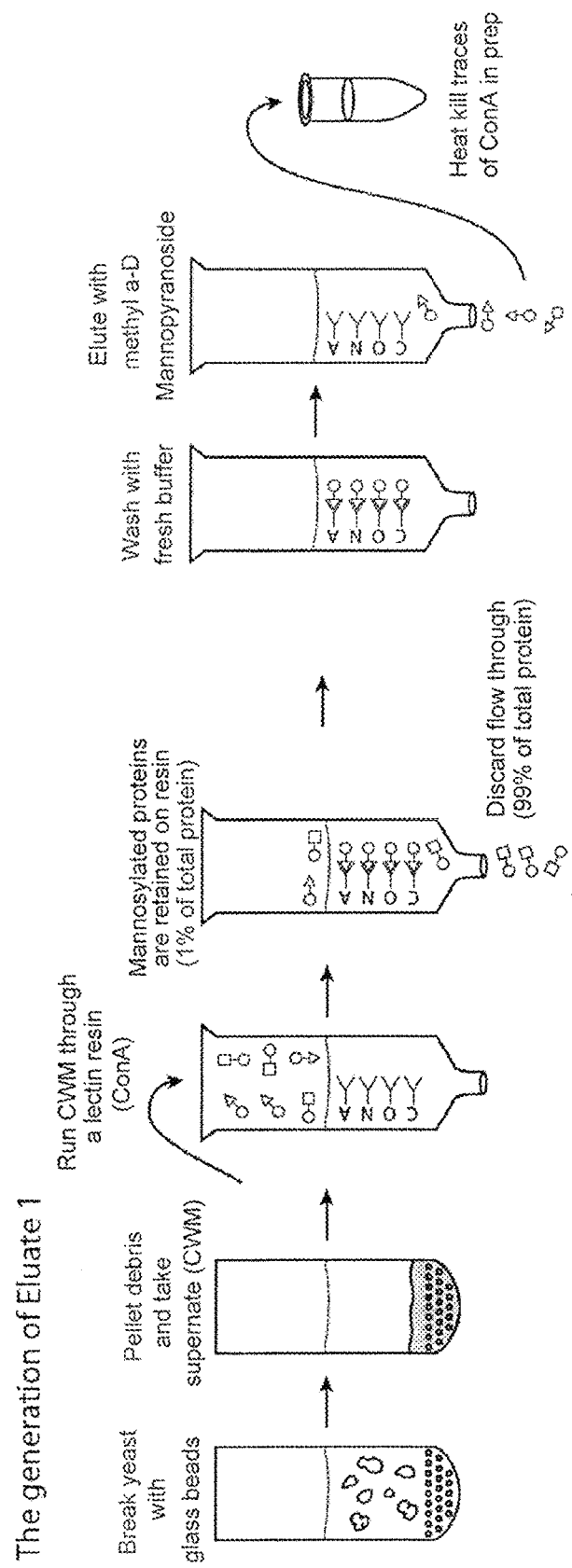
FIG. 1A is a graph showing identity of shared fungal antigen (Ag). Flow diagram that illustrates the generation of eluate #1 from the BAD1 vaccine strain #55.
Figure 1B:
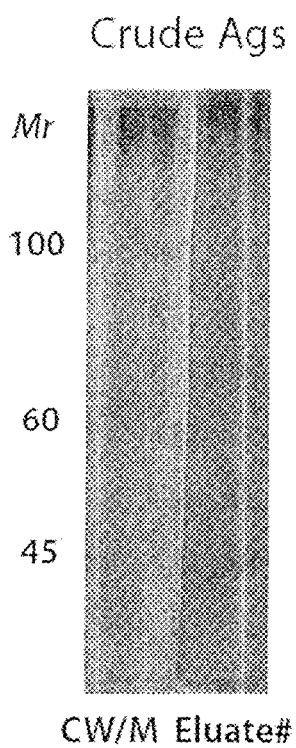
FIG. 1B Figure is a graph showing identity of shared fungal antigen (Ag). Silver nitrate stain of PAGE of *B. dermatitidis* Ags CW/M and Eluate #1 (left to right).

The use of the term "or" in the claims is used to mean "and/or" unless explicitly indicated to refer to alternatives only or the alternatives are mutually exclusive. It is specifically contemplated that any listing of items using the term "or" means that any of those listed items may also be specifically excluded from the related embodiment.

Throughout this application, the term "about" is used to indicate that a value includes the standard deviation of error for the device or method being employed to determine the value.

As used herein the specification, "a" or "an" may mean one or more, unless clearly indicated otherwise. As used herein in the claims, when used in conjunction with the word "comprising," the words "a" or "an" may mean one or more than one.

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has" or "includes" one or more steps is not limited to possessing only those one or more steps and also covers other unlisted steps.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. For example, any method discussed herein may employ any nanoparticle described herein.

The terms "polypeptide," "peptide," and "protein," as used herein, refer to a polymer comprising amino acid residues predominantly bound together by covalent amide bonds. By the term "protein," we mean to encompass all the above definitions. The terms apply to amino acid polymers in which one or more amino acid residue may be an artificial chemical mimetic of a naturally occurring amino acid, as well as to naturally occurring amino acid polymers and non-naturally occurring amino acid polymers. As used herein, the terms may encompass amino acid chains of any length, including full length proteins, wherein the amino acids are linked by covalent peptide bonds. The protein or peptide may be isolated from a native organism, produced by recombinant techniques, or produced by synthetic production techniques known to one skilled in the art.

The term "lyophilization," as used herein, refers to freezing of a material at low temperature followed by dehydration by sublimation, usually under a high vacuum. Lyophilization is also known as freeze drying. Many techniques of freezing are known in the art of lyophilization such as tray-freezing, shelf-freezing, spray-freezing, shell-freezing and liquid nitrogen immersion. Each technique will result in a different rate of freezing. Shell-freezing may be automated or manual. For example, flasks can be automatically rotated by motor driven rollers in a refrigerated bath containing alcohol, acetone, liquid nitrogen, or any other appropriate fluid. A thin coating of product is evenly frozen around the inside "shell" of a flask, permitting a greater volume of material to be safely processed during each freeze drying run. Tray-freezing may be performed by, for example, placing the samples in lyophilizer, equilibrating 1 hr at a shelf temperature of 0° C., then cooling the shelves at 0.5° C./min to −40° C. Spray-freezing, for example, may be performed by spray-freezing into liquid, dropping by ~20 µl droplets into liquid $N_2$, spray-freezing into vapor over liquid, or by other techniques known in the art.

The term "antibody," as used herein, refers to a class of proteins that are generally known as immunoglobulins. The term "antibody" herein is used in the broadest sense and specifically includes full-length monoclonal antibodies, polyclonal antibodies, multispecific antibodies (e.g., bispecific antibodies), and antibody fragments, so long as they exhibit the desired biological activity. Various techniques relevant to the production of antibodies are provided in, e.g., Harlow, et al., ANTIBODIES: A LABORATORY MANUAL, Cold Spring Harbor Laboratory Press, Cold Spring Harbor, N.Y., (1988).

The term "fusion protein," as used herein, refers to a hybrid polypeptide which comprises protein domains from at least two different proteins. Fusion proteins or chimeric proteins (literally, made of parts from different sources) are proteins created through the joining of two or more genes that originally coded for separate proteins. Translation of this fusion gene results in a single or multiple polypeptides with functional properties derived from each of the original proteins. Recombinant fusion proteins are created artificially by recombinant DNA technology for use in biological research or therapeutics. Chimeric or chimera usually designate hybrid proteins made of polypeptides having different functions or physico-chemical patterns. Chimeric mutant proteins occur naturally when a complex mutation, such as a chromosomal translocation, tandem duplication, or retrotransposition creates a novel coding sequence containing parts of the coding sequences from two different genes. Naturally occurring fusion proteins are commonly found in cancer cells, where they may function as oncoproteins. In one embodiment of the present invention, fusion proteins comprise at least one engineered intein.

The term "recombinant protein," as used herein, refers to a polypeptide of the present disclosure which is produced by recombinant DNA techniques, wherein generally, DNA encoding a polypeptide is inserted into a suitable expression vector which is in turn used to transform a heterologous host cell (e.g., a microorganism or yeast cell) to produce the heterologous protein.

The term "recombinant nucleic acid" or "recombinant DNA," as used herein, refers to a nucleic acid or DNA of the present disclosure which is produced by recombinant DNA techniques, wherein generally, DNA encoding a polypeptide is inserted into a suitable expression vector which is in turn used to transform a host cell to produce the heterologous protein.

The term "binding peptide," as used herein, refers to peptides that bind MHCII molecules to form pMHCII tetramers. In one embodiment, the binding peptides are calnexin peptides, preferably calnexin peptide #1, that is, residues 103-115 of the calnexin protein; SEQ ID NOs:1-11.

As used herein, the term "patient" refers to a human or non-human mammalian patient in need of vaccination. The vaccines of the present invention may be intended for use by any species, including, for example, human, feline, canine, equine, porcine, bovine, ovine. Preferably, the vaccines of the present invention may be intended for use by human.

The term "fungi" or "funguses", as used herein, refers to a member of a large group of eukaryotic organisms that may include microorganisms, e.g., yeasts and molds. These organisms may be classified as a kingdom of fungi, which is separate from plants, animals, and bacteria. One major difference between fungi and the others is that fungal cells have cell walls that contain chitin, unlike the cell walls of plants, which contain cellulose.

These and other differences show that the fungi form a single group of related organisms, named the Eumycota (true fungi or Eumycetes), that share a common ancestor (a monophyletic group). This fungal group may be distinct from the structurally similar myxomycetes (slime molds) and oomycetes (water molds). Genetic studies have shown that fungi are more closely related to animals than to plants. In the present invention, the terms "fungi", "funguses", or "fungal" may refer to fungi which may cause infection in humans and animals.

In the embodiments of the present invention, fungi may include dimorphic fungi and non-dimorphic fungi.

The term "dimorphic fungi", as used herein, refers to fungi which may exist as mold/hyphal/filamentous form or as yeast. An example is *Penicillium marneffei*. At room temperature, it may grow as a mold. At body temperature, it may grow as a yeast. The exception to these conditions are *Candida* spp. *Candida* grows as a mold at body temperatures and as a yeast at room temperatures. Several species of dimorphic fungi may be potential pathogens, including *Coccidioides immitis, Paracoccidioides brasiliensis, Candida albicans, Ustilago maydis, Blastomyces dermatitidis, Histoplasma capsulatum*, and *Sporothrix schenckii*.

The term "Calnexin", as used herein, refers to a 67 kDa integral protein of the endoplasmic reticulum (ER) (Williams D. B., 2006; Myhill N., Lynes E. M., et al., 2008).

Calnexin may appear variously as a 90 kDa, 80 kDa or 75 kDa band on western blotting depending on the source of the antibody. Calnexin may consist of a large (50 kDa)N-terminal calcium-binding lumenal domain, a single transmembrane helix and a short (90 residues), acidic cytoplasmic tail. Calnexin may be one of the chaperone molecules, which may be characterized by their main function of assisting protein folding and quality control, ensuring that only properly folded and assembled proteins proceed further along the secretory pathway.

The function of Calnexin may include retaining unfolded or unassembled N-linked glycoproteins in the ER. Antibodies against Calnexin may be used as markers for the ER in immmunofluorescence experiments. Calnexin may bind only those N-glycoproteins that have GlcNAc2Man9Glc1 oligosaccharides. Oligosaccharides with three sequential glucose residues may be added to asparagine residues of the nascent proteins in the ER. The monoglucosylated oligosaccharides that are recognized by Calnexin result from the trimming of two glucose residues by the sequential action of two glucosidases, I and II. Glucosidase II may also remove the third and last glucose residue. ATP and calcium ions may be two of the cofactors involved in substrate binding for Calnexin.

Calnexin may also function as a chaperone for the folding of MHC class I alpha chain in the membrane of the ER. After folding is completed Calnexin is replaced by calreticulin, which assists in further assembly of MHC class I.

The term "Calnexin fragment" as used herein, refers to at least one portion or domain of the full-length version of wild-type Calnexin, or at least one portion or domain of the modified version or recombinant Calnexin. A Calnexin fragment may retain at least 90% activity of the wild-type version of Calnexin. A preferable fragment is at least 13 amino acids.

The term "Calnexin peptide," as used herein, refers to a peptide directly from calnexin or a peptide which has an amino acid sequence substantially identical to part of the calnexin protein sequence.

In one embodiment of the present invention, certain calnexin peptides are the primary places for calnexin to bind with MHCII molecules. FIG. 6 and the Example show calnexin peptides #1-#10 (Peptides 1-10) are predicted binding sequences from calnexin.

The term "substantially identical," as used herein, refers to a peptide having a sequence identity of at least 80%, at least 85%, at least 90%, preferably at least 92%, more preferably at least 94%, even more preferably at least 96%, even more preferably at least 98%, and even more preferably 99% or 100% to a natural peptide from calnexin.

The term "functionally equivalent," as used herein, refers to a Calnexin fragment or a modified version of wild-type Calnexin that retains at least 90% activity of the wild-type version of Calnexin. In one embodiment, one may wish to use only selected domains of the native Calnexin protein.

The term "activity," as used herein, refers to antigenic reactivity of Calnexin fragments against fungi, as demonstrated below in the examples.

As used herein, an "antigenic peptide" is a peptide presented on an MHC II complex that is recognized by a T cell. As used herein, a "peptide" refers to two or more amino acids joined together by an amide bond. In certain embodiments, peptides comprise up to or include 50 amino acids. In certain embodiments, a peptide, such as an antigenic peptide, is at most or at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length, or any range derivable therein. In certain embodiments, the amino acid is at least 13 amino acids in length. As used herein, an "amino acid" refers to any of the 20 naturally occurring amino acids found in proteins. In one preferred embodiment, the antigenic peptide in the present invention is calnexin peptide, more preferably calnexin peptide #1, that is, residues 103-115 of the calnexin protein; SEQ ID NOs: 1-5, 7-8, and 12.

The term "therapeutically effective amount," as used herein, refers to an amount of an antigen or vaccine that would induce an immune response in a subject receiving the antigen or vaccine which is adequate to prevent signs or symptoms of disease, including adverse health effects or complications thereof, caused by infection with a pathogen, such as a virus or a bacterium. Humoral immunity or cell mediated immunity or both humoral and cell mediated immunity may be induced. The immunogenic response of an animal to a vaccine may be evaluated, e.g., indirectly through measurement of antibody titers, lymphocyte proliferation assays, or directly through monitoring signs and symptoms after challenge with wild-type strain. The protective immunity conferred by a vaccine may be evaluated by measuring, e.g., reduction in clinical signs such as mortality, morbidity, temperature number, overall physical condition, and overall health and performance of the subject. The amount of a vaccine that is therapeutically effective may vary depending on the particular virus used, or the condition of the subject, and may be determined by a physician.

The term "protected," as used herein, refers to immunization of a patient against a disease. The immunization may be caused by administering a vaccine comprising an antigen.

Specifically, in the present invention, the immunized patient is protected from fungal infection.

The term "vaccine," as used herein, refers to a composition that includes an antigen, as defined herein. Vaccine may also include a biological preparation that improves immunity to a particular disease. A vaccine may typically contain an agent that resembles a disease-causing microorganism, and the agent may often be made from weakened or killed forms of the microbe, its toxins or one of its surface proteins. The agent may stimulate the body's immune system to recognize the agent as foreign, destroy it, and "remember" it, so that the immune system can more easily recognize and destroy any of these microorganisms that it later encounters. Vaccines may be prophylactic, e.g., to prevent or ameliorate the effects of a future infection by any natural or "wild" pathogen, or therapeutic, e.g., to treat the disease. Administration of the vaccine to a subject results in an immune response, generally against one or more specific diseases. The amount of a vaccine that is therapeutically effective may vary depending on the particular virus used, or the condition of the patient, and may be determined by a physician. The vaccine may be introduced directly into the subject by the subcutaneous, oral, oronasal, or intranasal routes of administration.

The term "administration," as used herein, refers to the introduction of a substance, such as a vaccine, into a subject's body through or by way of a route that does not include the digestive tract. The administration, e.g., parenteral administration, may include subcutaneous administration, intramuscular administration, transcutaneous administration, intradermal administration, intraperitoneal administration, intraocular administration, intranasal administration and intravenous administration.

The vaccine or the composition according to the invention may be administered to an individual according to methods known in the art. Such methods comprise application e.g. parenterally, such as through all routes of injection into or through the skin: e.g. intramuscular, intravenous, intraperitoneal, intradermal, mucosal, submucosal, or subcutaneous. Also, the vaccine may be applied by topical application as a drop, spray, gel or ointment to the mucosal epithelium of the eye, nose, mouth, anus, or vagina, or onto the epidermis of the outer skin at any part of the body. Other possible routes of application are by spray, aerosol, or powder application through inhalation via the respiratory tract. In this last case the particle size that is used will determine how deep the particles will penetrate into the respiratory tract. Alternatively, application may be via the alimentary route, by combining with the food, feed or drinking water e.g. as a powder, a liquid, or tablet, or by administration directly into the mouth as a: liquid, a gel, a tablet, or a capsule, or to the anus as a suppository. The term "animal-based protein", as used herein, refers to proteins that are sourced from ruminant milk, and other sources, for example the muscle meat, of an animal, particularly a mammal. Suitable animal-based proteins may include, but are not limited to, digested protein extracts such as N—Z-Amine®, N—Z-Amine AS® and N—Z-Amine YT® (Sheffield Products Co., Norwich, N.Y.), which are casein enzymatic hydrolysates of bovine milk.

The term "vegetable-based protein," as used herein, refers to proteins from vegetables. A vegetable-based protein may include, without limitation, soy protein, wheat protein, corn gluten, rice protein and hemp protein, among others. Preferred vegetable based proteins in the present invention are soy proteins and corn gluten. Corn gluten is a mixture of various corn-derived proteins. The soy proteins can include 100% soy protein (available as VegeFuel® by Twinlab), textured soy protein, and soybean enzymatic digest. Textured soy protein is a soy protein that is made from defatted soy flour that is compressed and processed into granules or chunks. Soybean enzymatic digest describes soybean peptones that result from the partial hydrolysis of soybean proteins.

As used herein, the term "major histocompatibility complex" or "MHC" refers to a set of cell surface molecules encoded by a large gene family in all vertebrates. MHC molecules may mediate interactions of leukocytes, also called white blood cells (WBCs), which are immune cells, with other leukocytes or body cells. MHC determines compatibility of donors for organ transplant as well as one's susceptibility to an autoimmune disease via cross-reacting immunization. In humans, MHC is also called human leukocyte antigen (HLA).

Protein molecules-either of the host's own phenotype or of other biologic entities—are continually synthesized and degraded in a cell. Occurring on the cell surface, each MHC molecule displays a molecular fraction, called epitope, of a protein. The presented antigen can be either self or nonself.

The MHC gene family may be divided into three subgroups: class I, class II and class III. Diversity of antigen presentation, mediated by MHC classes I and II, may be attained in at least three ways: (1) an organism's MHC repertoire is polygenic (via multiple, interacting genes); (2) MHC expression is codominant (from both sets of inherited alleles); (3) MHC gene variants are highly polymorphic (diversely varying from organism to organism within a species).

Of the three MHC classes identified, human attention commonly focuses on classes I and II. By interacting with CD4 molecules on surfaces of helper T cells, MHC class II mediates establishment of specific immunity (also called acquired immunity or adaptive immunity).

As used herein, the term "peptide-MHCII tetramers" or "pMHCII tetramers" refers to molecule complexes of peptides with MHCII molecules, each of which includes four peptides and four MHCII molecules. The pMHC tetramers may bind multiple MHCs at a time to a T-cell (ideally, 3 of the 4 MHCs would bind) and so increase the binding avidity and circumvent the problem of dissociation.

In one embodiment, the binding peptides are calnexin peptides, preferably calnexin peptides #1-10 as shown in FIG. 6. In one more preferred embodiment, the binding peptides are calnexin peptides #1. Table 1 shows exemplary amino acid sequences of calnexin peptide #1.

The pMHCII tetramers may also comprise a streptavidin complex. Streptavidin is a molecule that forms homotetramer complexes, with each monomer having an unusually high affinity for biotin. One may bioengineer *E. Coli* to produce soluble MHCII molecules with a biotinylation protein domain, meaning a part of the MHCII can be replaced by covalently bound biotin (via BirA enzyme activity). The MHCII molecules may then be mixed with the antigenic peptide of interest, forming peptide-MHCII (pMHCII) complexes. The biotinylated domain may allow for up to 4 pMHCIIs to bind to a fluorescently tagged streptavidin complex with high affinity. The resulting pMHCII-streptavidin-fluorophore tetramer may be added to a sample of cells. The pMHCII tetramers bind to T-cells that are specific for both the MHC type and peptide being used in the tetramer.

Once the tetramers are bound, T-cells are often stained with other fluorophores and the sample may be washed to remove non-bound tetramers and ligands. The stained sample is then run through a flow cytometer for detection and sorting. In one embodiment, the fluorophore on any bound tetramers may be excited to give a signal, indicating that the tetramer is bound to a T-cell, and thus that the bound T-cell is specific for the peptide antigen of interest. Ultimately, a signal means that there exists some cell-mediated immune response to the pathogen from which the antigenic peptide is derived, and the strength of the signal gives the strength of the immune response.

The term "immune status" or "immunocompetence," as used herein, refers to the ability of the body to produce a normal immune response following exposure to an antigen. Immunocompetence is the opposite of immunodeficiency or immuno-incompetent or immuno-compromised.

The present invention is generally applied to humans. In certain embodiments, non-human mammals, such as rats, may also be used for the purpose of demonstration. One may use the present invention for veterinary purpose. For example, one may wish to treat commercially important farm animals, such as cows, horses, pigs, rabbits, goats, and sheep. One may also wish to treat companion animals, such as cats and dogs.

Vaccines of the Present Invention

In one embodiment, the present invention relates to a vaccine against fungi comprising a Calnexin fragment. In one embodiment, the vaccine comprising a Calnexin fragment may be applicable to any fungi. In another embodiment, the vaccine comprising a Calnexin fragment may be applicable to any dimorphic fungi. In another embodiment, the vaccine comprising a Calnexin fragment may be applicable to a dimorphic fungus selected from a group consisting of *Histoplasma, Coccidiodes, Paracoccidioides, Penicillium, Blastomyces*, and *Sporothrix*.

In another embodiment, the vaccine comprising a Calnexin fragment may be applicable to any non-dimorphic fungi. In another embodiment, the vaccine comprising a Calnexin fragment may be applicable to a non-dimorphic fungus selected from a group consisting of *Aspergillus, Pneumocystis, Magnaportha, Exophiala, Neuroaspora, Cryptococcus, Schizophyllum*, and *Candida*.

In one embodiment of the present invention, the Calnexin fragment is part of a full-length native version or a functionally equivalent version of full-length Calnexin. The Calnexin fragment may be produced and isolated from any fungi, e.g., those as discussed above and below. In one specific embodiment, the Calnexin fragment may be produced from any dimorphic fungi, e.g., those as discussed above. In yet another embodiment, the Calnexin fragment may be produce and isolated from any non-dimorphic fungi, e.g., those as discussed above. Further, the Calnexin fragment may also be produced from any other non-fungi sources. For example, the Calnexin fragment may be produced from bacteria and the as-produced Calnexin fragment may not be glycosylated. Thus, the as-produced Calnexin fragment may need to be glycosylated before it can be used as a vaccine.

In one specific embodiment, the Calnexin fragment of the present invention comprises or consists of the 13 amino acid sequence LVVKNPAAHHAIS (SEQ ID NO:1). Table 1 shows a comparison of a Calnexin fragment of Calnexin peptide #1, the 13 amino acid sequence among fungi species and *Homo sapiens* (Calmegin). As shown in Table 1, to be a suitable vaccine, the Calnexin fragment, comprising the completely conserved 13 amino acid sequence LVVKNPAAHHAIS (SEQ ID NO:1), may be produced from fungi species. The Calnexin fragment, comprising the completely conserved 13 amino acid sequence LVVKNPAAHHAIS (SEQ ID NO:1), may be produced from *Blastomyces dermatitidis* of strains 26199, 18808, Er-3, 14081; *Histoplasma capsulatum* of strains G186AR, Nam1, H88, and H143, *Aspergillus* sp.1 of strains group.1, *A. flavus*, and group.1, *A. oryzae, A. terreus*, and *Magnaporthe oryzae*_70-15. In another preferred embodiment, the Calnexin fragment of the present invention comprises one or more of peptide 2 (calnexin peptide #2), peptide 3 (calnexin peptide #3), peptide 4 (calnexin peptide #4), peptide 5 (calnexin peptide #5), peptide 6 (calnexin peptide #6), peptide 7 (calnexin peptide #7), peptide 8 (calnexin peptide #8), peptide 9 (calnexin peptide #9), and peptide 10 (calnexin peptide #10) as shown in FIG. 6. In another embodiment, the Calnexin fragment of the present invention consists of peptide 2 (calnexin peptide #2), peptide 3 (calnexin peptide #3), peptide 4 (calnexin peptide #4), peptide 5 (calnexin peptide #5), peptide 6 (calnexin peptide #6), peptide 7 (calnexin peptide #7), peptide 8 (calnexin peptide #7), peptide 9 (calnexin peptide #9), and peptide 10 (calnexin peptide #10) as shown in FIG. 6.

TABLE 1

| Calnexin peptide #1, 13 amino acid sequence | | | | | | | | | | | | | | |
|---|---|---|---|---|---|---|---|---|---|---|---|---|---|---|
| Genus species_strain | | | | | | | | | | | | | | 1807 reactive |
| *Blastomyces dermatitidis* (SEQ ID NO: 1)[a] | L | V | V | K | N | P | A | A | H | H | A | I | S | + |
| *Histoplasma capsulatum* (SEQ ID NO: 1)[b] | – | – | – | – | – | – | – | – | – | – | – | – | – | + |
| *Paracoccidioides brasiliensis* Pb18 (SEQ ID NO: 2) | – | – | I | – | – | A | – | – | – | – | – | – | – | |
| *Paracoccidioides lutzii* _ Pb01 (SEQ ID NO: 2) | – | – | I | – | – | A | – | – | – | – | – | – | – | + |
| *Coccidioides immitis.*_RS (SEQ ID NO: 3) | – | – | – | – | – | A | – | – | – | – | – | – | – | |
| *Coccidioides posadasii* (SEQ ID NO: 3)[c] | – | – | – | – | – | A | – | – | – | – | – | – | – | + |
| *Penicillium marneffei* (SEQ ID NO: 4) | | – | L | – | – | – | – | – | – | – | – | – | – | |

TABLE 1-continued Calnexin peptide #1, 13 amino acid sequence

| Genus species_strain | 1 | 2 | 3 | 4 | 5 | 6 | 7 | 8 | 9 | 10 | 11 | 12 | 13 | 1807 reactive |
|---|---|---|---|---|---|---|---|---|---|---|---|---|---|---|
| Penicillium chrysogenum (SEQ ID NO: 3) | - | - | - | - | - | A | - | - | - | - | - | - | - | |
| Aspergillus sp. 1. (SEQ ID NO: 1)[d] | - | - | - | - | - | - | - | - | - | - | - | - | - | |
| Aspergillus sp. 2 (SEQ ID NO: 5)[e] | - | - | - | - | - | V | - | - | - | - | - | - | - | + |
| Pneumocystis carinii_Rat Form 1 (SEQ ID NO: 6) | - | - | L | - | - | E | - | - | - | - | - | - | - | - |
| Magnaporthe oryzae_70-15 (SEQ ID NO: 1) | - | - | - | - | - | - | - | - | - | - | - | - | - | |
| Exophiala dermatitidis_NIH/UT8656 (SEQ ID NO: 3) | - | - | - | - | - | A | - | - | - | - | - | - | - | |
| Neurospora crassa_OR74A (SEQ ID NO: 3) | - | - | - | - | - | A | - | - | - | - | - | - | - | |
| Cryptococcus neoformans (SEQ ID NO: 7) | - | - | L | - | T | K | - | - | - | - | - | - | - | |
| Schizophyllum commune_H4-8 (SEQ ID NO: 8) | - | - | A | - | T | K | - | - | - | - | - | - | - | |
| Candida albicans_5314 (SEQ ID NO: 9) | - | - | M | - | S | R | - | S | - | Y | - | - | - | - |
| Homo sapiens (Calmegin) (SEQ ID NO: 10) | - | - | L | - | S | R | - | K | - | - | - | - | - | |
| Homo sapiens (Calnexin) (SEQ ID NO: 11) | - | - | L | M | S | R | - | K | - | - | - | - | - | |
| Geomyces destructans (SEQ ID NO: 3)[f] | - | - | - | - | - | A | - | - | - | - | - | - | - | |

[a]*B. dermatitidis* strains: 26199, 18808, Er-3, 14081
[b]*H capsulatum* strains: G186AR, Nam1, H88, H143
[c]*C. posadasii* strains: C35 Δ SOWgp, Silveira
[d]*Aspergillus* species group. 1: *A. flavus, A, oryzae, A. terreus*
[e]*Aspergillus* species group 2: *A. nidulans, A. kawachii, A. niger, A. fumagatus* 293, *A. clavatus*
[f]*Geomyces destructans* now called *Pseudogymnoascus destructans*

In another embodiment of the present invention, a suitable Calnexin fragment, comprising 13 amino acid sequence of LVVKNPAAHHAIS (SEQ ID NO:1), may have at least one modified amino acid sequence among the 13 amino acid sequence. In one specific embodiment, the suitable Calnexin fragment may comprise LVVKNAAAHHAIS from *Coccidioides immitis*. RS (SEQ ID NO: 3). In another specific embodiment, the suitable Calnexin fragment may comprise LVVKNAAAHHAIS (SEQ ID NO:3) from *Coccidioides posadasii* of strains C35 Δ SOWgp and Silveira. In another specific embodiment, the suitable Calnexin fragment may comprise LVLKNPAAHHAIS from *Penicillium marneffei* (SEQ ID NO: 4). In another specific embodiment, the suitable Calnexin fragment may comprise LVVKNAAAHHAIS from *Penicillium chrysogenum* (SEQ ID NO: 3). In yet another specific embodiment, the suitable Calnexin fragment may comprise LVVKNVAAHHAIS (SEQ ID NO:5) from *Aspergillus* sp.2 of strains group.2, *A. nidulans*, group.2, *A. kawachii*, group.2, *A. niger*, group.2, *A. fumagatus* 293, or group.2, *A. clavatus*. In yet another specific embodiment, the suitable Calnexin fragment may comprise LVVKNAAAHHAIS from *Exophiala dermatitidis* NIH UT8656 (SEQ ID NO: 3). In yet another specific embodiment, the suitable Calnexin fragment may comprise LVVKNAAAHHAIS from *Neuroaspora crassa*_OR74A (SEQ ID NO: 3). In another embodiment, the suitable Calnexin fragment may comprise LVVKNAAAHHAIS from *Geomyces destructans*, which are now called *Pseudogymnoascus destructans* (SEQ ID NO: 3).

In another embodiment of the present invention, a suitable Calnexin fragment, comprising the 13 amino acid sequence of LVVKNPAAHHAIS (SEQ ID NO:1), may have at least two changed amino acid sequences among the 13 amino acid sequence. In one specific embodiment, the suitable Calnexin fragment may comprise LVIKNAAAHHAIS from *Paracoccidioides brasiliensis*_Pb18 (SEQ ID NO: 2). In another specific embodiment, the suitable Calnexin fragment may comprise LVIKNAAAHHAIS from *Paracoccidioides lutzii* Pb01 (SEQ ID NO: 2). Applicants found that the Calnexin fragment comprising the 13 amino acid sequence of LVLKNEAAHHAIS (SEQ ID NO: 6) from *Pneumocystis carinii* was not reactive.

In another embodiment of the present invention, a suitable Calnexin fragment, comprising the 13 amino acid sequence of LVVKNPAAHHAIS (SEQ ID NO:1), may have at least three changed amino acid sequences among the 13 amino acid sequence. In one specific embodiment, the suitable Calnexin fragment may comprise LVLKTKAAHHAIS from *Cryptococcus neoformans* (SEQ ID NO: 7). In another specific embodiment, the suitable Calnexin fragment may comprise LVAKTKAAHHAIS from *Schizophyllum commune* H4-8 (SEQ ID NO: 8).

In another embodiment of the present invention, a suitable Calnexin fragment, comprising 13 amino acid sequence of LVVKNPAAHHAIS (SEQ ID NO:1), may have more than three changed amino acid sequences among the 13 amino acid sequence.

In one preferred embodiment, a suitable Calnexin fragment may comprise a sequence selected from the group consisting of SEQ ID NOs: 1-2, 3, and 5.

In another preferred embodiment, a suitable Calnexin fragment may comprise a sequence selected from the group consisting of SEQ ID NOs: 1, 2, 3, and 7.

In one embodiment, Applicants found or envisioned that the Calnexin fragment comprising LVLKNEAAHHAIS (SEQ ID NO: 6) from *Pneumocystis* carinii_Rat Form 1, the Calnexin fragment comprising LVMKSRASHYAIS (SEQ ID NO: 9) from *Candida* albicans_5314, and the Calnexin fragment comprising LVLKSRAKHHAIS (SEQ ID NO: 10) from *Homo sapiens* (Calmegin) were not reactive with the 1807 cells. Thus, the Calnexin fragments from these species may not be suitable for a vaccine of the present invention.

In another embodiment, a suitable Calnexin fragment in the vaccine of the present invention may comprise a full-length native version of a Calnexin. In one specific embodiment, the full length native version of a Calnexin may comprise a sequence from *Blastomyces dermatitidis* of strains 26199 (SEQ ID NO: 12) or 18188 (SEQ ID NO: 12). In another embodiment, a suitable Calnexin fragment in the vaccine of the present invention may comprise a functionally equivalent version of full-length wild-type Calnexin.

Applicants envision that many peptide sequences of Calnexin fragments would be suitable vaccines for human in the present invention. FIGS. 7A, 7B, 7C, 7D, 7E, 7F, 7G and 7H show predicted peptide sequences of Calnexin fragments for 51 Human HLA DRB1 alleles, where the predicted peptide sequences of Calnexin fragments would fit in the known epitope binding domain of all the 51 Human HLA DRB1 alleles. In one embodiment, a suitable Calnexin fragment for human vaccination may comprise a sequence selected from a group consisting of each of the 51 amino acid sequences shown in Figures FIGS. 7A, 7B, 7C, 7D, 7E, 7F, 7G and 7H. In another embodiment, a suitable Calnexin fragment for human vaccination may comprise a sequence selected from a group consisting of each of the 51 amino acid sequences at least having the highlighted amino acid sequences as shown in Figures FIGS. 7A, 7B, 7C, 7D, 7E, 7F, 7G and 7H.

In one embodiment, a suitable calnexin fragment for human vaccination may comprise a sequence selected from a group consisting of at least one of the highlighted amino acid sequences as shown in Figures FIGS. 7A, 7B, 7C, 7D, 7E, 7F, 7G and 7H. In one embodiment, a suitable calnexin fragment for human vaccination may comprise a sequence selected from a group consisting of at least two of the highlighted amino acid sequences as shown in FIG. 7 FIGS. 7A, 7B, 7C, 7D, 7E, 7F, 7G and 7H. Applicants envision that the amino acid sequences highlighted in blue color can likely bind (based on motifs) to human HLA class II molecules and thus may be antigens for stimulating human CD4 T cells and eliciting calnexin antigen-dependent cellular immunity to fungi. In one embodiment, the suitable calnexin fragment may comprise or consist of a sequence selected from a group consisting of the sequences presented in Figures FIGS. 7A, 7B, 7C, 7D, 7E, 7F, 7G and 7H. Specifically, the group may consist of those sequences highlighted in Figures FIGS. 7A, 7B, 7C, 7D, 7E, 7F, 7G and 7H.

In another embodiment, the present invention relates to a method of vaccination for protecting a patient from fungal infections. The method of vaccination in the present invention may generally be applicable to any fungi comprising any dimorphic or non-dimorphic fungi. In a preferred embodiment, the method of vaccination may be used to protect a patient from the infections of dimorphic fungi. In one specific embodiment, the method of vaccination may be applicable to a dimorphic fungus selected from a group consisting of *Histoplasma, Coccidiodes, Paracoccidioides, Penicillium, Blastomyces*, and *Sporothrix*. In another embodiment, the method of vaccination may be applicable to a non-dimorphic fungus selected from a group consisting of *Aspergillus, Pneumocystis, Magnaportha, Exophiala, Neuroaspora, Cryptococcus, Schizophyllum*, and *Candida*.

A Calnexin fragment suitable for a vaccine in the present invention may be in any form as discussed above. In one embodiment, a vaccine of a Calnexin fragment may be expressed in commercially available sources, e.g., *E. coli*. The vaccine of a Calnexin fragment may be then isolated and purified from the sources. The protein expression, isolation, and purifications are well know to a person having ordinary skill in the art. The Example demonstrated methods of expression, isolation, and purifications of a Calnexin fragment according to one embodiment of the present invention.

A vaccine comprising a Calnexin fragment may also comprise other suitable ingredients. In one embodiment, a vaccine may also comprise a carrier molecule as a stabilizer component. As the types of vaccines enclosed in the present invention may be rapidly degraded once injected into the body, the vaccine may be bound to a carrier molecule for stabilizing the vaccine during delivery and administration. A suitable carrier or stabilizer may comprise fusion proteins, polymers, liposome, micro or nanoparticles, or any other pharmaceutically acceptable carriers. A suitable carrier or stabilizer molecule may comprise a tertiary amine N-oxide, e.g., trimethylamine-N-oxide, a sugar, e.g., trehalose, a poly(ethylene glycol) (PEG), an animal-based protein, e.g., digested protein extracts such as N—Z-Amine®, N—Z-Amine AS® and N—Z-Amine YT® (Sheffield Products Co., Norwich, N.Y.), a vegetable-based protein, e.g., soy protein, wheat protein, corn gluten, rice protein and hemp protein, and any other suitable carrier molecules.

Suitable Carrier Or Vehicle

Suitable agents may include a suitable carrier or vehicle for delivery. As used herein, the term "carrier" refers to a pharmaceutically acceptable solid or liquid filler, diluent or encapsulating material. A water-containing liquid carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. A tabulation of ingredients listed by the above categories, may be found in the *U.S. Pharmacopeia National Formulary*, 1857-1859, (1990).

Some examples of the materials which can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen free water; isotonic saline; Ringer's solution, ethyl alcohol and phosphate buffer solutions, as well as other non toxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents, preservatives and antioxidants can also be present in the compositions, according to the desires of the formulator.

Examples of pharmaceutically acceptable antioxidants include water soluble antioxidants such as ascorbic acid, cysteine hydrochloride, sodium bisulfite, sodium metabisulfite, sodium sulfite and the like; oil-soluble antioxidants such as ascorbyl palmitate, butylated hydroxyanisole (BHA), butylated hydroxytoluene (BHT), lecithin, propyl gallate, alpha-tocopherol and the like; and metal-chelating agents such as citric acid, ethylenediamine tetraacetic acid (EDTA), sorbitol, tartaric acid, phosphoric acid and the like.

Stabilization Agent

In another configuration, the present formulation may also comprise other suitable agents that stabilize the formulations. For example, an approach for stabilizing solid protein formulations of the invention is to increase the physical stability of purified, e.g., lyophilized, protein. This will inhibit aggregation via hydrophobic interactions as well as via covalent pathways that may increase as proteins unfold. Stabilizing formulations in this context may often include polymer-based formulations, for example a biodegradable hydrogel formulation/delivery system. The critical role of water in protein structure, function, and stability is well known. Typically, proteins are relatively stable in the solid state with bulk water removed. However, solid therapeutic protein formulations may become hydrated upon storage at elevated humidities or during delivery from a sustained release composition or device. The stability of proteins generally drops with increasing hydration. Water may also play a significant role in solid protein aggregation, for example, by increasing protein flexibility resulting in enhanced accessibility of reactive groups, by providing a mobile phase for reactants, and by serving as a reactant in several deleterious processes such as beta-elimination and hydrolysis.

An effective method for stabilizing peptides and proteins against solid-state aggregation for delivery may be to control the water content in a solid formulation and maintain the water activity in the formulation at optimal levels. This level depends on the nature of the protein, but in general, proteins maintained below their "monolayer" water coverage will exhibit superior solid-state stability.

A variety of additives, diluents, bases and delivery vehicles may be provided within the invention that effectively control water content to enhance protein stability. These reagents and carrier materials effective as anti-aggregation agents in this sense may include, for example, polymers of various functionalities, such as polyethylene glycol, dextran, diethylaminoethyl dextran, and carboxymethyl cellulose, which significantly increase the stability and reduce the solid-phase aggregation of peptides and proteins admixed therewith or linked thereto. In some instances, the activity or physical stability of proteins may also be enhanced by various additives to aqueous solutions of the peptide or protein drugs. For example, additives, such as polyols (including sugars), amino acids, proteins such as collagen and gelatin, and various salts may be used.

Certain additives, in particular sugars and other polyols, may also impart significant physical stability to dry, e.g., lyophilized proteins. These additives may also be used within the invention to protect the proteins against aggregation not only during lyophilization but also during storage in the dry state. For example sucrose and Ficoll 70 (a polymer with sucrose units) exhibit significant protection against peptide or protein aggregation during solid-phase incubation under various conditions. These additives may also enhance the stability of solid proteins embedded within polymer matrices.

Yet additional additives, for example sucrose, stabilize proteins against solid-state aggregation in humid atmospheres at elevated temperatures, as may occur in certain sustained-release formulations of the invention. Proteins such as gelatin and collagen also serve as stabilizing or bulking agents to reduce denaturation and aggregation of unstable proteins in this context. These additives can be incorporated into polymeric melt processes and compositions within the invention. For example, polypeptide microparticles can be prepared by simply lyophilizing or spray drying a solution containing various stabilizing additives described above. Sustained release of unaggregated peptides and proteins can thereby be obtained over an extended period of time.

Various additional preparative components and methods, as well as specific formulation additives, are provided herein which yield formulations for mucosal delivery of aggregation-prone peptides and proteins, wherein the peptide or protein is stabilized in a substantially pure, unaggregated form using a solubilization agent. A range of components and additives are contemplated for use within these methods and formulations. Exemplary of these solubilization agents are cyclodextrins (CDs), which selectively bind hydrophobic side chains of polypeptides. These CDs have been found to bind to hydrophobic patches of proteins in a manner that significantly inhibits aggregation. This inhibition is selective with respect to both the CD and the protein involved. Such selective inhibition of protein aggregation may provide additional advantages within the intranasal delivery methods and compositions of the invention.

Additional agents for use in this context include CD dimers, trimers and tetramers with varying geometries controlled by the linkers that specifically block aggregation of peptides and protein. Yet solubilization agents and methods for incorporation within the invention involve the use of peptides and peptide mimetics to selectively block protein-protein interactions. In one aspect, the specific binding of hydrophobic side chains reported for CD multimers may be extended to proteins via the use of peptides and peptide mimetics that similarly block protein aggregation. A wide range of suitable methods and anti-aggregation agents may be available for incorporation within the compositions and procedures of the invention.

Stabilizing Delivery Vehicle, Carrier, Support or Complex-Forming Species

In another embodiment, the present formulation may also comprise other suitable agents such as a stabilizing delivery vehicle, carrier, support or complex-forming species. The coordinate administration methods and combinatorial formulations of the instant invention may optionally incorporate effective lipid or fatty acid based carriers, processing agents, or delivery vehicles, to provide improved formulations for delivery of Calnexin or functionally equivalent fragment proteins, analogs and mimetics, and other biologically active agents. For example, a variety of formulations and methods are provided for delivery which comprise one or more of these active agents, such as a peptide or protein, admixed or encapsulated by, or coordinately administered with, a liposome, mixed micellar carrier, or emulsion, to enhance chemical and physical stability and increase the half-life of the biologically active agents (e.g., by reducing susceptibility to proteolysis, chemical modification and/or denaturation) upon mucosal delivery.

Within certain aspects of the invention, specialized delivery systems for biologically active agents may comprise small lipid vesicles known as liposomes or micelles. These are typically made from natural, biodegradable, non-toxic, and non-immunogenic lipid molecules, and can efficiently entrap or bind drug molecules, including peptides and proteins, into, or onto, their membranes. The attractiveness of liposomes as a peptide and protein delivery system within the invention is increased by the fact that the encapsulated proteins can remain in their preferred aqueous environment within the vesicles, while the liposomal membrane protects them against proteolysis and other destabilizing factors. Even though not all liposome preparation methods known are feasible in the encapsulation of peptides and proteins due to their unique physical and chemical properties, several methods allow the encapsulation of these macromolecules without substantial deactivation.

Additional delivery vehicles carrier, support or complex-forming species for use within the invention may include long and medium chain fatty acids, as well as surfactant mixed micelles with fatty acids. Most naturally occurring lipids in the form of esters have important implications with regard to their own transport across mucosal surfaces. Free fatty acids and their monoglycerides which have polar groups attached have been demonstrated in the form of mixed micelles to act on the intestinal barrier as penetration enhancers. This discovery of barrier modifying function of free fatty acids (carboxylic acids with a chain length varying from 12 to 20 carbon atoms) and their polar derivatives has stimulated extensive research on the application of these agents as mucosal absorption enhancers.

For use within the methods of the invention, long chain fatty acids, especially fusogenic lipids (unsaturated fatty acids and monoglycerides such as oleic acid, linoleic acid, linoleic acid, monoolein, etc.) provide useful carriers to enhance delivery of Calnexin or a functionally equivalent fragment, and other biologically active agents disclosed herein. Medium chain fatty acids (C6 to C12) and monoglycerides have also been shown to have enhancing activity in intestinal drug absorption and can be adapted for use within the mucosal delivery formulations and methods of the invention. In addition, sodium salts of medium and long chain fatty acids are effective delivery vehicles and absorption-enhancing agents for mucosal delivery of biologically active agents within the invention. Thus, fatty acids can be employed in soluble forms of sodium salts or by the addition of non-toxic surfactants, e.g., polyoxyethylated hydrogenated castor oil, sodium taurocholate, etc. Other fatty acid and mixed micellar preparations that are useful within the invention include, but are not limited to, Na caprylate (C8), Na caprate (C10), Na laurate (C12) or Na oleate (C18), optionally combined with bile salts, such as glycocholate and taurocholate.

The vaccine of the present invention may advantageously include a pharmaceutically acceptable excipient such as a suitable adjuvant. Suitable adjuvants include an aluminium salt such as aluminium hydroxide gel (alum) or aluminium phosphate (as described in WO93/24148), but may also be a salt of calcium, iron or zinc, or may be an insoluble suspension of acylated tyrosine, or acylated sugars, cationically or anionically derivatised polysaccharides, or polyphosphazenes. The suitable adjuvants may also comprise mannose-containing, carbohydrate based adjuvants such as fungal mannans.

The vaccine formulation may additionally include a biologically acceptable buffer to maintain a pH close to neutral (7.0-7.3). Such buffers preferably used are typically phosphates, carboxylates, and bicarbonates. More preferred buffering agents are sodium phosphate, potassium phosphate, sodium citrate, calcium lactate, sodium succinate, sodium glutamate, sodium bicarbonate, and potassium bicarbonate. The buffer may comprise about 0.0001-5% (w/v) of the vaccine formulation, more preferably about 0.001-1% (w/v). The buffer(s) may be added as part of the stabilizer component during the preparation thereof, if desired. Other excipients, if desired, may be included as part of the final vaccine formulation.

The remainder of the vaccine formulation may be an acceptable diluent, to 100%, including water. The vaccine formulation may also be formulated as part of a water-in-oil, or oil-in-water emulsion.

Also provided as part of the invention is a method of preparation of the vaccine formulation herein described. Preparation of the vaccine formulation preferably takes place in two phases. The first phase typically involves the preparation of the stabilizer component. The first phase may typically involve the preparation of the stabilizer component. The stabilizer component may comprise any suitable components as discussed above. For example, a vegetable-based protein stock solution may be prepared by dissolving the vegetable-based protein in a diluent. The preferred diluent may be water, preferably distilled and/or purified so as to remove trace impurities (such as that sold as purified Super Q®). In a separate vessel an animal-based protein may be dissolved in a diluent, additionally with the sugar component and buffer additives. Preferably, an equal volume of the vegetable-based protein stock solution is added to the animal-based protein solution. It is desirable that after HCl/KOH adjustment to achieve a pH of approximately 7.2±0.1, the stabilizer component may be sterilized via autoclave. The stabilizer solution may be refrigerated for an extended period prior to introduction of the Calnexin fragment.

The second phase of preparation of the vaccine formulation may include introduction of the Calnexin fragment with the stabilizer component, thereby yielding the vaccine formulation. Preferably, the Calnexin fragment may be diluted with a buffer solution prior to its introduction to the stabilizer component.

Once this vaccine formulation solution has been achieved, the formulation may be separated into vials or other suitable containers. The vaccine formulation herein described may then be packaged in individual or multi-dose ampoules, or be subsequently lyophilized (freeze-dried) before packaging in individual or multi-dose ampoules. The vaccine formulation herein contemplated also includes the lyophilized version. The lyophilized vaccine formulation may be stored for extended periods of time without loss of viability at ambient temperatures. The lyophilized vaccine may be reconstituted by the end user, and administered to a patient.

The vaccine of the present invention may be either in a solid form or in a liquid form. Preferably, the vaccine of the present invention may be in a liquid form. The liquid form of the vaccine may have a concentration of 50-4,000 nanomolar (nM), preferably between 50-150 nM. In some embodiments, the concentration will be between 1-50,000 nM.

To vaccinate a patient, a therapeutically effective amount of vaccine comprising Calnexin fragments may be administered to a patient. The therapeutically effective amount of vaccine may typically be one or more doses, preferably in the range of about 0.01-10 mL, most preferably 0.1-1 mL, containing 20-200 micrograms, most preferably 1-50 micrograms of vaccine formulation/dose. The therapeutically effective amount may also depend on the vaccination species. For example, for smaller animals such as mice, a preferred dosage may be about 0.01-1 mL of a 1-50 microgram solution of antigen. For a human patient, a preferred dosage may be about 0.1-1 mL of a 1-50 microgram solution of antigen. The therapeutically effective amount may also depend on other conditions including characteristics of the patient (age, body weight, gender, health condition, etc.), the species of fungi, and others.

A vaccine of the present invention may be administered by using any suitable means as disclosed above. Preferably, a vaccine of the present invention may be administered by intranasal delivery or intramuscular administration, e.g., needle injection.

After vaccination using a vaccine of the present invention, a patient may be immunized from at least one of fungi. In one specific embodiment, a patient after vaccination may be immunized from at least one of dimorphic fungi. In one preferred embodiment, a patient after vaccination may be immunized from multiple dimorphic fungi of *Histoplasma, Coccidiodes, Paracoccidioides, Penicillium, Blastomyces,* and *Sporothrix*.

In one embodiment, the present invention relates to a therapeutic device for vaccination a patient against fungal infection. In one embodiment, the therapeutic device may comprise any suitable devices charged with a preparation of Calnexin or a functionally equivalent fragment. In another embodiment, the therapeutic device may comprise any suitable devices charged with a preparation of Calnexin or a functionally equivalent fragment and at least one additional active compound.

The instant invention may also include kits, packages and multicontainer units containing the above described pharmaceutical compositions, active ingredients, and/or means for administering the same for use in the prevention and treatment of diseases and other conditions in mammalian subjects. Briefly, these kits include a container or formulation that contains Calnexin or a functionally equivalent fragment, and/or other biologically active agents in combination with mucosal delivery enhancing agents disclosed herein formulated in a pharmaceutical preparation for delivery.

Methods for Determining the Immune Status of a Patient

In one aspect, the present application discloses diagnostic methods for determining immune status of a patient. Applicants envision that the present methods would be used to access the status of receipt in a tissue transplantation procedure.

In one embodiment, the present application discloses proteins or peptides and methods of using such proteins or peptides to evaluate the immune status of a patient. In one embodiment, proteins or peptides may be used to detect endogenous calnexin specific CD4 T cells. As discussed above, Applicants identified calnexin as a major shared antigen that is recognized by T cells that mediate protection against pathogenic fungi that are members of the broad fungal taxonomic group called Ascomycetes.

In one embodiment, the family of Ascomycetes may comprise *Blastomyces dermatitidis, Histoplasma capsulatum, Aspergillus fumigatus, Fonsecea pedrosoi,* and *Geomyces destructans* (the latter is the "white nose fungus", which is decimating bat populations in North America), to name a few.

In one preferred embodiment, the proteins or peptides may comprise peptide-MHCII tetramers (pMHC tetramers). The binding peptide in pMHC tetramers may be any calnexin peptide as discussed above. In one embodiment, the binding peptides may be any of calnexin peptides 1-10 as shown in FIG. 6.

In one preferred embodiment, the binding peptide in pMHC tetramers may be calnexin peptide #1 (that is, residues 103-115 of the calnexin protein; SEQ ID NOs: 1-5, 7-8, and 12).

Calnexin peptide #1 specific T cells recognize many of these fungi and confer protection against them. As used herein, calnexin peptide #1 specific T cells refers to the T cells that are directed against the calnexin peptide #1 (that is, residues 103-115 of the calnexin protein; SEQ ID NOs: 1-5, 7-8, and 12). The examples of calnexin peptide #1 are shown in the Table 1.

Helper T cells play an essential role in protecting the host from infection and cancer. Each helper T cell expresses a unique receptor (TCR), which via the aid of the CD4 coreceptor is capable of binding to a specific foreign peptide embedded in a Major Histocompatibility Complex II (MHCII) molecule on the surface of another host cell—the so-called antigen-presenting cell. Recognition of the relevant peptide-MHCII ligand causes a helper T cell to produce various lymphokines that help B cells produce antibodies and enhance the microbicidal activities of phagocytes and cytotoxic lymphocytes. Therefore, The pMHC tetramers may be used to track the emergence and persistence of these T cells after exposure to the fungus in question.

In one aspect, the present invention disclose pMHCII tetramers and method of using pMHCII tetramers to evaluate immune status of a patient.

In one embodiment, the pMHCII tetramers may include any calnexin peptides as discussed above as binding peptides. In one preferred embodiment, the calnexin peptide in the pMHCII tetramers is calnexin peptide #1, which include residues 103-115 of the calnexin protein. Preferably, the calnexin peptide comprises or consists of a sequence selected from a group consisting of SEQ ID NOs: 1-5, 7-8, and 12. The calnexin peptide may be linked to a MHCII molecule through a flexible linker. Any suitable flexible linker as appreciated by one skilled in the art may be used to link the calnexin peptide to the MHCII molecule.

In one embodiment, the fungus in question may include any fungi as discussed above and any others as appreciated by one person having ordinary skill in the art.

The pMHCII tetramers may be produced from any suitable methods as appreciated by one person having ordinary skill in the art. For example, the pMHCII tetramers may be synthesized by using the method described previously (jenkinslab.umn.edu/Jenkins_Lab_2/assets/pdf/Jenkins %20tetramer %20production %2004-25-10.pdf).

In one preferred embodiment, the pMHCII tetramers may comprise at least one fluorescent label. For example, the design of the tetramer may incorporate Fos-Jun leucine zipper motifs to force dimerize the coexpressed MHCII α and β chains (Teyton, et. al., *J. Exp. Med.* 183:2087), and the *E. coli* BirA signal sequence (Schatz, et. al., Protein Science 8:921) on the a chain to allow for site-specific biotinylation. The resulting biotinylated peptide:MHCII (pMHCII) heterodimers may be tetramerized with fluorochrome-labeled streptavidin.

In one embodiment, the present proteins or peptides such as the pMHC tetramers may be used to identify "endogenous" calnexin peptide #1 specific T cells that reside in the body of a patient before infection.

In one embodiment, the present proteins or peptides such as the pMHC tetramers may be used to quantify "endogenous" calnexin peptide #1 specific T cells that reside in the body of a patient before infection.

In one embodiment, the present proteins or peptides such as the pMHC tetramers may be used to monitor the response of calnexin peptide #1 specific T cells.

In one embodiment, the present proteins or peptides such as the pMHC tetramers may be used to monitor expansion and characteristics of the calnexin peptide #1 specific T cells after infection and vaccination.

In one embodiment, the present application discloses compositions to identify and track calnexin peptide specific T cells in a patient. In one embodiment, the compositions may comprise proteins or peptides. Specifically, the suitable proteins or peptides may comprise pMHC tetramers as discussed above.

The present invention provides compositions, e.g., pharmaceutically acceptable compositions, which include pMHC tetramers formulated together with a pharmaceutically acceptable carrier. As used herein, "pharmaceutical compositions" encompass labeled pMHC tetramers for visualization of calnexin peptide specific T cells, e.g., in vivo imaging as well as therapeutic compositions.

A composition comprising pMHC tetramers may also comprise other suitable ingredients. The present composition of pMHC tetramers may comprise other pharmaceutically acceptable carriers and/or other pharmaceutically acceptable salts.

As used herein, the term "pharmaceutically acceptable carrier" refers to any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the antigenic peptide, i.e., the calnexin protein may be coated in a material to protect the peptide from the action of acids and other natural conditions that may inactivate the peptide.

A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The composition can be formulated as a solution, microemulsion, dispersion, liposome, or other ordered structure suitable to high drug concentration.

In one embodiment, the composition may also comprise a carrier molecule as a stabilizer component. As the types of proteins or peptides enclosed in the present invention may be rapidly degraded once injected into the body, the proteins or peptides may be bound to a carrier molecule for stabilizing the proteins or peptides during delivery and administration. A suitable carrier or stabilizer may comprise fusion proteins, polymers, liposome, micro or nanoparticles, or any other pharmaceutically acceptable carriers. A suitable carrier or stabilizer molecule may comprise a tertiary amine N-oxide, e.g., trimethylamine-N-oxide, a sugar, e.g., trehalose, a poly(ethylene glycol) (PEG), an animal-based protein, e.g., digested protein extracts such as N—Z-Amine®, N—Z-Amine AS® and N—Z-Amine YT® (Sheffield Products Co., Norwich, N.Y.), a vegetable-based protein, e.g., soy protein, wheat protein, corn gluten, rice protein and hemp protein, and any other suitable carrier molecules. The composition may also comprise any suitable carrier or vehicle, such as those as discussed above. The composition may also comprise other stabilization agents, such as those as discussed above.

In one embodiment, the composition may also comprise suitable stabilizing delivery vehicle, carrier, support or complex-forming species, such as those as discussed above. For example, the composition may additionally comprise at least one of a stabilizer, a buffer, or an adjuvant.

In one embodiment, the present application discloses methods for evaluating the immune status of a patient.

In one specific embodiment, the present methods for evaluating the immune status of a patient may be accomplished by detecting and evaluating "endogenous" calnexin peptide #1 specific T cells in a patient.

In one embodiment, a method for evaluating the immune status of a patient against a fungus comprises the steps of 1) obtaining pMHCII tetramers; 2) exposing a sample of a patient to a suitable amount of pMHCII tetramers; 3) identifying helper T cells such as "endogenous" calnexin peptide #1 specific T cells in the patient's sample; 4) quantifying helper T cells such as "endogenous" calnexin peptide #1 specific T cells in the patient's sample; and 5) monitoring the response, expansion and characteristics of helper T cells such as calnexin peptide #1 specific T cells the after infection and vaccination, wherein the immune status of a patient against the fungus is obtained by comparing the quantity, expansion and characteristics of the helper T cells before and after infection and vaccination.

In one embodiment, the pMHCII tetramers of the present invention may be produced by any methods as discussed above or by any other suitable methods as appreciated by one person having ordinary skill in art.

In one specific embodiment, the binding peptide in the pMHCII tetramers is a calnexin peptide. Any calnexin peptide as discussed above may be used as the binding peptide in the pMHCII tetramers. In one preferred embodiment, the binding peptide in the pMHCII tetramers is calnexin peptide #1, i.e., residues 103-115 of the calnexin protein. More preferably, the calnexin peptide #1 comprises or consists of a sequence selected from a group consisting of SEQ ID NOs: 1-5, 7-8, and 12.

In one specific embodiment, the sample of the present invention is a fresh blood sample from a patient. Applicants envision that other biological samples may also be used for the present invention. The other biological samples may include any biological fluids that comprise the helper T cells, preferably "endogenous" calnexin peptide #1 specific T cells.

After the pMHCII tetramers and the patient sample are obtained, the patient's sample is exposed to a suitable amount of the pMHCII tetramers. The reaction of the helper T cells, such as calnexin peptide #1 specific T cells to the antigentic peptide in the pMHCII tetramers is monitored to evaluate immune status of the patient. In one embodiment, the reaction of the helper T cells to the pMHCII tetramers may be monitored by detecting, identifying, evaluating enumerating and quantifying the helper T cells, such as calnexin peptide #1 specific T cells.

In one embodiment, the immune status of a patient against a fungus may be evaluated by monitoring the response, expansion and characteristics of the helper T cells after infection and vaccination.

The term "detecting," "identifying," "evaluating," "enumerating," or "quantifying," as used herein, refers to its broadest sense to include assays which qualitatively or quantitatively or semi-quantitatively test for the presence or level of the helper T cells in the presence of the pMHCII tetramers and hence the number of the pMHCII tetramers (e.g., CD44+)—positive cells, or, assays which qualitatively or quantitatively test for the presence or level of the pMHCII tetramers using reagents capable of distinguishing between the two forms.

In one embodiment, the response, expansion and characteristics of the helper T cells after infection and vaccination may be monitored by using a detection marker, a reporter molecule or fluorescent label. The term "detection marker," "reporter molecule" or "fluorescent label," as used herein, refers to a molecule or particle which, by its chemical nature, provides an analytically identifiable signal which allows the detection of positive helper T cells. As will be well recognized, a wide variety of different reporter systems are available and those allowing rapid visual detection are clearly the most useful in the context of point of care diagnostics.

For example, the detection marker may be a colloidal particle or microparticle. Colloidal metal and metalloid particles may include those comprising gold, silver, platinum, iron, copper, selenium; metal complexes such as cyclopentadienylmanganese(I) tricarbonyl, gold cluster; and microparticles such as latex and dyed latex particles.

In one embodiment, the present invention may also extend to qualitative or quantitative detection using any of the commonly used reporter molecules in immunoassay such as enzymes, fluorophores or radionuclide containing molecules and chemiluminescent molecules. In the case of an enzyme immunoassay, an enzyme is conjugated to a second antibody generally by means of glutaraldehyde or periodate. Commonly used enzymes include horseradish peroxidase, glucose oxidase, beta galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates which yield a fluorescent product rather than the chromogenic substrates listed above. In all cases, the enzyme labelled antibody is added to the first antibody antigen complex, allowed to bind, and the excess reagent is washed away. A solution containing the appropriate substrate is then added to the complex of antibody-antigen antibody. The substrate will react with the enzyme linked to the second antibody, giving a qualitative visual signal, which may be further quantified, usually spectrophotometrically, to give an indication of the amount of antigen which is present in the sample. Alternatively, fluorescent compounds, such as fluorescein and rhodamine are chemically coupled to antibodies without altering their binding capacity. When activated by a illumination with light of a particular wave length, the fluorochrome labelled antibody absorbs the light energy inducing a state of excitability in the molecule followed by emission of the light at a characteristic wavelength visually detectable with a microscope.

In one specific embodiment, the peptide-MHCII tetramers may comprise at least one fluorescent label. The fluorescent peptide-MHCII tetramers may bind to helper T cells such as "endogenous" calnexin peptide #1 specific T cells. One may identify the help T cells through a fluorescence detection technique.

The peptide-MHCII tetramers of the present invention may be directly or indirectly labeled with a detectable substance to facilitate detection of the positive helper T cells. Suitable detectable substances include various enzymes, prosthetic groups, fluorescent materials, luminescent materials and radioactive materials.

Complex formation between the calnexin peptide #1 specific T cells and peptide-MHCII tetramers may be detected by measuring or visualizing either the T cells bound to the peptide-MHCII tetramers or unbound T cells. Conventional detection assays can be used, e.g., an enzyme-linked immunosorbent assays (ELISA), a radioimmunoassay (RIA) or tissue immunohistochemistry. Further to labeling the T cells, the presence of a peptide-MHCII tetramer may be assayed in a sample by a competition immunoassay utilizing standards labeled with a detectable substance and an unlabeled T cell.

Fluorophore and chromophore labeled peptide-MHCII tetramers can be prepared. Since antibodies and other proteins absorb light having wavelengths up to about 310 nm, the fluorescent moieties should be selected to have substantial absorption at wavelengths above 310 nm and preferably above 400 nm. The peptide-MHCII tetramers can be labeled with fluorescent chromophore groups by conventional procedures as appreciated by one skilled in the art. One group of fluorescers having a number of the desirable properties described above is the xanthene dyes, which include the fluoresceins and rhodamines. Another group of fluorescent compounds are the naphthylamines. Once labeled with a fluorophore or chromophore, the peptide-MHCII tetramers can be used to detect the presence or localization of the T cells in a sample, e.g., using fluorescent microscopy (such as confocal or deconvolution microscopy).

In one embodiment, the response, expansion and characteristics of the helper T cells after infection and vaccination may be monitored by using Chromatographic assays. Immunoassay or enzyme-based chromatographic assays are particularly preferred and these are described in Wild D "The Immunoassay Handbook", Nature Publishing Group, 2001 and by reference to U.S. Pat. Nos. 4,016,043; 4,590,159; 5,266,497; 4,962,023; 5,714,389; 5,877,028, 5,922,537, 6,168,956 and 6,548,309, 6,180,417, and 5,266,497 incorporated herein and information disclosed by references cited therein. Various modifications of immunochromatographic methods are described in Published US Patent Application Nos. 20010006821, 20040087036 and 20040214347 which are incorporated herein in their entirety. Immunogold filtration methods for multiple analyte analyses are described in Published US Patent Application No. 20030165970 incorporated herein.

In one embodiment, the method may be applied to evaluate the immune status against any fungi such as dimorphic fungi or non-dimorphic fungi. In one embodiment, the method may be applied to evaluate the immune status against a dimorphic fungus selected from a group consisting of *Histoplasma, Coccidiodes, Paracoccidioides, Penicillium, Blastomyces,* and *Sporothrix*.

In another embodiment, the method may be applied to evaluate the immune status against a fungus selected from a group consisting of *Blastomyces dermatitidis, Histoplasma capsulatum, Aspergillus fumigatus, Fonsecea pedrosoi,* and *Geomyces destructans*.

In one aspect, the present application discloses a kit for evaluating the immune status of a patient against a fungus. The kit may comprise (1) a container or formulation wherein the container or formulation comprises peptide-MHCII tetramers, (2) means for exposing peptide-MHCII tetramers to a sample of a patient, and (3) means for detecting helper T cells in the patient's sample, wherein the immune status of a patient against the fungus is obtained by comparing the quantity, expansion and characteristics of the helper T cells before and after infection and vaccination. In one embodiment, the peptide-MHCII tetramers are binding to the helper T cells.

In one specific embodiment, the binding peptide in the pMHCII tetramers is a calnexin peptide. Any calnexin peptide as discussed above may be used as the binding peptide in the pMHCII tetramers. In one preferred embodiment, the binding peptide in the pMHCII tetramers is calnexin peptide #1, i.e., residues 103-115 of the calnexin protein. More preferably, the calnexin peptide #1 comprises or consists of a sequence selected from a group consisting of SEQ ID NOs: 1-5, 7-8, and 12.

In one embodiment, the sample is a fresh blood sample of a patient.

In one embodiment, the peptide-MHCII tetramers may be either a powder or a solution. In one specific embodiment, the means for delivering peptide-MHCII tetramers is selected from a group consisting of subcutaneous administration, intramuscular administration, transcutaneous administration, intradermal administration, intraperitoneal administration, intraocular administration, intranasal administration and intravenous administration.

In another embodiment, the kit may used to evaluating the immune status of a patient against a fungus selected from a group consisting of *Blastomyces dermatitidis, Histoplasma capsulatum, Aspergillus fumigatus, Fonsecea pedrosoi,* and *Geomyces destructans*.

In another embodiment, the kit may used to evaluating the immune status of a patient against a fungus selected from a group consisting of *Blastomyces dermatitidis, Histoplasma capsulatum, Aspergillus fumigatus, Fonsecea pedrosoi,* and *Geomyces destructans*.

In one embodiment, the means for detecting helper T cells in the patient's sample may include any methods as discussed above.

In one embodiment, the peptide-MHCII tetramers may comprise at least one fluorescent label. In one specific embodiment, the means of detection may be a fluorescence technique.

In one embodiment, the kit may include Chromatographic assays as discussed above to monitor and evaluate the response, expansion and characteristics of the helper T cells after infection and vaccination.

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Materials and Methods

Fungi.

Strains used were ATCC 26199 (Harvey, Schmid, et al., 1978), a wild-type strain of *Blastomyces dermatitidis*, and the isogenic, attenuated mutant lacking BAD1, designated strain #55 (Brandhorst, Wüthrich, et al., 1999), as well as *Histoplasma capsulatum* strain G217B, *Coccidiodes posadasii* (isolate C735) and *Candida albicans* strain #5314 (Wüthrich, Hung, et al., 2011); *P. destructans* ATCC 20631-21; *A. fumigatus* Af293; and *F. pedrosoi* strain ATCC 46428. *B. dermatitidis* was grown as yeast on Middlebrook 7H10 agar with oleic acid-albumin complex (Sigma) at 39° C. *H. capsulatum* was grown as yeast at 37° C. and 5% $CO_2$ on brain-heart infusion agar (BHI) slants. *C. albicans* was grown on YPD plates. The saprobic phase of *C. posadasii* (isolate C735) was grown on GYE medium (1% glucose, 0.5% yeast extract, 1.5% agar) at 30° C. for 3 to 4 weeks to generate a confluent layer of arthroconidia (spores) on the agar surface. Formalin killed spherules (FKS) of *C. posadasii* were generated as described (Levine, Cobb, et al., 1960; Levine, Kong, et al., 1965). *P. destructans* was kindly provided by David Blehart (USGS—National Wildlife Health Center) and grown on Sabouraud dextrose agar for 60 days at 7-10° C. *F. pedrosoi* was kindly provided by Gordon Brown (Aberdeen, Scotland) and grown on potato agar plates or in liquid potato broth containing 50 μg/ml chloramphenicol in a shaking incubator at 30° C. Conidia were filtered to remove hyphae and washed with PBS before use. *A. fumigatus* was kindly provided by Nancy Keller (UW-Madison) and cultured on glucose minimal medium at 37° C. Spores were collected in $H_2O$-Tween 20 (0.01%).

Mouse Strains.

Inbred C57BL/6, IL-17a$^{tm1.1(icre)Stck}$/J (stock #16879) and Gt(ROSA)26Sor$^{tm1(EYFP)Cos}$ reporter mice (stock #6148) were obtained from Jackson laboratory, Bar Harbor, ME. Breeding IL-17a$^{tm1.1(icre)Stck}$/J to Gt(ROSA)26 Sor$^{tm1(EYFP)Cos}$ reporter mice enabled us to fluorescently label and track IL-17A expressing cells as described for fate mapping (Hirota et al., 2011). *Blastomyces*-specific TCR Tg 1807 mice were bred to B6.PL (Thy1.1$^+$) mice to obtain Thy1.1$^+$ 1807 cells (Wüthrich, Ersland, et al., 2012). Mice were 7-8 weeks old at the time of these experiments. Mice were housed and cared for as per guidelines of the University of Wisconsin Animal Care Committee, who approved this work.

Generation of Eluate #1.

Cell wall membrane (CW/M) antigen (Ag) was extracted from BAD1-null vaccine yeast as previously described (Wüthrich, et al., 2000). Briefly, yeast were broken open with glass beads, debris pelleted, and the aqueous supernatant harvested. CW/M Ag was diluted to a protein concentration of 1.5 mg/ml in binding buffer containing 20 mM Tris, pH7.6, 0.3 mM NaCl, 1 mM $MnCl_2$, 1 mM $MgCl_2$, 1 mM $CaCl_2$) and centrifuged to remove insoluble complexes. To enrich the mannosylated proteins in the CW/M Ag preparation we used a Con A column (FIGS. 1A, 1B, 1C, 1D, and 1E). To prepare the column, we washed 0.75 ml Con A-Sepharose resin with 5 ml of binding buffer at least three times, each time the resin was pelleted by centrifugation at 1,000×g for 3 min. After equilibration of the resin with an equal volume of binding buffer, the CW/M Ag extract was allowed to bind for 60 to 120 min under agitation at 4° C. The resin was then centrifuged at 1,000×g for 3 min, and washed twice for 10 min with 15 ml of binding buffer containing 0.1% Tween 20. After a final wash with detergent free binding buffer, the bound fraction was eluted by incubating it for 10 min in 5 ml 20 mM Tris-HCL buffer pH 7.6 containing 500 mM a-D-methylmannopyranoside and 0.3 M NaCl. After pelleting the resin at 2,000×g for 3 min, the supernatant was saved as eluate #1 and aliquoted for subsequent use. To inactivate Con A that might have leached from the resin, eluate #1 aliquots were heat treated for 15 min at 85° C.

Enrichment of the Shared Ag by Gel-Free Separation and Identification by Mass Spec Analysis.

Eluate #1 was applied to a Gel-free 8100 fractionation system (Protein Discovery, Knoxville, TN), and separated on a 10% Tris-Acetate cartridge. Fractions were collected that corresponded to separately eluted MW markers. These fractions were surveyed for protein content by PAGE analysis and silver stain. The fractions that activated 1807 T cells (quantified by production of INF-γ) were concentrated by FASP for mass spectroscopy analysis (below).

Filter Aided Sample Preparation [FASP] Method.

FASP sample preparation (Universal sample preparation method for proteome analysis (Wisniewski, Zougman, et al., 2009) and mass spectrometric analysis was done at the Mass Spectrometry Facility at the Biotechnology Center, University of Wisconsin-Madison. Peptides were analyzed by nanoLC-MS/MS using the Agilent 1100 NANOFLOW high performance liquid chromatography system (Agilent Technologies) connected to a hybrid linear ion trap-ORBITRAP mass spectrometer (LTQ-ORBITRAP XL, Thermo Fisher Scientific) equipped with a nanoelectrospray ion source. In short, samples were bound to 10 kDa MW cut-off Microcon filters (Millipore Corp., Bedford MA) and washed twice with 500 µL of 25 mM $NH_4HCO_3$ (pH8.5). Sample was denatured for 2 min in 100 µL of 8M Urea/50 mM $NH_4HCO_3$ (pH8.5) then spun 6 min at 14,000×g. Disulfides were reduced at 37° C. in 100p of 6.4M Urea/40 mM $NH_4HCO_3$ (pH8.5)/5 mM DTT for 45 min then spun 2 min at 14,000×g. Cys alkylation was performed at room temperature in the dark for 15 min in 100 µl of 6.4M Urea/40 mM $NH_4HCO_3$ (pH8.5)/11 mM IAA then spun 2 min at 14,000×g and washed once with 100 µL of 8M Urea/50 mM $NH_4HCO_3$ (pH8.5) and once with 25 mM $NH_4HCO_3$ (pH8.5). Digestion with 200 ng trypsin (Promega Corporation, Madison WI) was performed in 50p of 1M Urea/20 mM $NH_4HCO_3$ (pH8.5)/5% ACN overnight at 37° C. Peptides were spun through the membrane and washed through with 50p of 25 mM $NH_4HCO_3$ (pH8.5), 5 min at 14,000×g. Eluted peptide solution was acidified with 2.5% TFA [Trifluoroacetic Acid] to 0.3% final and C18 solid phase extracted with OMIX SPE tips (Agilent Technologies, Santa Clara, CA). Peptides were eluted off the C18 column with 20 ul of acetonitrile/$H_2O$/TFA (60%:40%:0.1%) into 1.5 mL Protein LoBind tube (Eppendorf) dried in the SpeedVac to ~2 µl, diluted to 18 µl with 0.05% TFA and 8 µl loaded for nanoLC-MS/MS analysis.

NanoLC-MS/MS.

Peptides were analyzed by nanoLC-MS/MS using the Agilent 1100 NANOFLOW high performance liquid chromatography system (Agilent Technologies) connected to a hybrid linear ion trap-ORBITRAP mass spectrometer (LTQ-ORBITRAP XL, Thermo Fisher Scientific) equipped with a nanoelectrospray ion source. HPLC was performed using an in-house fabricated 15-cm C18 column packed with MAGIC C18AQ 3 µm particles (MICHROM Bioresources Inc., Auburn, CA). Solvents were 0.1% formic acid in water (solvent A) and 0.1% formic acid, 95% acetonitrile in water (solvent B). The gradient consisted of 20 min loading and desalting at 1% solvent B, an increase to 40% B over 195 min, to 60% B over 20 min, and to 100% B over 5 min.

MS survey scans from m/z 300 to 2000 were collected in centroid mode at a resolving power of 100,000. Dynamic exclusion was employed to increase dynamic range and maximize peptide identifications, excluding precursors up to 0.55 m/z below and 1.05 m/z above previously selected precursors (40 sec expiration). Data was referenced against *B. dermatitidis* amino acid sequence database (19,126 protein entries) using in-house Mascot search engine 2.2.07 (Matrix Science, London, UK). Peptide mass tolerance was set at 20 ppm and fragment mass at 0.6 Da. Quantification was done with Scaffold software (version 3.6.3, Proteome Software Inc., Portland, OR). Protein identifications were reported above 95.0% probability within 0.9% False Discovery Rate and comprising at least 2 identified peptides. Probabilities were assigned by the Protein Prophet algorithm (Nesvizhskii, Keller, et al., 2003).

Generation and Purification of Recombinant Calnexin.

*Paracoccidioides brasiliensis* Calnexin was amplified from the pGEM-Calnexin plasmid (dos Santos Feitosa, de Almeida Soares, et al., 2007), generously provided by Jose Daniel Lopes, using oligonucleotides designed to omit the stop codon and add NheI and SalI restriction sites to the 5' and 3' ends, respectively. The resulting 1.7 kb fragment was ligated into the pET28c vector digested with NheI and XhoI, in frame with a C-terminal 6×His tag. The pET28c-Calnexin construct was transformed into BL21(DE3) *E. coli* for expression of recombinant Calnexin. Calnexin-expressing *E. coli* was grown at 37° C. in LB medium supplemented with 50 ug/ml kanamycin to an OD600 of ~0.9, at which point isopropyl-β-D-1-thiogalactopyranoside (IPTG) was added to a final concentration of 0.2 mM. Cells were induced for 24 hours at 15° C. Cells were harvested and resuspended in lysis buffer (50 mM Tris-HCl (pH 7.5), 200 mM NaCl, 0.1% Triton X-100, 5 mM DTT, and 0.1 mg/ml lysozyme supplemented with complete EDTA-free Protease Inhibitor Cocktail Tablet (Roche)), followed by sonication and centrifugation. Calnexin was purified from the supernatant using a Ni-NTA column (Qiagen) and the wash and elution buffers were used according to manufacturer instructions for purification under native conditions. Calnexin eluate was then dialyzed into 1×PBS using 3,500 MWCO dialysis tubing (Pierce).

Generation of Anti-Calnexin Polyclonal Antibody and Staining of Yeast.

Mice were vaccinated with 200 µg recombinant Calnexin (rCalnexin) thrice. For the first immunization, the protein was emulsified in CFA, the following two boosters were formulated in IFA (Wüthrich, Filutowicz, et al., 2000). Two weeks after the last boost, mice were bled and the serum harvested. Oligospecific anti-Calnexin antibodies were purified from the serum using affinity-purification. Briefly, >200 µg purified recombinant Calnexin was run on an SDS-10% polyacrylamide gel at 20 mAmp for one hour, transferred to PVDF membrane (Millipore), and stained in Ponceau S. The band corresponding to Calnexin was excised from the membrane and probed overnight at 4° C. with anti-Calnexin mouse serum diluted 1:2 in PBS. After washing once in PBS+0.1% Tween 20 and three times in PBS, the anti-Calnexin antibodies were eluted from the membrane in 100 mM glycine (pH 2.6). Following neutralization with 100 mM Tris-HCl (pH 8), the purified antibody was functionally verified by spectrophotometric analysis and Western blot.

For staining yeast, B. dermatitidis strain #55 was grown in liquid HMM for three days at 37° C., passed back to an OD600 of 0.8 and grown for an additional two days. Aliquots of $10^6$ yeast were washed in PBS, resuspended in 90 μl PBS+10 μl anti-Calnexin antibody, and incubated at 4° C. for one hour. Cells were washed in PBS, and then incubated at room temperature for 40 minutes with rhodamine red-conjugated goat anti-mouse (Molecular Probes) diluted 1:100 in PBS containing 0.5% BSA and 2 mM EDTA. After washing in PBS, the yeast were fixed in 2% PFA, pelleted, and resuspended in PBS. Fluorescent microscopy was carried out on an Olympus BX60 using mirror cube U-MWIG, with images taken under a 40× objective using QCapture Pro software.

Comparison of Calnexin Sequence Among Different Fungi and Prediction of its Class II Epitopes.

To determine the degree of conservation of the Calnexin protein among the systemic dimorphic fungi, the deduced Calnexin protein sequences of B. dermatitidis strain 26199, H. capsulatum strain G217B, C. posadasii strain C735 and P. brasiliensis strain PB01 were aligned using ClustalW (Thompson, Higgins, et al., 1994) in the MacVector software package (v. 12.5.1; MacVector Inc., Carey, NC). To aid in determining possible epitopes within the Calnexin protein sequence, two different algorithms were used to predict binding peptides for the mouse C57/B6 MHC-class-II-allele, $H_2$-IAb. In the first algorithm the Calnexin protein sequence of B. dermatitidis was analyzed using the Immune Epitope Database (IEDB) Analysis Resource (tools.immuneepitope.org/main/html/tcell_tools.html). The output of this software designates each peptide and its $IC_{50}$ value. Several peptides, with nine amino-acid-core sequences that had $IC_{50}$ values less than 500 nM (considered strong to moderate binding affinity) were predicted, and clustered into six regions of extended peptides within the B. dermatitidis Calnexin protein sequence (FIG. 6). A second algorithm developed in the Laboratory of Marc Jenkins, University of Minnesota, which is based only on peptides that have been eluted from affinity purified $H_2$-IAb molecules and sequenced by mass spec (Mark Jenkins, personal communication), generated ten strong-binding nanomers, with greater than 5 standard deviations above random peptides. The peptides were named Peptide 1 through Peptides 10, based on the strength of predicted binding to $H_2$-IAb (FIG. 6).

The ten predicted nanomers were synthesized as 13aa peptide-harboring an additional two flanking amino acids at each end—by GeneScript USA Inc. (Piscataway, NJ; genscript.com) and used to test epitope-specific 1807 T-cell activation.

GP-calnexin-MSA/yR, GMP-calnexin-MSA/yR, GP-MSA/yR, and GP-MSA/yR Vaccine Formulations. Glucan Particles (GP) and Glucan Mannan Particles (GMP) were purified from Baker's yeast using chemical and organic extractions (Soto and Ostroff, 2008; Young et al., 2007). GPs and GMPs containing encapsulated r-calnexin-mouse serum albumin (MSA; Equitech-Bio, Kerrville, TX) and yeast RNA (yR; Sigma, St. Louis, MO) (G(M)P-calnexin-MSA/yR) or control MSA/yR (G(M)P-MSA/tR) were synthesized (Huang et al., 2010; Soto and Ostroff, 2008). Vaccine formulations were adjusted to $10^9$ particles/ml in saline for injection (Baxter, Deerfield, IL) and flash frozen in single use aliquots to deliver 10 μg calnexin complexed with 50 μg MSA/$10^8$ particles per 0.1 ml dose. Vaccine Ag identity and encapsulation efficiency (>95%) were established by SDS-PAGE. GMP calnexin peptide 1-MSA/yR vaccine formulations were synthesized as described for calnexin protein.

Generation of MHC class II tetramer. To create tetramer, we covalently linked the peptide Ag by a fusion to the N-terminus of the MHCIIb chain via a flexible glycine-serine linker as described jenkinslab.umn.edu/Jenkins_Lab_2/assets/pdf/Jenkins %20tetramer %20production %2004-25-10.pdf and (Moon et al., 2007). Briefly, to clone the calnexin peptide #1 sequence into the I-Ab b chain vector (pRMHa-3 I-Ab beta 2W-109C) we designed a set of overlapping oligos encoding the new peptide sequence (underlined) plus flanking sequences encompassing the restriction sites XmaI and SpeI (italicized). The oligos tdsP813 CCGGGACTGAGGGC CTCGTGGTGAAGAATCCCGCCGCCCACCACGCGAT TCCGGC*TGT*GGAGGTA (SEQ ID NO: 14) (sense strand) and tdsP814 CTAGTACCTCC*ACA*GCC GGAAATCGCGTGGTGGGCGGCGGGATTCTTCACCA CGAGG CCCTCAGTC (SEQ ID NO: 15) (anti-sense 5' to 3') contain a cysteine residue (italicized and underlined) in the linker sequence, which stabilizes the peptide in the MHC binding pocket. The cloning was verified by sequencing and the peptide:I-Ab molecules expressed in Drosophila S2 cells as described (Moon et al., 2007).

Enrichment, staining and analysis of rare epitope-specific T cells. To enrich epitope-specific T cells in mice we used a magnetic bead-based procedure that results in about a 100-fold increase in the frequency of the target population (Moon et al., 2009; Moon et al., 2007). Enriched cells were stained with a cocktail of fluorochrome-labeled antibodies specific for B220, CD11b, CD11c, F4/80, CD3, CD8, CD4 and CD44. The entire stained sample was collected on an LSRII flow cytometer and live cells analyzed by FlowJo software (Treestar) following the gating strategy described (Moon et al., 2009). The total number of tetramer positive cells from a mouse was calculated from the percent of tetramer-positive events multiplied by the total number of cells in the enriched fraction as described (Moon et al., 2009) and in the enriched plus unbound fraction when larger numbers of tetramer positive cells are present. Briefly, a single cell suspension from the spleen and vaccine site draining lymph nodes was prepared in 0.2 ml Fc block. PE-conjugated tetramer was added at a concentration of 10 nM and the cells were incubated at room temperature for 1 h, washed in 10 ml of ice-cold sorter buffer (PBS+2% fetal bovine serum). Tetramer stained cells were then resuspended in 400 μl of sorter buffer and mixed with 100 μl of anti-PE antibody conjugated magnetic microbeads (Miltenyi) and incubate on ice for 20 min, followed by two washes with 10 ml of sorter buffer and passed over a magnetized LS column (Miltenyi). The column was washed with 3 ml of sorter buffer three times and the bound cells eluted with a plunger.

Stimulation of 1807 T Cells In Vitro.

To test the antigenic properties of the Calnexin protein and peptides we loaded bone marrow derived dendritic cells (BMDC) with the respective antigens and cultured them with naïve 1807 T cells to assess T-cell activation and cytokine production. After three days of co-culture, the cell culture supernatants were harvested and analyzed for cytokines by ELISA and 1807 T cells stained for the activation markers CD44 and CD62L (Wüthrich, Ersland, et al., 2012). In some experiments, the Blastomyces CW/M-reactive T-cell clone #5, whose TCR was cloned to generate 1807 transgenic mice (Wüthrich, Filutowicz, et al., 2007), was used as a reporter T-cell to identify the presence of the antigen. Cell-culture supernatants were generated in 96-well plates in 0.2 ml containing 1×10$^5$ BMDC, 0.05 to 10 µg/ml of CW/M antigen (Wüthrich, Filutowicz, et al., 2000), 0.05 to 50 µg/ml Calnexin and Drk1 (as a negative control) (Nemecek, Wüthrich, et al., 2006) and 0.001 to 100 µM Calnexin peptides #1-10 (FIG. 6). Supernatants were collected after 72 hours of co-culture. IFN-γ and IL-17A were measured by ELISA (R&D System, Minneapolis, MN) according to manufacturer specifications (detection limits were 0.05 ng/ml).

Generation of a Water-Soluble Extract from Vaccine Yeast.

Yeast surface proteins were extracted three times with three yeast-pellet volumes of water by agitating the yeast for one hour at 4° C. The yeast were separated from the supernatant by centrifugation and filtration through a 0.2 µm filter. The water soluble-extract was concentrated by a Centricon column with a 30 kD cutoff.

Vaccination and Infection.

Mice were Vaccinated as Described (Wüthrich, Filutowicz, et al., 2000), Twice, Two weeks apart, subcutaneously (s.c.) with 20 to 200 µg recombinant Calnexin emulsified in complete Freund's adjuvant or with 10$^8$ heat killed *C. albicans* yeast and mineral oil. Mice were infected intratracheally (i.t.) with 2×10$^3$ or 2×10$^4$ wild-type yeast of *B. dermatitidis* strain 26199, 2×10$^5$ *H. capsulatum* G217B, 2×10$^5$ FKS or 60 spores of the virulent *C. posadasii* isolate C735 (Wüthrich, Filutowicz, et al., 2000; Wisniewski, Zougman, et al., 2009; Nesvizhskii, Keller, et al., 2003; dos Santos Feitosa, de Almeida Soares, et al., 2007; Thompson, Higgins, et al., 1994; Wüthrich, Filutowicz, et al., 2007; Nemecek, Wüthrich, et al., 2006; Wüthrich Gern, et al., 2011). To assess the infiltration of primed CD4 T cells into the lungs, challenged mice were analyzed at day 4 post-infection. To analyze the extent of lung infection, homogenized lungs were plated and yeast colony forming units (CFU) enumerated on BHI agar (Difco, Detroit, MI), sheep-blood containing Mycosel plates, or GYE plates containing 50 µg/ml of chloramphenicol (Wüthrich, Gern, et al., 2011).

Adoptive Transfer of 1807 Cells and Experimental Challenge.

To assess the T helper cytokine phenotype of Calnexin-specific CD4$^+$ T cells after vaccination with Calnexin and various adjuvants, we transferred 10$^6$ naïve 1807 Tg cells into C57BL/6 wild-type mice before vaccination. On the same day, recipients were vaccinated, boosted two weeks later and challenged two weeks after the boost.

Intracellular Cytokine Stain.

Lung cells were harvested at day 4 post-infection. Cells (0.5×10$^6$ cells/ml) were stimulated for 4 hours with anti–CD3 (clone 145-2C11; 0.1 µg/mL) and anti–CD28 (clone 37.51; 1 µg/mL) in the presence of Golgi-Stop (BD Biosciences). Stimulation with fungal ligands yielded comparable cytokine production by transgenic T-cells compared to CD3/CD28 stimulation (data not shown). After cells were washed and stained for surface CD4 and CD8 using anti–CD4 PerCp, anti–CD8 PeCy7, and anti–CD44-FITC mAbs (Pharmingen), they were fixed and permeabilized in Cytofix/Cytoperm at 4° C. overnight. Permeabilized cells were stained with anti-IL-17A PE and anti-IFN-γ-Alexa 700 (clone XMG1.2) conjugated mAbs (Pharmingen) in FACS buffer for 30 min at 4° C., washed, and analyzed by FACS. Cells were gated on CD4 and cytokine expression in each gate analyzed. The number of cytokine positive CD4$^+$ T cells per lung was calculated by multiplying the percent of cytokine-producing cells by the number of CD4$^+$ cells in the lung.

Cytokine Protein Measurements of In Vivo Primed T Cells.

Cell-culture supernatants were generated in 24-well plates in 1 mL containing 5×10$^6$ splenocytes and lymph node cells and various concentrations of *Blastomyces* CW/M antigen (Wüthrich, Filutowicz, et al., 2000), rCalnexin, Drk1, and Calnexin peptides. Supernatant was collected after 72 hours of co-culture. IFN-γ and IL-17A were measured by ELISA as above.

In vitro stimulation and identification of activated human T cells. Peripheral blood mononuclear cells (PBMC) were isolated from heparinized whole blood collected over histopaque 1119 and 1077. Studies were approved by UW-Madison IRB (protocol 2014-1167). Patients provided informed consent. PBMC were stimulated with 10 µg/ml r-calnexin, 10$^7$/ml heat killed *C. albicans* or crude or purified fungal Ag (10 µg/ml *Blastomyces* CW/M, 5 µg/ml *Histoplasma* CW/M, 100 µg/ml *Blastomyces* alkali-soluble, water-soluble (ASWS) Ag, 10 µg/ml Coccidioidin, and 5 µg/ml *Histoplasma* Hsp60) plus 5 U/ml IL-2 and 1 µg/ml α-human CD40 mAb for 14 hr at 37° C./5% CO$_2$. After stimulation, cells were bead-enriched by CD154$^+$ selection (Miltenyi). Enriched cells were stained with live/dead blue fluorescent dye (Life Technologies), and α-CD8 PerCP, –CD4 PeCy-7, –CD3 BV785, –B220 Pacblue, –CD154 PE and –CD137 APC. B220$^-$, CD8$^-$, CD3$^+$, CD4$^+$ T cells were analyzed for CD137 and CD154 expression using FlowJo.

Statistical Analysis.

The number and percentage of activated, proliferating or cytokine producing T-cells and differences in number of CFU were analyzed using the Wilcoxon rank test for non-parametric data (Fisher and vanBelle, 1993) or the T-test when data were normally distributed. A P value of <0.05 is considered statistically significant.

SUMMARY

We described an effective live, attenuated vaccine against infection with *Blastomyces dermatitidis* (Wüthrich et al., 2000). This dimorphic fungus causes the systemic mycosis blastomycosis and exhibits genetic and morphological similarities to six related dimorphic fungi that cause human disease: *Histoplasma capsulatum, Coccidioides posadasii* and *immitis, Penicillium marneffei, Sporothrix schenkii* and *Paracoccidioides brasiliensis*. The dimorphic fungi are in the fungal taxon Ascomycota, which includes diverse members such as *A. fumigatus* and also the white nose fungus, *Pseudogymnoascus destructans*, the cause of epidemic fatal disease spreading among bats across the U.S. Analysis of the attenuated vaccine against blastomycosis revealed that resistance is mediated by CD4$^+$ T cells; cloning of the protective T cells disclosed the identity of the T cell receptor (TCR) and enabled the generation of a TCR (Tg) transgenic mouse, termed 1807. TCR Tg 1807 cells recognize and respond to all the dimorphic fungi of North America (*Blastomyces, Histoplasma, Coccidiodes*) and confer resistance against lethal experimental infection with each of them (Wüthrich et al., 2011a; Wüthrich et al., 2011b). These findings imply that the T cells recognize a conserved Ag in dimorphic fungi and perhaps fungal Ascomycetes.

Here, we sought to identify a conserved Ag in pathogenic fungi. We used broadly reactive, protective 1807 cells to probe for such an Ag. We report that calnexin, which is generally thought of as an intracellular resident of endoplasmic reticulum, is displayed on the fungal surface and represents the shared Ag of 1807 cells. We also describe that the calnexin epitope is highly conserved in the taxon Ascomycota. Finally, by using calnexin-peptide MHCII tetramers, we show that fungal display of this sequence across numerous ascomycetes induces the expansion of calnexin-specific CD4+ T cells that can be harnessed for vaccine immunity against multiple fungal pathogens.

Results

Steps Used to Identify Calnexin as the Shared Antigen (Ag).

Figure 1C:
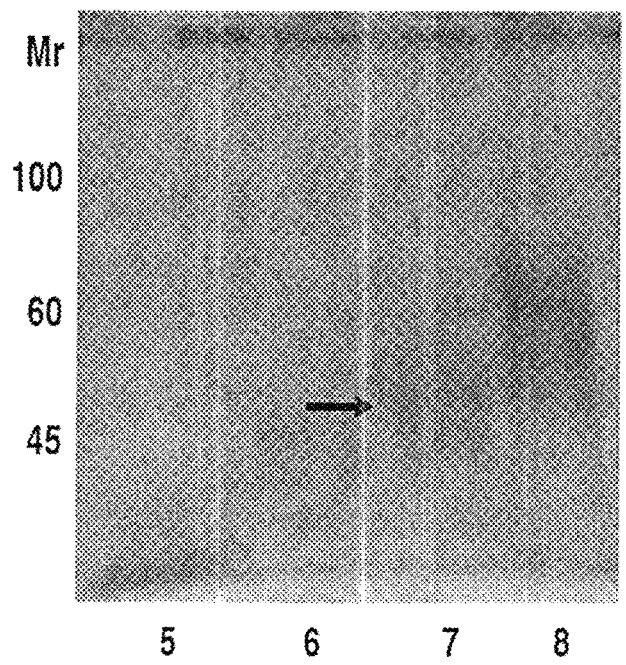
FIG. 1C is a graph showing identity of shared fungal antigen (Ag). Gel free separation of Eluate #1 into fractions by molecular weight.
Figure 1D:
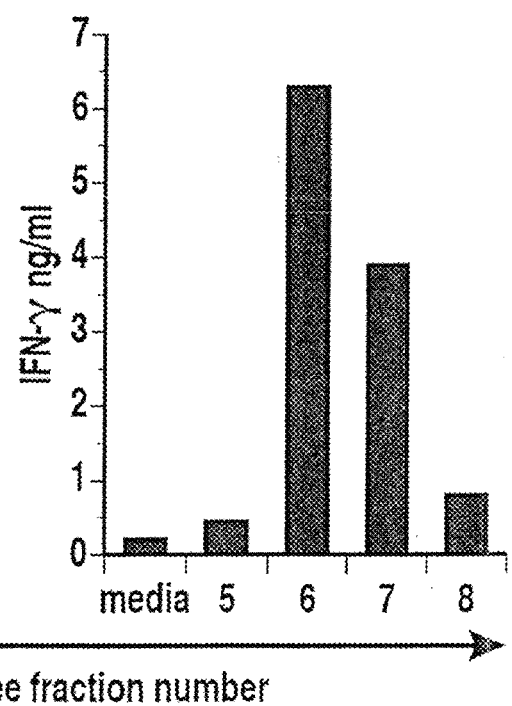
FIG. 1D is a graph showing identity of shared fungal antigen (Ag). Stimulation of 1807 TCR Tg cells in vitro by gel free fractions from panel C, as measured by IFN-γ response. The T cells by Calnexin peptide 1. $10^5$ BMDC were loaded with various concentrations of antigens or peptides shown and then co-cultured with $3 \times 10^5$ CD4+ purified 1807 T cells. Three days later, T-cells were analyzed for activation by flow cytometry.
Figure 1E:
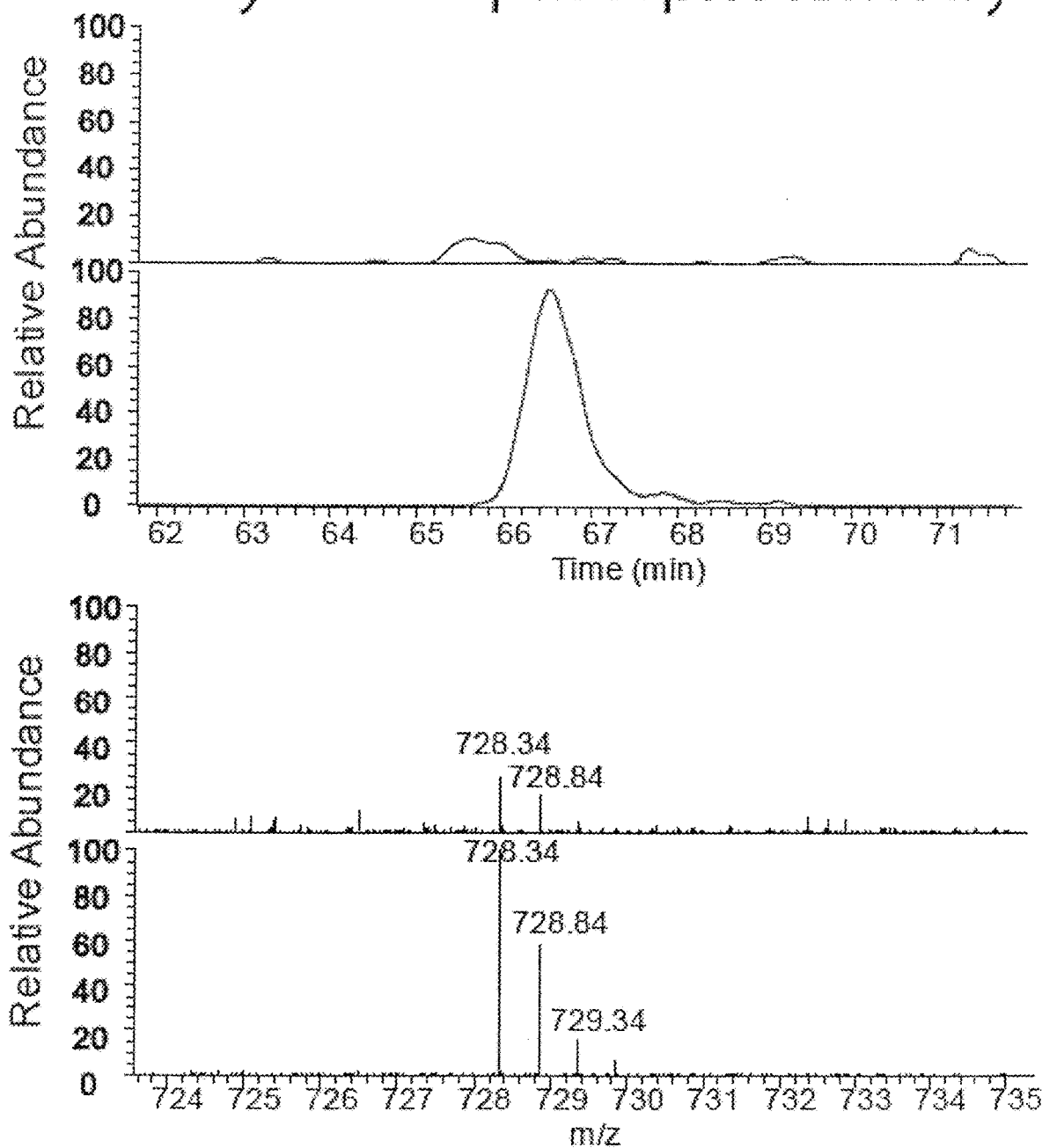

1807 TCR Tg cells recognize a protective antigen that is shared among systemic dimorphic fungi (Wüthrich, Hung, et al., 2011; Wüthrich, Ersland, et al., 2012). To identify the shared antigen, we prepared a cell wall membrane (CW/M) extract from B. dermatitidis vaccine yeast as previously described (Wüthrich, Filutowicz, et al., 2000). After running CW/M through a Con A column that retains mannosylated proteins, we collected Eluate 1, which contained 1% of the protein present in the starting material (FIG. 1A). Traces of active Con A released from the column into Eluate #1 were heated to destroy its mitogenic activity (not shown). Eluate #1 (FIG. 1B) was further fractioned in a gel free system to separate individual constituents by size (FIG. 1C). Fractions 6 and 7 stimulated 1807 T cells to produce IFN-γ, whereas medium alone as a control, and fractions 5 and 8 did not (FIG. 1D). To identify the T cell reactive Ag, we subjected fraction 7 to mass spec analysis. Proteins were identified by cross-referencing the mass of detected peptides against a database of the B. dermatitidis proteome. Proteins present in non-stimulatory fractions and proteins diverging from the mass parameters of the gel-free fraction were discounted. This technique yielded a roster of five protein candidates potentially representing the shared antigen. Calnexin was one of these five proteins (FIG. 1E).

Proof that Calnexin is the Shared Antigen

Figure 2B:
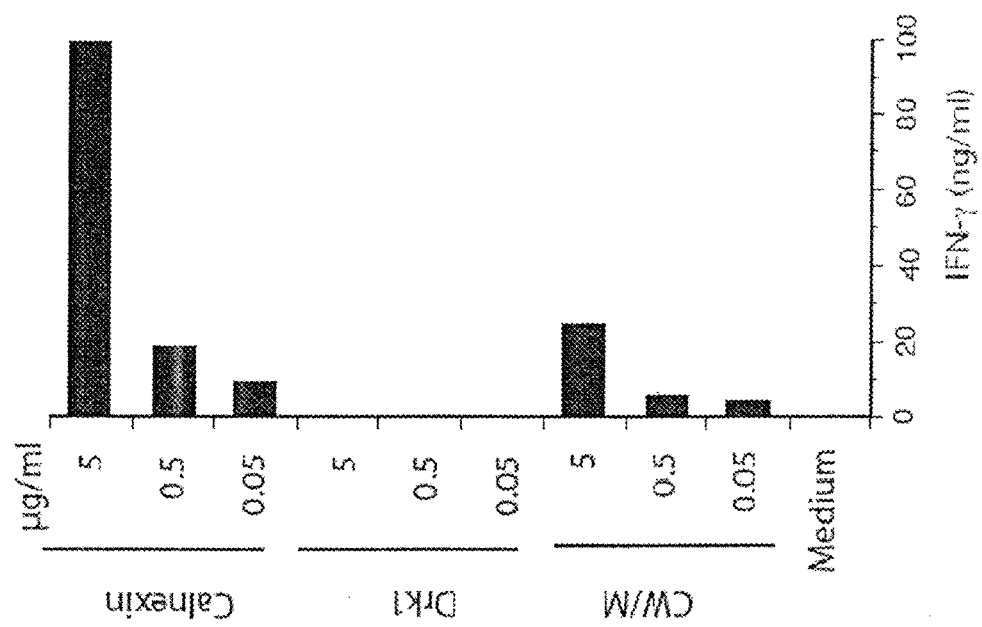
Figure 2A:
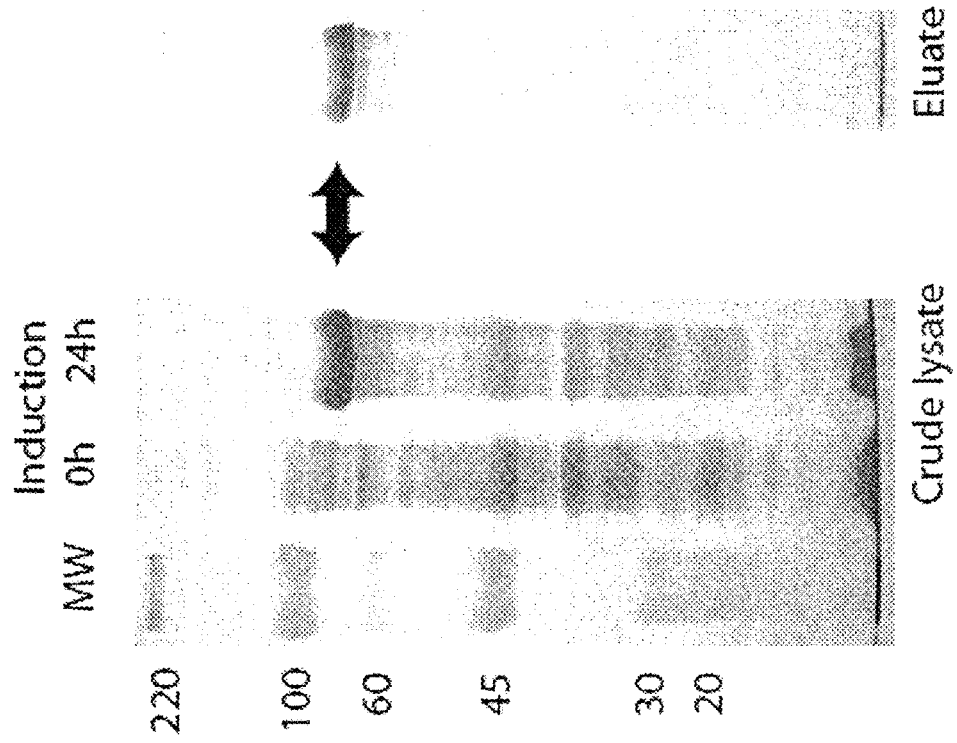

To investigate whether Calnexin is the shared Ag that stimulates 1807 T cells, we cloned the gene into the plasmid pET28c and used IPTG to induce gene expression in transfected E. coli. 24 h later, the crude lysate from E. coli harbored an additional prominent band that migrated between 60-70 kD, which corresponds with the predicted molecular weight of 63 kD for recombinant Calnexin (rCalnexin) (FIG. 2A). We purified the recombinant protein over a Ni-NTA column (FIG. 2A) and used the eluate to stimulate 1807 cells in an in vitro co-culture system with BMDC. In response to rCalnexin, 1807 T cells produced IFN-γ in a dose-dependent manner. The response to rCalnexin exceeded the response to CW/M extract, which also harbors Calnexin, but at a lower concentration (FIG. 2B). In contrast, recombinant Drk1—a hybrid histidine kinase of B. dermatitidis (Nemecek, Wüthrich, et al., 2006) expressed and purified from E. coli as a control—did not induce IFN-γ production by 1807 T cells. Thus, rCalnexin (not LPS from E. coli) induced cytokine production by 1807 T cells specifically and in a dose-dependent manner.

Figure 2C:
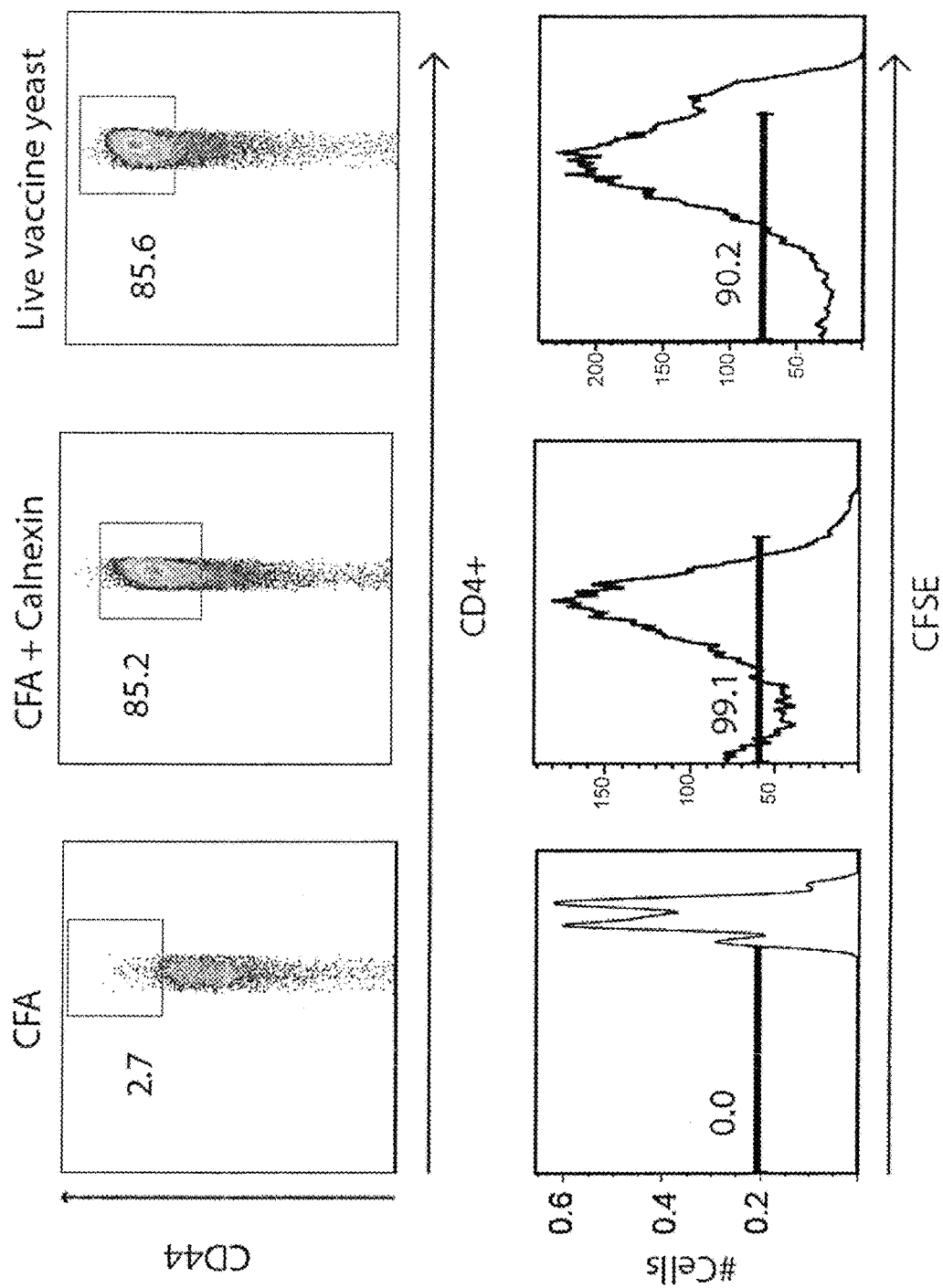

To investigate whether rCalnexin induces activation and proliferation of 1807 cells in vivo, we adoptively transferred 1807 Tg T cells into naïve wild-type recipient mice prior to vaccination. Similar to live B. dermatitidis vaccine yeast, rCalnexin emulsified in complete Freund's adjuvant activated and stimulated proliferation of >85% of the transferred 1807 cells (FIG. 2C), whereas adjuvant alone did not. These results identify Calnexin as the shared Ag that is recognized by 1807 TCR Tg T cells, which confer resistance to multiple systemic dimorphic fungi (Wüthrich, Hung, et al., 2011; Wüthrich, Ersland, et al., 2012).

Identification of Calnexin's Peptide Epitope

To identify the 1807 T cell reactive peptide epitope, we first aligned the amino acid sequence of the fungal species that we have reported stimulate 1807 T cells in vivo (Wüthrich, Hung, et al., 2011), including B. dermatitidis, H. capsulatum, C. posadasii and P. brasiliensis. We investigated regions of sequence conservation that might represent the shared epitope for the 1807 T-cell receptor. We found that Calnexin is highly conserved across the entire Calnexin sequence among this group of dimorphic fungi (FIG. 6). Thus, the identification of highly conserved areas of the protein was not a sufficient measure to hone in on the 1807 epitope-containing sequence. To narrow the focus of possible peptides to test for 1807 reactivity, we subjected Blastomyces Calnexin to two class II I-Ab restricted-epitope prediction algorithms (FIG. 6). The IEBD algorithm predicted six regions of overlapping peptides with binding affinities values ($IC_{50}$) less that 500 nM. In a second analysis, an algorithm developed in Marc Jenkins' laboratory (unpublished data) refined the above analysis, and predicted ten strong $H_2$-IAb epitopes in B.dermatitidis Calnexin (FIG. 6). We chemically synthesized peptides of thirteen amino acids in length, representing these ten predicted epitopes (named Peptide #1 though Peptide #10), and tested them to determine the cognate epitope for the 1807 T-cell receptor.

Figure 3A:
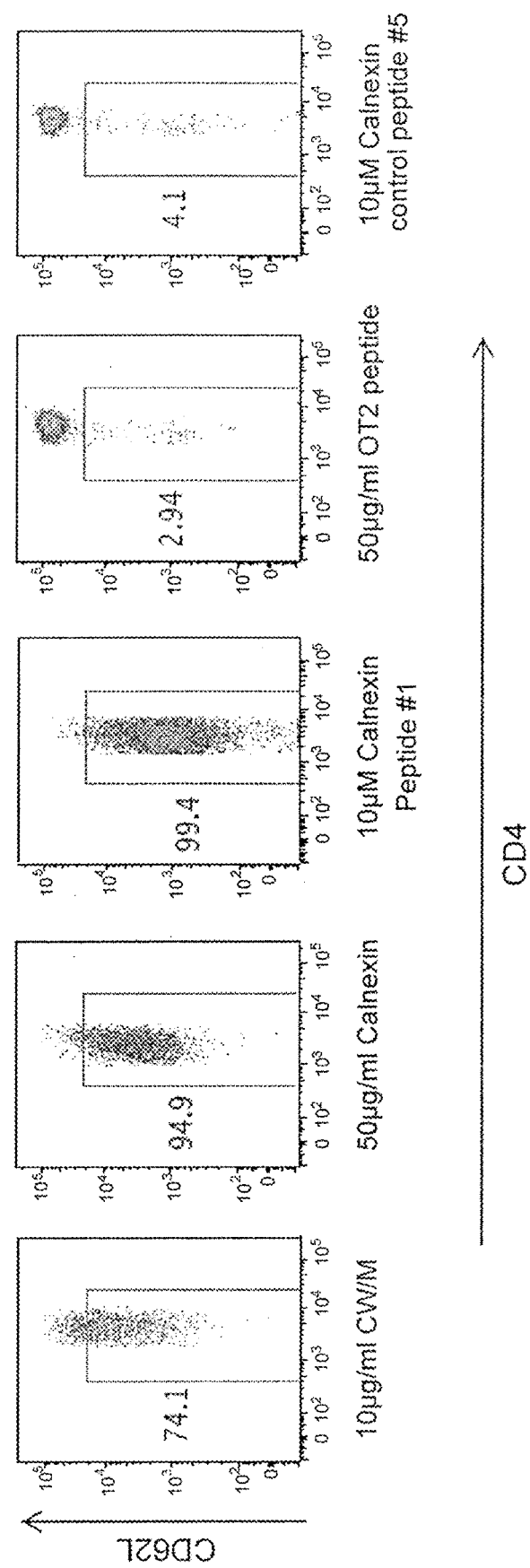
FIG. 3B is part of a set of graphs showing identification of Calnexin's 1807 TCR epitope. Naïve 1807 T cells were co-cultured as in Panel A, and cell culture supernatants analyzed for IFN-γ by ELISA.
FIG. 3C is part of a set of graphs showing identification of Calnexin's 1807 TCR epitope. In vivo activation of 1807 T cells by Calnexin peptide #1.
Figure 3B:
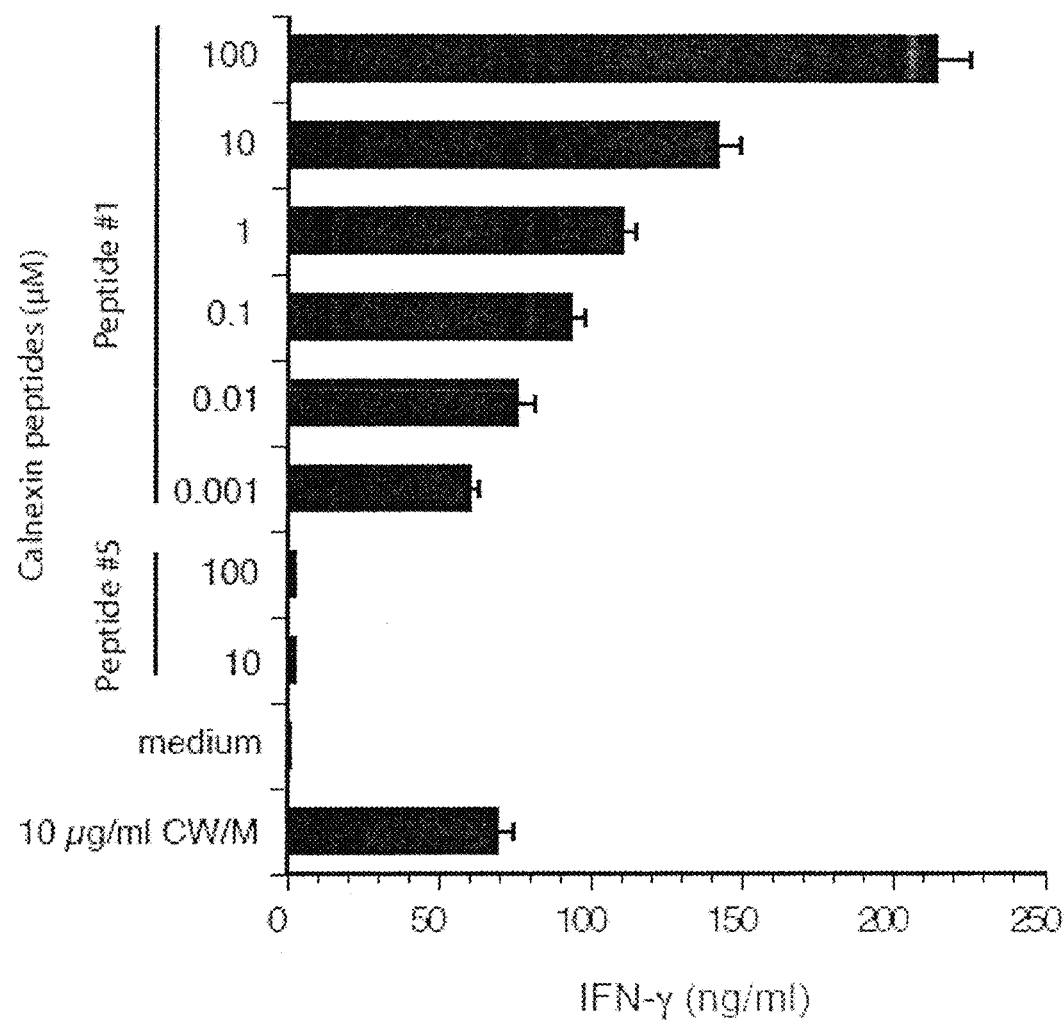
Figure 3C:
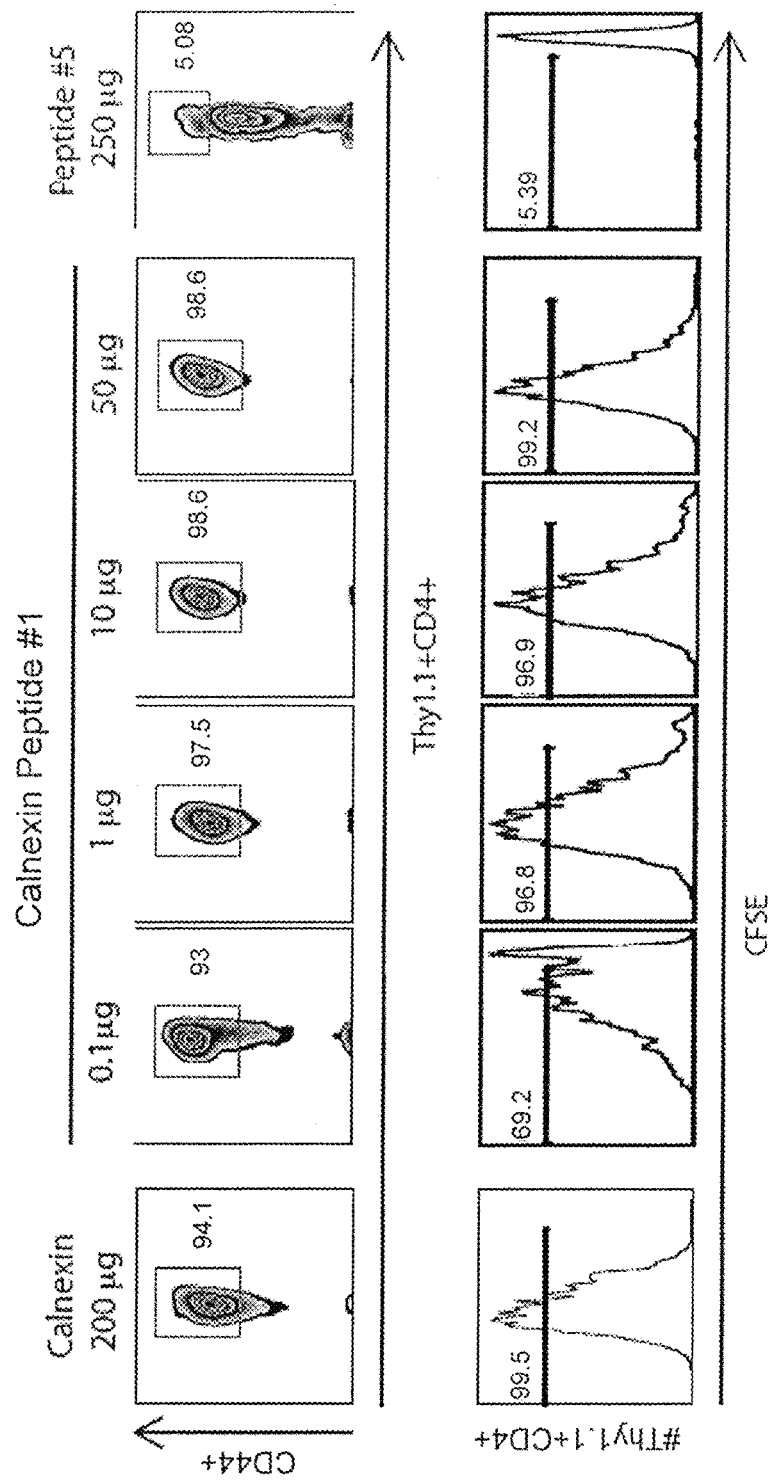

To test whether the synthetic peptides activate naïve 1807 T cells in vitro, we loaded BMDC with individual peptides and co-cultured them with 1807 cells. Peptide #1 (comprised of the sequence LVVKNPAAHHAIS (SEQ ID NO: 1) activated naïve 1807 T cells as measured by their reduced expression of CD62L (FIG. 3A) and increased expression of CD44 (data not shown). An irrelevant control, ovalbumin (OT-II) peptide, and all other synthetic calnexin peptides did not activate 1807 cells. Peptide #1 also stimulated the production of IFN-γ by 1807 cells in a concentration-dependent manner (FIG. 3B). As little as 1 to 10 nM of peptide #1 stimulated as much IFN-γ as 10 μg/ml of CW/M Ag, which has been shown to induce substantial amounts of the cytokine (data not shown). None of the other calnexin peptides induced IFN-γ production by 1807 cells. In vivo, 0.1 to 1 μg of peptide #1 was enough to activate and induce the proliferation of naïve 1807 T cells (FIG. 3C). Thus, peptide #1 is the T-cell epitope recognized by 1807 cells.

Evidence that Calnexin is Displayed on the Yeast Surface

Figure 4A:
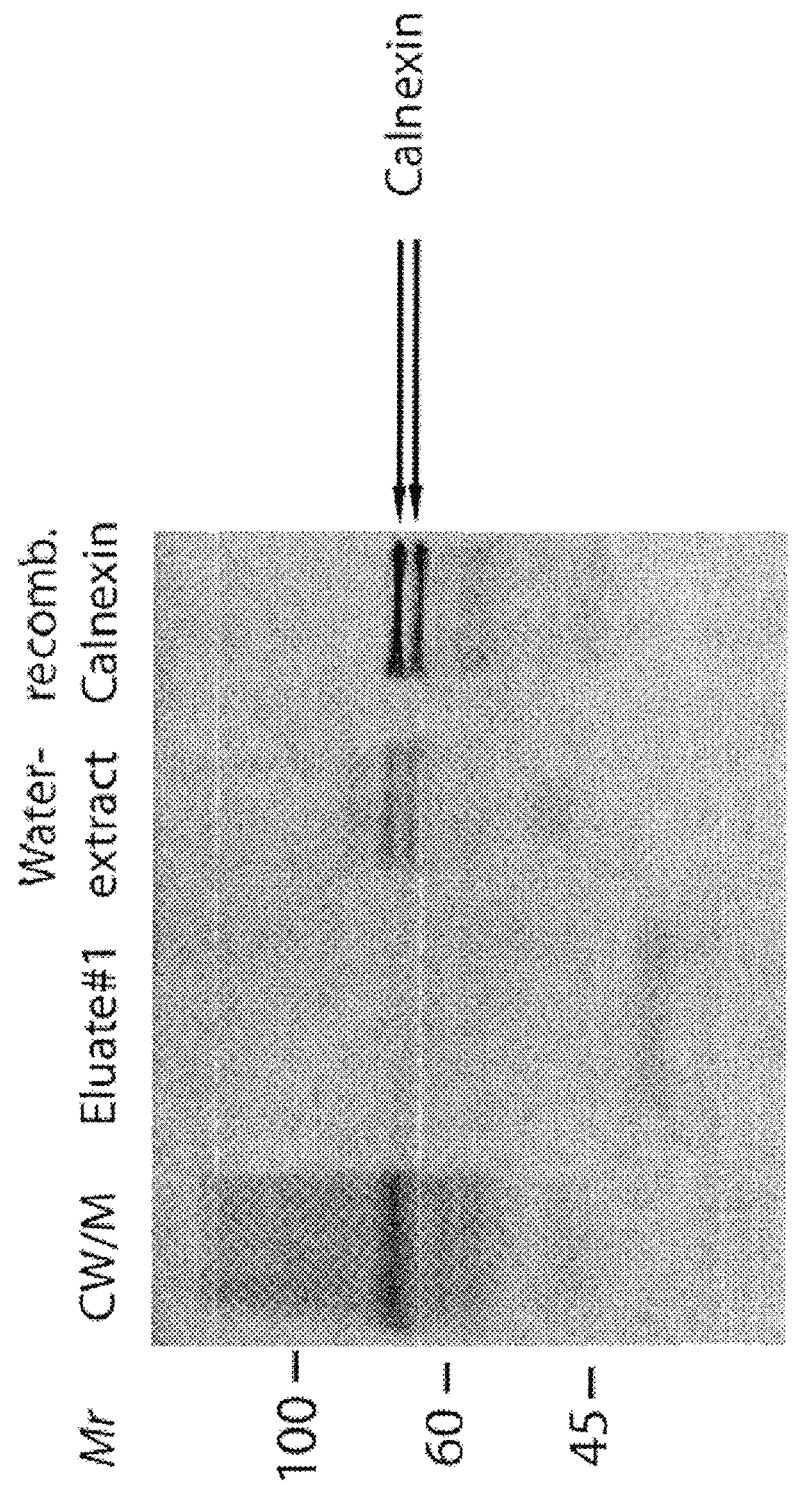

Among fungal pathogens, most of the virulence factors and antigenic proteins are secreted or associated with the cell wall or surface. Despite the fact that Calnexin is a molecular chaperone and folding sensor that regulates the transport of proteins from the ER to the Golgi apparatus (Ellgaard and Helenius, 2003), vaccination with B. dermatitidis yeast efficiently stimulates 1807 T cell responses in vivo. To address this unexpected finding, we investigated whether calnexin is displayed on the yeast surface. During our early search for the shared Ag, we found that a water-soluble extract of surface proteins from the vaccine yeast activated 1807 T cells (data not shown). Western-blot analysis of the water-soluble extract detected a doublet that migrated on SDS-PAGE at the same position as rCalnexin produced by E. coli (FIG. 4A). To investigate whether B. dermatitidis vaccine yeast harbor Calnexin on their surface, we stained yeast with polyclonal anti-Calnexin antibodies. Both in vitro and in vivo grown vaccine yeast stained positively with the anti-Calnexin serum (FIG. 4B and FIG. 4C). The virulent parental strain 26199 that is used for the pulmonary challenge of mice also harbored Calnexin on the yeast surface when harvested and stained at day 4 post-infection (FIG. 4C). Since calnexin is shared among ascomycetes, we tested whether it is also expressed on the surface of *Aspergillus fumigatus*. Exposure of hyphae and spores to anti-calnexin antibody showed punctate surface staining and fluorescence (FIG. 4C). Thus, calnexin is detectable on the surface of *B. dermatitidis* yeast and *A. fumigatus* hyphae and spores.

Functional Relevance of Calnexin and Peptide T Cell Responses.

Figure 5A:
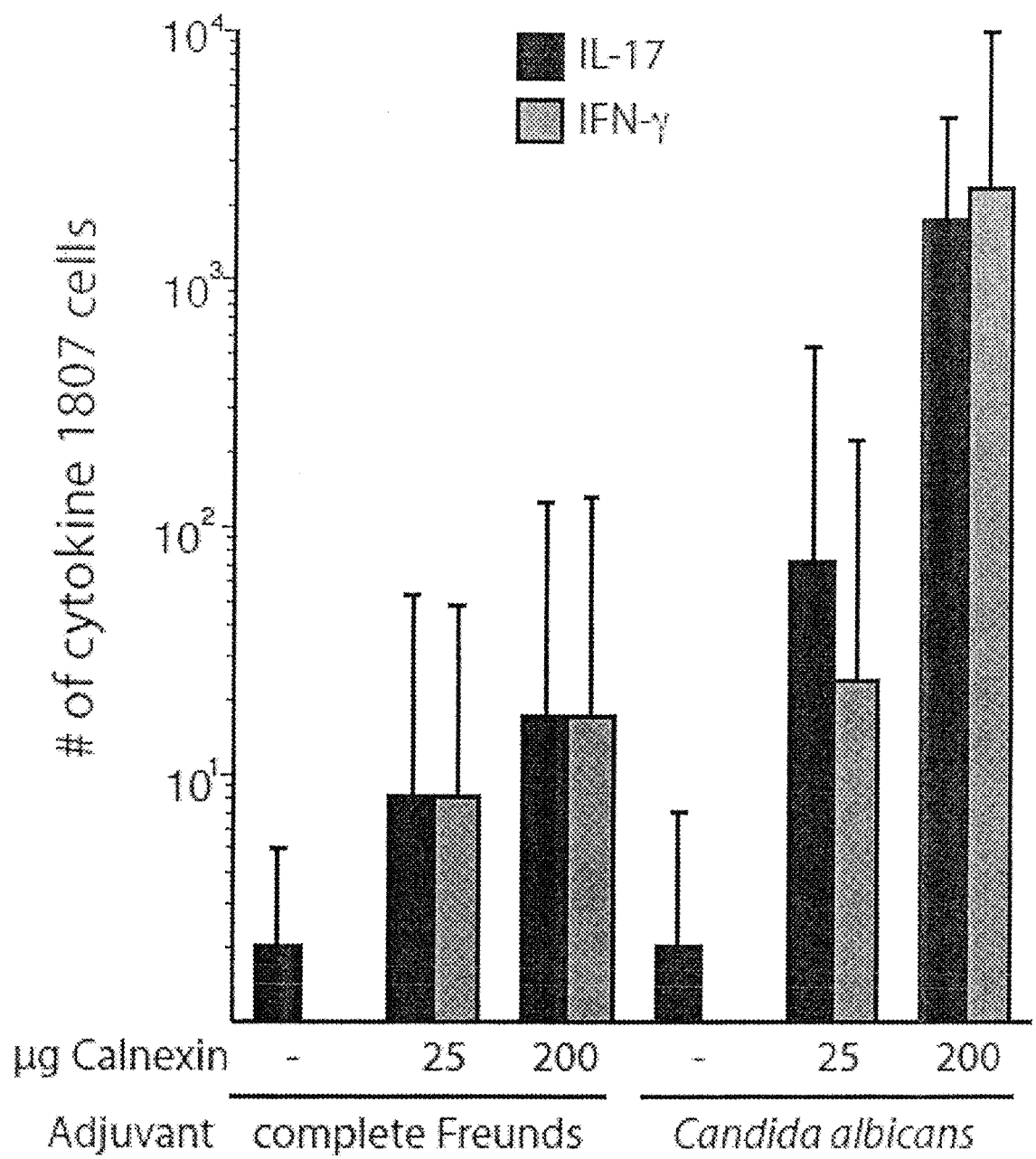
FIGS. 5A and 5B are a set of graphs of experimental observations showing response to Calnexin.
Figure 5B:
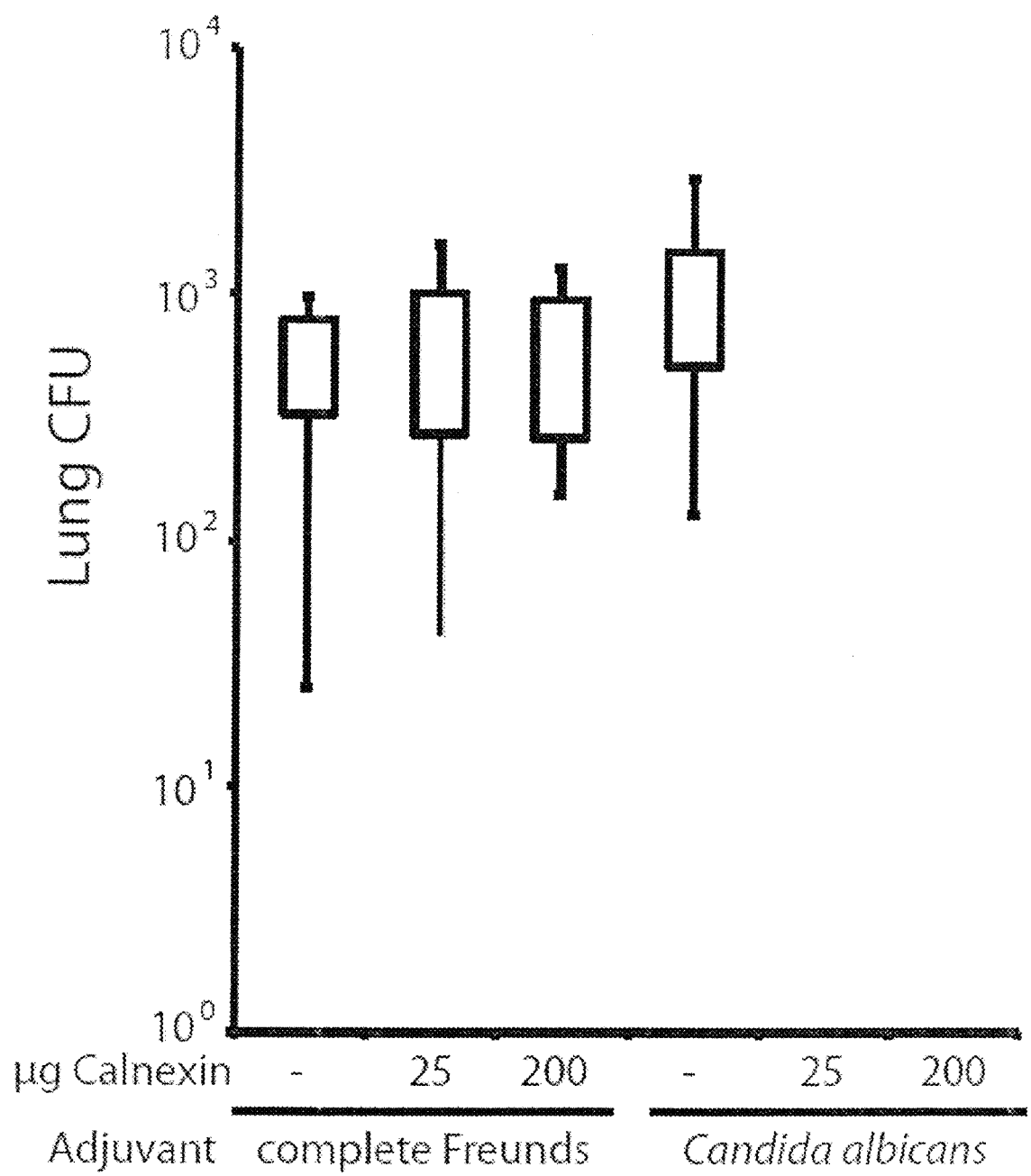

To determine whether vaccination with Calnexin induces protective immunity against lethal *B. dermatitidis* infection, we immunized mice with soluble recombinant protein plus either complete Freund's adjuvant (CFA) or heat killed *C. albicans* yeast (contains fungal PAMPs) to polarize naïve T cells into Th1 cells or Th17, respectively (LeibundGut-Landmann, Gross, et al., 2007). To evaluate whether these vaccine formulations efficiently stimulate the generation and recruitment of Th17 and Th1 cells to the lung upon recall, we adoptively transferred naïve 1807 T cells into mice prior to vaccination and determined the number of cytokine producing 1807 T cells at day 4 post-infection. Mice vaccinated with Calnexin recruited Th17 and Th1 cells into the lung in a dose and Ag-specific manner. The antigen formulation prepared with heat killed *C. albicans* yeast expanded more 1807 T cells than that prepared with CFA (FIG. 5A). Most strikingly, mice that were vaccinated with rCalnexin and *C. albicans* yeast as the adjuvant completely cleared lung infection by day 4 post-infection, whereas mice vaccinated with either *Candida* adjuvant alone or Calnexin and CFA together did not (FIG. 5B). These data indicate that recombinant Calnexin protein has the capacity to protect vaccinated mice against lethal pulmonary infection when Ag-specific T cells have been primed in sufficient numbers.

Peptide Prediction Of Calnexin Fragments To Human.

Applicants performed an analysis of the predicted peptides that could work with the known epitope binding domain of several Human HLA DRB1 alleles, using the publicly available ProPred software (imtech.res.in/raghava/propred/). The results were shown in FIGS. 7A, 7B, 7C, 7D, 7E, and 7F. In the output, the Blasto Calnexin sequence was shown on a separate line for each of 51 DRB1 alleles, and peptides that are predicted to fit in the MHCII groove of that allele were indicated in blue, with red used to indicate a so-called anchor amino acid that would be at position one of the 9 amino acid core sequence. A peptide of interest is "promiscuous" if it is predicted to interact with many different human MHCII molecules. Since the human HLA locus is so polymorphic, a good vaccine for humans will have to have epitopes that are promiscuous, and can work with many different HLA MHC molecules in order to stimulate an immune response. The results in FIGS. 7A, 7B, 7C, 7D, 7E, 7F, 7G and 7H shows that Blasto Calnexin does, indeed, have several peptide sequences (blue) that are predicted to fit into the MHC groove for presentation to T-Cells. Of particular interest is that there is a predicted epitope for the sequence of Peptide1 (which was predicted for B6 mouse HLA interaction, and has been experimentally shown to do so with 1807 cells) at position 103 to 115. There were several other promiscuous epitopes throughout the Calnexin sequence as predicted by the ProPred software.

Peptide MHCII Tetramers To Detect Endogenous Calnexin Specific Cd4 T Cells

Applicants have taken advantage of the discovery of calnexin as a major shared antigen that is recognized by T cells that mediate protection against pathogenic fungi that are members of the broad fungal taxonomic group called Ascomycetes. Having already discovered that calnexin peptide #1 specific T cells recognize many of these fungi and confer protection against them, Applicants created an immunogical tool—peptide-MHCII tetramers (pMHC tetramers)—to track the emergence and persistence of these T cells after exposure to the fungus in question. The synthesis of pMHCII tetramers has been previously described. The present application discloses methods of creating reagents to identify and track calnexin peptide specific T cells.

Applicants have now used the tetramers to find and quantify "endogenous" calnexin peptide #1 specific T cells that reside in the body before infection, and then to monitor their response, expansion and characteristics after infection and vaccination. Applicants initiated this work by studying mice before and after infection with *Blastomyces dermatitidis* or after vaccination with calnexin recombinant protein or attenuated *B. dermatitidis*. Applicants envision that the process of the experiments may be extended to other fungi that are members of the family of ascomycetes. Other fungi may include *Histoplasma capsulatum*, Aspergillusfumigatus, *Fonsecea pedrosoi*, and *Geomyces destructans* (the latter is the "white nose fungus", which is decimating bat populations in North America), to name a few. Applicants results suggest that infection with these fungi activates and expands endogenous calnexin peptide #1 specific T cells.

The tetramers that we are developing pave the way toward a clinical application. Individuals with cancer or other disorders who are to receive bone marrow or stem cell transplants may be at risk for opportunistic fungal infection with *Aspergillus* species. These infections may carry high morbidity and mortality rates that reach 80-90%. It would be clinically advantageous to use the tetramer to screen and discern whether a bone marrow or stem cell donor has evidence of strong immunity against *Aspergillus* as a way of planning the clinical management of the recipient. For example, the tetramers in the present application may be used to, 1) gauge the risk of *Aspergillus* infection in the transplanted recipient (who will receive the immune or non-immune cells); 2) to plan anti-fungal prophylaxis strategies for the at-risk recipient, or 3) plan vaccination of the donor (pre-transplant) to induce calnexin or peptide #1 antigen-specific T cells.

Calnexin Peptide #1 in Fungi and Activation of T Cells In Vivo.

Figure 11:
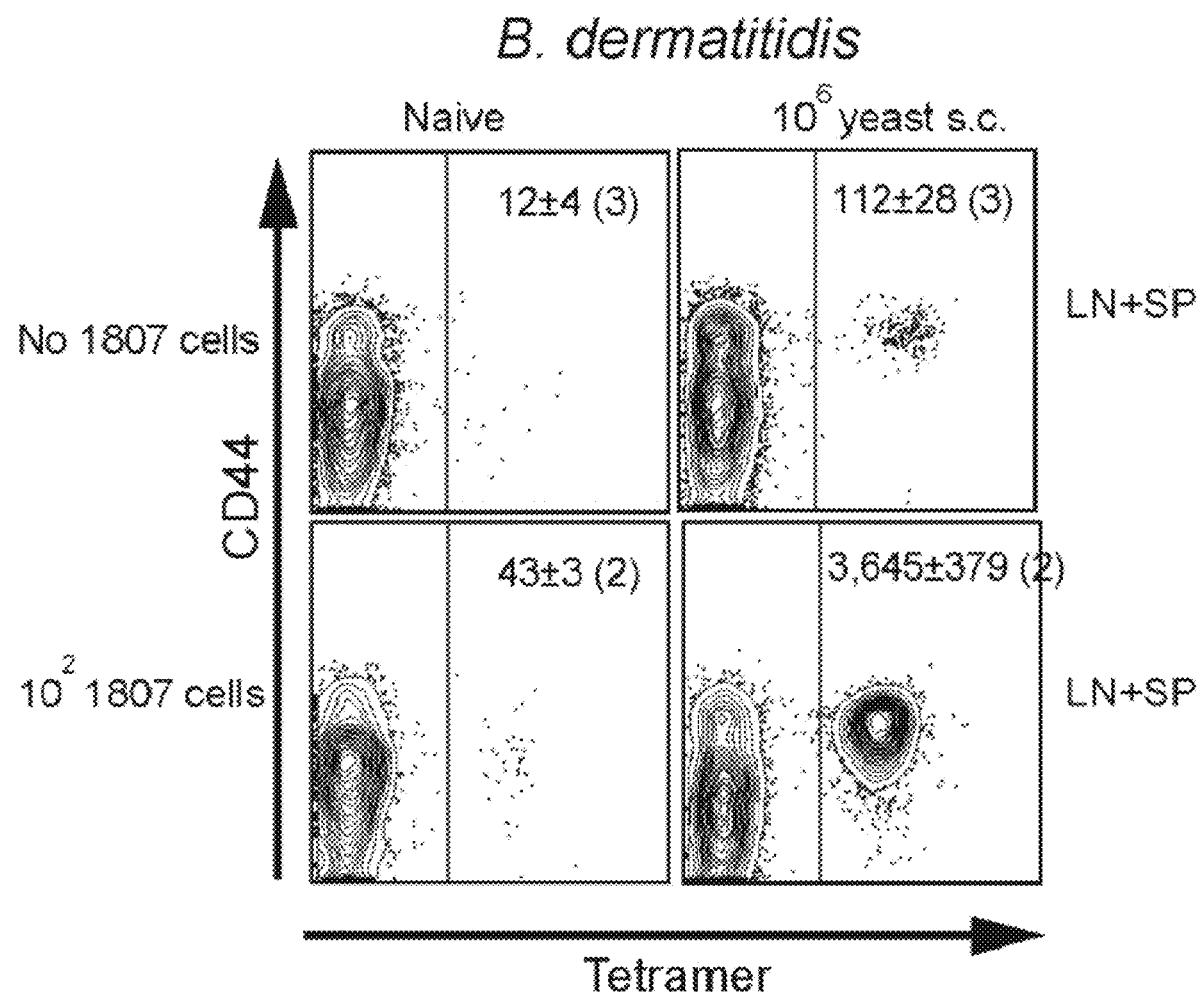
FIG. 11 is a set of graphs showing tetramer enrichment of endogenous, fungal-specific T cells ex vivo. Mice received naïve 1807 T cells or not and were infected by doses and routes shown for B. dermatitidis yeast, F. pedrosoi spores, A. fumigatus spores, H. capsulatum yeast and P. destructans spores. 7 d post-infection, the skin draining lymph nodes (LN), spleen (SP) or lungs were collected. The number of calnexin peptide #1-specific CD4+ T cells were analyzed and quantified after tetramer enrichment as detailed in the Methods. Tetramerpositive cells are shown to the right of the gate in each dot plot. The number represents the geometric mean±SEM of tetramer-positive cells, with number of mice studied in parenthesis.
Figure 15:
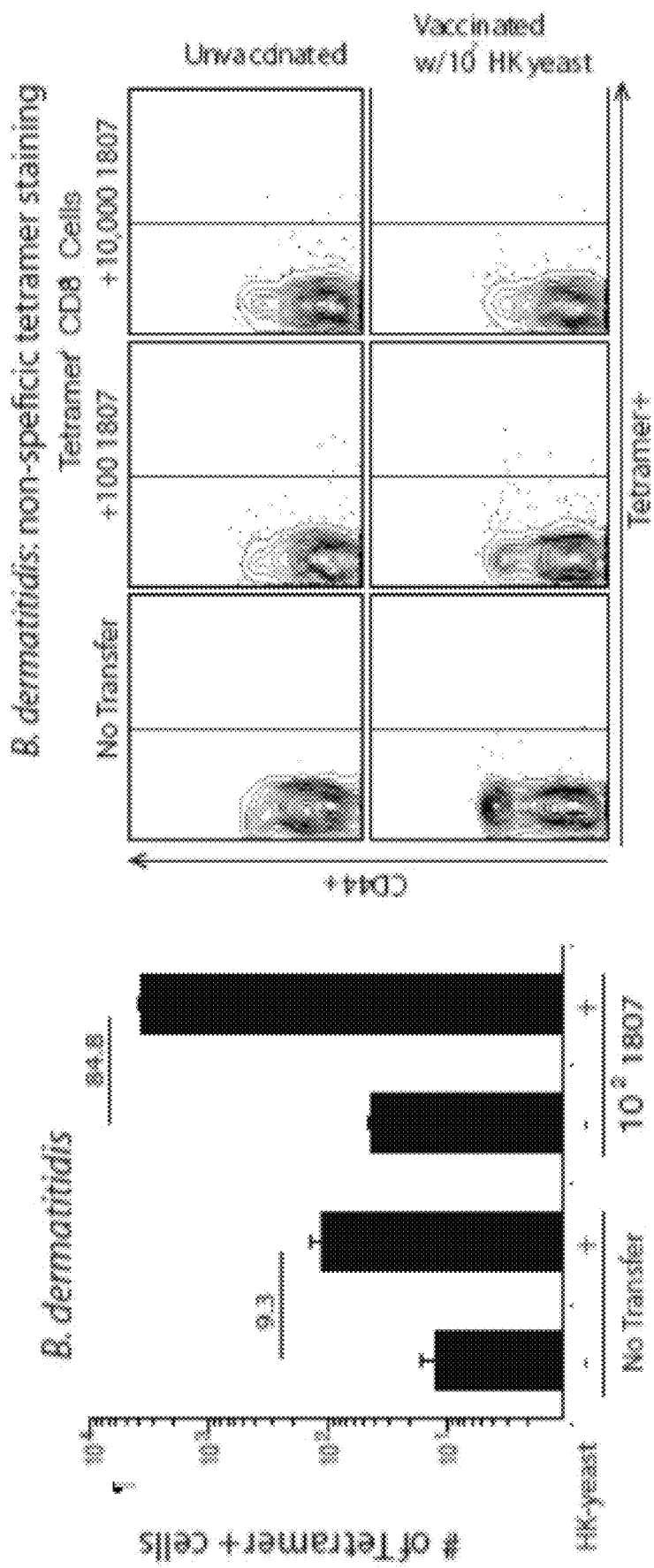
FIG. 15 are a set of graphs showing expansion of calnexin specific endogenous and 1807 cells in response to ascomycete fungi. Mice received naïve 1807 cells or not and were infected with the fungi shown in FIG. 12. 7d post-infection, the skin draining lymph nodes (LN), spleen (SP) or lungs were collected and the number of calnexin peptide #1-specific CD4+T cells were analyzed by tetramer enrichment. The fold change in tetramer-positive cells from fungus-exposed vs. naïve controls were calculated by dividing the geometric means and are indicated in the histograms. To validate the specificity of the tetramer staining, dot plots in the upper right show tetramer vs. CD44 staining of CD8+ T cells in mice exposed to *Blastomyces*.
Figure 16A:
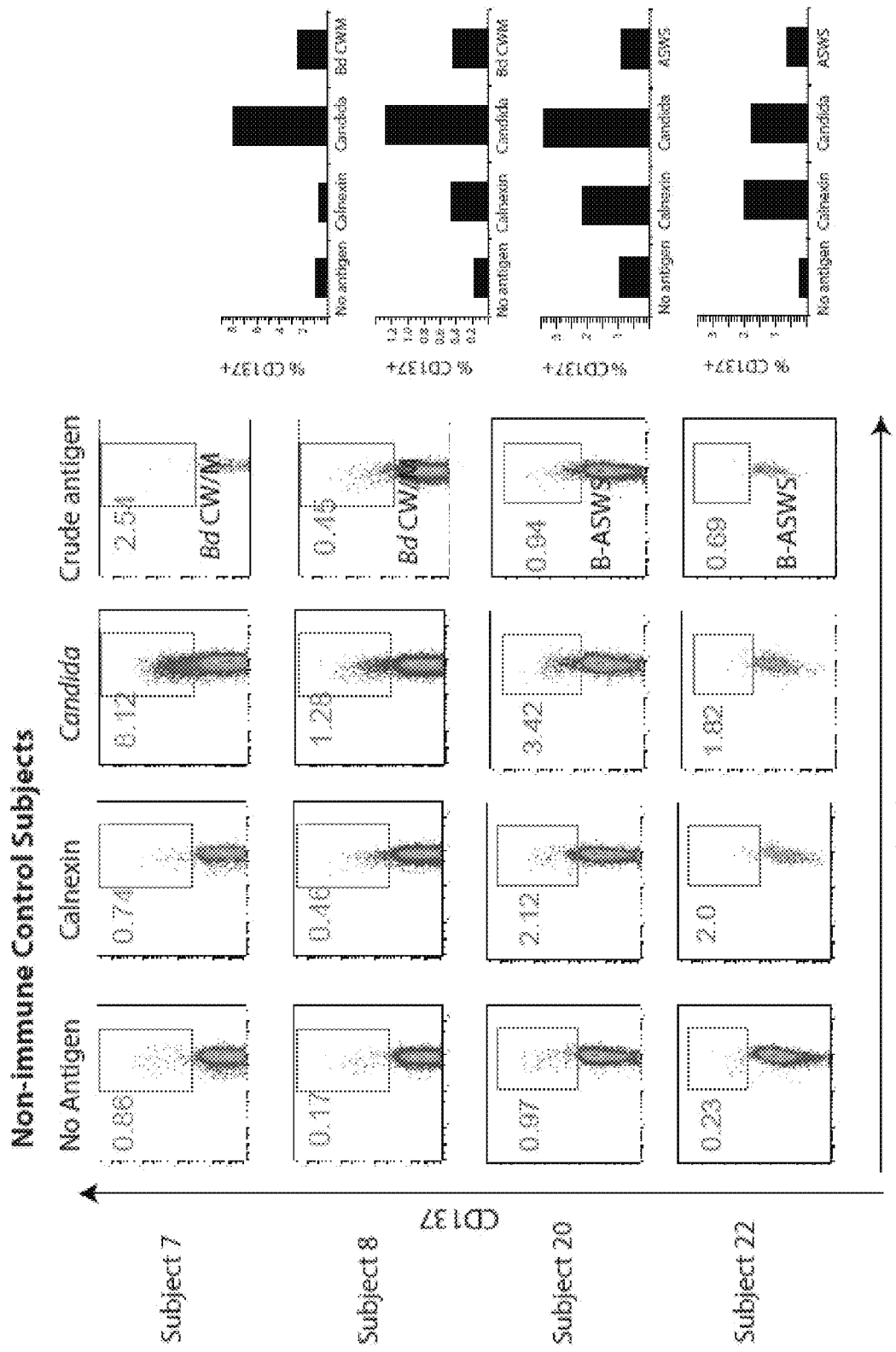
FIGS. 16A, 16B, 16C and 16D are a set of graphs showing response of immune and non-immune human subjects to calnexin and other fungal antigens. PBMC was collected from subjects with proven infection or a history of prior exposure to *H. capsulatum* (Hc), *B. dermatitidis* (Bd), *C. posadasii* (Cp) or *P. marne_ei* (Pm) (immune subjects) and healthy normal control subjects (non-immune subjects). PMBC were stimulated overnight with medium alone, r-calnexin or control Ag shown. Activated CD4+ T cells were enriched based on CD154 expression (Methods). Enriched cells were stained for a second activation marker CD137. The frequencies of anti–CD154 enriched CD8–/CD3+/CD4+ cells that express CD137 are shown in dot plots (left) and histograms (right). A positive response to the relevant crude fungal Ag (far right) was defined as >3-fold more than the response in medium alone. Thus, none of the non-immune subjects were positive, whereas all of the immune subjects were positive to the corresponding crude fungal Ag. Non-immune (FIG. 16A) and immune (FIG. 16B) subjects were assayed for the responses to r-calnexin (10 μg/ml) and a positive control (*Candida*). One of four non-immune subjects responded to calnexin (#22), while five of six immune subjects responded to calnexin (#18 did not respond).
Figure 16B:
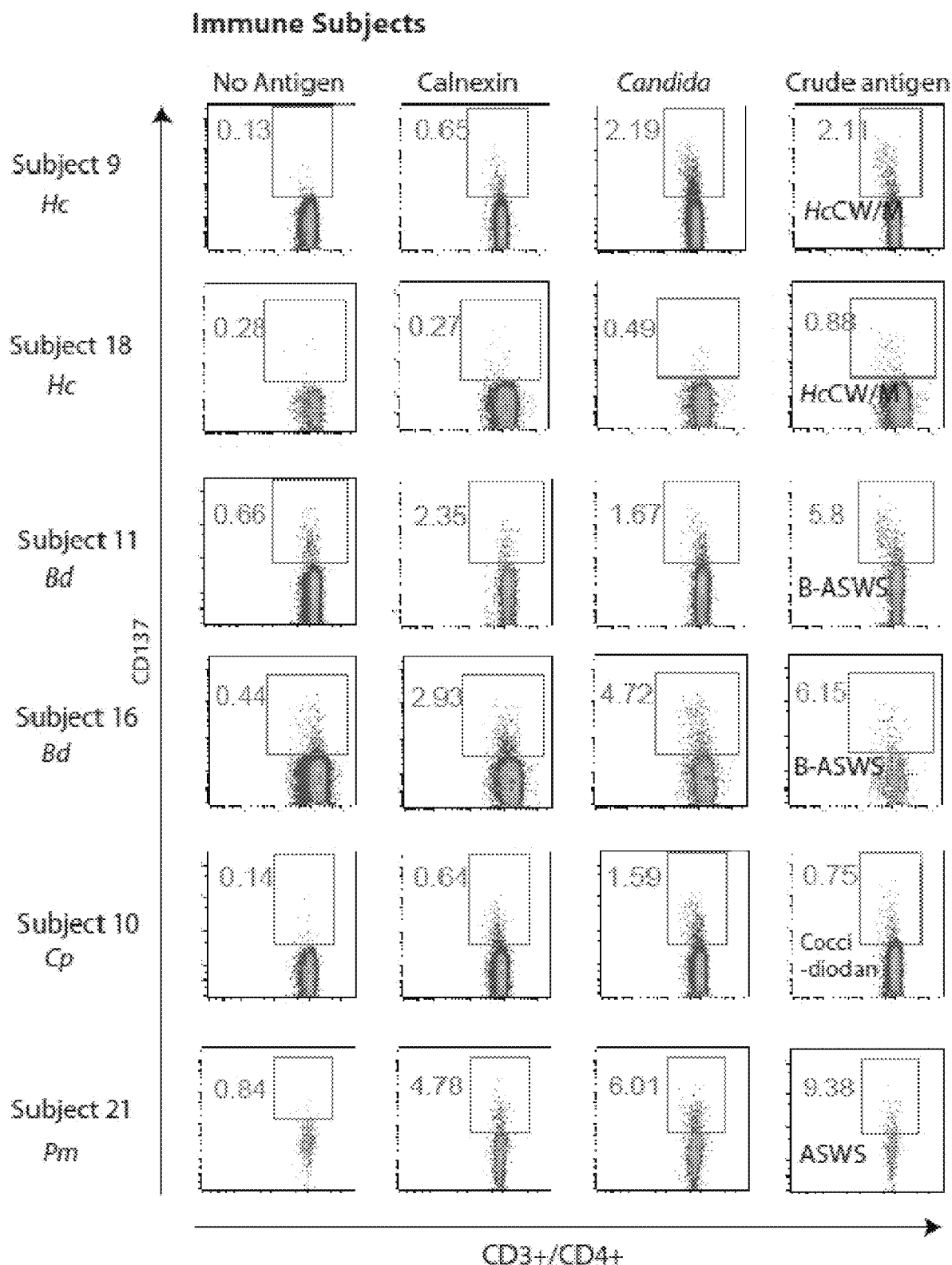
Figure 16C:
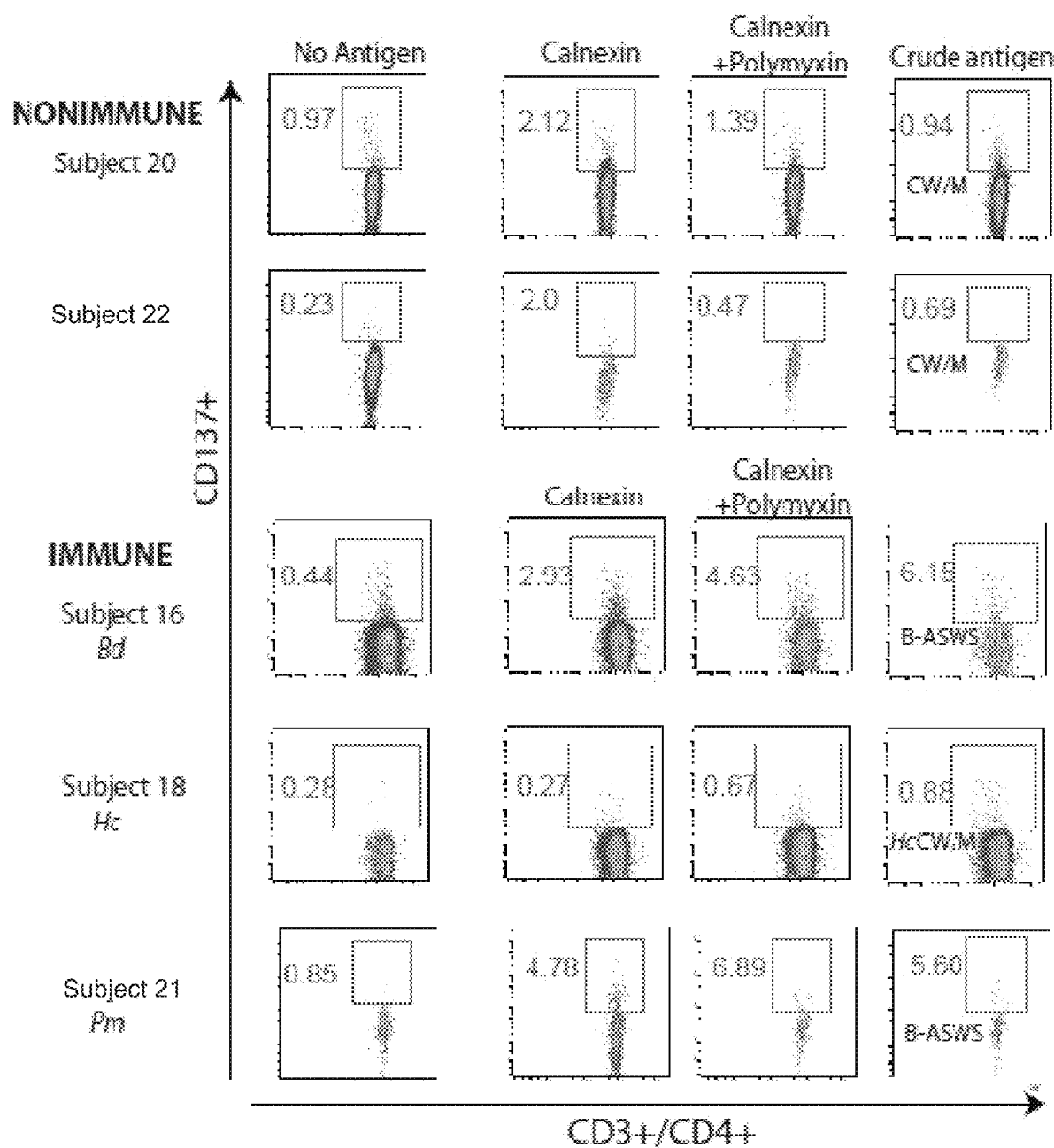
Figure 16D:
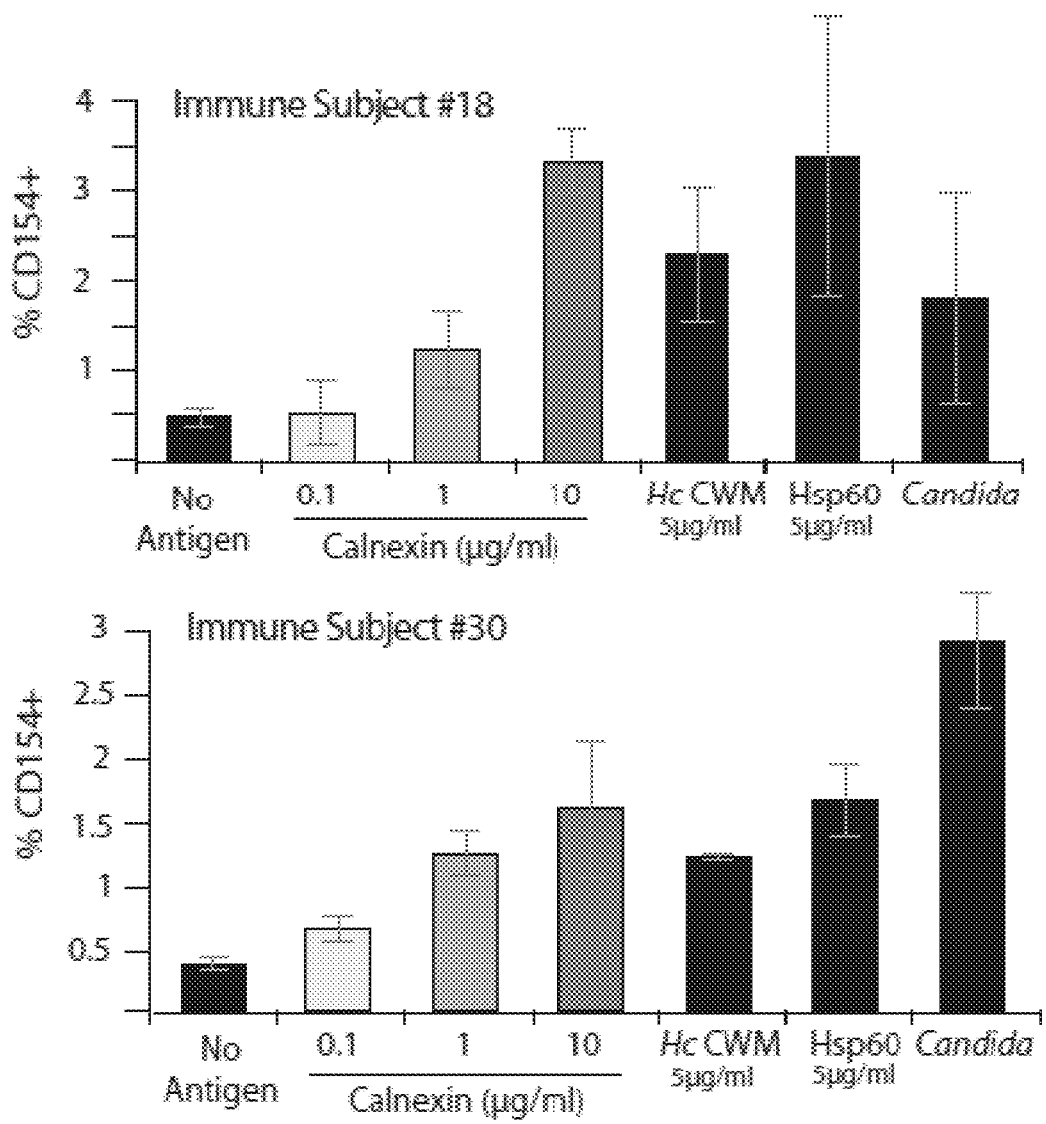

We analyzed conservation of the sequence of peptide #1 broadly throughout fungi. The 13 aa sequence is found in four phyla including Ascomycota, Basidiomycota, Chytridiomycota and Glomeromycota (Tables 1 and 2). The highest conservation of the peptide was found in ascomycetes. To investigate biological relevance, and test whether medically important fungi with conserved peptide #1 sequences trigger the expansion and activation of TCR Tg 1807 and endogenous, polyclonal, peptide #1-specific $CD4^+$ T-cells in vivo, we transferred naïve 1807 T cells into mice before infection or vaccination with these fungi. One week later, we analyzed activation of 1807 and also endogenous Ag-specific $CD4^+$ T-cells using a newly generated, calnexin peptide-MHC class II tetramer. *B. dermatitidis*, *A. fumigatus*, *H. capsulatum*, *C. posadasii*, *Fonsecaea pedrosoi* causing chromoblastomycosis (da Gloria Sousa et al., 2011), and *Pseudogymnoascus* (*Geomyces*) *destructans* causing white nose syndrome and death in bats in the U.S. (Lorch et al., 2011) expanded and activated 1807 and tetramer positive $CD4^+$ T cells in vivo (FIGS. 11 and 15, and data not shown). Fungi that did not trigger expansion of tetramer positive $CD4^+$ T cells included *Candida albicans*, *Cryptococcus neoformans*, and *Pneumocystis jiroveci*, none of which are ascomycetes. Naïve mice harbored 29±10 tetramer positive $CD4^+$ T cells per animal; hardly any tetramer positive CD8⁺ T-cells were detected in vaccinated mice (FIG. 15A). Thus, the tetramer recognizes and binds the T-cell receptor of calnexin peptide #1-specific CD4⁺ T-cells in a specific manner and can be used as a tool to monitor Ag-specific T cells in vivo in response to a number of pathogenic fungal ascomycetes.

The Basis for Variable Expansion of Peptide-Specific T Cells by Fungi.

We sought to explain the effect of calnexin peptide #1 variation in fungi. It is likely that the nonamer core for peptide #1 is VKNPAAHHA(SEQ ID NO: 16; Table 1). For the class II MHC, I-Ab, P1, 3, 4, 5, 7, 9 make contacts with I-Ab, and P2, 5, 7, and 8 are usually the most important TCR contacts, especially P5 (Nelson et al., 2014). Calnexin from *C. immitis* and *Aspergillus* can be detected by VKN-PAAHHA (SEQ ID NO: 16):I-Ab-specific T cells because A or V at P4 are permissive for I-Ab binding and these peptides have the same TCR contact amino acids at P2, 5, 7, and 8 as calnexin from *B. dermatitidis*. Conversely, *P. carinii* may not be recognized because E at P4 is not permissive for I-Ab binding, and the peptide likely does not bind I-Ab. Calnexin from *C. albicans* is not recognized because R at P4 is not permissive for I-Ab binding, and thus, this peptide likely does not bind I-Ab. *Candida* also has a Y for H substitution at P8, which should make the peptide unrecognizable to VKNPAAHHA (SEQ ID NO: 16):I-Ab-specific T cells even if it does bind to I-Ab.

Response to Calnexin in Humans.

In a pilot study, we assayed the CD4⁺ T cell response to calnexin in human subjects with either a history of confirmed infection due to dimorphic fungi or residence in an endemic area and laboratory evidence of prior infection (immune) vs. healthy subjects that lacked the above features (non-immune) (FIGS. 16A, 16B, 16C and 16D). Five of six immune subjects responded to calnexin vs. one of four non-immune subjects. The response to calnexin in immune subjects was dose-dependent, similar to that for the immunodominant fungal Ag heat shock protein 60 (Hsp60) and not due to contaminating LPS.

Functions of Calnexin Specific T Cell Responses.

Figure 12A:
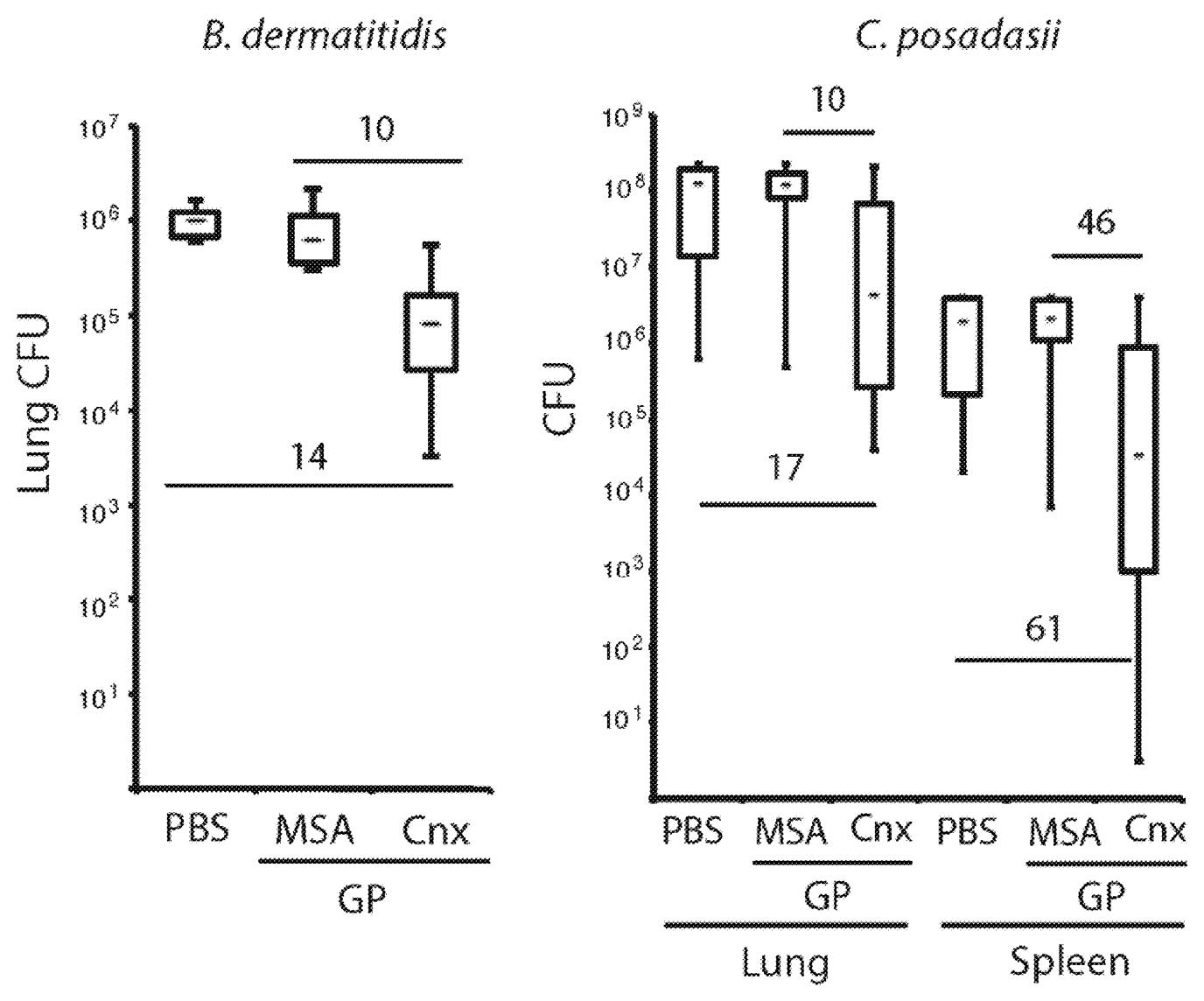
Figure 12B:
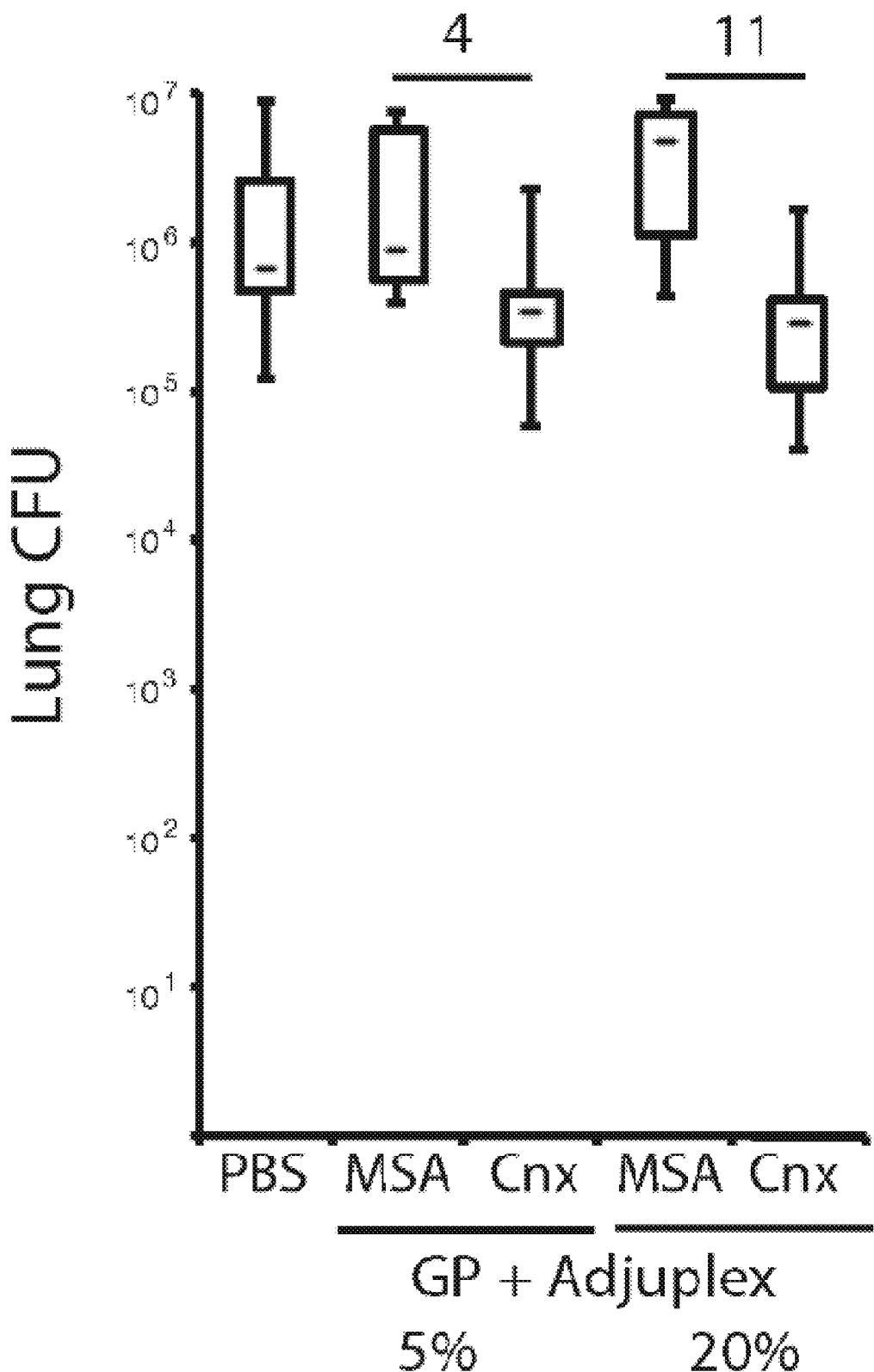
Figure 12C:
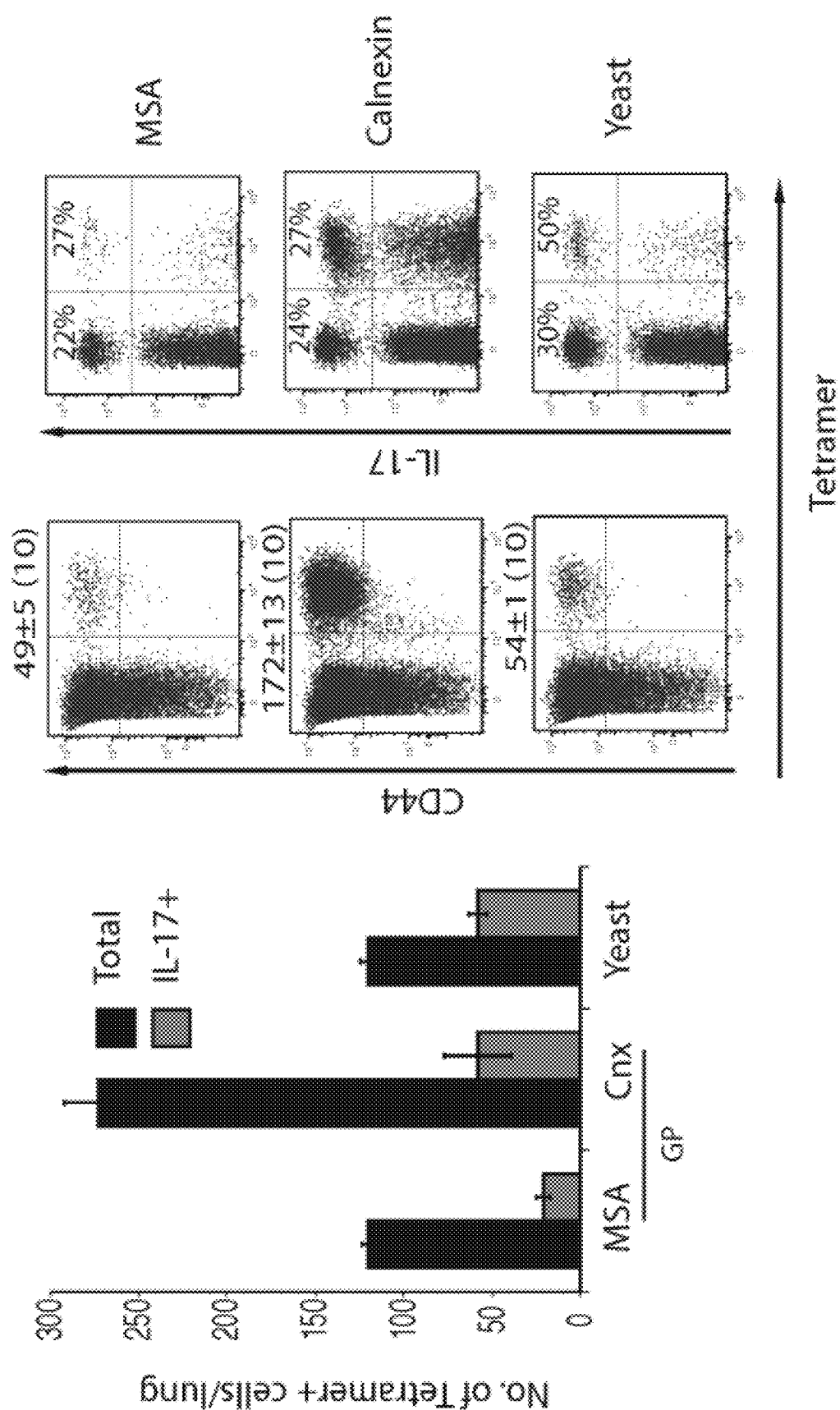
Figure 17A:
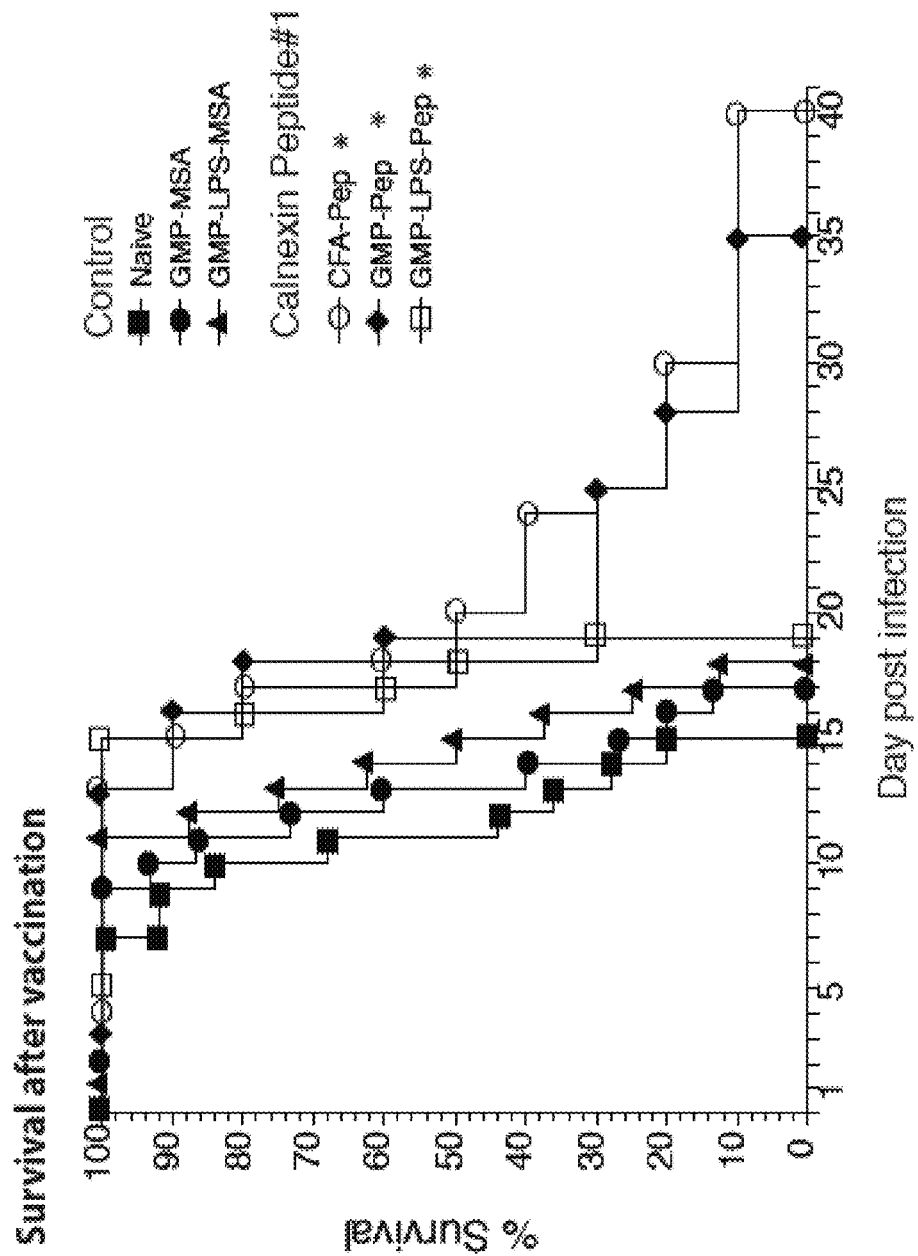
FIGS. 17A and 17B are a set of graphs showing calnexin-induced resistance: correlation of CFU and survival.
Figure 17B:
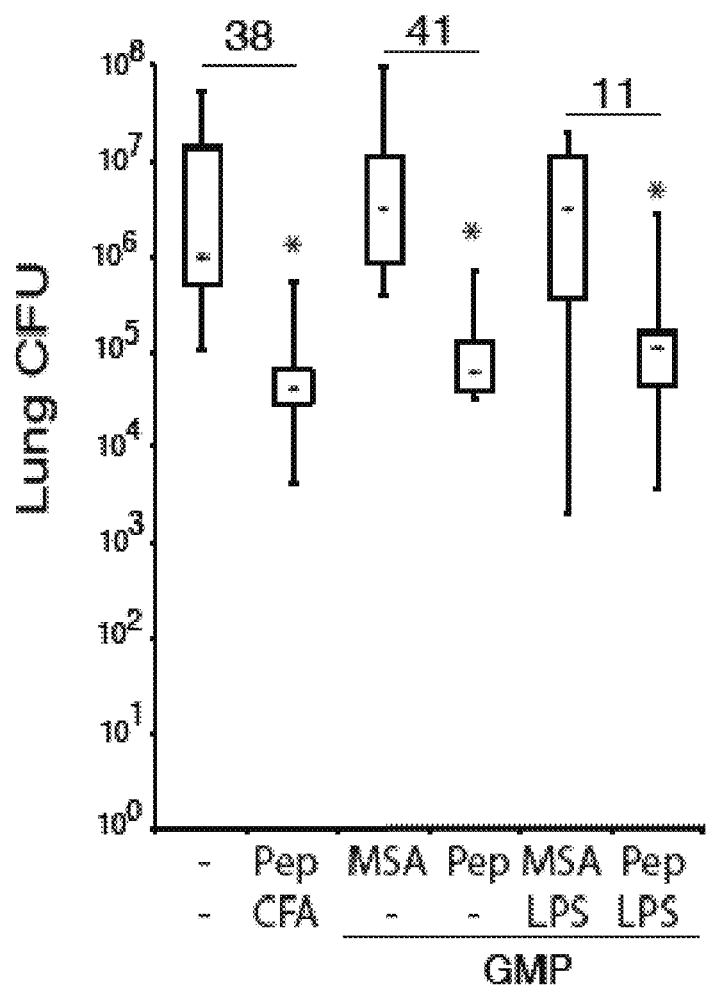
Figure 18A:
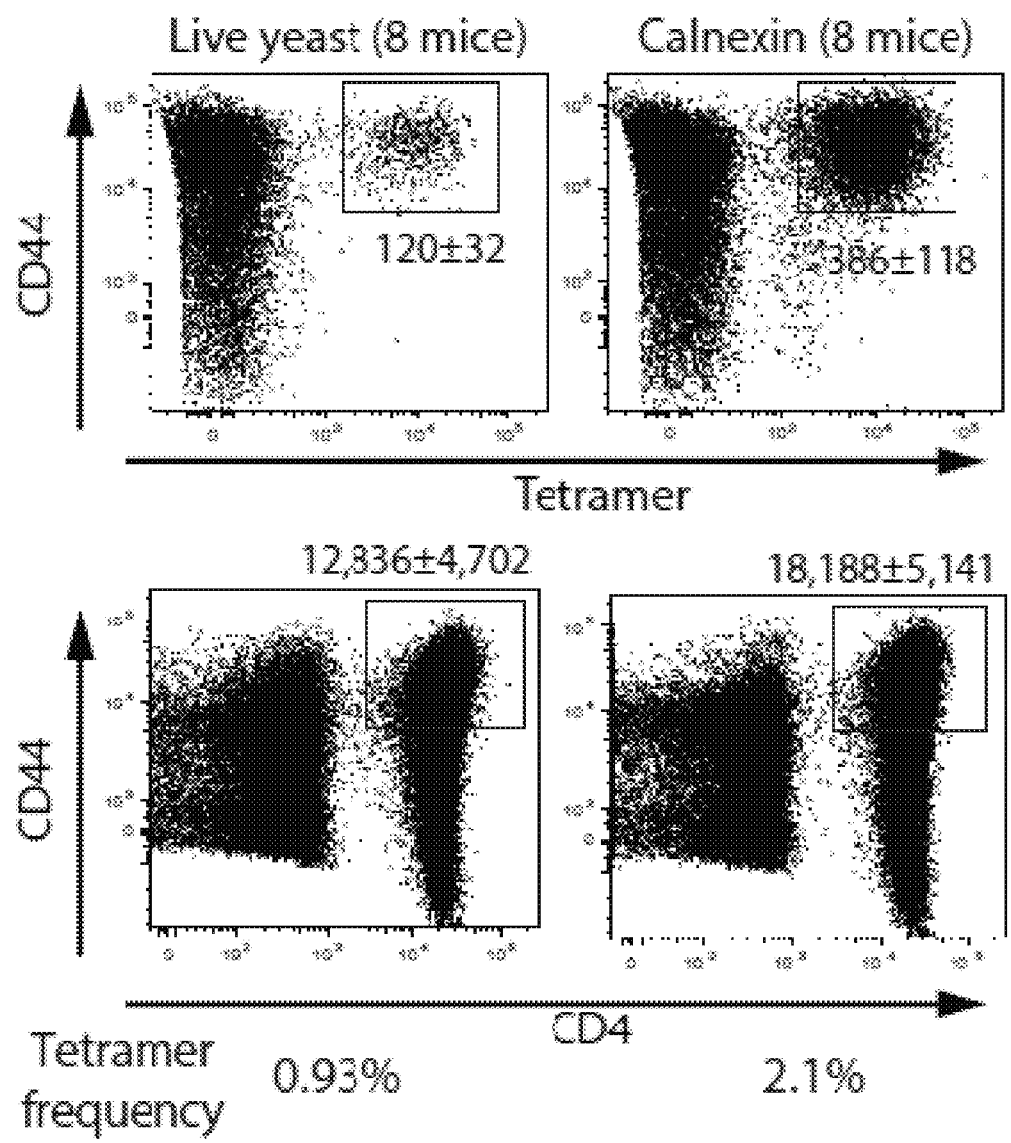
FIGS. 18A and 18B are a set of graphs showing features of endogenous calnexin-specific T cells: immunodominance and chemokine receptor expression.
Figure 18B:
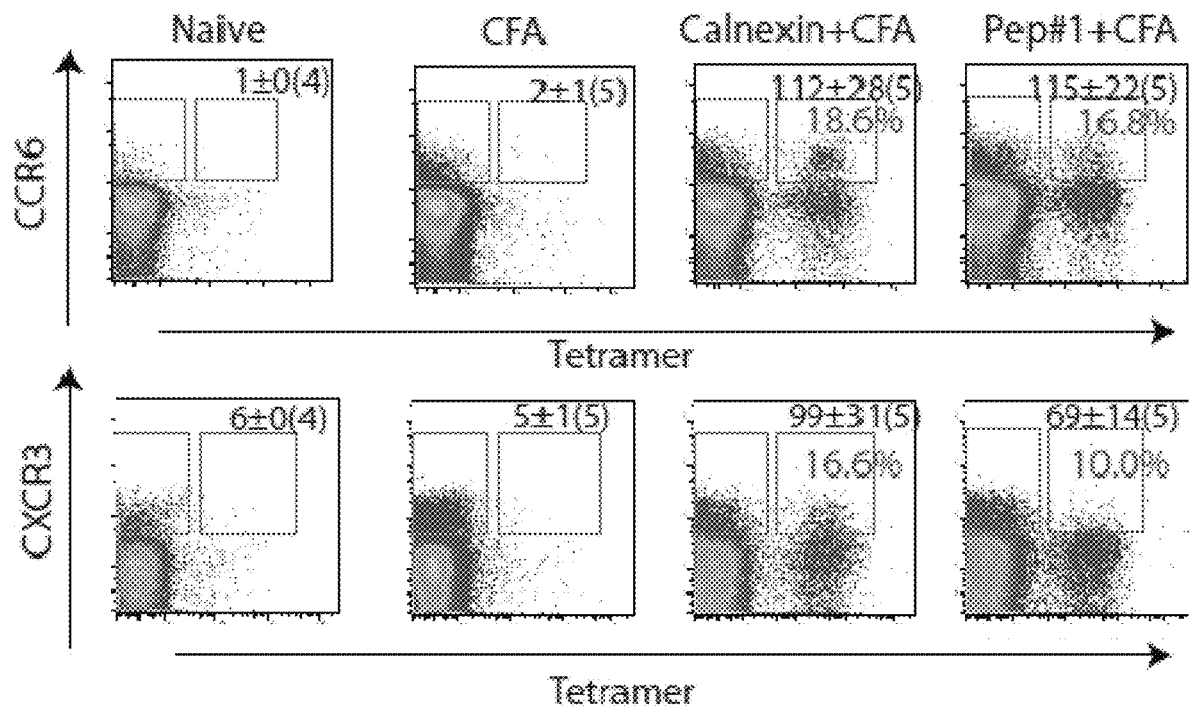

To test whether vaccination with calnexin induces protective immunity against lethal, pulmonary fungal infection, we immunized mice with r-calnexin. We investigated selected adjuvants empirically such as glucan particles (GP) to promote type 17 immunity and ADJUPLEX adjuvant, type 1 immunity. Vaccination with calnexin formulated in GP or ADJUPLEX adjuvant reduced lung and spleen CFU≥10-fold vs. control mice after infection with *B. dermatitidis* or *C. posadasii* (FIGS. 12A and 12B); reduced lung CFU correlated with prolonged survival (FIG. 17A). Vaccination with calnexin lead to increased numbers of tetramer-positive cells recruited to the lung at day 4 post-infection (FIG. 12C). Of the CD441 CD4⁺ T cells recruited to lung after fungal challenge of *Blastomyces* yeast-vaccinated mice, about 1% are tetramer positive and that proportion more than doubles after vaccination with calnexin (FIG. 18A). After vaccination with calnexin, 15-20% of the tetramer-positive cells in the draining lymph nodes display the chemokine receptors CCR6 or CXCR3 (FIG. 18B), which are respectively linked with Th17 and Th1 cell recruitment (Hirota et al., 2007; Nanjappa et al., 2012a; Nanjappa et al., 2012b). Nearly 30% of tetramer-positive cells recruited to the lung were IL-17 producers in calnexin-vaccinated mice (FIG. 12C). Thus, vaccination with calnexin induces the development of Ag-specific CD4⁺ T cells that are recruited to the lung after challenge and this response is linked to reduced CFU and prolonged survival in association with features of Th17 and Th1 immunity.

The Role of T Cell Precursor Frequency and Expansion in Calnexin Induced Protection.

The frequency of naïve CD4⁺ T cell populations affects the size of the T-cell response after immunization with the relevant peptide (Moon et al., 2007). We tested whether better expansion and recruitment of calnexin peptide #1 specific CD4⁺ T cells would improve vaccine protection. With calnexin vaccination above, we observed ≈100-200 tetramer positive cells recruited to the lung after infection, but only about 50 of these cells produced IL-17, implying that type 17 responses could be further enhanced.

Figure 13A:
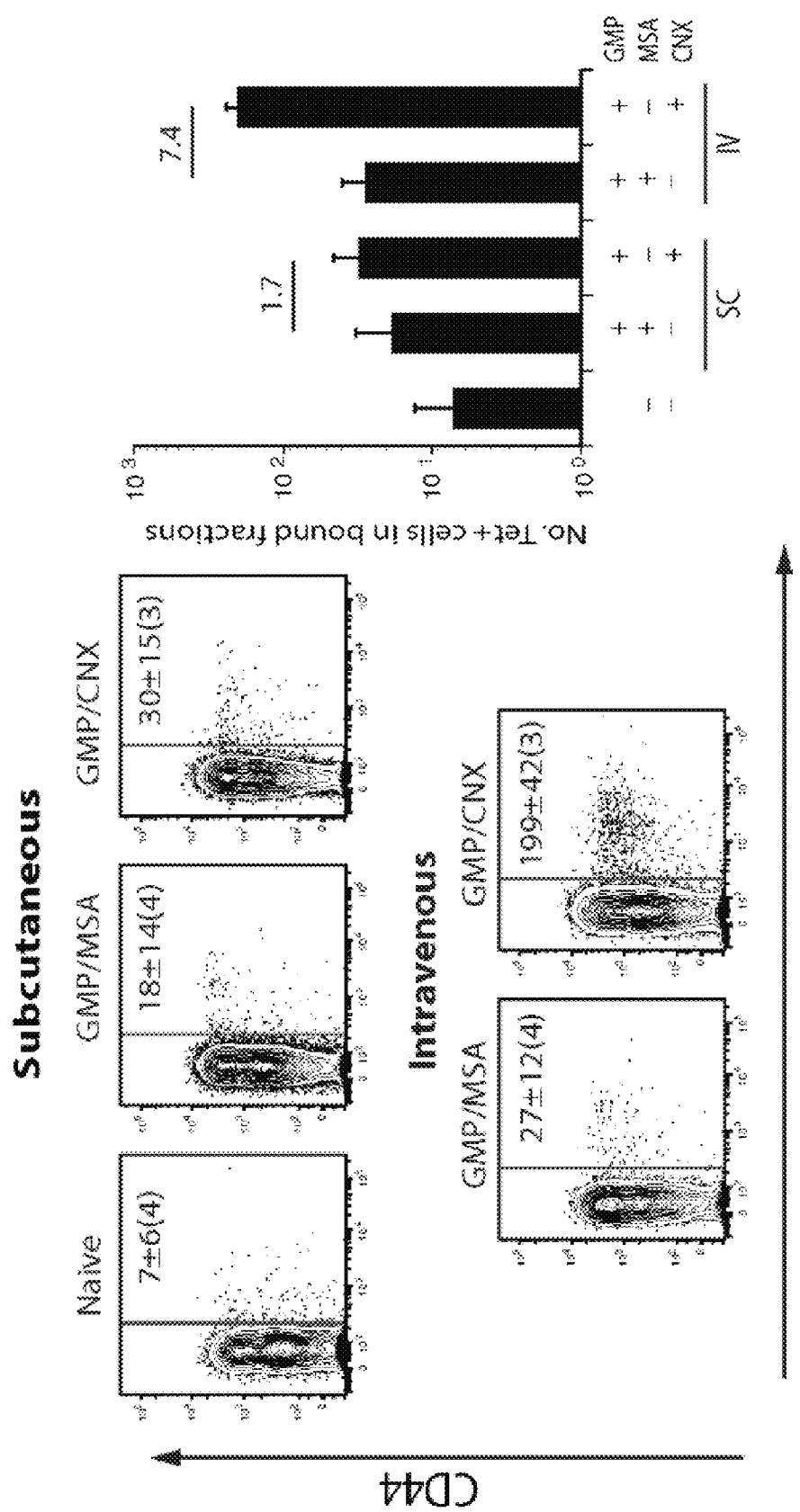
FIGS. 13A, 13B and 13C are a set of graphs showing intravenous delivery of calnexin peptide, expansion of endogenous, tetramer-specific T cells, and resistance to infection. A. Wild type C57BL6 mice were vaccinated s.c. or i.v. with 10⁸ glucan mannan particles (GMP) loaded with 10 μg of r-calnexin (Cnx) or MSA as a negative control.
Figure 13B:
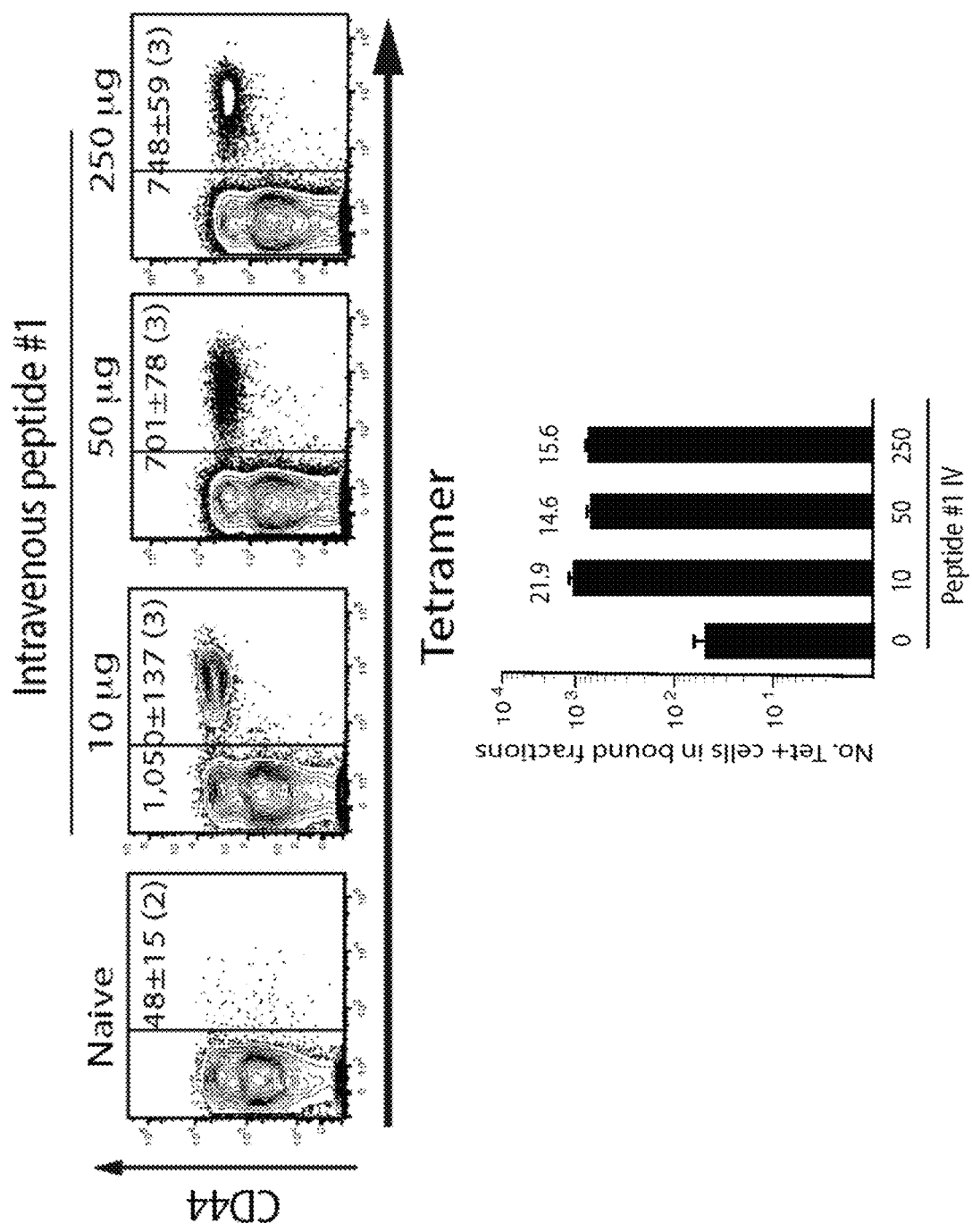
Figure 13C:
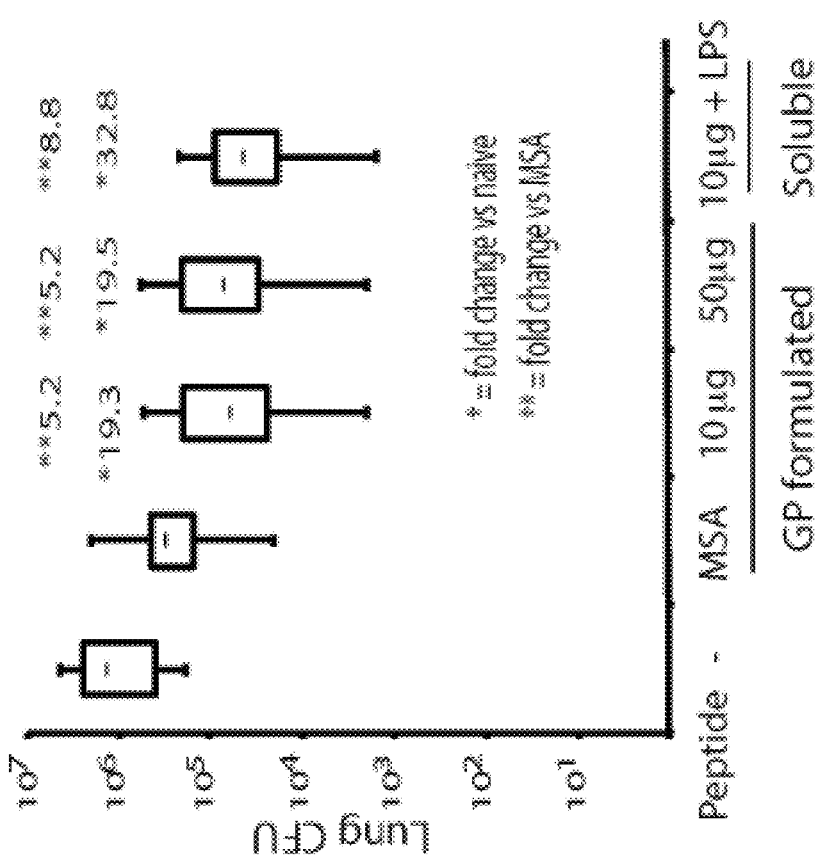

We first compared different routes of vaccine delivery. The intravenous (i.v.) route with particles bearing calnexin triggered better expansion than the subcutaneous (s.c.) route (FIG. 13A). Delivery of soluble peptide #1 with LPS i.v. prompted a further increase in the number of tetramer-positive cells at the peak of expansion (FIG. 13B), especially at the lowest dose of 10 μg peptide. Improved expansion of calnexin-specific T cells did not translate into better protection against infection compared to the preceding approaches (FIG. 13C), perhaps because only a small fraction of tetramer-positive cells were recalled to the lungs and fate-mapping mice demonstrated that essentially none maintained production of IL-17. Thus, i.v. delivery promoted better expansion, but differentiation or persistence of IL-17 effectors wavered despite vaccine protection.

Enhanced Vaccine-Induced Expansion of Calnexin Specific T Cells.

Figure 14C:
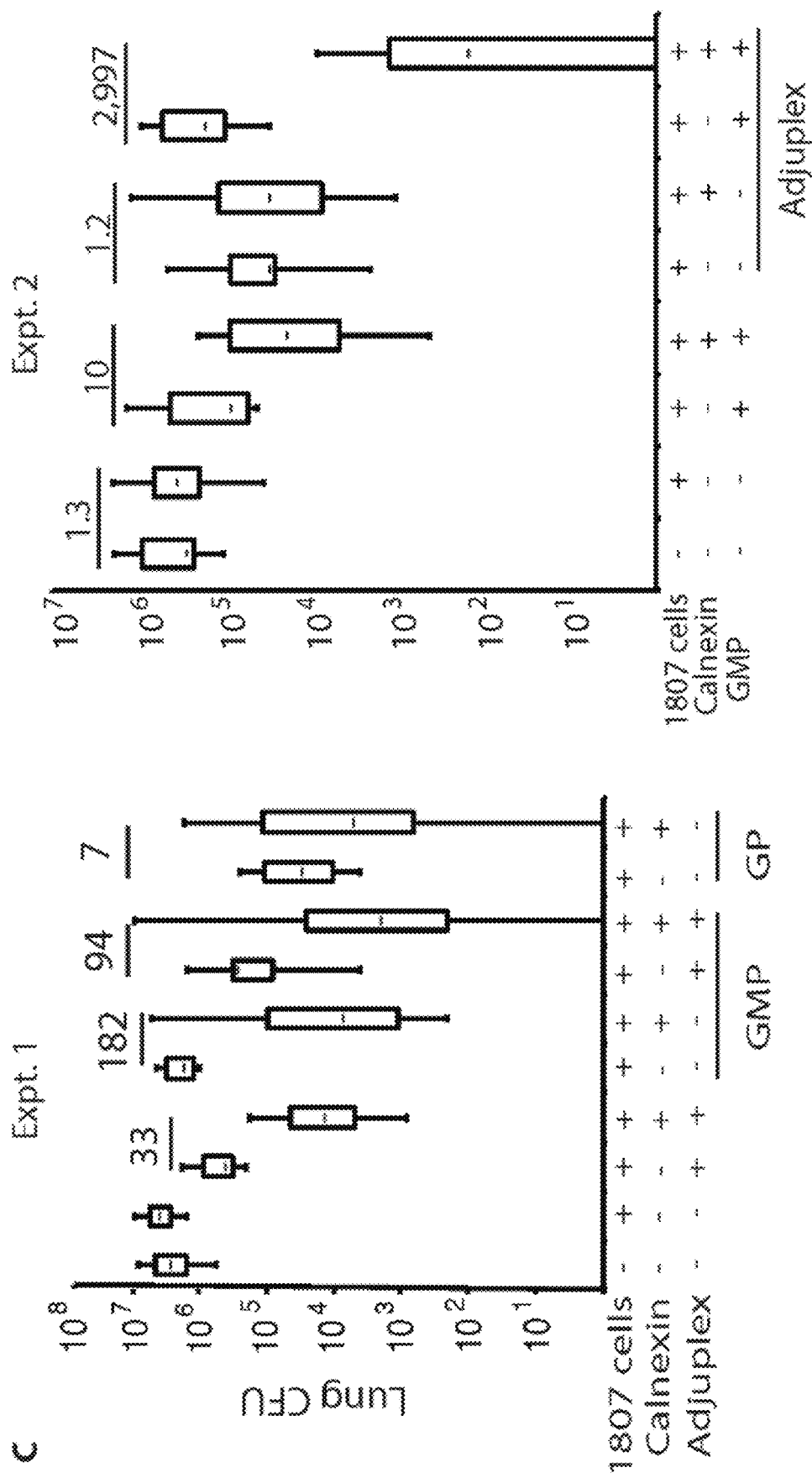

We sought an alternate approach to promote expansion, differentiation and maintenance of calnexin-specific T cells to explore their role in vaccine protection. We transferred naïve 1807 T cells prior to s.c. vaccination to increase the pool of Ag-experienced CD4⁺ T cells that persist. In mice given GP-encapsulated calnexin, we enumerated the number of activated (CD44⁺) and cytokine-producing 1807 T cells upon recall in the lung at day 4 post-infection. The number of CD44⁺ Ag-specific lung CD4⁺ T cells increased 41-fold in mice that received 1807 T cells (11,240±298 1807 cells; FIG. 14A) vs. those that did not (273±19 tetramer positive cells; FIG. 12C). Encouraged by this finding, we empirically tested different calnexin vaccine formulations to boost the number of Ag-experienced 1807 cells in the lung upon recall and sway their polarization. Mannan was added to GP to sway type 17 responses and ADJUPLEX adjuvant to drive type 1 responses. Glucan mannan particles (GMP), ADJUPLEX adjuvant and the combination of the two together yielded maximal numbers of IL-17- and IFN-γ producing 1807 T cells in the lung (FIG. 14B), with >10⁴ recalled 1807 T cells showing an activated phenotype and >10³ T cells each producing IL-17 or IFN-γ. To test whether increased numbers of calnexin-primed CD4⁺ T cells translate into improved vaccine resistance, we determined the lung burden after infection in mice that received transferred, naïve 1807 T cells before vaccination. Calnexin formulated with GMP and ADJUPLEX adjuvant together yielded ≈3,000-fold less lung CFU than adjuvant-control mice (FIG. 14C). Thus, calnexin is a conserved Ag capable of inducing vaccine resistance against infection with multiple fungal ascomycetes if the conditions are optimized for precursor frequency, expansion and maintenance of T cells that produce IL-17, IFN-γ or both.

DISCUSSION

We report the discovery of an immunodominant Ag—calnexin—that is conserved among numerous members of the fungal taxon Ascomycota. The peptide sequence that induces CD4+ T cell responses is conserved among the endemic, systemic dimorphic fungi, as well as clinically important *Aspergillus* species, *Fonsecea pedrosoi*, and even *P. destructans*, also referred to as the white nose fungus, which is sweeping across North America and devastating bat populations. This sequence is functionally important for inducing the expansion of Ag-specific T cells following exposure to each of these fungi, and the responses stemmed progression of ascomycete fungal infections that we studied, including *Blastomyces* and *Coccidioides*. The calnexin sequence diverges in fungi of other taxa, such as the basidiomycetes, and importantly also in mammals. The calnexin CD4+ T cell epitope is conserved for the inbred mouse strain studied here. Likewise, humans that have recovered from certain fungal infections demonstrate recall responses to calnexin in their CD4+ T cells.

Most of the major fungal antigens reported to date are either secreted or cell wall associated molecules (Rappleye and Goldman, 2008). In *Blastomyces*, the chief Ag BAD-1 is both released and yeast cell wall associated. In *Histoplasma*, the skin test Ag histoplasmin is a cell culture filtrate that contains H and M Ags, which are encoded by a β-glucosidase and catalase, respectively (Deepe and Durose, 1995; Zancope-Oliveira et al., 1999). In *Cryptococcus* sp., mannoproteins in or on the cell wall, or accumulated in the supernatant, trigger immunity to this fungus (Levitz and Specht, 2006). In *Candida*, the principal Ag targets of vaccines currently under study are Als3, which is a surface adhesin, and Sap2, which is a secreted aspartyl proteinase (Cassone and Casadevall, 2012). Thus, we were surprised that a protein such as calnexin, which monitors protein folding and glycosylation in the ER of cells, would serve as a major trigger of host cellular immune responses. We found that although calnexin normally resides in interior cell compartments, anti-calnexin antisera detected this protein on the surface of *Blastomyces* yeast and *Aspergillus* spores and hyphae. While unexpected, this result is not unprecedented. In *Histoplasma*, HIS62, a heat-shock protein (HSP), triggers CD4+ T cells that confer immunity in response to the fungus (Gomez et al., 1991). HSPs have been detected on the surface of *Histoplasma* yeast and mediate adherence to host integrin receptors (Long et al., 2003). Likewise, histone-like proteins have been detected on the surface of this fungus and antibodies directed against these proteins confer immunity (Nosanchuk et al., 2003). The localization of calnexin on the fungal surface could be due to protein shedding from dead or dying fungi, followed by non-specific adherence to the surface of viable cells. Alternatively, surface localization could be due to the trafficking of intracellular molecules through the cell wall in vesicles, as described in other fungi (Casadevall et al., 2009). The route notwithstanding, intracellular proteins including calnexin may unexpectedly appear at the fungal surface and induce immune recognition by the host.

In mapping the T cell epitope of calnexin, we synthesized peptide-MHCII tetramers and exploited this tool to study endogenous CD4+ T cells specific for this sequence on multiple pathogenic fungi. The pool of naïve calnexin specific cells in a C57BL/6 mouse is about 30 CD4+ T cells. This pool of T cells expands in response to exposure to a wide range of fungal ascomycetes, including the white nose fungus *P. destructans*. Our results supporting the conserved nature of the Ag were confirmed with TCR transgenic T cells that were adoptively transferred in parallel into infected mice. While the availability of transgenic T cells enables the monitoring of Ag specific immune responses, transfer of large numbers of T cells has pitfalls and limitations that may introduce artifacts that distort or misrepresent the true nature of the immune response to microbes (Moon et al., 2009). Peptide-MHCII tetramers offer a powerful tool to circumvent such limitations. We validated this tool for detecting and tracking endogenous fungal Ag specific CD4+ T cell responses to multiple fungi, in a manner that has not been previously available for the study of immunity to fungi. This tool will offer investigators studying various fungal pathogens a level of resolution that has not previously been possible. We show that this tool can be applied to study fungal diseases that vary from the endemic, systemic mycoses such as blastomycosis and histoplasmosis, to the opportunistic fungal disease Aspergillosis, to the tropical mycosis chromoblastomycosis, and unexpectedly, even to the fatal bat disease caused by the white nose fungus.

We used calnexin peptide-MHCII tetramers to track the behavior of IL-17-producing, Ag-specific CD4+ T cells with the benefit of fate mapping mice. We previously demonstrated that IL-17 production by CD4+ T cells is indispensable in vaccine immunity against dimorphic fungi that cause North American systemic mycoses (Nanjappa et al., 2012a; Wüthrich et al., 2011a). We have found that IL-17 producing T cells are maintained and persist after vaccination with attenuated yeast in CD4-sufficient and -deficient mice (Nanjappa et al., 2012a; Wüthrich et al., 2011a). In contrast, others have reported that IL-17 producing T cells are short lived and dwindle due to death or conversion to type 1 cytokine producing T cells (Hirota et al., 2011; Pepper et al., 2010). Here, we exploited tetramers to track fungal Ag-specific, IL-17 producing T cells after vaccination. Calnexin vaccination induced T cells to differentiate into IL-17 producers, and tetramer positive cells recalled to the lung after challenge included IL-17 producers. These cells dwindled after i.v. peptide vaccination. In contrast, mice that received transferred 1807 T cells and s.c. vaccination with GMP and ADJUPLEX adjuvant evinced a large population of IL-17 producers during recall. Thus, fungal Ag-specific CD4+ T cells that produce IL-17 in response to vaccination were maintained in the latter setting. In a murine model of cutaneous *Candida* infection, IL-17 producing CD4+ T cells did not persist (Hirota et al., 2011). Our findings are in line with data in humans where *Candida* responsive, IL-17 producing T cells persist (Acosta-Rodriguez et al., 2007). Tetramers developed here should allow us to elucidate strategies to promote the persistence of memory T cells that confer anti-fungal immunity after vaccine administration.

In view of the conserved nature of calnexin, and its potential clinical utility for vaccination against pathogenic fungi, we immunized mice with calnexin or its epitopes and tested efficacy against pulmonary challenge with *Blastomyces* or *Coccidioides*. We encapsulated calnexin in GPs due to the potential advantages of polarizing the immune response toward IL-17 producing CD4+ T cells (Soto and Ostroff, 2008). Calnexin vaccine protected mice against lethal blastomycosis or coccidioidomycosis, reducing lung CFU by at least 1 log vs. control mice. In addition to calnexin delivery in GPs, we explored adjuvants such as mannan, LPS and ADJUPLEX adjuvant that may polarize T cells differently; each gave similar levels of calnexin-induced resistance and our results suggest a role for both type 17 and type 1 immunity. Thus, calnexin could prove to be a valuable component for a "pan-fungal" vaccine.

The size of the pool of naïve precursors specific for calnexin peptide #1 is an average size (Nelson et al., 2014) of 30 cells. Because the size of this precursor pool dictates the ultimate number of Ag-specific T cells in the expanded pool after vaccination (Moon et al., 2007), we sought to expand this pool to boost calnexin vaccine efficacy. Delivery of peptide via the i.v. route lead to an expanded pool of calnexin-specific T cells. In the latter circumstance, the pool of calnexin-specific T cells increased to >1000 cells in the draining lymph nodes and spleen of calnexin-vaccinated mice, or more than 20-fold higher than the number of cells in control mice. However, tetramers showed that Ag-specific effectors were poorly maintained based on recall and vaccine efficacy was unchanged.

We investigated cell transfer as an alternate maneuver to increase the size of the precursor pool and boost vaccine efficacy. Transfer of 1807 T cells lead to a 10-fold enhancement of calnexin peptide-specific T cells recruited to the lungs on challenge; ~10,000 of these cells exhibited an activated (CD44+) phenotype and ~10% produced IL-17 or IFN-γ (1,000 each). These mice also had vaccine given s.c. in GMPs in association with ADJUPLEX adjuvant so that the independent role of each of these conditions–precursor number vs. adjuvant–could not be discerned. These combined conditions yielded improved vaccine efficacy, with levels that far exceeded other conditions, resulting in a 3-4 log reduction in lung CFU in a model of lethal experimental fungal infection. We cannot exclude that TCR affinity played a role in better protection after transfer of transgenic T cells and vaccination. Nevertheless, T cell transfer has been used to treat immune suppressed patients with CMV infections in the setting of bone marrow or stem cell transplantation (Blyth et al., 2013; Peggs et al., 2011). Such patients receive donor T cells after expansion of Ag specific T cells in vitro, followed by magnetic bead enrichment of activated cytokine producing T cells. Another major risk in these patients is pulmonary aspergillosis (Singh and Paterson, 2005). Because calnexin is conserved in *Aspergillus* and displayed on the fungal surface, and because the fungus induces expansion of calnexin specific CD4+ T cells during infection, transfer of calnexin-specific T cells that are activated, expanded, and enriched in vitro may offer novel immunotherapeutic benefit to patients with invasive fungal infection (Beck et al., 2006).

TABLE 2

Short sequence BLASTp of *Blastomyces dermatitidis* calnexin peptide #1 against deduced fungal protein sequences at NCBI.

| Organism | Accession | \multicolumn{13}{c}{Calnexin peptide #1} | SEQ ID NO: |
|---|---|---|---|---|---|---|---|---|---|---|---|---|---|---|
| | | L | V | V | K | N | P | A | A | H | H | A | I | S | |
| Ajellomyces capsulatus | XP_001538455 | - | - | - | - | - | - | - | - | - | - | - | - | - | 1 |
| Ajellomyces dermatitidis | XP_002627579 | - | - | - | - | - | - | - | - | - | - | - | - | - | 1 |
| Arthroderma benhamiae | XP_003013696 | - | - | - | - | - | - | - | - | - | - | - | - | - | 1 |
| Arthroderma gypseum | XP_003177596 | - | - | - | - | - | - | - | - | - | - | - | - | - | 1 |
| Arthroderma otae | XP_002851011 | - | - | - | - | - | - | - | - | - | - | - | - | - | 1 |
| Aspergillus flavus | XP_002383280 | - | - | - | - | - | - | - | - | - | - | - | - | - | 1 |
| Aspergillus oryzae | XP001816793 | - | - | - | - | - | - | - | - | - | - | - | - | - | 1 |
| Aspergillus terreus | XP_001212344 | - | - | - | - | - | - | - | - | - | - | - | - | - | 1 |
| Beauveria bassiana | EJP61334 | - | - | - | - | - | - | - | - | - | - | - | - | - | 1 |
| Botryotinia fuckeliana | XP_001560997 | - | - | - | - | - | - | - | - | - | - | - | - | - | 1 |
| Claviceps purpurea | CCE30657 | - | - | - | - | - | - | - | - | - | - | - | - | - | 1 |
| Colletorichum gloeosporioides | EQB45337 | - | - | - | - | - | - | - | - | - | - | - | - | - | 1 |
| Colletotrichum higginsianum | CCF46037 | - | - | - | - | - | - | - | - | - | - | - | - | - | 1 |
| Colletotrichum orbiculare | ENH88310 | - | - | - | - | - | - | - | - | - | - | - | - | - | 1 |
| Cordyceps militaris | XP_006671496 | - | - | - | - | - | - | - | - | - | - | - | - | - | 1 |
| Endocarpon pusillum | ERF68760 | - | - | - | - | - | - | - | - | - | - | - | - | - | 1 |
| Fusarium fujikuroi | CCT62441 | - | - | - | - | - | - | - | - | - | - | - | - | - | 1 |
| Fusarium graminearum | XP_380667 | - | - | - | - | - | - | - | - | - | - | - | - | - | 1 |
| Fusarium oxysporum | ENH61055 | - | - | - | - | - | - | - | - | - | - | - | - | - | 1 |
| Fusarium pseudograminearum | EKJ78469 | - | - | - | - | - | - | - | - | - | - | - | - | - | 1 |
| Magnaporthe oryzae | XP_003714591 | - | - | - | - | - | - | - | - | - | - | - | - | - | 1 |
| Metarhizium acridum | EFY90279 | - | - | - | - | - | - | - | - | - | - | - | - | - | 1 |
| Metarhizium anisopliae | EFZ00440 | - | - | - | - | - | - | - | - | - | - | - | - | - | 1 |

TABLE 2-continued

Short sequence BLASTp of *Blastomyces dermatitidis* calnexin
peptide #1 against deduced fungal protein sequences at NCBI.

| Organism | Accession | L | V | V | K | N | P | A | A | H | H | A | I | S | SEQ ID NO: 1 |
|---|---|---|---|---|---|---|---|---|---|---|---|---|---|---|---|
| *Nectria haematococca* | XP_003053601 | - | - | - | - | - | - | - | - | - | - | - | - | - | 1 |
| *Ophiocordyceps sinensis* | EQK97868 | - | - | - | - | - | - | - | - | - | - | - | - | - | 1 |
| *Pestalotiopsis fici* | ETS87047 | - | - | - | - | - | - | - | - | - | - | - | - | - | 1 |
| *Thielavia terrestris* | XP_003656746 | - | - | - | - | - | - | - | - | - | - | - | - | - | 1 |
| *Trichoderma reesei* | EGR52201 | - | - | - | - | - | - | - | - | - | - | - | - | - | 1 |
| *Trichophyton equinum* | EGE03014 | - | - | - | - | - | - | - | - | - | - | - | - | - | 1 |
| *Trichophyton rubrum* | XP_003231908 | - | - | - | - | - | - | - | - | - | - | - | - | - | 1 |
| *Trichophyton tonsurans* | EGE00302 | - | - | - | - | - | - | - | - | - | - | - | - | - | 1 |
| *Trichophyton verrucosum* | XP_003024212 | - | - | - | - | - | - | - | - | - | - | - | - | - | 1 |
| *Uncinocarpus reesii* | XP_002541105 | - | - | - | - | - | - | - | - | - | - | - | - | - | 1 |
| *Colletotrichum graminicola* | EFQ26293 | - | - | I | - | - | - | - | - | - | - | - | - | - | 17 |
| *Chaetomium globosum* | XP_001220707 | - | - | I | - | - | - | - | - | - | - | - | - | - | 17 |
| *Puccinia graminis* | XP_003324724 | - | - | - | - | S | - | - | - | - | - | - | - | - | 18 |
| *Melampsora larici-populina* | EGG03582 | - | - | - | - | S | - | - | - | - | - | - | - | - | 18 |
| *Yarrowia lipolytica* | XP_500829 | - | - | - | - | S | - | - | - | - | - | - | - | - | 18 |
| *Talaromyces stipitatus* | XP_002341910 | - | - | L | - | - | - | - | - | - | - | - | - | - | 4 |
| *Talaromyces marneffei* | XP_002151134 | - | - | L | - | - | - | - | - | - | - | - | - | - | 4 |
| *Cyphellophora europaea* | ETN45895 | - | - | L | - | - | - | - | - | - | - | - | - | - | 4 |
| *Gaeumannomyces graminis* | EJT81584 | - | - | L | - | - | - | - | - | - | - | - | - | - | 4 |
| *Byssochlamys spectabilis* | GAE00076 | - | - | - | - | - | A | - | - | - | - | - | - | - | 3 |
| *Cladophialophora carrionii* | ETI28715 | - | - | - | - | - | A | - | - | - | - | - | - | - | 3 |
| *Coccidioides immitis* | XP_001246842 | - | - | - | - | - | A | - | - | - | - | - | - | - | 3 |
| *Coccidioides posadasii* | XP_003066418 | - | - | - | - | - | A | - | - | - | - | - | - | - | 3 |
| *Eutypa lata* | EMR712898 | - | - | - | - | - | A | - | - | - | - | - | - | - | 3 |
| *Exophiala dermatitidis* | EHY5477 | - | - | - | - | - | A | - | - | - | - | - | - | - | 3 |
| *Marssonina brunnea* | EKD19175 | - | - | - | - | - | A | - | - | - | - | - | - | - | 3 |
| *Myceliophthora thermophile* | XP_0036587800 | - | - | - | - | - | A | - | - | - | - | - | - | - | 3 |
| *Neurospora crassa* | XP_964700 | - | - | - | - | - | A | - | - | - | - | - | - | - | 3 |
| *Neurospora tetrasperma* | EGO53734 | - | - | - | - | - | A | - | - | - | - | - | - | - | 3 |
| *Penicillium chrysogenum* | XP_002564324 | - | - | - | - | - | A | - | - | - | - | - | - | - | 3 |
| *Penicillium digitatum* | EKV07146 | - | - | - | - | - | A | - | - | - | - | - | - | - | 3 |
| *Podospora anserine* | XP_001912989 | - | - | - | - | - | A | - | - | - | - | - | - | - | 3 |
| *Pseudogymnoascus destructans* | ELR08206 | - | - | - | - | - | A | - | - | - | - | - | - | - | 3 |
| *Sclerotinia borealis* | ESZ98300 | - | - | - | - | - | A | - | - | - | - | - | - | - | 3 |
| *Sclerotinia sclerotiorum* | XP_001594877 | - | - | - | - | - | A | - | - | - | - | - | - | - | 3 |

TABLE 2-continued

Short sequence BLASTp of *Blastomyces dermatitidis* calnexin peptide #1 against deduced fungal protein sequences at NCBI.

| Organism | Accession | L | V | V | K | N | P | A | A | H | H | A | I | S | SEQ ID NO: 1 |
|---|---|---|---|---|---|---|---|---|---|---|---|---|---|---|---|
| *Sordaria macrospora* | XP_003347545 | – | – | – | – | – | A | – | – | – | – | – | – | – | 3 |
| *Togninia minima* | EON96783 | – | – | – | – | – | A | – | – | – | – | – | – | – | 3 |
| *Trichoderma atroviride* | EHK48053 | – | – | – | – | – | A | – | – | – | – | – | – | – | 3 |
| *Verticillium dahlia* | EGY22689 | – | – | – | – | – | A | – | – | – | – | – | – | – | 3 |
| *Grosmannia clavigera* | EFX05243 | – | – | – | – | – | K | – | – | – | – | – | – | – | 19 |
| *Sporothrix schenckii* | ERS98008 | – | – | – | – | – | K | – | – | – | – | – | – | – | 19 |
| *Aspergillus nidulans* | XP_661196 | – | – | – | – | – | V | – | – | – | – | – | – | – | 5 |
| *Aspergillus clavatus* | XP_001272136 | – | – | – | – | – | V | – | – | – | – | – | – | – | 5 |
| *Aspergillus fumigatus* | XP_751547 | – | – | – | – | – | V | – | – | – | – | – | – | – | 5 |
| *Aspergillus kawachii* | GAA81928 | – | – | – | – | – | V | – | – | – | – | – | – | – | 5 |
| *Aspergillus niger* | XP_001389264 | – | – | – | – | – | V | – | – | – | – | – | – | – | 5 |
| *Chaetomium thermophilum* | EGS18750 | – | – | – | – | – | V | – | – | – | – | – | – | – | 5 |
| *Neosartorya fischeri* | XP_001266757 | – | – | – | – | – | V | – | – | – | – | – | – | – | 5 |
| *Penicillium oxalicum* | EPS33667 | – | – | – | – | – | V | – | – | – | – | – | – | – | 5 |
| *Tuber melanosporum* | XP_002840340 | – | – | – | – | – | V | – | – | – | – | – | – | – | 5 |
| *Trichoderma virens* | EHK24760 | – | – | I | – | – | A | – | – | – | – | – | – | – | 2 |
| *Paracoccidioides lutzii* | XP_002791126 | – | – | I | – | – | A | – | – | – | – | – | – | – | 2 |
| *Paracocciodioides brasiliensis* | EEH45415 | – | – | I | – | – | A | – | – | – | – | – | – | – | 2 |
| *Meyerozyma guilliermondii* | EDK36034 | – | – | M | – | T | – | – | – | – | – | – | – | – | 20 |
| *Debaryomyces hansenii* | XP_459463 | – | – | L | – | T | – | – | – | – | – | – | – | – | 21 |
| *Arthrobotrys oligospor* | EGX49671 | – | – | – | – | D | K | – | – | – | – | – | – | – | 22 |
| *Pichia pastoris* | XP_002491218 | – | – | – | – | S | E | – | – | – | – | – | – | – | 23 |
| *Batrachochytrium dendrobatidis*[C] | XP_006683250 | – | – | – | – | T | T | – | – | – | – | – | – | – | 24 |
| *Bipolaris maydis* | EMD94330 | – | – | I | – | D | Q | – | – | – | – | – | – | – | 25 |
| *Agaricus bisporus*[B] | XP_006453987* | – | – | A | – | S | – | – | S | – | – | – | – | – | 26 |
| *Ophiostoma piceae* | EPE04709 | – | – | L | – | – | K | – | – | – | – | – | – | – | 27 |
| *Schizosaccharomyces japonicas* | XP_002173890 | – | – | M | – | D | A | – | – | – | – | – | – | – | 28 |
| *Schizosaccharomyces octosporus* | EPX70576 | – | – | M | – | D | A | – | – | – | – | – | – | – | 28 |
| *Phaeosphaeria nodorum* | XP_001794804 | – | – | I | – | D | K | – | – | – | – | – | – | – | 29 |
| *Neofusicoccum parvum* | EOD50245 | – | – | I | – | D | K | – | – | – | – | – | – | – | 29 |
| *Macrophomina phaseolina* | EKG22397 | – | – | I | – | D | K | – | – | – | – | – | – | – | 29 |
| *Pyrenophora teres* | XP_003295857 | – | – | I | – | D | K | – | – | – | – | – | – | – | 29 |
| *Pyrenophora tritici-repentis* | XP_001938332 | – | – | I | – | D | K | – | – | – | – | – | – | – | 29 |
| *Setosphaeria turcica* | EOA89024 | – | I | – | – | D | K | – | – | – | – | – | – | – | 30 |
| *Wickerhamomyces ciferrii* | CCH44989 | – | – | L | – | T | – | – | – | – | – | – | – | – | 21 |

TABLE 2-continued

Short sequence BLASTp of *Blastomyces dermatitidis* calnexin peptide #1 against deduced fungal protein sequences at NCBI.

| | | Calnexin peptide #1 | | | | | | | | | | | | | SEQ ID NO: |
|---|---|---|---|---|---|---|---|---|---|---|---|---|---|---|---|
| Organism | Accession | L | V | V | K | N | P | A | A | H | H | A | I | S | 1 |
| *Coniosporium apollinis* | EON64158 | – | – | I | – | D | K | – | – | – | – | – | – | – | 29 |
| *Schizosaccharomyces pombe* | NP_593612 | – | – | M | – | D | E | – | – | – | – | – | – | – | 31 |
| *Millerozyma farinose* | XP_004197197 | – | – | M | – | K | A | – | – | – | – | – | – | – | 32 |
| *Schizosaccharomyces cryophilus* | EPY51734 | – | – | M | – | D | E | – | – | – | – | – | – | – | 31 |
| *Glarea lozoyensis* | EHK96071 | – | – | M | – | D | V | – | – | – | – | – | – | – | 33 |
| *Pneumocystis jirovecii* | CCJ28190 | – | – | L | – | K | Q | – | – | – | – | – | – | – | 34 |
| *Stereum hirsutum*[B] | EIM92379 | – | – | A | – | D | K | – | – | – | – | – | – | – | 35 |
| *Sphaerulina musiva* | EMF10900 | – | – | L | – | D | K | – | – | – | – | – | – | – | 36 |
| *Pseudocercospora fijiensis* | EME79270 | – | – | A | – | D | K | – | – | – | – | – | – | – | 35 |
| *Dothistroma septosporum* | EME43956 | – | – | L | – | D | K | – | – | – | – | – | – | – | 36 |
| *Zymoseptoria tritici* | XP_003853151 | – | – | L | – | D | K | – | – | – | – | – | – | – | 36 |
| *Leptosphaeria maculans* | XP_003839005 | – | – | L | – | D | K | – | – | – | – | – | – | – | 36 |
| *Baudoinia compniacensis* | EMC95130 | – | – | L | – | D | K | – | – | – | – | – | – | – | 36 |
| *Blumeria graminis* | EPQ66287 | – | – | L | – | T | Q | – | – | – | – | – | – | – | 37 |
| *Tremella mesenterica*[B] | EIW72285 | – | – | M | – | S | K | – | – | – | – | – | – | – | 38 |
| *Fomitiporia mediterranea*[B] | EJC98754 | – | – | A | – | S | K | – | – | – | – | – | – | – | 39 |
| *Punctularia strigosozonata*[B] | EIN14355 | – | – | A | – | S | K | – | – | – | – | – | – | – | 39 |
| *Laccaria bicolor*[B] | XP_001874124 | – | – | A | – | S | K | – | – | – | – | – | – | – | 39 |
| *Coprinopsis cinerea*[B] | XP_002912210 | – | – | A | – | S | K | – | – | – | – | – | – | – | 39 |
| *Moniliophthora roreri*[B] | ESK96243 | – | – | A | – | S | K | – | – | – | – | – | – | – | 39 |
| *Trichosporon asahii*[B] | EKD02066 | – | – | L | – | S | K | – | – | – | – | – | – | – | 40 |
| *Scheffersomyces stipites*[B] | XP_001386232 | – | – | L | – | S | K | – | – | – | – | – | – | – | 40 |
| *Piriformospora indica*[B] | CCA68922 | – | – | A | – | S | K | – | – | – | – | – | – | – | 39 |
| *Heterobasidion irregulare*[B] | ETW86792* | – | – | A | – | S | K | – | – | – | – | – | – | – | 39 |
| *Ogataea parapolymorpha* | ESW97477 | – | – | A | – | T | E | – | – | – | – | – | – | – | 41 |
| *Ogataea angusta* | CAL64800 | – | – | A | – | T | E | – | – | – | – | – | – | – | 41 |
| *Coniophora puteana*[B] | EIW87079 | – | – | A | – | T | K | – | – | – | – | – | – | – | 8 |
| *Schizophyllum commeune*[B] | XP_003037049 | – | – | A | – | T | K | – | – | – | – | – | – | – | 8 |
| *Dichomitus squalens*[B] | EJF67129 | – | – | A | – | T | K | – | – | – | – | – | – | – | 8 |
| *Trametes versicolor*[B] | EIW64029 | – | – | A | – | T | K | – | – | – | – | – | – | – | 8 |
| *Cryptococcus neoformans*[B] | XP_570776 | – | – | L | – | T | K | – | – | – | – | – | – | – | 7 |
| *Cryptococcus gattii*[B] | XP_003194070 | – | – | L | – | T | K | – | – | – | – | – | – | – | 7 |
| *Phanerochaete carnosa*[B] | EKM61428 | – | – | A | – | T | K | – | – | – | – | – | – | – | 8 |
| *Pneumocystis murina* | EMR11423 | – | – | L | – | T | K | – | – | – | – | – | – | – | 7 |
| *Rhodosporidium toruloides*[B] | EMS26034 | – | – | L | – | T | K | – | – | – | – | – | – | – | 7 |
| *Dactylellina haptotyla* | EPS40966 | – | – | – | – | D | K | – | R | – | – | – | – | – | 42 |

TABLE 2-continued

Short sequence BLASTp of *Blastomyces dermatitidis* calnexin
peptide #1 against deduced fungal protein sequences at NCBI.

| Organism | Accession | Calnexin peptide #1 | | | | | | | | | | | | | SEQ ID NO: |
|---|---|---|---|---|---|---|---|---|---|---|---|---|---|---|---|
| | | L | V | V | K | N | P | A | A | H | H | A | I | S | 1 |
| *Candida temuis* | XP_006686125 | – | – | L | – | T | K | – | – | – | – | – | – | – | 7 |
| *Ceriporiopsis subvermispora*[B] | EMD42320* | – | – | A | – | T | K | – | – | – | – | – | – | – | 8 |
| *Fibroporia radiculosa*[B] | CCM03669* | – | – | A | – | T | K | – | – | – | – | – | – | – | 8 |
| *Serpula lacrymans*[B] | EGO05279* | – | – | A | – | T | K | – | – | – | – | – | – | – | 8 |
| *Gloeophyllum trabeum*[B] | EPQ60121* | – | – | A | – | T | K | – | – | – | – | – | – | – | 8 |
| *Fomitopsis pinicola*[B] | EPT03461 | – | – | A | – | T | K | – | – | – | – | – | – | – | 8 |
| *Dekkera bruxellensis* | EIF46712 | – | – | – | – | S | E | – | – | L | – | – | – | – | 43 |
| *Mixia osmundae*[B] | GAA96853 | – | – | – | A | S | K | – | – | – | – | – | – | – | 44 |
| *Rhizoctonia solani*[B] | CCO31780 | – | – | A | – | S | K | – | S | – | – | – | – | – | 45 |
| *Spathaspora passalidarum* | EGW35646 | – | – | L | – | S | K | – | – | – | – | – | – | A | 46 |
| *Auricularia delicate*[B] | EJD54856 | – | – | A | – | S | K | – | T | – | – | – | – | – | 47 |
| *Rhizophagus irregularis*[G] | ESA03120 | – | I | – | D | S | K | – | – | – | – | – | – | – | 48 |
| *Pyronema omphalodes* | CCX15881 | – | – | A | – | – | V | – | – | F | – | – | – | – | 49 |
| *Moniliophthora perniciosa*[B] | XP_002392753* | – | – | A | – | S | K | – | – | – | Q | – | – | – | 50 |
| *Dacryopinax sp.*[B] | EJU02798 | – | – | A | – | T | K | – | G | – | – | – | – | – | 51 |

NOTES:
NCBI BLASTp with parameters adjusted (automatically by BLASTp) to search for short input sequences.
Only amino acids different from *Bd.* calnexin peptide 1 are indicated by letter; – = no diff.
Duplicate hits of different seq files for the same species are not shown.
[B]Phyllum Basidiomycota, [C]Chytridiomycota, [G]Phylum Glomeromycota; all the others are Ascomycota
For hits that are identical to *B. derm.* Peptide 1, the species are listed in alphabetical order; for hits with a single amino acid substitution, the hits are sorted by substituted amino acid, for hits with a single amino acid substitution at position six, the species are first sorted by substituted amino acid, and then alphabetically; Hits with more than one substitution are listed in the order as they appear in the BLASTp output.

REFERENCES

1. Harvey, R. P., Schmid, E. S., Carrington, C. C., and Stevens, D. A. 1978. Mouse model of pulmonary blastomycosis: utility, simplicity, and quantitative parameters. *American Review of Respiratory Disease* 117:695-703.
2. Brandhorst, T. T., Wüthrich, M., Warner, T., and Klein, B. 1999. Targeted gene disruption reveals an adhesin indispensable for pathogenicity of *Blastomyces dermatitidis*. *J Exp Med* 189:1207-1216.
3. Wüthrich, M., Hung, C. Y., Gem, B. H., Pick-Jacobs, J. C., Galles, K. J., Filutowicz, H. I., Cole, G. T., and Klein, B. S. 2011. A TCR Transgenic Mouse Reactive with Multiple Systemic Dimorphic Fungi. *J Immunol* 187:1421-1431.
4. Levine, H. B., Cobb, J. M., and Smith, C. E. 1960. Immunity to coccidioi-domycosis induced in mice by purified spherule, arthrospore, and mycelial vaccines. *Trans N Y Acad Sci* 22:436-449.
5. Levine, H. B., Kong, Y. C., and Smith, C. 1965. Immunization of Mice to *Coccidioides Immitis*: Dose, Regimen and Spherulation Stage of Killed Spherule Vaccines. *J Immunol* 94:132-142.
6. Wüthrich, M., Ersland, K., Sullivan, T., Galles, K., and Klein, B. S. 2012. Fungi subvert vaccine T cell priming at the respiratory mucosa by preventing chemokine-induced influx of inflammatory monocytes. *Immunity* 36:680-692.
7. Wüthrich, M., Filutowicz, H. I., and Klein, B. S. 2000. Mutation of the WI-1 gene yields an attenuated *Blastomyces dermatitidis* strain that induces host resistance. *J Clin Invest* 106:1381-1389.
8. Wisniewski, J. R., Zougman, A., Nagaraj, N., and Mann, M. 2009. Universal sample preparation method for proteome analysis. *Nat Methods* 6:359-362.
9. Nesvizhskii, A. I., Keller, A., Kolker, E., and Aebersold, R. 2003. A statistical model for identifying proteins by tandem mass spectrometry. *Anal Chem* 75:4646-4658.
10. dos Santos Feitosa, L., de Almeida Soares, C. M., Dos Santos, M. R., Bailao, A. M., Xander, P., Mortara, R. A., and Lopes, J. D. 2007. Cloning, characterization and expression of a calnexin homologue from the pathogenic fungus *Paracoccidioides brasiliensis*. *Yeast* 24:79-87.
11. Thompson, J. D., Higgins, D. G., and Gibson, T. J. 1994. CLUSTAL W: improving the sensitivity of progressive multiple sequence alignment through sequence weighting, position-specific gap penalties and weight matrix choice. *Nucleic Acids Res* 22:4673-4680.
12. Wüthrich, M., Filutowicz, H. I., Allen, H. L., Deepe, G. S., and Klein, B. S. 2007. V{beta}1+J{beta}1.1+/V{alpha}2+J{alpha}49+CD4+ T Cells Mediate Resistance against Infection with *Blastomyces dermatitidis*. *Infect Immun* 75:193-200.

13. Nemecek, J. C., Wüthrich, M., and Klein, B. S. 2006. Global control of dimorphism and virulence in fungi. *Science* 312:583-588.
14. Wüthrich, M., Gern, B., Hung, C. Y., Ersland, K., Rocco, N., Pick-Jacobs, J., Galles, K., Filutowicz, H., Warner, T., Evans, M., et al. 2011. Vaccine-induced protection against 3 systemic mycoses endemic to North America requires Th17 cells in mice. *J Clin Invest* 121:554-568.
15. Wüthrich, M., Gern, B., Hung, C. Y., Ersland, K., Rocco, N., Pick-Jacobs, J., Galles, K., Filutowicz, H., Warner, T., Evans, M., et al. 2011. Vaccine-induced protection against 3 systemic mycoses endemic to North America requires Th17 cells in mice. *J Clin Invest*.
16. Fisher, L. D., and van Belle, G. 1993. Biostatistics: A Methodology for the Health Sciences. John Wiley & Sons, New York:611-613.
17. Ellgaard, L., and Helenius, A. 2003. Quality control in the endoplasmic reticulum. *Nat Rev Mol Cell Biol* 4:181-191.
18. LeibundGut-Landmann, S., Gross, O., Robinson, M. J., Osorio, F., Slack, E. C., Tsoni, S. V., Schweighoffer, E., Tybulewicz, V., Brown, G. D., Ruland, J., et al. 2007. Syk- and CARD9-dependent coupling of innate immunity to the induction of T helper cells that produce interleukin 17. *Nat Immunol* 8:630-638.
19. Myhill Nathan, Lynes Emily M., Nanji Jalal A., Blagoveshchenskaya Anastassia D., Fei Hao, Simmen Katia Carmine, Cooper Timothy J., Thomas Gary, Simmen Thomas, The Subcellular Distribution of Calnexin Is Mediated by PACS-2. *Molecular Biology of the Cell* 2008, 19, 2777-2788.
20. Williams David B. Beyond lectins: the calnexin/calreticulin chaperone system of the endoplasmic reticulum. *Journal of Cell Science*, 2006, 119, 615-623
21. Acosta-Rodriguez, E. V., Rivino, L., Geginat, J., Jarrossay, D., Gattorno, M., Lanzavecchia, A., Sallusto, F., and Napolitani, G. (2007). Surface phenotype and antigenic specificity of human interleukin 17-producing T helper memory cells. Nature immunology 8, 639-646.
22. Beck, O., Topp, M. S., Koehl, U., Roilides, E., Simitsopoulou, M., Hanisch, M., Sarfati, J., Latge, J. P., Klingebiel, T., Einsele, H., et al. (2006). Generation of highly purified and functionally active human TH1 cells against *Aspergillus fumigatus*. Blood 107, 2562-2569.
23. Blyth, E., Clancy, L., Simms, R., Ma, C. K., Burgess, J., Deo, S., Byth, K., Dubosq, M. C., Shaw, P. J., Micklethwaite, K. P., et al. (2013). Donor-derived CMV-specific T cells reduce the requirement for CMV-directed pharmacotherapy after allogeneic stem cell transplantation. Blood 121, 3745-3758.
24. Casadevall, A., Nosanchuk, J. D., Williamson, P., and Rodrigues, M. L. (2009). Vesicular transport across the fungal cell wall. Trends in microbiology 17, 158-162.
25. Cassone, A., and Casadevall, A. (2012). Recent progress in vaccines against fungal diseases. Current opinion in microbiology 15, 427-433. 26 da Gloria Sousa, M., Reid, D. M., Schweighoffer, E., Tybulewicz, V., Ruland, J., Langhorne, J., Yamasaki, S., Taylor, P. R., Almeida, S. R., and Brown, G. D. (2011). Restoration of pattern recognition receptor costimulation to treat chromoblastomycosis, a chronic fungal infection of the skin. Cell Host Microbe 9, 436-443.
27. Deepe, G. S., Jr., and Durose, G. G. (1995). Immunobiological activity of recombinant H antigen from *Histoplasma capsulatum*. Infection and immunity 63, 3151-3157.
28. Edwards, J. E., Jr. (2012). Fungal cell wall vaccines: an update. Journal of medical microbiology 61, 895-903.
29. Ellgaard, L., and Helenius, A. (2003). Quality control in the endoplasmic reticulum. Nat Rev Mol Cell Biol 4, 181-191.
30. Fisher, L. D., and van Belle, G. (1993). Biostatistics: A Methodology for the Health Sciences. John Wiley & Sons, New York, 611-613.
31. Gomez, F. J., Gomez, A. M., and Deepe, G. S., Jr. (1991). Protective efficacy of a 62-kilodalton antigen, HIS-62, from the cell wall and cell membrane of *Histoplasma capsulatum* yeast cells. Infection and immunity 59, 4459-4464.
32. Hirota, K., Duarte, J. H., Veldhoen, M., Hornsby, E., Li, Y., Cua, D. J., Ahlfors, H., Wilhelm, C., Tolaini, M., Menzel, U., et al. (2011). Fate mapping of IL-17-producing T cells in inflammatory responses. Nature immunology 12, 255-263.
33. Hirota, K., Yoshitomi, H., Hashimoto, M., Maeda, S., Teradaira, S., Sugimoto, N., Yamaguchi, T., Nomura, T., Ito, H., Nakamura, T., et al. (2007). Preferential recruitment of CCR6-expressing Th17 cells to inflamed joints via CCL20 in rheumatoid arthritis and its animal model. The Journal of experimental medicine 204, 2803-2812.
34. Huang, H., Ostroff, G. R., Lee, C. K., Specht, C. A., and Levitz, S. M. (2010). Robust stimulation of humoral and cellular immune responses following vaccination with antigen-loaded beta-glucan particles. MBio 1.
35. Levitz, S. M., and Specht, C. A. (2006). The molecular basis for the immunogenicity of *Cryptococcus neoformans* mannoproteins. FEMS yeast research 6, 513-524.
36. Long, K. H., Gomez, F. J., Morris, R. E., and Newman, S. L. (2003). Identification of heat shock protein 60 as the ligand on *Histoplasma capsulatum* that mediates binding to CD18 receptors on human macrophages. J Immunol 170, 487-494.
37. Lorch, J. M., Meteyer, C. U., Behr, M. J., Boyles, J. G., Cryan, P. M., Hicks, A. C., Ballmann, A. E., Coleman, J. T., Redell, D. N., Reeder, D. M., et al. (2011). Experimental infection of bats with *Geomyces destructans* causes white-nose syndrome. Nature 480, 376-378.
38. Moon, J. J., Chu, H. H., Hataye, J., Pagan, A. J., Pepper, M., McLachlan, J. B., Zell, T., and Jenkins, M. K. (2009). Tracking epitope-specific T cells. Nat Protoc 4, 565-581.
39. Moon, J. J., Chu, H. H., Pepper, M., McSorley, S. J., Jameson, S. C., Kedl, R. M., and Jenkins, M. K. (2007). Naïve CD4(+) T cell frequency varies for different epitopes and predicts repertoire diversity and response magnitude. Immunity 27, 203-213.
40. Nanjappa, S. G., Heninger, E., Wüthrich, M., Gasper, D. J., and Klein, B. S. (2012a). Tc17 cells mediate vaccine immunity against lethal fungal pneumonia in immune deficient hosts lacking CD4+ T cells. PLoS pathogens 8, e1002771.
41. Nanjappa, S. G., Heninger, E., Wüthrich, M., Sullivan, T., and Klein, B. (2012b). Protective antifungal memory CD8(+) T cells are maintained in the absence of CD4(+) T cell help and cognate antigen in mice. J Clin Invest 122, 987-999.
42. Nelson, R. W., Beisang, D., Tubo, N. J., Dileepan, T., Wiesner, D. L., Nielsen, K. N., Spanier, J. A., Fife, B. T., Moon, J. J., Wuethrich, M., et al. (2014). TCR cross-reactivity between similar foreign and self peptides influences naïve cell population size and autoimmunity. Immunity. In Press.

43. Nemecek, J. C., Wüthrich, M., and Klein, B. S. (2006). Global control of dimorphism and virulence in fungi. Science 312, 583-588.
44. Nosanchuk, J. D., Steenbergen, J. N., Shi, L., Deepe, G. S., Jr., and Casadevall, A. (2003). Antibodies to a cell surface histone-like protein protect against *Histoplasma capsulatum*. J Clin Invest 112, 1164-1175.
45. Park, B. J., Wannemuehler, K. A., Marston, B. J., Govender, N., Pappas, P. G., and Chiller, T. M. (2009). Estimation of the current global burden of cryptococcal meningitis among persons living with HIV/AIDS. AIDS 23, 525-530.
46. Peggs, K. S., Thomson, K., Samuel, E., Dyer, G., Armoogum, J., Chakraverty, R., Pang, K., Mackinnon, S., and Lowdell, M. W. (2011). Directly selected cytomegalovirus-reactive donor T cells confer rapid and safe systemic reconstitution of virus-specific immunity following stem cell transplantation. Clin Infect Dis 52, 49-57.
47. Pepper, M., Linehan, J. L., Pagan, A. J., Zell, T., Dileepan, T., Cleary, P. P., and Jenkins, M. K. (2010). Different routes of bacterial infection induce long-lived TH1 memory cells and short-lived TH17 cells. Nature immunology 11, 83-89.
48. Pfaller, M. A., Moet, G. J., Messer, S. A., Jones, R. N., and Castanheira, M. (2011). *Candida* Bloodstream Infections: Comparison of Species Distributions and Antifungal Resistance Patterns in Community-Onset and Nosocomial Isolates in the SENTRY Antimicrobial Surveillance Program, 2008-2009. Antimicrobial Agents and Chemotherapy 55, 561-566.
49. Rappleye, C. A., and Goldman, W. E. (2008). Fungal stealth technology. Trends in immunology 29, 18-24.
50. Singh, N., and Paterson, D. L. (2005). *Aspergillus* infections in transplant recipients. Clinical microbiology reviews 18, 44-69.
51. Soto, E. R., and Ostroff, G. R. (2008). Characterization of multilayered nanoparticles encapsulated in yeast cell wall particles for DNA delivery. Bioconjug Chem 19, 840-848.
52. Torosantucci, A., Bromuro, C., Chiani, P., De Bernardis, F., Berti, F., Galli, C., Norelli, F., Bellucci, C., Polonelli, L., Costantino, P., et al. (2005). A novel glyco-conjugate vaccine against fungal pathogens. The Journal of experimental medicine 202, 597-606.
53. Walsh, T. J., Anaissie, E. J., Denning, D. W., Herbrecht, R., Kontoyiannis, D. P., Marr, K. A., Morrison, V. A., Segal, B. H., Steinbach, W. J., Stevens, D. A., et al. (2008). Treatment of aspergillosis: clinical practice guidelines of the Infectious Diseases Society of America. Clin Infect Dis 46, 327-360.
54. Young, S. H., Ostroff, G. R., Zeidler-Erdely, P. C., Roberts, J. R., Antonini, J. M., and Castranova, V. (2007). A comparison of the pulmonary inflammatory potential of different components of yeast cell wall. J Toxicol Environ Health A 70, 1116-1124.
55. Zancope-Oliveira, R. M., Reiss, E., Lott, T. J., Mayer, L. W., and Deepe, G. S., Jr. (1999). Molecular cloning, characterization, and expression of the M antigen of *Histoplasma capsulatum*. Infection and immunity 67, 1947-1953.

We claim:

1. A method for evaluating an immune status of a patient immunized against a fungus, the method comprising the steps of:
   a) obtaining peptide-MHCII tetramers, wherein the peptide-MHCII tetramers comprise a peptide selected from the group consisting of SEQ ID NOs:1-5, 7, and 8;
   b) exposing a patient's sample to a suitable amount of the pMHCII tetramers wherein the patient's sample comprises helper T cells;
   c) identifying helper T cells in the patient's sample specific for the peptide-MHCII tetramers;
   d) quantifying the helper T cells identified in step (c) in the patient's sample;
   e) vaccinating the patient against a fungus;
   f) repeating steps (b)-(d) after vaccinating against the fungus,
   wherein the immune status of a patient against the fungus is obtained by comparing the quantity of the helper T cells specific for the peptide-MHCII tetramers before and after vaccinating the patient against the fungus.

2. The method of claim 1, wherein the sample is a fresh blood sample.

3. The method of claim 1, wherein the peptide-MHCII tetramers comprise at least one fluorescent label.

4. The method of claim 1, wherein identifying helper T cells in the patient's sample comprises using a spectroscopy technique to identify helper T cells.

5. The method of claim 4, wherein the spectroscopy technique is fluorescence.

6. The method of claim 1, wherein the fungus is either a dimorphic fungus or non-dimorphic fungus.

7. The method of claim 6, wherein the dimorphic fungus is selected from a group consisting of *Histoplasma, Coccidiodes, Paracoccidioides, Penicillium, Blastomyces,* and *Sporothrix*.

8. The method of claim 1, wherein the fungus is selected from a group consisting of *Blastomyces dermatitidis, His-*

*toplasma capsulatum, Aspergillus fumigatus, Fonsecea pedrosoi,* and *Geomyces destructans.*

9. The method of claim 1, wherein the peptide-MHCII tetramers comprise a calnexin peptide selected from the group consisting of SEQ ID NOs:1-5, 7, and 8 covalently linked by a flexible linker to a MHCII β chain; and
a MHCII α chain.

10. The method of claim 1, wherein step d) further comprises detecting expression of one or more markers in the T cells, the markers selected from the group consisting of: interferon gamma (IFN-γ), interleukin 17 (IL-17), CD44, CCR6, CXCR3, and CD62 ligand (CD62L).

11. The method of claim 10, wherein detecting expression comprises detecting expression by flow cytometry.

12. A method comprising the steps of:
a) obtaining peptide-MHCII tetramers, wherein the peptide-MHCII tetramers comprise a peptide selected from the group consisting of SEQ ID NOs:1-5, 7, and 8;
b) exposing a patient's sample to a suitable amount of the peptide-MHCII tetramers, wherein the patient's sample comprises helper T cells;
c) identifying helper T cells in the patient's sample specific for the peptide-MHCII tetramers.

13. The method of claim 12, further comprising:
d) quantifying the helper T cells in the patient's sample specific for the peptide-MHCII tetramers.

14. The method of claim 12, wherein the patient is in need of a bone marrow or stem cell transplant.

15. The method of claim 12, wherein the patient has been diagnosed with cancer, has undergone organ transplantation, has been diagnosed with acquired immune deficiency syndrome (AIDS), is undergoing hemodialysis, has a catheter, is suffering from severe trauma or burns, has been diagnosed with diabetes mellitus, or has indwelling intravenous tubes.

\* \* \* \* \*

UNITED STATES PATENT AND TRADEMARK OFFICE
CERTIFICATE OF CORRECTION

PATENT NO. : 11,789,019 B2
APPLICATION NO. : 16/529151
DATED : October 17, 2023
INVENTOR(S) : Bruce Steven Klein et al.

It is certified that error appears in the above-identified patent and that said Letters Patent is hereby corrected as shown below:

In the Specification

Column 6, Line 62, "10 g" should be --10μg--.

Column 7, Line 7, "26 g" should be --25μg--.

Column 7, Line 34, "μlus" should be --plus--.

Column 7, Line 50, "10 g" should be --10μg--.

Column 8, Line 45, "10 g" should be --10μg--.

Column 8, Line 54, "(25 g)" should be --(25μg)--.

Column 27, Line 4, "a" should be --α--.

Column 33, Line 44, "100p" should be --100μl--.

Column 33, Line 55, "50p" should be --50μl--.

Column 42, Lines 19-20, "Aspergillusfumigatus" should be --*Aspergillus fumigatus*--.

Column 43, Line 54, "CD441" should be --CD44$^{hi}$--.

Signed and Sealed this
Twenty-sixth Day of March, 2024

Katherine Kelly Vidal
*Director of the United States Patent and Trademark Office*